(12) United States Patent
Bumgardner et al.

(10) Patent No.: US 11,878,088 B2
(45) Date of Patent: Jan. 23, 2024

(54) CHITOSAN NANOFIBER COMPOSITIONS, COMPOSITIONS COMPRISING MODIFIED CHITOSAN, AND METHODS OF USE

(71) Applicant: The University of Memphis Research Foundation, Memphis, TN (US)

(72) Inventors: Joel D. Bumgardner, Memphis, TN (US); Hengjie Su, Memphis, TN (US); Tomoko Fujiwara, Memphis, TN (US); Daniel G. Abebe, Memphis, TN (US); Kwei-Yu Liu, Memphis, TN (US)

(73) Assignee: The University of Memphis Research Foundation, Memphis, TN (US)

( * ) Notice: Subject to any disclaimer, the term of this patent is extended or adjusted under 35 U.S.C. 154(b) by 44 days.

(21) Appl. No.: 17/539,672

(22) Filed: Dec. 1, 2021

(65) Prior Publication Data

US 2022/0160935 A1 May 26, 2022

Related U.S. Application Data

(62) Division of application No. 15/120,990, filed as application No. PCT/US2015/018170 on Feb. 27, 2015, now Pat. No. 11,229,721.

(60) Provisional application No. 61/980,278, filed on Apr. 16, 2014, provisional application No. 61/975,881, filed on Apr. 6, 2014, provisional application No. 61/946,704, filed on Feb. 28, 2014.

(51) Int. Cl.
| | |
|---|---|
| A61L 27/20 | (2006.01) |
| A61L 15/28 | (2006.01) |
| C08B 37/08 | (2006.01) |
| D01D 5/00 | (2006.01) |
| D01F 4/00 | (2006.01) |
| A61K 9/70 | (2006.01) |

(52) U.S. Cl.
CPC ............ *A61L 27/20* (2013.01); *A61L 15/28* (2013.01); *C08B 37/003* (2013.01); *D01D 5/0007* (2013.01); *D01F 4/00* (2013.01); *A61K 9/70* (2013.01); *A61L 2400/12* (2013.01); *A61L 2430/02* (2013.01)

(58) Field of Classification Search
CPC ...... A61L 27/20; A61L 15/28; A61L 2400/12; A61L 2430/02; C08B 37/003; D01D 5/0007; D01F 4/00; A61K 9/70
See application file for complete search history.

(56) References Cited

U.S. PATENT DOCUMENTS

| | | | |
|---|---|---|---|
| 4,607,125 A | 8/1986 | Mott | |
| 6,184,037 B1 | 2/2001 | Rolland et al. | |
| 6,242,529 B1 | 6/2001 | Marritt et al. | |
| 11,229,721 B2 | 1/2022 | Bumgardner et al. | |
| 2002/0018732 A1 | 2/2002 | Hung et al. | |
| 2002/0152560 A1 | 10/2002 | Soane et al. | |
| 2007/0196401 A1 | 8/2007 | Naruse et al. | |
| 2008/0254125 A1 | 10/2008 | Freier | |
| 2013/0266790 A1 | 10/2013 | Han et al. | |
| 2013/0274892 A1 | 10/2013 | Lelkes et al. | |
| 2013/0344763 A1 | 12/2013 | Steckl et al. | |
| 2014/0046236 A1 | 2/2014 | Filée et al. | |
| 2014/0242145 A1 | 8/2014 | Yoo et al. | |

FOREIGN PATENT DOCUMENTS

| | | |
|---|---|---|
| EP | 2361144 A2 | 8/2011 |
| FR | 2857970 A1 | 1/2005 |
| WO | WO-2009011944 A2 * | 1/2009 ............ A61K 8/027 |

OTHER PUBLICATIONS

Sun et al ("Preparation, properties and applications of chitosan based nanofibers fabricated by electrospinning", express Polymer Letters, vol. 5, No. 4, (2011)) (Year: 2011).*
Craveiro et al., Derwent Abstract, BR-9805480-A, Sep. 12, 2000.
Neamnark et al., "Electrospinning of hexanoyl chitosan," Carbohydrate Polymers, 2006, vol. 66, pp. 298-305.
Norowski et al., "Suture pullout strength and in vitro fibroblast and RAW 264.7 monocyte biocompatibility of genipin crosslinked nanofibrous chitosan mats for guided tissue regeneration," Journal of Biomaterials Research Part A, 2012, vol. 100A, No. 11, pp. 2890-2896.

(Continued)

*Primary Examiner* — Leigh C Maier
*Assistant Examiner* — Everett White
(74) *Attorney, Agent, or Firm* — Melissa Hunter-Ensor; Maximilian Benz; Greenberg Traurig, LLP

(57) ABSTRACT

The invention includes chitosan nanofibers having enhanced structural integrity, compositions comprising such chitosan nanofibers, and related methods of use. In a particular aspect, electrospun chitosan nanofibers can be reversibly acylated to enhance structural integrity and promote healing and the formation of tissues in a subject. In another aspect, electrospun chitosan nanofibers comprising at least a portion of the amino groups protected, such as through N-tert-butoxycarbonyl groups, demonstrate enhanced structural integrity and promote healing and the formation of tissues in a subject. The invention also includes compositions and methods for producing a modified chitosan material having anti-inflammatory and pro-healing characteristics and methods of using the modified chitosan materials in a film, a gel, a membrane, microfibers, nanofibers, nano- or micro-particles/spheres and/or sponges. In some aspects, microspheres and methods of producing microspheres comprising modified chitosan are included.

10 Claims, 91 Drawing Sheets

(56) References Cited

OTHER PUBLICATIONS

Pavinatto et al., "Interaction of O-acylated chitosans with biomembrane models: Probing the effects from hydrophobic interactions and hydrogen bonding," Colloids and Surfaces B: Biointerfaces, 2014, vol. 114, pp. 53-59.
Schiffman et al., "One-Step Electrospinning of Cross-Linked Chitosan Fibers," Biomacromolecules, 2007, vol. 8, No. 9, pp. 2665-2667.
Sun et al., "Preparations, properties and applications of chitosan based nanofibers fabricated by electrospinning," eXPRESS Polymer Letters, 2011, vol. 5, No. 4, pp. 342-361.
International Search Report and Written Opinion dated Jul. 16, 2015 in corresponding International PCT Patent Application No. PCT/US2015/018170 (17 pages).

\* cited by examiner

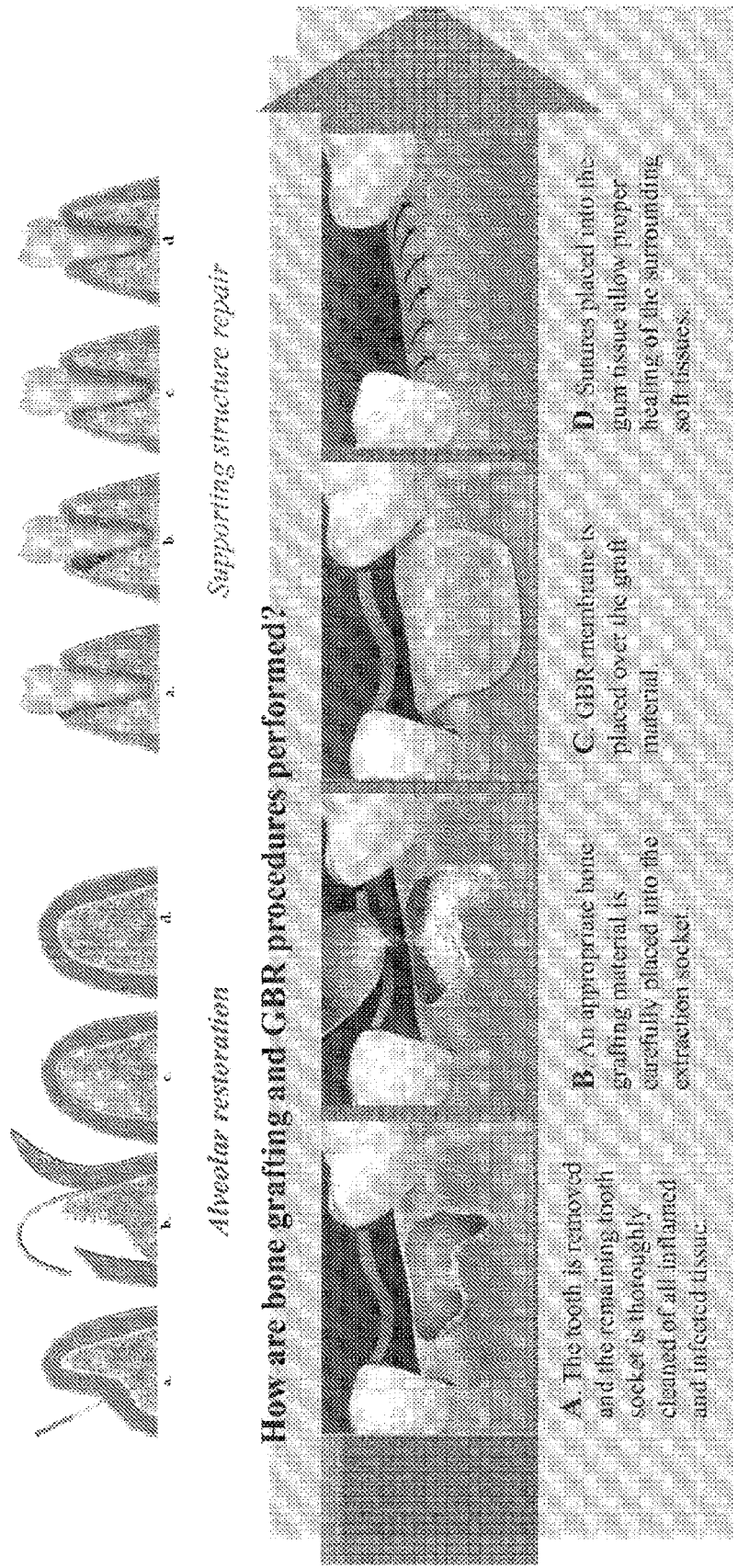

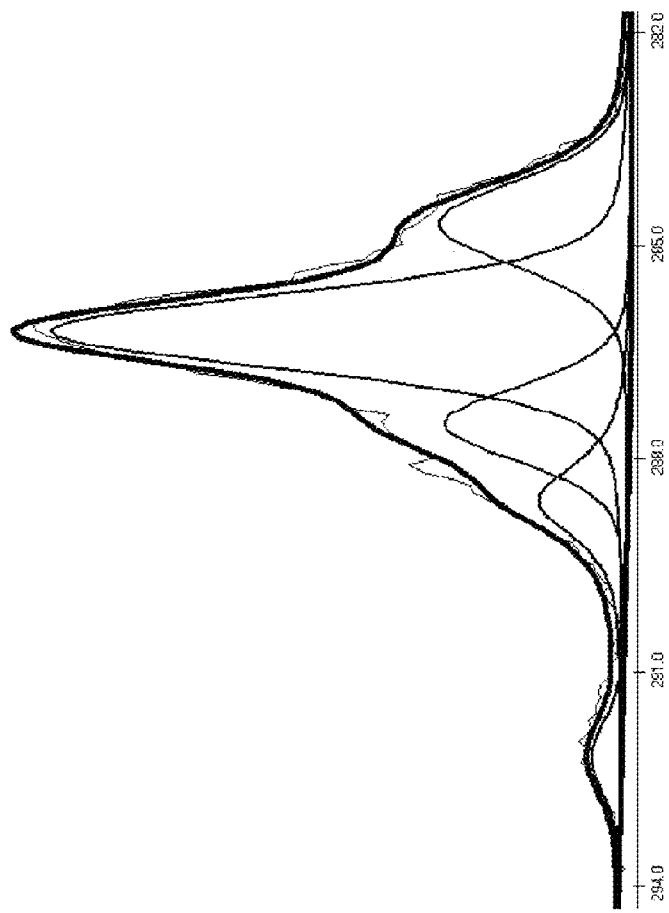
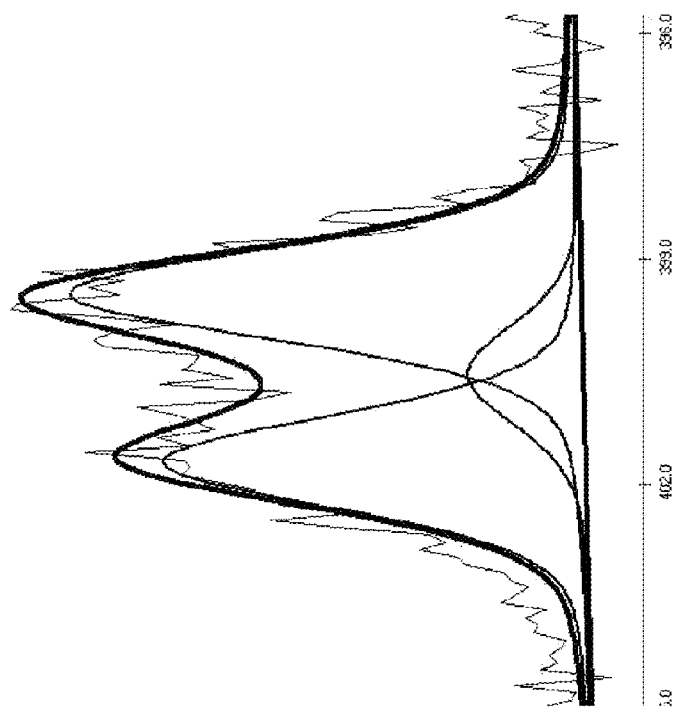
FIG. 9B

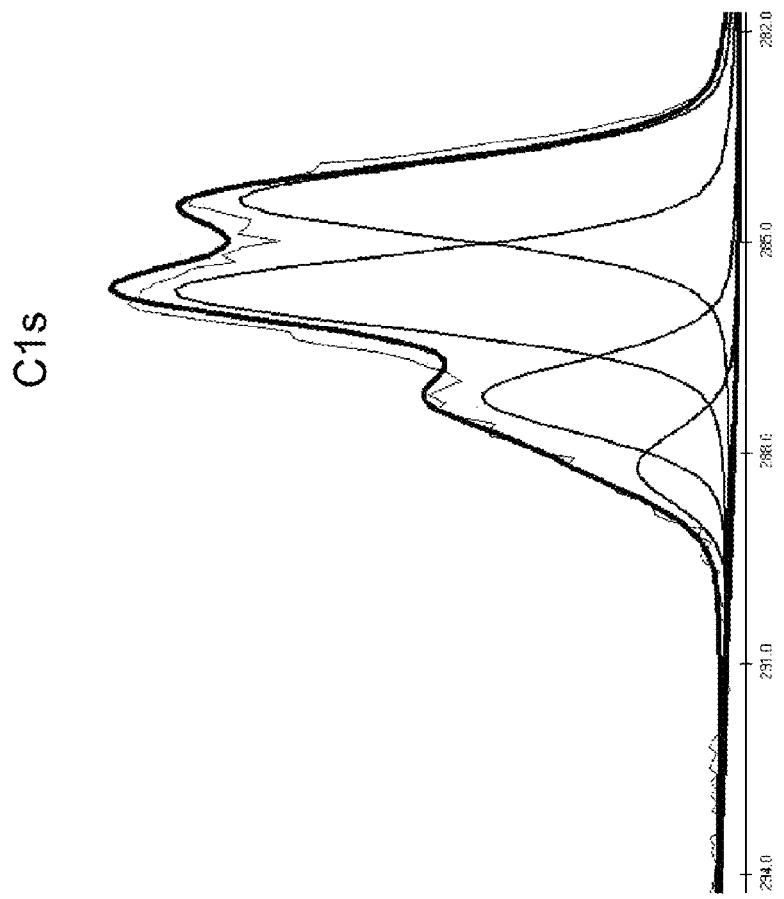
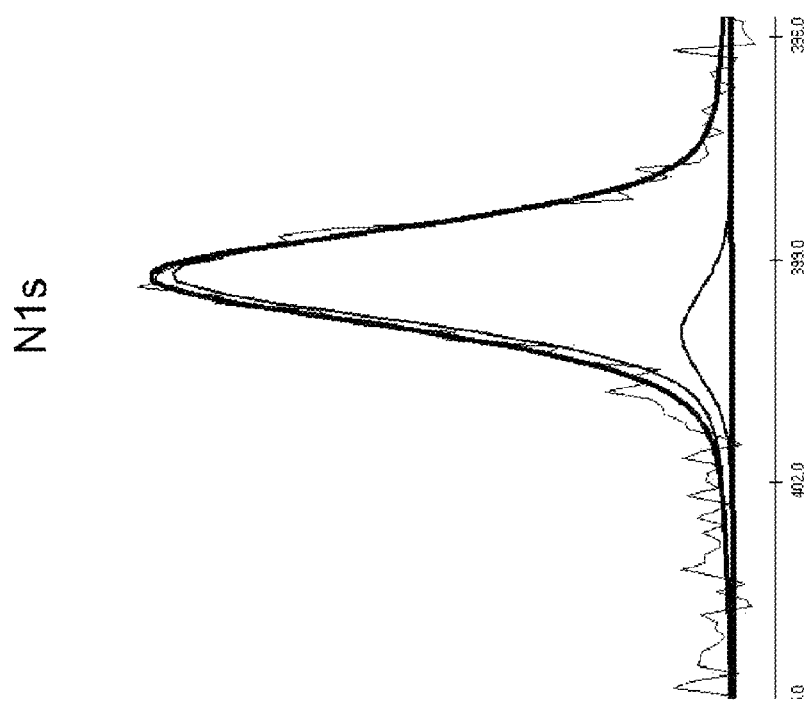
FIG. 9C

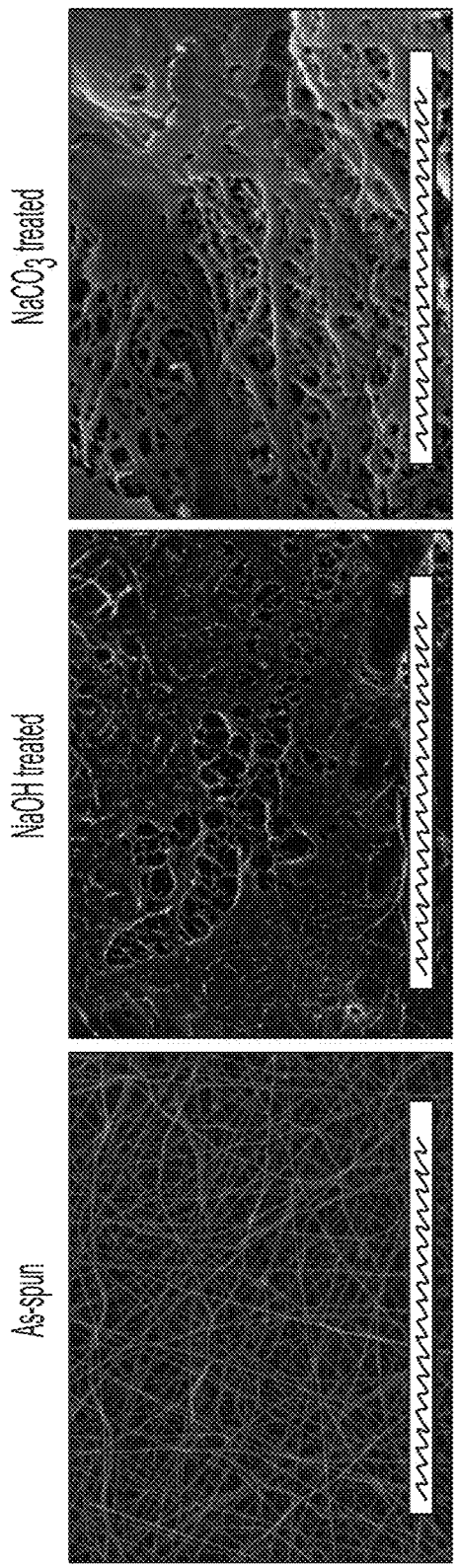

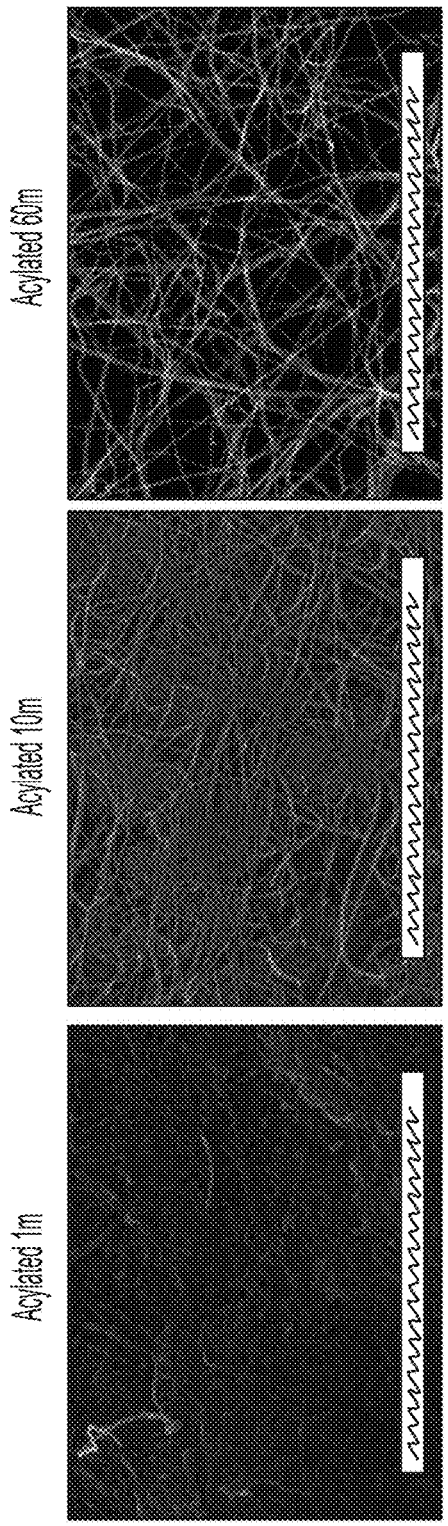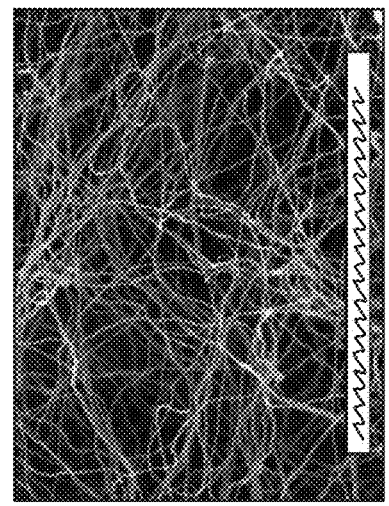
FIG. 11D  FIG. 11E  FIG. 11F  FIG. 11G

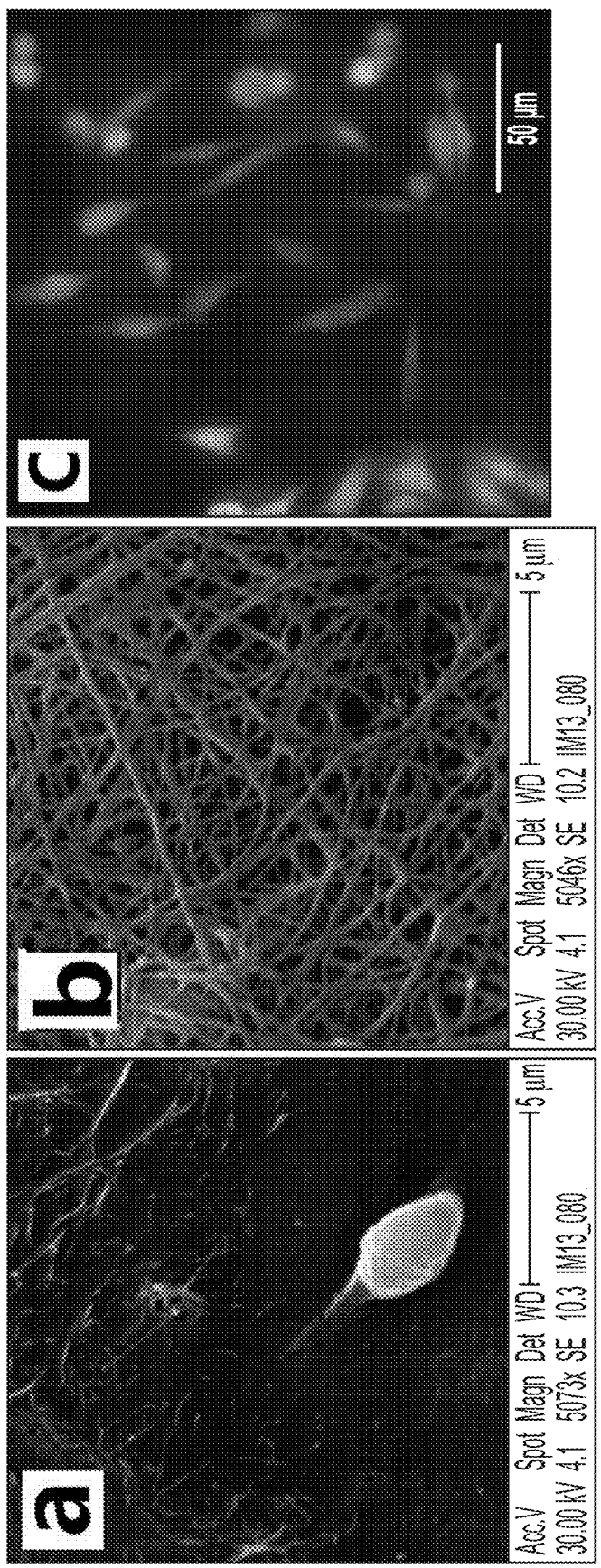

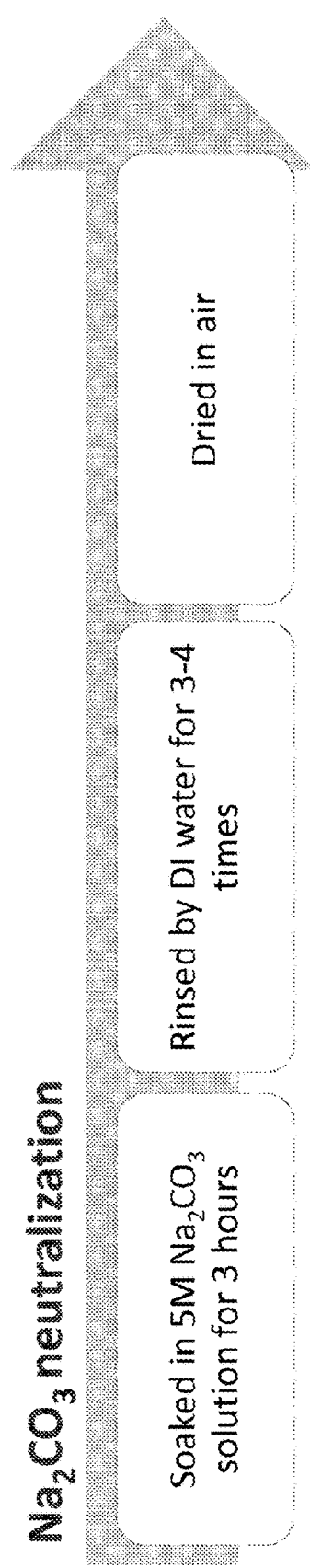
FIG. 29

FTIR

- Fourier transform infrared spectroscopy (FTIR) spectra showed removal of TFA salts. Peaks at 720, 796 and 836 cm-1 related to TFA salts disappeared after the TEA treatment.
- After the tBoc treatment, the peaks around 1600 cm$^{-1}$ showed an increased height in the spectrum, which indicated the presence of the tBoc molecule.
- Since tBoc molecules are hydrophobic, their presence on the chitosan fibers would result in an increased water contact angle and a more hydrophobic surface.

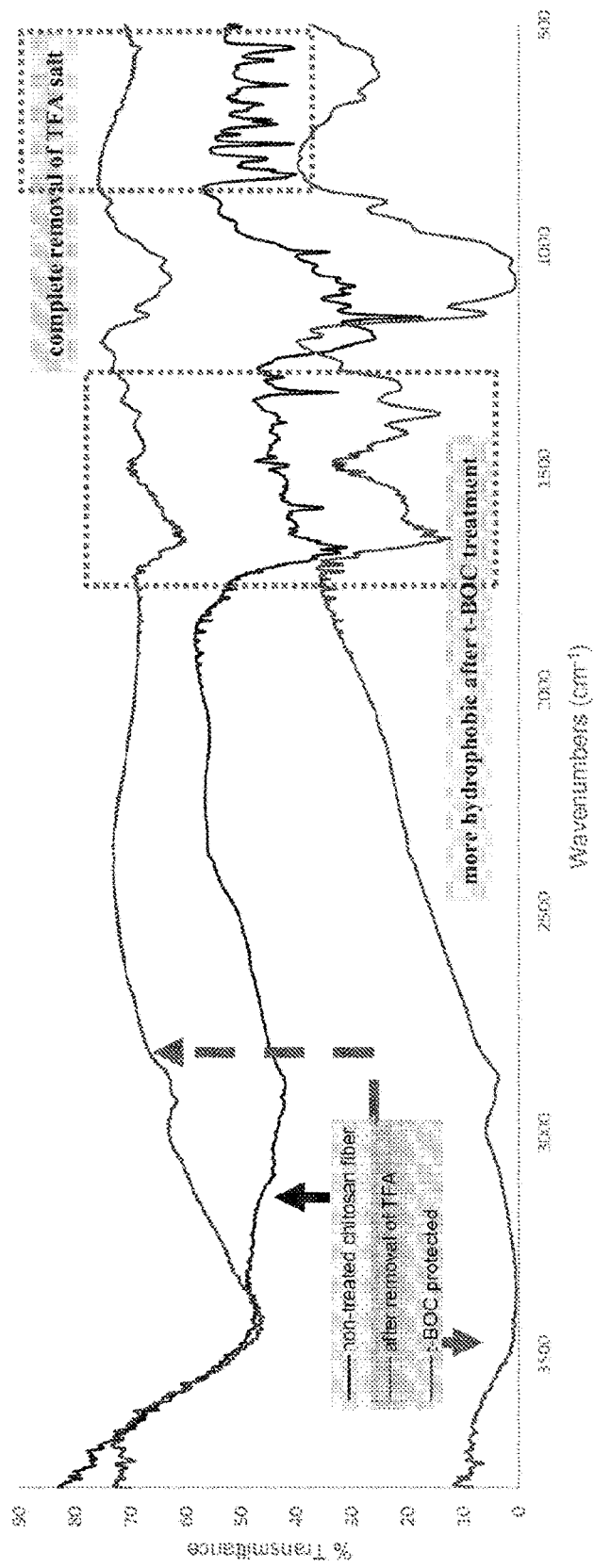

FIG. 31

- The whole steps needed to be repeated 3 times for electrospinning 30 mL chitosan solution to attain an un-neutralized membrane in thickness of $0.7 \pm 0.1$ mm and approximately 15 cm in diameter.

FIG. 36B
Contact angle
- After TEA/tBoc treatment, water contact angle was larger than that of $Na_2CO_3$ treatment membrane. ($p = 6.74 \times 10^{-5}$)
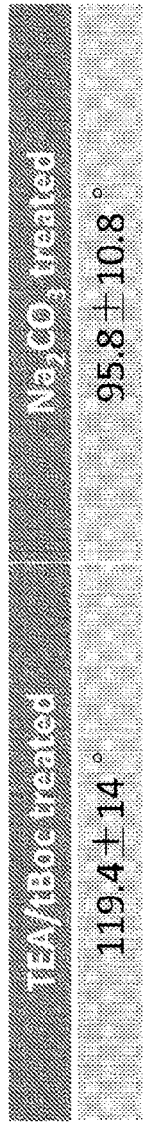
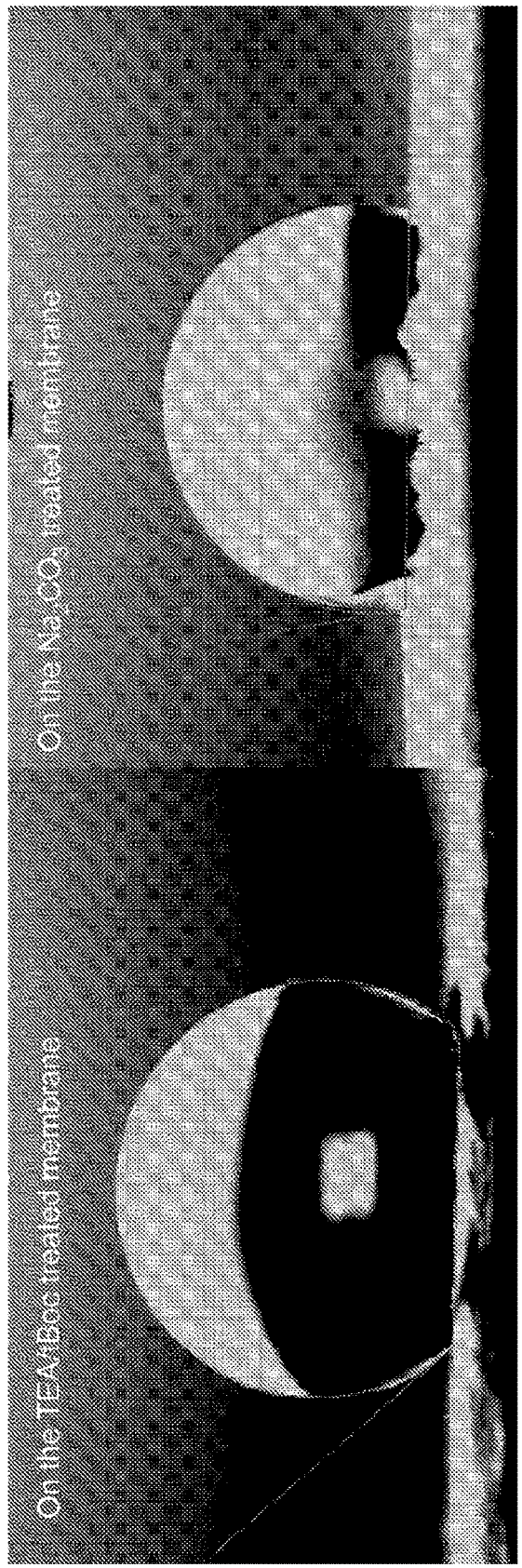

Summary of Histology Scores

| | 3 week animals | | | 12 week animals | | |
|---|---|---|---|---|---|---|
| | Butyryl-modified | collagen | TEA/tBoC treated | Butyryl-modified | collagen | TEA/tBoC treated |
| | 1 | 2 | 1 | 2 | 1 | 2 |
| | 1 | 1 | 1 | 1 | 2 | 1 |
| | 1 | 3 | 2 | 2 | 1 | 1 |
| | 1 | 2 | 1 | 2 | 2 | 1 |
| | 3 | 3 | 2 | 1 | 1 | 1 |
| mean | 1.4 | 2.2 | 1.4 | 1.6 | 1.4 | 1.2 |
| std dev | 0.9 | 0.8 | 0.5 | 0.5 | 0.5 | 0.4 |
| median | 1.0 | 2.0 | 1.0 | 2.0 | 1.0 | 1.0 |

Chi-square analysis; no difference in scores between groups at 3 week or at 12 weeks

FIG. 36E

Summary of Histology Scores

*Confidence interval*

| | 3 weeks | 12 weeks |
|---|---|---|
| Butyrl-modified | 0.29 to 2.51 (mean = 1.4) | 0.92 to 2.28 (mean = 1.6) |
| Collagen | 1.16 to 3.24 (mean = 2.2) | 0.72 to 2.08 (mean = 1.4) |
| TEA/tBoc | 0.72 to 2.08 (mean = 1.4) | 0.64 to 1.76 (mean = 1.2) |

Chi-square analysis; no difference in scores between groups at 3 week or at 12 weeks

FIG. 36F

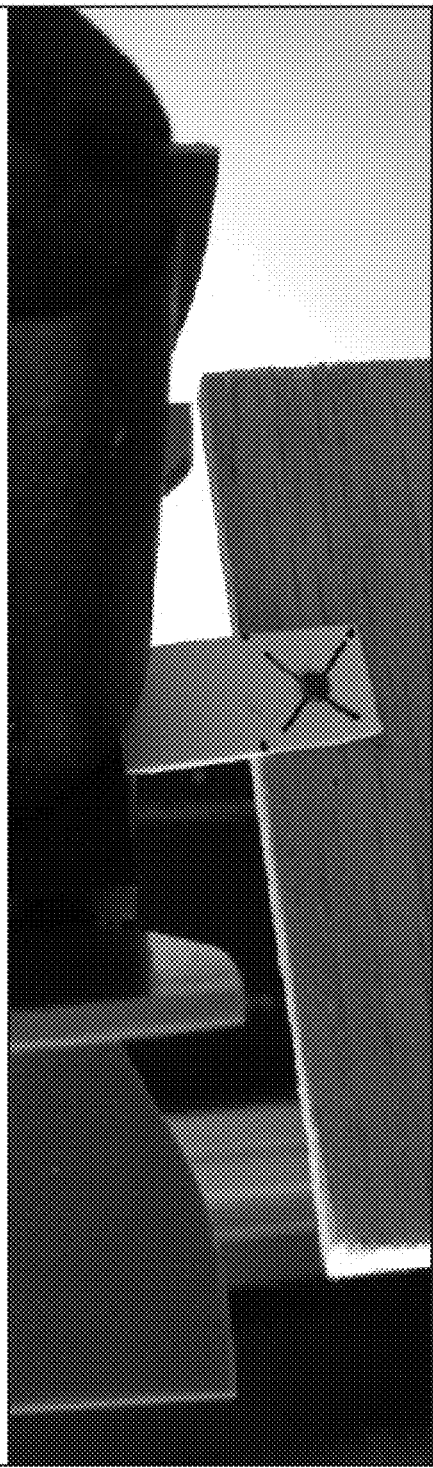
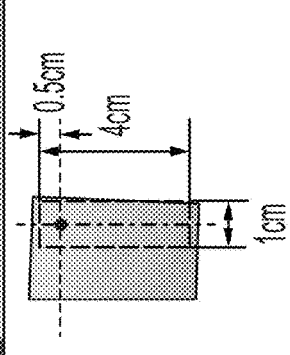
FIG. 37E

The torn pattern

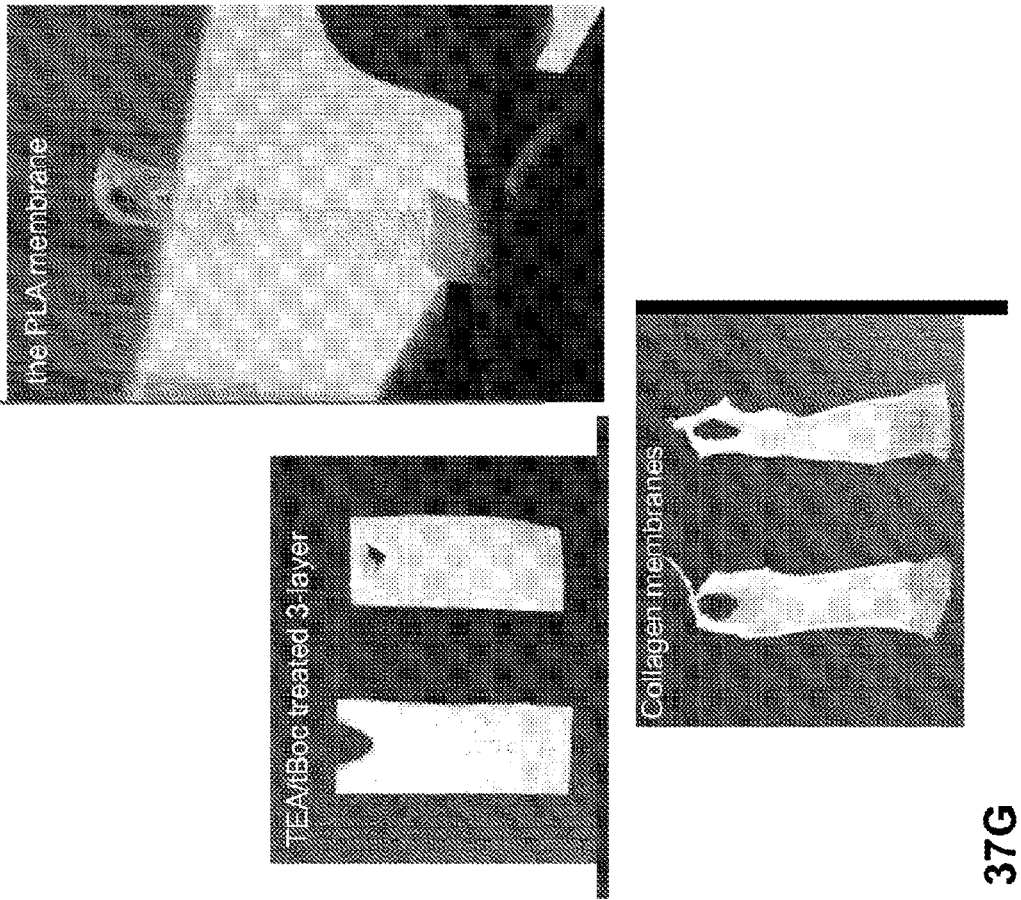

The torn patterns related to the clinical handle ability.

- The Bio-Gide® collagen membrane presented extremely elasticity during the tacking process.
- TEA/tBoc treated triple layers membranes had the similar torn patterns with the collagen membranes but lower elasticity.
- The GUIDOR® polylactic acid (PLA) membrane was torn in the middle part of the membrane instead of the tacking edge.
- With the similar tearing strength, TEA/tBoc treated triple layers membranes would be easier fixed in the wound and keep better coverage function than the GUIDOR® PLA membranes.

FIG. 37G

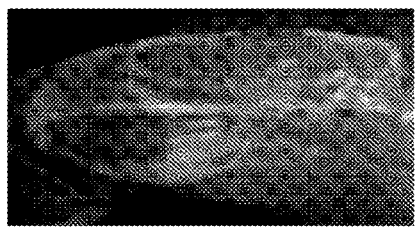
X-ray of defect site at implant placement
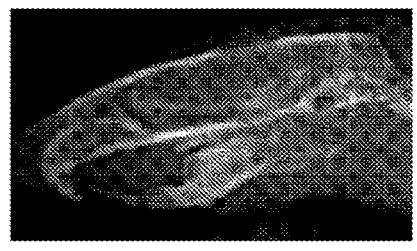
X-ray of defect site at 3 weeks
3 weeks_Collagen
Normal healing response.
FIG. 38E

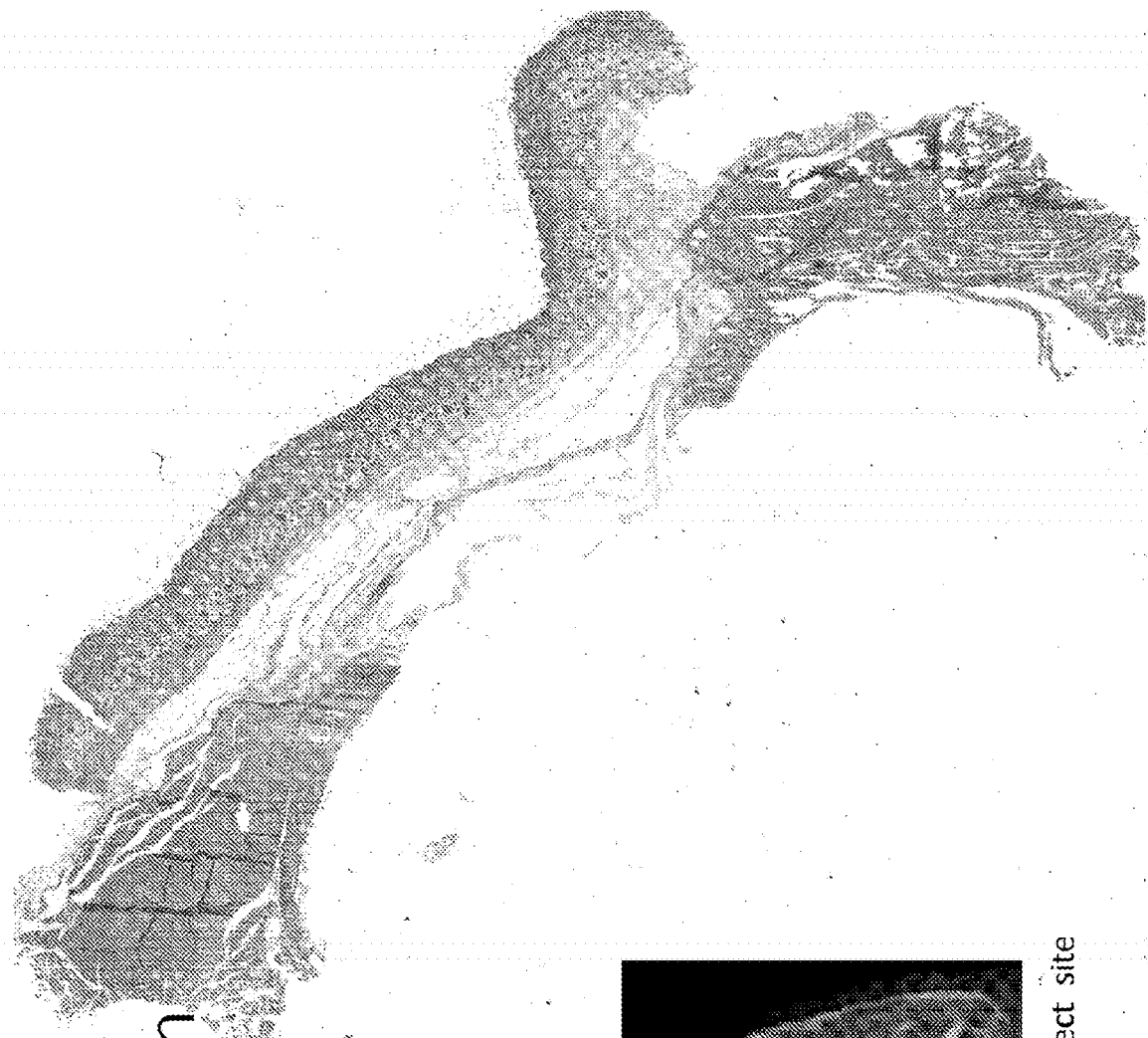
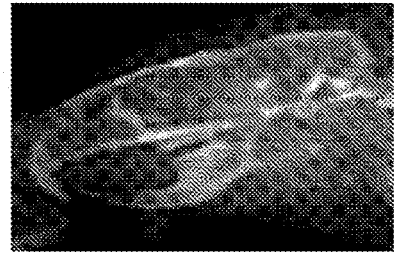
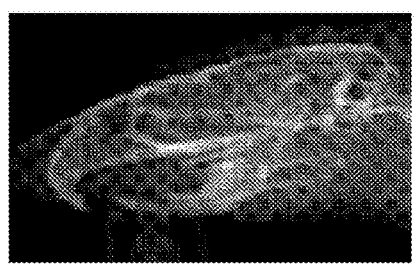
3 weeks_Butyric-modified chitosan membrane
X-ray of defect site at implant placement
X-ray of defect site at 3 weeks
FIG. 38F    normal healing response, New bone is beginning to bridge the defect.

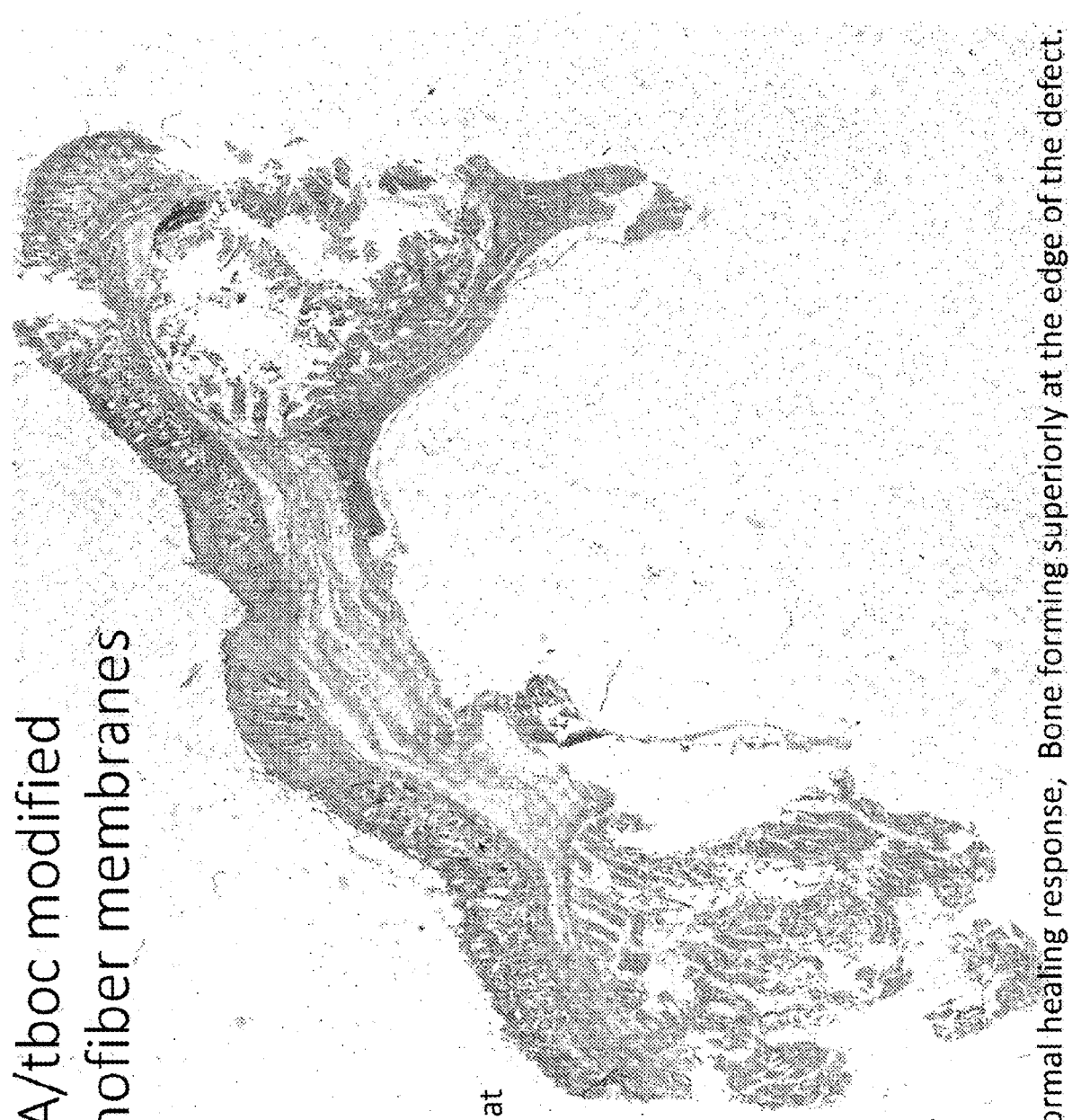
FIG. 38G  3 weeks_TEA/tboc modified chitosan nanofiber membranes. normal healing response, Bone forming superiorly at the edge of the defect.

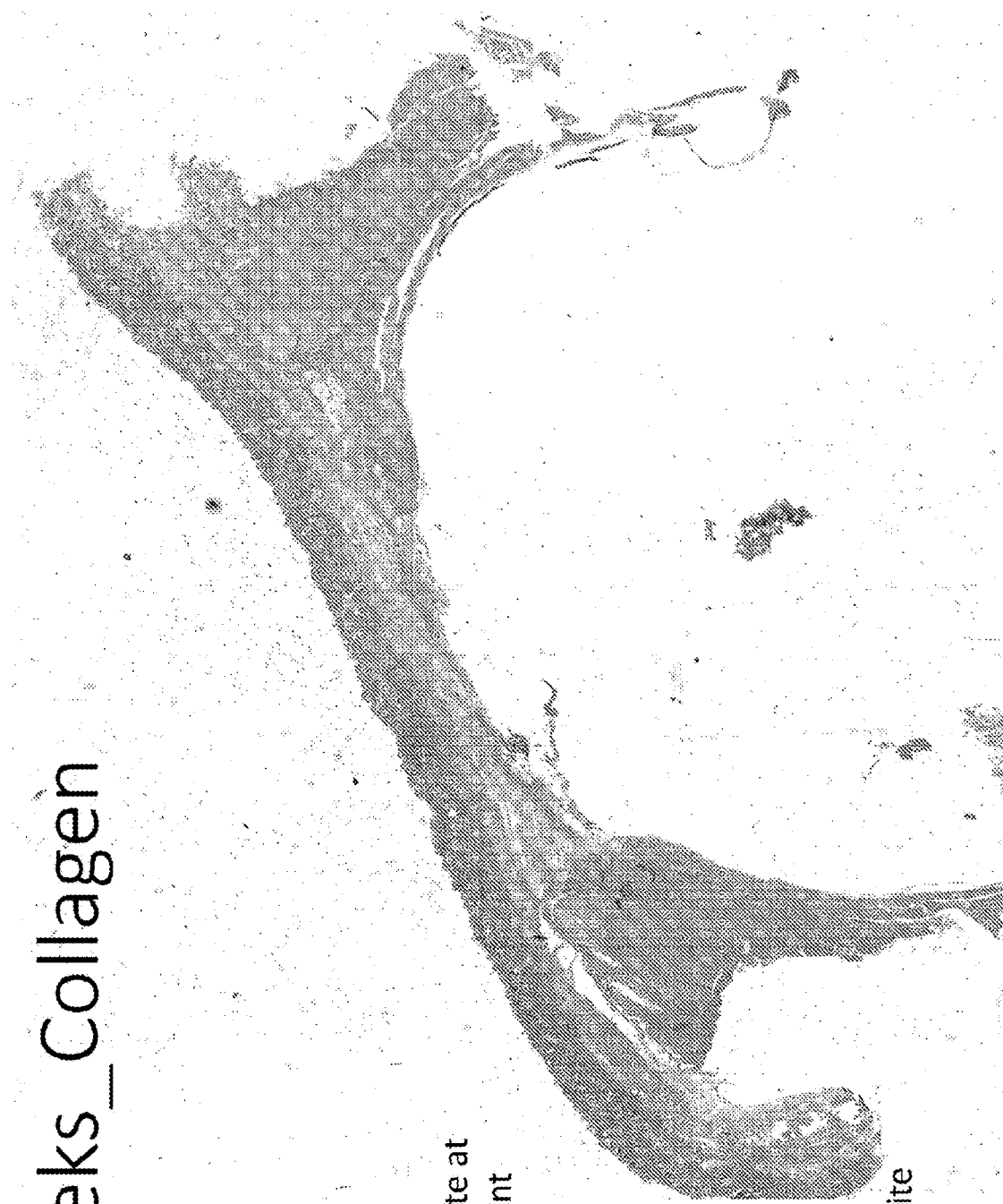
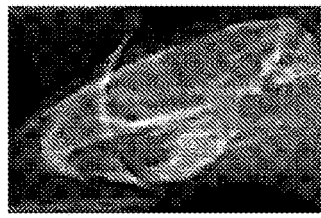
X-ray of defect site at implant placement
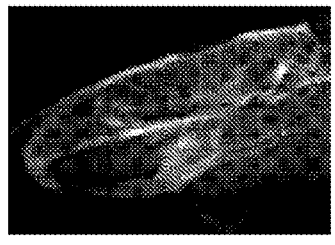
X-ray of defect site at 12 weeks
FIG. 38H  New bone showing definitive proliferation into the defect

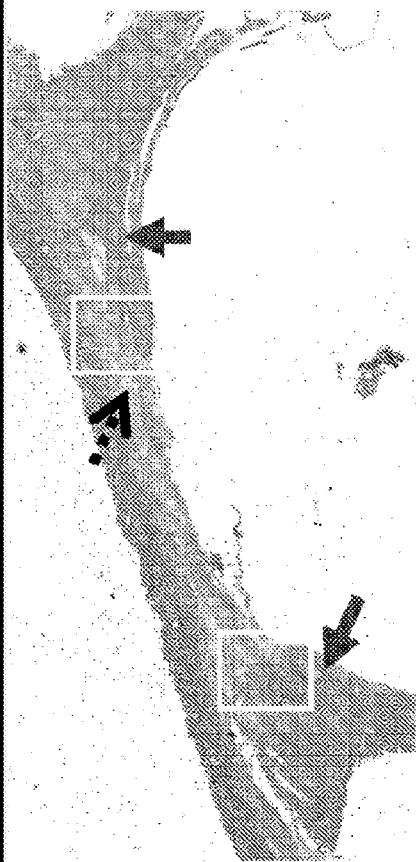
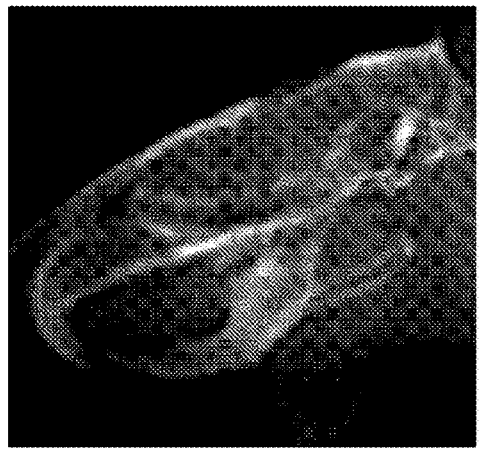
Collagen membrane – 12 wk
↑ New bone
◁┈ membrane
FIG. 38I

CHITOSAN NANOFIBER COMPOSITIONS, COMPOSITIONS COMPRISING MODIFIED CHITOSAN, AND METHODS OF USE

CROSS REFERENCE TO RELATED APPLICATIONS

This application is a divisional of U.S. patent application Ser. No. 15/120,990, filed Aug. 23, 2016, which is the U.S. National Phase Application, pursuant to 35 U.S.C. § 371, of PCT International Patent Application No.: PCT/US2015/018170, filed Feb. 27, 2015, designating the United States and published in English, which claims the benefit of and priority to U.S. Provisional Patent Application No. 61/980,278, filed Apr. 16, 2014; U.S. Provisional Patent Application No. 61/975,881, filed Apr. 6, 2014; and U.S. Provisional Patent Application No. 61/946,704, filed Feb. 28, 2014, the contents of each of which are incorporated herein by reference in their entirety.

BACKGROUND OF THE INVENTION

Guided tissue regeneration (GTR) membranes are used to direct the healing and formation of tissues by helping to prevent the overgrowth of fast healing epithelial tissues into areas of more slowly healing tissues. When the membranes are used to regenerate and restore dental, craniofacial, orthopedic bone volume, and shape and function loss due to disease or injury, the surgical technique is referred to as guided bone regeneration. In guided bone regeneration, the membranes are used to stabilize bone graft material in the defect site, to provide a barrier to prevent soft tissue infiltration and to preserve the space for bone regeneration. Guided bone regeneration (GBR) membranes are widely used with bone graft applications. They are used in approximately 50% of all dental implants, to regenerate bone defects due to chronic periodontitis and edentulism. The membranes are also widely used in craniofacial traumatic injuries especially when bone grafting is required and are beginning to be used for regenerating bone in large traumatic orthopedic injuries.

Current clinically-used membranes made from expanded polytetrafluoroethylene (ePTFE), a non-degradable woven material, require a second surgery for removal and are reported to have exposure/infection rates as high as 20-44%. The removal surgery may disrupt healing in the graft area and is a burden to both patient and physician. Commercially available biodegradable collagen membranes do not require removal, but their degradation is rapid and unpredictable and may not maintain barrier function for the full healing and regeneration period of 4-6 months. Collagen membranes, crosslinked with glutaraldehyde, have slower degradation rates, but they also have poor tissue response, become exposed more often and elicit less bone formation than uncrosslinked collagen membranes. Additional problems with collagen and ePTFE membranes include infection, wound dehiscence and membrane exposure, and premature membrane degradation, especially when exposed to the oral cavity.

Electrospun nanofibers that mimic the structure and function of the natural extracellular matrix (ECM) are of great interest in tissue engineering as scaffolding materials to restore, maintain or improve the function of human tissue. Recently, there has been a growing interest in nanofibers made of chitosan, a cationic polysaccharide derived from the exoskeletons of crustaceans.

Current methods for producing chitosan nanofibers by electrospinning result in poor structure, in which beads are extensively present and or are highly susceptible to swelling/dissolution. It is difficult to obtain chitosan nanofibers that are homogenous, free of beads, and that do not dissolve or swell significantly in water. All of these are important requirements of nanofibers suitable for biomedical applications.

Implanting biomedical devices/biomaterials to replace/restore tissue function results in surgical wound or injury. The wound healing process is important to the clinical success and functional outcome of the biomedical device. An important and normal step in wound healing is inflammation. Macrophage cells play a central role in directing the inflammatory and wound healing responses. In response to the implanted device or material, the macrophages become activated and will release a variety of chemokines and cytokines to direct the cleaning up of damaged cells/tissues, removal of infectious material/agents and recruitment of fibroblasts and other cells to close the wound and replace missing tissue matrix. This is the acute inflammatory process and it typically lasts for minutes to days depending on the extent of injury.

Chronic inflammation occurs as a result of persistent inflammatory stimuli to the macrophages due to a variety of causes such as the type of implant material, micromotion, infection of the implant, implant site and or implant material degradation/leachable components. Chronic inflammation results in tissue damage, failure of the wound to close and heal properly, poor integration/adaption of implant materials/devices into host tissues and leads to compromised/failed implant function/performance.

For closure of the wound and healing to occur, the acute inflammation stage needs to subside in favor of proliferation and function of cells responsible for elaboration of tissue extracellular matrix. During the transition from acute inflammation to wound closure/healing, macrophage cells transition from an initial inflammatory state involved in removing damaged/diseased tissues and bacteria from the site (referred to as M1 macrophages) to a healing state supporting and directing the healing response for new tissue and new blood vessel formation for the newly forming tissues (referred to as M2 macrophages). The ability of implant materials to help support the transition/formation to the M2 macrophage phenotype would be a great benefit to encouraging healing and normal tissue formation around implant devices and or materials used to for repairing/regenerating tissues by helping to promote healing as opposed to an extended/chronic inflammatory response.

Current anti-inflammatory treatments that are used with implant devices/materials are pharmacologically based and are generally administered systemically. These agents are typically directed towards reducing the inflammatory response associated with M1 type macrophages but are not necessarily directed at promoting the pro-healing activity of M2 macrophages.

Therefore, a biomaterial that promotes healing/tissue formation over inflammatory processes will be of significant benefit to the success of a broad spectrum of biomedical implant materials and devices.

SUMMARY OF THE INVENTION

As described below, the present invention features methods for producing chitosan nanofibers having enhanced structural integrity and/or morphology (e.g., maintenance of nanofiber morphology/structure), membranes comprising such chitosan nanofibers, and methods of using the chitosan membranes to promote healing of a tissue in a subject. The invention includes chitosan nanofibers having enhanced structural integrity, compositions comprising such nanofibers, and related methods of use.

The present invention also features methods for producing a modified chitosan material having anti-inflammatory and pro-healing characteristics and methods of using the modified chitosan materials in a film, a gel, a sponge, a membrane, microfibers, nanofibers, and/or nano- or micro-particles/spheres.

Compositions and materials defined by the invention were prepared or otherwise manufactured in connection with the examples provided below. Other features and advantages of the invention will be apparent from the detailed description, and from the claims herein.

One aspect of the invention includes a method of preparing chitosan nanofibers comprising electrospinning an acidic solution comprising chitosan into chitosan nanofibers, acylating one or more of the electrospun chitosan nanofibers with an acylating agent, and washing the acylated chitosan nanofibers with a hydrophilic solvent.

Another aspect of the invention includes a method of protecting structural integrity of electrospun chitosan nanofibers from dissolution comprising reversibly acylating the chitosan nanofibers.

Yet another aspect of the invention includes a membrane comprising the electrospun chitosan nanofibers made by any of the methods included herein.

In another aspect, the invention includes a membrane comprising electrospun chitosan nanofibers that are reversibly acylated to retain nanofiber structure and integrity when the membrane is exposed to a hydrophilic solvent.

In yet another aspect, the invention includes a membrane comprising electrospun chitosan nanofibers that are reversibly acylated with at least one acyl group.

In still yet another aspect, the invention includes a composition comprising electrospun chitosan nanofibers that are reversibly acylated with at least one acyl group.

In various embodiments of the above aspects or any other aspect of the invention delineated herein, the acidic solution comprises trifluoroacetic acid. In another embodiment, the chitosan nanofibers are electrospun in a solution comprising trifluoroacetic acid. In another embodiment, the acidic solution further comprises at least one selected from the group consisting of a natural material, a synthetic material, and an agent. In yet another embodiment, the electrospinning of the acidic solution yields immobilized salt residues on the chitosan nanofibers.

In various embodiments of the above aspects or any other aspect of the invention delineated herein, the step of acylating comprises exposing the electrospun chitosan nanofibers to an acylating catalyst and acylating agent. In one embodiment, the acylating catalyst is selected from the group consisting of pyridine, 4-dimethylamino-pyridine (DMAP), triethylamine, diisopropylethylamine (DIPEA), lutidine, aluminum chloride, aluminum trifluoride, triphenylphosphine, tributylphosphine, and combinations thereof. In another embodiment, acylating agent comprises a butyric anhydride, acyl chloride, symmetric or mixed acid anhydride, vinyl ester, cyanomethyl ester, S-phenyl thioester, piperidino ester, pyrid-3-yl ester, 4-nitrophenyl ester, 2,4,6-trichlorophenyl ester, 2,3,4,5,6-pentachlorophenyl ester, 2,3,4,5,6-pentafluorophenyl ester, phtalimido ester, succinimido ester, 4-oxo-3,4-dihydrobenzotriazin-3-yl ester, benzotriazolyl ester, and combinations thereof.

In various embodiments of the above aspects or any other aspect of the invention delineated herein, the chitosan nanofibers comprise an acyl group selected from the group consisting of formyl, acetyl, propionyl, butyryl, isobutyryl, pivaloyl, pentanoyl, hexanoyl, and benzoyl group. In one embodiment, the acylated chitosan nanofibers comprise an acyl group selected from the group consisting of formyl, acetyl, propionyl, butyryl, isobutyryl, pivaloyl, pentanoyl, hexanoyl, and benzoyl group. In another embodiment, the chitosan nanofibers are more hydrophobic than unacylated chitosan nanofibers. In yet another embodiment, the acylated chitosan nanofibers are more hydrophobic than unacylated chitosan nanofibers.

In various embodiments of the above aspects or any other aspect of the invention delineated herein, the step of washing comprises hydrolizing the immobilized salt residues from the chitosan nanofibers. In one embodiment, the nanofibers comprise immobilized trifluoroacetate salt residues on the surface of the nanofibers. In another embodiment, the method includes contacting the acylated chitosan nanofibers with a hydrophilic solvent. In yet another embodiment, the immobilized trifluoroacetate salt residues are hydrolyzed when exposed to a hydrophilic solvent. In still yet another embodiment, the exposure to the hydrophilic solvent hydrolyzes trifluoroacetate salt residues immobilized on the nanofibers.

In various embodiments of the above aspects or any other aspect of the invention delineated herein, nanofibers have a mean diameter in the range of about 100 to about 200 nm. In one embodiment, the nanofibers exhibit minimal swelling when exposed to the hydrophilic solvent. In another embodiment, the nanofibers exhibit minimal dissolution when exposed to the hydrophilic solvent. In yet another embodiment, the nanofibers exhibit minimal loss of nanofiber structure when exposed to the hydrophilic solvent.

In various embodiments of the above aspects or any other aspect of the invention delineated herein, the method further comprises deacylating the acylated chitosan nanofibers. In one embodiment, the step of deacylating comprises exposing the acylated chitosan nanofibers to a deacylating agent. In another embodiment, the deacylating agent is selected from the group consisting of potassium hydroxide, lithium hydroxide, sodium hydroxide, rubidium hydroxide, cesium hydroxide, calcium hydroxide, strontium hydroxide, barium hydroxide, other basic solution, and combinations thereof.

In various embodiments of the above aspects or any other aspect of the invention delineated herein, the reversible acylation prevents or minimizes swelling of the nanofibers when exposed to the hydrophilic solvent. In one embodiment, the reversible acylation protects the nanofibers from dissolution when exposed to the hydrophilic solvent. In yet another embodiment, the reversible acylation protects the nanofibers from loss of nanofiber structure when exposed to the hydrophilic solvent.

In various embodiments of the above aspects or any other aspect of the invention delineated herein, the membrane and composition further comprise at least one selected from the group consisting of a natural material, a synthetic material, and an agent. In one embodiment, the method includes incorporating an agent around and/or in the nanofibers. In another embodiment, the agent is around and/or in the nanofibers.

In various embodiments of the above aspects or any other aspect of the invention delineated herein, the membrane and composition is a barrier membrane.

In various embodiments of the above aspects or any other aspect of the invention delineated herein, the method further comprises drying the acylated chitosan nanofibers.

In another aspect, the invention includes an electrospun chitosan nanofiber with a water contact angle of at least 90 degrees. In various embodiments of the above aspects or any other aspect of the invention delineated herein, the water contact angle ranges from about 93.7 to about 100.3 degrees In another aspect, the invention includes an electrospun chitosan nanofiber comprising a x-ray diffraction spectrum of FIG. 27.

In yet another aspect, the invention includes an electrospun chitosan nanofiber comprising a Fourier transform infrared spectroscopy of FIG. 6 or FIG. 7.

Yet another aspect of the invention includes a method for promoting or directing healing of a tissue in a subject at a target site comprising contacting the site with a barrier membrane comprising electrospun chitosan nanofibers produced according to any of the methods included herein.

In still yet another aspect, the invention includes a method of promoting or directing formation of tissues in a subject at a target site comprising contacting the site with a membrane comprising electrospun chitosan nanofibers produced according to any of the methods included herein.

In various embodiments of the above aspects or any other aspect of the invention delineated herein, the tissue is selected from the group consisting of epithelial, abdominal, gynecological, dental, craniofacial, connective and bone tissue. In one embodiment, the subject is suffering from chronic periodontitis, edentulism, and bone regeneration. In another embodiment, the step of contacting the site comprises implanting the membrane for guided bone regeneration.

Another aspect of the invention includes a kit comprising chitosan nanofibers, acylating catalyst, acylating agent, hydrophilic solvent. In various embodiments of the above aspects or any other aspect of the invention delineated herein, the kit further comprises a deacylating agent. In one embodiment, the kit further comprises at least one selected from the group consisting of a natural material, a synthetic material, and an agent.

One aspect of the invention includes a method of preparing chitosan nanofibers comprising electrospinning an acidic solution comprising chitosan to produce chitosan nanofibers with immobilized salts; removing one or more immobilized salts on the electrospun chitosan nanofibers with an organic solvent, thus generating one or more free amino groups on the nanofibers; and contacting one or more free amino groups on the nanofibers.

Another aspect of the invention includes a method of protecting structural integrity of electrospun chitosan nanofibers from dissolution comprising reacting at least a portion of the chitosan nanofibers with an amino protecting reagent.

Yet another aspect of the invention includes a membrane comprising the electrospun chitosan nanofibers made by any of the methods included herein.

In another aspect, the invention includes a membrane comprising electrospun chitosan nanofibers with at least a portion of the chitosan nanofibers amino protected with N-tert-butoxycarbonyl (t-Boc) groups to retain structure and integrity when the barrier membrane is exposed to a hydrophilic solvent.

In yet another aspect, the invention includes a membrane comprising electrospun chitosan nanofibers comprising N-tert-butoxycarbonyl groups.

In still yet another aspect, the invention includes a composition comprising electrospun chitosan nanofibers comprising N-tert-butoxycarbonyl groups.

In various embodiments of the above aspects or any other aspect of the invention delineated herein, the acidic solution comprises trifluoroacetic acid, acetic acid, formic acid, nitric acid, or hydrochloric acid. In another embodiment, the chitosan nanofibers are electrospun in a solution comprising trifluoroacetic acid or hydrochloric acid. In yet another embodiment, the electrospinning of the acidic solution yields immobilized salt residues on the chitosan nanofibers. In yet another embodiment, the immobilized salt residues comprise salts of the amino groups on the chitosan nanofibers.

In various embodiments of the above aspects or any other aspect of the invention delineated herein, the organic solvent comprises a neat organic base or a solution of an organic base in at least one organic solvent. In other embodiments, the organic solvent comprises triethylamine, trimethylamine, diisopropylethylamine or pyridine. In yet other embodiments, the organic solvent comprises acetone, tetrahydrofuran, ethyl acetate, diethylether or dichloromethane. In one embodiment, the amino protecting reagent comprises a carbonate ester reagent. In another embodiment, the carbonate ester reagent is di-tert-butyl dicarbonate. In yet another embodiment, the reaction with di-tert-butyl dicarbonate yields N-tert-butoxycarbonyl on the chitosan nanofibers.

In various embodiments of the above aspects or any other aspect of the invention delineated herein, the amino protection comprises contacting the chitosan nanofibers with a carbonate ester reagent, such as di-tert-butyl dicarbonate. In another embodiment, the reaction with the amino protecting reagent yields amino protected chitosan nanofibers. In yet another embodiment, the acylated chitosan nanofibers are more hydrophobic than unacylated chitosan nanofibers. In still yet another embodiment, the amino protected chitosan nanofibers are more hydrophobic than unreacted chitosan nanofibers.

In various embodiments of the above aspects or any other aspect of the invention delineated herein, the invention comprises contacting the amino protected chitosan nanofibers with a hydrophilic solvent. In another embodiment, the reaction prevents or minimizes swelling of the chitosan nanofibers when exposed to the hydrophilic solvent. In yet another embodiment, the reaction protects the chitosan nanofibers from dissolution when exposed to the hydrophilic solvent.

In various embodiments of the above aspects or any other aspect of the invention delineated herein, the amino protected chitosan nanofibers are on an exterior surface of the barrier membrane. In one embodiment, the amino protected chitosan nanofibers create a hydrophobic barrier for the barrier membrane against hydrophilic solvents.

In various embodiments of the above aspects or any other aspect of the invention delineated herein, at least a portion of the amino groups on the chitosan nanofibers are protected with N-tert-butoxycarbonyl groups. In still yet another embodiment, the chitosan nanofibers with N-tert-butoxycarbonyl groups are on an exterior surface of the composition.

In various embodiments of the above aspects or any other aspect of the invention delineated herein, the nanofibers have a mean diameter in the range of about 40 to about 130 nm.

In various embodiments of the above aspects or any other aspect of the invention delineated herein, the composition exhibits minimal swelling when exposed to a hydrophilic solvent. In another embodiment, the composition exhibits minimal chitosan nanofiber dissolution when exposed to a hydrophilic solvent. In yet another embodiment, the composition exhibits minimal loss of chitosan nanofiber structure when exposed to a hydrophilic solvent.

In various embodiments of the above aspects or any other aspect of the invention delineated herein, the amino protection prevents or minimizes swelling of the barrier membrane when exposed to a hydrophilic solvent. In one embodiment, the amino protection protects the barrier membrane from chitosan nanofiber dissolution when exposed to a hydrophilic solvent. In yet another embodiment, the amino protection protects the barrier membrane from loss of chitosan nanofiber structure when exposed to a hydrophilic solvent.

In various embodiments of the above aspects or any other aspect of the invention delineated herein, the method includes incorporating an agent around and/or in the nanofibers. In another embodiment, the membrane and composition further comprise an agent around and/or in the nanofibers.

In various embodiments of the above aspects or any other aspect of the invention delineated herein, the membrane and composition is a barrier membrane.

Yet another aspect of the invention includes a method for promoting or directing healing of a tissue in a subject at a target site comprising contacting the site with a barrier membrane comprising electrospun chitosan nanofibers produced according to any of the methods included herein.

In still yet another aspect, the invention includes a method of promoting or directing formation of tissues in a subject at a target site comprising contacting the site with a membrane comprising electrospun chitosan nanofibers produced according to any of the methods included herein.

In various embodiments of the above aspects or any other aspect of the invention delineated herein, the tissue is selected from the group consisting of epithelial, abdominal, gynecological, dental, craniofacial, connective and bone tissue. In one embodiment, the subject is suffering from chronic periodontitis, edentulism, and bone regeneration. In another embodiment, the step of contacting the site comprises implanting the membrane for guided bone regeneration.

Another aspect of the invention includes a kit comprising chitosan nanofibers and an amino protecting reagent. In various embodiments of the above aspects or any other aspect of the invention delineated herein, the amino protecting reagent comprises a carbonate ester reagent. In one embodiment, the carbonate ester reagent is di-tert-butyl dicarbonate.

The invention includes a chitosan material with anti-inflammatory and pro-healing characteristics. In one embodiment, the process of modifying the chitosan with raspberry ketone involves reacting the ketone group of raspberry ketone with a free amine of chitosan, which results in the production of an imine bond.

One aspect of the invention includes a method of modifying chitosan comprising obtaining an oxygen depleted acidic solution comprising chitosan and mixing the oxygen depleted chitosan solution with a phenyl-containing carbonyl derivative; wherein the phenyl-containing carbonyl derivative reacts with at least one free amino group on the chitosan to create an imine bond, thus modifying the chitosan. In one embodiment, this reaction may be facilitated by pyridine or pyridine derivatives 4-dimethylaminopyridine (DMAP) and 4-(1-pyrrolidinyl) pyridine.

In another aspect, the invention includes a modified chitosan comprising an iminyl group.

In one aspect, the invention includes a method of producing a chitosan composition (e.g., microspheres, nanoparticles, films, gels, sponges, fibers, and the like) comprising modifying at least one free amino group on the chitosan with an iminyl group, and crosslinking the modified chitosan to form chitosan microspheres.

In yet another aspect, the invention includes a method of producing microspheres of chitosan comprising modifying at least one free amino group on the chitosan with an iminyl group, and crosslinking the modified chitosan to form chitosan microspheres.

In still another aspect, the invention includes a chitosan microsphere comprising the modified chitosan made by any method described herein.

In still yet another aspect, the invention includes a chitosan microsphere comprising chitosan modified with an iminyl group.

In various embodiments of the above aspects or any other aspect of the invention delineated herein, the acidic solution comprises acetic acid. In another embodiment, obtaining the oxygen depleted chitosan solution comprises removing $O_2$ gas and replacing the $O_2$ gas with $N_2$ gas. In yet another embodiment, mixing the oxygen depleted chitosan solution with the phenyl-containing carbonyl derivative comprises heating the mixture.

In another embodiment, the iminyl group has a structure as shown in Structure II:

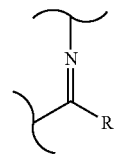

Structure II wherein R can be selected from the group consisting of H, $C_1$-$C_6$ alkyl, $C_1$-$C_6$ alkoxy, phenyl, and any combination thereof. In yet another embodiment, the iminyl group is derived from a phenyl-containing carbonyl derivative, such as a raspberry ketone. In still another embodiment, the phenyl-containing carbonyl derivative has a structure as shown in Structure I:

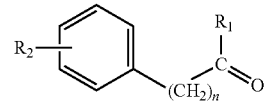

Structure I wherein $R_1$ and $R_2$ are each independently selected from the group consisting of H, $C_1$-$C_6$ alkyl, and $C_1$-$C_6$ alkoxy; and n is an integer selected from 1, 2, 3, 4, 5, and 6

In still another embodiment, the modification increases anti-inflammatory properties as compared to unmodified chitosan. In another embodiment, the modification increases pro-healing properties of the modified chitosan as compared to unmodified chitosan. In yet another embodiment, the modification decreases macrophage production of nitric oxide.

In another embodiment, modifying the chitosan comprises obtaining an oxygen depleted acidic solution comprising chitosan and mixing the oxygen depleted chitosan solution with a phenyl-containing carbonyl derivative;

wherein the phenyl-containing carbonyl derivative reacts with at least one free amino group on the chitosan to create an imine bond, thus modifying the chitosan. In one embodiment, the modified chitosan is crosslinked by exposure to a crosslinking agent.

In yet another embodiment, the microsphere has a diameter in the range of about 50 nm to about 500 µm.

In another embodiment, the microsphere further comprises an agent. In one embodiment, the microsphere forms a biodegradable shell around the agent or the agent is incorporated into the microsphere.

In another aspect, the invention includes a method for preventing inflammation or promoting healing of tissue at a target site in a subject comprising contacting the site with modified chitosan, wherein the modified chitosan is produced according to any method described herein.

In yet another aspect, the invention includes a method of decreasing nitric oxide levels at a target site in a subject comprising contacting the site with modified chitosan, wherein the modified chitosan is produced according to any method described herein.

In various embodiments of the above aspects or any other aspect of the invention delineated herein, the modified chitosan is in the form of microspheres.

In another aspect, the invention includes a kit comprising chitosan and a phenyl-containing carbonyl derivative.

In various embodiments of the above aspects or any other aspect of the invention delineated herein, the kit further comprises a crosslinking agent.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "acylation" is meant the process of derivatizing chitosan with one or more acyl groups. An acylating agent reacts with chitosan, providing the acyl group that is transferred to chitosan. An acylating catalyst is used to increase the rate of transfer of the acyl group from the acylating agent to chitosan. In certain embodiments, the reaction between chitosan and the acylating catalysts does not require the presence of an acylating agent. In other embodiments, the reaction between chitosan and the acylating agents does not require the presence of an acylating catalyst.

By "acylated chitosan" is meant a chitosan fiber derivatized with one or more acyl groups.

By "acylating agent" is meant a compound that provides an acyl group that can be transferred onto the chitosan nanofibers in an acylation reaction. Examples of acylating agents include, but are not limited to, acyl chloride, symmetric or mixed acid anhydride, vinyl ester, cyanomethyl ester, S-phenyl thioester, piperidino ester, pyrid-3-yl ester, 4-nitrophenyl ester, 2,4,6-trichlorophenyl ester, 2,3,4,5,6-pentachlorophenyl ester, 2,3,4,5,6-pentafluorophenyl ester, phtalimido ester, succinimido ester, 4-oxo-3,4-dihydrobenzotriazin-3-yl ester, and benzotriazolyl ester. In certain embodiments, the symmetric or mixed acid anhydride comprises a fatty acid anhydride. In other embodiments, the acyl group is derived from a fatty acid. In yet other embodiments, the acyl group is derived from an aliphatic carboxylic acid. In yet other embodiments, the acyl group is derived from a $C_2$-$C_{30}$ aliphatic carboxylic acid, for example, a $C_2$-$C_4$, $C_4$-$C_6$, $C_6$-$C_8$, $C_8$-$C_{12}$, $C_{13}$-$C_{21}$ or $C_{21}$-$C_{30}$ aliphatic carboxylic acid.

By "acylating catalyst" is meant a catalyst that increases the rate of the chemical reaction to transfer an acyl group from the acylating agent onto chitosan. In one embodiment, an acylating catalyst is a nucleophilic catalyst. Examples of acylating catalysts include, but are not limited to, pyridine, 4-dimethylamino-pyridine (DMAP), triethylamine, diisopropylethylamine (DIPEA), lutidine, aluminum chloride, aluminum trifluoride, triphenylphosphine and tributylphosphine.

By "acyl group" is meant a functional group represented by R—(C=O)—, wherein R is H, alkyl, cycloalkyl, alkenyl, cycloalkenyl, alkynyl, cycloalkynyl, aryl, heteroaryl or heterocyclyl, each of each groups may be optionally substituted. Examples of acyl groups include, but are not limited to, formyl, acetyl, propionyl, butyryl, isobutyryl, pivaloyl, pentanoyl, hexanoyl, and benzoyl groups.

By "amino protecting reagent" is meant a reagent that is capable of reacting with one or more of the free amino groups on a chitosan nanofiber to yield stably protected=amino groups and prevents hydrolysis or any other unwanted reaction of the chitosan nanofibers.

By "amino protected chitosan nanofibers" is meant chitosan nanofibers reacted with an amino protecting reagent, whereby one or more free amino groups on the chitosan nanofibers are protected. In an exemplary embodiment, di-tert-butyl dicarbonate is reacted with the amines on the chitosan nanofibers to yield N-tert-butoxycarbonyl (also known as t-Boc) derivatives on the chitosan nanofiber.

By "barrier membrane" is meant any material used to protect or promote healing or prevent tissue invasion or adhesions at a site. The barrier membrane includes an implantable device that is used in craniofacial, periodontal, or orthopedic surgery to prevent cell migration into a site of tissue regeneration. For example, barrier membranes are commonly used in periodontal surgery to separate the epithelium from slower growing tissue and preventing the epithelium from migrating to a site where bone regeneration is desired. The barrier membrane also includes an implantable device for preventing tissue adhesion in abdominal and gynecological cavities. For example, abdominal adhesions can result from inflammation, infection, treatments, or unknown reasons and barrier membranes are implanted to reduce adhesion formation.

By "carbonate ester" is meant an amino protecting reagent comprising the functionality —O—C(=O)—O— that reacts with the free amino group. In one embodiment, a chitosan nanofiber has a diameter in the range of about 40 nm to about 400 nm (e.g., 130 nm). An exemplary example of a carbonate ester includes, but is not limited to, di-tert-butyl dicarbonate. In certain embodiments, di-tert-butyl dicarbonate reacts with free amino groups on the chitosan nanofiber to yield N-tert-butoxycarbonyl or t-Boc derivatives.

By "chitosan" is meant a chitin-derived polymer. Chitin is a linear polysaccharide consisting of (1-4)-linked 2-acetamido-2-deoxy-b-D-glucopyranose. Preferably, chitosan is at least about 50% deacylated.

By "chitosan nanofiber" is meant a chitosan fiber with a diameter in the range of about 5 nm to about 1000 nm. In particular embodiments, a chitosan nanofiber has a diameter in the range of about 40 nm to about 400 nm (e.g., 130 nm). In certain embodiments, a chitosan nanofiber has a diameter in the range of about 50 nm to about 500 nm. In an exemplary embodiment, the chitosan nanofiber is produced from a chitosan solution through electrospinning. The resulting chitosan nanofiber has a substantially uniform diameter.

By "chitosan microsphere" is meant spherical shell or bead comprising chitosan with a small diameter usually in the micron or nanometer range. Microspheres can be hollow and filled with an agent (as a drug or antibody) that is released once the chitosan microsphere is degraded. Microspheres may incorporate the agent into the microsphere and the agent is released as the chitosan degrades.

By "chitosan nanoparticle" is meant a chitosan particle with a diameter in the range of about 5 nm to about 1000 nm. In one embodiment, a chitosan nanoparticle has a diameter in the range of about 40 nm to about 130 nm. In an exemplary embodiment, the chitosan nanoparticle is produced from a water-in-oil emulsion process. The resulting chitosan nanoparticle has a substantially uniform diameter.

By "chitosan film" is meant a sheet of chitosan with thickness in the range of about 0.01 mm to about 5 mm. In one embodiment, a chitosan film has a thickness in the range of about 0.1 mm to about 1 mm. In an exemplary embodiment, the chitosan film is produced from a chitosan solution through solution casting. The resulting chitosan film has a substantially uniform thickness.

By "deacylation" is meant the process of removing one or more acyl groups from an acylated chitosan.

By "deacylating agent" is meant a compound that removes an acyl group from the chitosan nanofibers in a deacylation reaction. Examples of deacylating agent include, but are not limited to, a basic solution such as ammonium hydroxide, potassium hydroxide, lithium hydroxide, sodium hydroxide, rubidium hydroxide, cesium hydroxide, calcium hydroxide, strontium hydroxide, barium hydroxide, other basic solutions (such as potassium carbonate or sodium carbonate), and combinations thereof.

By "deacylated chitosan" is meant a chitosan fiber wherein one or more acyl groups have been removed. In particular embodiment, a deacylated chitosan fiber is at least about 70%, 80%, 90%, 95% or more deacylated.

By "degrades" is meant physically or chemically breaks down in whole or in part. Preferably, the degradation represents a physical reduction in the mass or structural integrity of a nanofiber by at least about 10%, 25%, 50%, 75%, 80%, 85%, 90%, 95% or 100%.

By "dissolution" is meant the loss of nanofibrous structure after exposure to a hydrophilic solvent, such as water. Resistance to dissolution is imparted when the nanofibers, films, spheres, and particles do not increase in size or do not have an electrophilic group that is susceptible to nucleophile attack by a water molecule or hydroxyl ion which results in loss of structure.

By "electrospin" or "electrospinning" is meant a process of producing chitosan nanofibers from a solution of chitosan by applying an electric charge to the chitosan solution.

By "exterior surface" is meant a thickness of the barrier membrane or composition of chitosan nanofibers exposed to the amino protecting reagent and capable of reacting with the amino protecting reagent. In certain embodiments, the amino protecting reagent is in an organic solvent which may not penetrate the entire thickness of the barrier membrane or composition, such that only the chitosan nanofibers exposed to the reagent are present on the exterior surface.

By "hydrophilic solvent" is meant a solution that is capable of dissolving hydrophilic compounds. Typically hydrophilic solvents are charge-polarized and capable of hydrogen bonding. An exemplary example of a hydrophilic solvent includes, but is not limited to, water.

By "hydrophobic barrier" is meant chitosan nanofibers on an exterior surface of the barrier membrane or composition that are amino protected such that they are not or less susceptible to hydrolysis, swelling or loss of nanofibrous structure when exposed to a hydrophilic solvent.

By "iminyl group" is meant a nitrogen-carbon double bond having the general formula shown in Structure II:

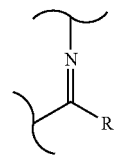

Structure II wherein R can be selected from the group consisting of H, $C_1$-$C_6$ alkyl, $C_1$-$C_6$ alkoxy, phenyl, and any combination thereof.

By "organic solvent" is meant a solvent capable of dissolving the amino protecting reagent. Examples of organic solvents include, but are not limited to, triethylamine, triethylamine in acetone, tetrahydrofuran, and toluene.

By "phenyl-containing carbonyl derivative" is meant to include a molecule having a general formula of Structure I:

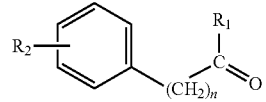

Structure I wherein $R_1$ and $R_2$ are each independently selected from the group consisting of H, $C_1$-$C_6$ alkyl, and $C_1$-$C_6$ alkoxy, and n is selected from an integer 1, 2, 3, 4, 5, and 6.

By "biodegradable" is meant susceptible to breakdown by biological activity. For example, biodegradable chitosan compositions are susceptible to breakdown by enzymes present in vivo (e.g., lysozyme, N-acetyl-o-glucosaminidase and lipases). Degradation of a chitosan composition of the invention need not be complete. A chitosan composition of the invention may be degraded, for example, by the cleavage of one or more chemical bonds (e.g., glycosidic bonds).

By "pro-healing" is meant aiding in the processes that promote healing of a tissue. Examples would be to prevent or decrease inflammatory reactions within a tissue by preventing or decreasing leukocyte infiltration, nitric oxide production and release by macrophages, edema, redness, pain, and/or edema, redness, pain, and/or fibrosis (scar tissue formation).

By "reversible acylation" is meant the process of adding one or more acyl groups to chitosan, where the attachment of the acyl group to chitosan is not permanent and the attached acyl group may be removed as necessary.

By "structural integrity" or "nanofibrous structure" is meant the physical properties associated with the chitosan nanofibers. In an exemplary embodiment, the chitosan nanofibers demonstrate no or minimal change in physical properties, such as fiber or particle diameter, film thickness, tensile strength, and/or elasticity, etc., when exposed to different solvents, such as hydrophilic solvents. In a preferred embodiment, the chitosan nanofibers exhibit no or minimal swelling or dissolution when exposed to a hydrophilic solvent.

By "unmodified chitosan" is meant chitosan not reacted with a modifying agent, such as a phenyl-containing carbonyl derivative.

By "unreacted chitosan nanofibers" is meant either the chitosan nanofibers not reacted with the amino protecting reagent or the as-spun chitosan nanofibers.

By "acidic solution" is meant a solution that has an acidic pH and is used to solubilize chitosan. Examples of acidic solutions include, but are not limited to, trifluoroacetic acid.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

By "antimicrobial" is meant an agent that inhibits or stabilizes the proliferation or survival of a microbe. In one embodiment, a bacteriostatic agent is an antimicrobial. In other embodiments, any agent that kills a microbe (e.g., bacterium, fungus, virus) is an antimicrobial.

By "anti-inflammatory" is meant the reduction in severity or symptoms of an inflammatory reaction in a tissue. An inflammatory reaction within tissue is generally characterized by leukocyte infiltration, nitric oxide production and release by macrophages, edema, redness, pain, and/or neovascularization. Inflammation can also be measured by analyzing levels of nitric oxide, inflammatory cytokines, or any other inflammatory marker.

By "anti-inflammatory agent" is meant an agent that reduces the severity or symptoms of an inflammatory reaction in a tissue. An inflammatory reaction within tissue is generally characterized by leukocyte infiltration, edema, redness, pain, and/or fibrosis. Inflammation can also be measured by analyzing levels of inflammatory cytokines or any other pro-inflammatory markers.

By "biodegradable" is meant susceptible to breakdown by biological activity. For example, biodegradable chitosan compositions are susceptible to breakdown by enzymes present in vivo (e.g., lysozyme, N-acetyl-o-glucosaminidase and lipases). Degradation of a chitosan composition of the invention need not be complete. A chitosan composition of the invention may be degraded, for example, by the cleavage of one or more chemical bonds (e.g., glycosidic bonds).

By "clinician" is meant any healthcare provider. Exemplary clinicians include, but are not limited to, doctors, veterinarians, osteopaths, physician's assistants, emergency medical technicians, medics, nurse practitioners, and nurses.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "degradation rate" is meant the time required to substantially degrade the composition. A composition is substantially degraded where at least about 75%, 85%, 90%, 95% or more has been degraded. Methods for measuring degradation of chitosan are known in the art and include measuring the amount of a nanofiber membrane, fibrous material, sponge, film, composite or other composition of the invention that remains following implantation in a subject or following in vitro exposure to an enzyme having chitosan-degrading activity.

By "disease" is meant any condition or disorder that damages or interferes with the normal function of a cell, tissue, or organ. Examples of diseases include, but are not limited to, bone defects, chronic periodontitis, edentulism, traumatic injury, ulcers, arthritis, and orthopedic injuries.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polysaccharide, protein, polypeptide, nucleic acid, or other molecule. This portion contains, preferably, at least 10%, 20%, 30%, 40%, 50%, 60%, 70%, 80%, or 90% of the entire length of the reference polysaccharide, protein, polypeptide, nucleic acid, or other molecule. A fragment may contain 10, 20, 30, 40, 50, 60, 70, 80, 90, or 100, 200, 300, 400, 500, 600, 700, 800, 900, or 1000 units of the polysaccharide, protein, polypeptide, nucleic acid, or other molecule.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" polysaccharide, protein, polypeptide, nucleic acid, or other molecule is sufficiently free of other materials such that any impurities do not materially affect the biological properties of the polysaccharide, protein, polypeptide, nucleic acid, or other molecule or cause other adverse consequences. That is, a polysaccharide, protein, polypeptide, nucleic acid, or other molecule is purified if it is substantially free of cellular material, viral material, or culture medium when produced by recombinant techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a polysaccharide, protein, polypeptide, nucleic acid, or other molecule gives rise to essentially one band in an electrophoretic gel. For a polysaccharide, protein, polypeptide, nucleic acid, or other molecule that can be subjected to modifications, for example, phosphorylation or glycosylation, different modifications may give rise to different isolated polysaccharides, proteins, polypeptides, nucleic acids, or other molecules, which can be separately purified.

As used herein, "obtaining" as in "obtaining an agent" includes synthesizing, purchasing, or otherwise acquiring the agent.

By "polymer" is meant a natural or synthetic organic molecule formed by combining smaller molecules in a regular pattern.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

By "prosthetic device" is meant an implanted medical device that substitutes for or supplements a missing or defective part of the body.

By "reduces" is meant a negative alteration of at least 10%, 25%, 50%, 75%, or 100%.

By "reference" is meant a standard or control condition.

By "small molecule" is meant any chemical compound.

By "subject" is meant a mammal, including, but not limited to, a human or non-human mammal, such as a bovine, equine, canine, ovine, or feline.

By "trauma" is meant any injury that damages a tissue or organ of a subject. The injury need not be severe. Therefore, a trauma includes any injury that breaks the skin.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A is an image of guided bone regeneration procedure. A tooth is removed and the remaining tooth socket is thoroughly cleaned of all inflamed and infected tissue.

FIG. 1B is an image showing an appropriate bone grafting material is carefully placed into the extraction socket.

FIG. 1C is an image showing the guided bone regeneration membrane is often placed over the grafted material.

FIG. 1D is an image showing sutures placed into the gum tissue allow proper healing of the surrounding soft tissues.

FIG. 9B shows the N 1s and C 1s peaks from x-ray photoelectron spectroscopy of as-spun electrospun chitosan nanofibers.

FIG. 9C shows the N 1s and C 1s peaks from x-ray photoelectron spectroscopy of acylated electrospun chitosan nanofibers.

FIG. 11A is an image of a scanning electron micrograph (SEM) of as-spun electrospun chitosan nanofibers.

FIG. 11B is an image of a scanning electron micrograph (SEM) of NaOH treated electrospun chitosan nanofibers.

FIG. 11C is an image of a scanning electron micrograph (SEM) of $Na_2CO_3$ solution treated electrospun chitosan nanofibers.

FIG. 11D is an image of a scanning electron micrograph (SEM) of electrospun chitosan nanofibers acylated for 1 minute followed by water immersion.

FIG. 11E is an image of a scanning electron micrograph (SEM) of electrospun chitosan nanofibers acylated for 10 minutes followed by water immersion.

FIG. 11F is an image of a scanning electron micrograph (SEM) of electrospun chitosan nanofibers acylated for 60 minutes followed by water immersion.

FIG. 11G is an image of a scanning electron micrograph (SEM) of electrospun chitosan nanofibers regenerated (deacylated) followed by water immersion.

FIG. 17A is an SEM image showing untreated electrospun chitosan nanofibers (CSEF) membranes lost fibrous structure after PBS immersion.

FIG. 17B is an SEM image showing acylated CSEF exhibited nano-fibrous morphology after PBS immersion.

FIG. 17C is an image of viable (fluorescent) osteoblast cells cultured on acylated CSEF after 5 days.

FIG. 29 is a schematic comparing the post processing protocol for TEA/t-BoC neutralization and $Na_2CO_3$ neutralization, respectively.

FIG. 31 is a series of FTIR spectra showing the effect removal of the immobilized TFA salts has on the electrospun chitosan nanofibers. Peaks at 720, 796 and 836 $cm^{-1}$ disappeared after the TEA/t-BOC treatment.

FIG. 36B are two images of the hydrophobicity of a TEA/tboc treated chitosan membrane (left) and $Na_2CO_3$ treated chitosan membrane (right) as measured by water contact angles.

FIGS. 36C-36F are graphs showing histomorphometric analyses and inflammatory response scoring.

FIG. 36C is a graph showing a histology analysis of new bone growth at 3 weeks and 12 weeks after butyric modified chitosan nanofiber membrane, TEA/tBoC treated chitosan nanofiber membrane and commercial collagen membrane implant placement, respectively.

FIG. 36D is a graph showing a histology analysis of remaining membrane at 3 weeks and 12 weeks after butyric modified chitosan nanofiber membrane, TEA/tBoC treated chitosan nanofiber membrane and commercial collagen membrane implant placement, respectively.

FIG. 36E is a graph showing a summary of histology scores for inflammatory responses; chi-square analysis shows no difference in scores between groups at 3 weeks and 12 weeks after butyric modified chitosan nanofiber membrane, TEA/tBoC treated chitosan nanofiber membrane and commercial collagen membrane implant placement, respectively.

FIG. 36F is a summary of histology scores showing a graph of the confidence interval; chi-square analysis shows no difference in scores between groups at 3 weeks and 12 weeks after butyric modified chitosan nanofiber membrane, TEA/tBoC treated chitosan nanofiber membrane and commercial collagen membrane implant placement, respectively.

FIG. 37A is an image of viable (fluorescent) osteoblast cells cultured on TEA/tboc treated chitosan nanofiber membranes after 5 days.

FIG. 37B is an image of viable (fluorescent) osteoblast cells cultured on $Na_2CO_3$ treated chitosan nanofiber membranes after 5 days.

FIGS. 37E-37J are images and graphs comparing surgical tacking strength and suture strength between TEA/tBoc treated, collagen, and GUIDO® PLA membranes.

FIG. 37E is a photographic image and a schematic of surgical tacking strength tests of chitosan membranes.

FIG. 37F is a graph comparing surgical tacking strength between dry and wet TEA/tBoc treated, collagen and GUIDO® PLA membranes, respectively.

FIG. 37G is three photographic images comparing surgical torn patterns related to the clinical handle ability between TEA/tBoc treated, collagen and GUIDO® PLA membranes.

FIG. 37H is a photographic image and a schematic of suture strength tests of chitosan membranes.

FIG. 37I is a graph comparing suture strength between triple layers TEA/tBoc treated, triple layers and one layer $Na_2CO_3$ treated, and collagen membranes.

FIG. 37J is three electron micrograph images showing suture tearing edges of TEA/tBoc treated and $Na_2CO_3$ treated membranes.

FIGS. 38E-38G are an evaluation of chitosan nanofiber membranes in rat calvarial model showing preliminary x-ray results, comparing butyric anhydride- and TEA/TBoC-modified nanofibrous chitosans to a commercial collagen membrane, depicting 3 week group x-rays and histology sections. X-rays were taken at implantation, i.e. 0 weeks, and at 3 weeks and histological sections at 3 weeks.

FIG. 38E depicts two x-ray images of the defect site at implant placement (top panel) and at 3 weeks post-surgery (bottom panel) and an image of a histology section 3 weeks after collagen implant placement. Normal healing response. Healing is indicated by the increase in radio-opaqueness in the defect area.

FIG. 38F depicts two x-ray images of the defect site at implant placement (left panel) and at 3 weeks post-surgery (right panel) and an image of a histology section 3 weeks after butyric modified chitosan membrane implant placement; radio-opaque area indicates bone formation. Normal healing response, new bone is beginning to bridge the defect.

FIG. 38G is two x-ray images of the defect site at implant placement (top panel) and at 3 weeks post-surgery (bottom panel) and an image of a histology section 3 weeks after TEA/tBoC-modified chitosan nanofiber membrane implant placement. Normal healing response, bone forming superiorly at the edge of the defect indicated by the increase in radio-opaqueness in the defect area.

FIGS. 38H-38M are an evaluation of chitosan nanofiber membranes in rat calvarial model showing preliminary x-ray results, comparing butyric anhydride- and TEA/TBoC-modified nanofibrous chitosans to a commercial collagen membrane, depicting 12 week group x-rays and histology sections. X-rays were taken at implantation, i.e. 0 weeks, and at 12 weeks and histological sections at 12 weeks.

FIG. 38H is two x-ray images of the defect site at implant placement (top panel) and at 12 weeks post-surgery (bottom panel) and an image of a histology section 12 weeks after collagen implant placement. New bone showing definitive proliferation into the defect as indicated by the increase in radio-opaqueness in the defect area.

FIG. 38I is an x-ray image of the defect site at 12 weeks post-surgery (bottom panel) and three images of histology sections 12 weeks after collagen implant placement. New bone formation is shown by the increase in radio-opaqueness in the defect area and by arrows in histology sections. Membrane is shown by dotted arrows in histology sections.

FIG. 38J is two x-ray images of the defect site at implant placement (top panel) and 12 weeks post-surgery (bottom panel) and an image of a histology section 12 weeks after butyric modified chitosan nanofiber membrane implant placement. Bone formation is shown along the membrane and closing the defect. New bone formation is shown by the increase in radio-opaqueness in the defect area.

FIG. 38K is an x-ray image of the defect site at 12 weeks post-surgery (bottom panel) and four images of histology sections 12 weeks after butyric modified chitosan nanofiber membrane implant placement. New bone formation is shown by the increase in radio-opaqueness in the defect area and by arrows in histology sections. Membrane is shown by dotted arrows in histology sections.

FIG. 38L is two x-ray images of the defect site at implant placement (top panel) and 12 weeks post-surgery (bottom panel) and an image of a histology section 12 weeks after TEA/tBoC-modified chitosan nanofiber membrane implant placement. New bone is forming along the membrane and beginning to move into the defect. New bone formation is shown by the continued increase in radio-opaqueness in the defect area.

FIG. 38M is an x-ray image of the defect site at 12 weeks post-surgery (bottom panel) and three images of histology sections 12 weeks after TEA/tBoC-treated chitosan nanofiber membrane implant placement. New bone formation is shown by the continued increase in radio-opaqueness in the defect area and by arrows in histology sections.

DETAILED DESCRIPTION OF THE INVENTION

Figure 1E:
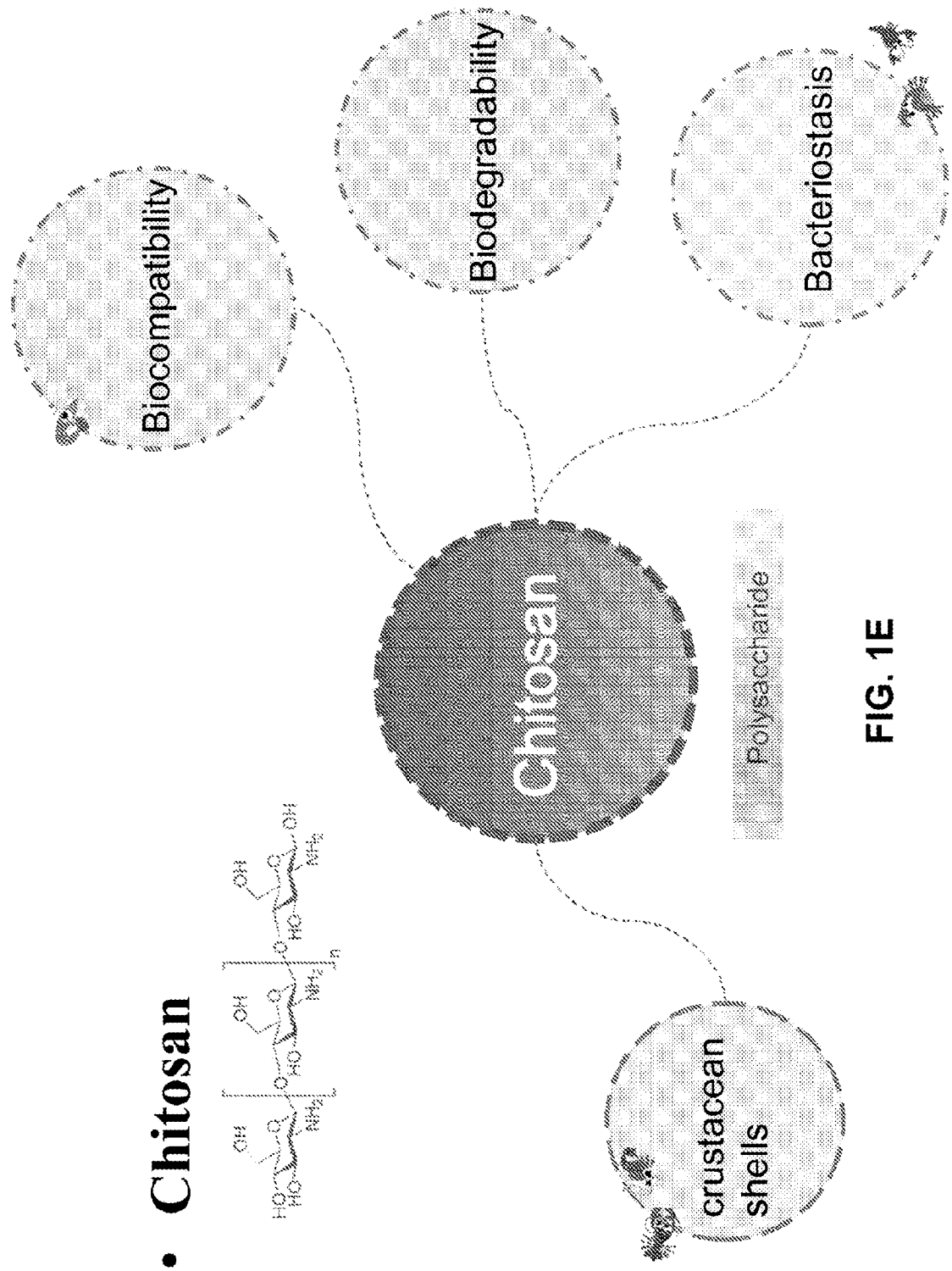
FIG. 1E is a drawing showing the chemical structure of chitosan and a schematic of chitosan's characteristics.

As described below, the present invention features chitosan compositions (e.g., barrier membranes) that maintain structural integrity when exposed to hydrophilic solvents and methods of making such compositions without dissolution of the chitosan caused by hydrolysis.

The invention is based, at least in part, on the discovery that acylation of electrospun chitosan nanofibers can prevent or minimize swelling and dissolution of the nanofibers when exposed to hydrophilic solvents used to neutralize and remove immobilized salts left by the acidic electrospinning solution.

The invention is also based, at least in part, on the discovery that protection of the amino groups on electrospun chitosan nanofibers can prevent or minimize swelling and dissolution of the nanofibers when exposed to hydrophilic solvents.

Chitosan

Chitosan is a naturally occurring linear polysaccharide composed of N-acetyl-glucosamine-co-N-glucosamine copolymers. Chitosan is derived from chitin, a naturally occurring polymer. Chitin is a white, hard, inelastic, nitrogenous polysaccharide isolated from fungi, mollusks, or from the exoskeletons of arthropods (e.g., crustaceans, insects).

Chitosan materials have shown great potential in guided tissue regeneration (GTR), particularly guided bone regeneration (GBR), applications because of their biocompatibility, controllable degradation, non-toxic degradation properties and are osteoconductive. Chitosan supports wound healing and osteogenesis because of its similarity to extracellular matrix polysaccharides such as hyaluronan and chondroitin sulfate. Chitosan may also be easily formed into nanofibrous membranes which have the advantage of mimicking the scale and topography of extracellular matrix fibers, providing high surface area for cell attachments and pore sizes for fluid/nutrient exchange between tissue compartments but not cell/tissue infiltration.

Chitosan Nanofibers

Conventional methods of producing chitosan nanofibers are inadequate. The selection of a suitable solvent system is a prerequisite for successful electrospinning. The ideal solvents should have two properties. One is to dissolve the polymer with high polymer concentration and low solution viscosity. The other is to carry the solvated polymer molecules towards the collector, then to leave the polymer fibers by rapid vaporization of the solvent molecules. So far, suitable electrospinning solvents for chitosan are rather limited. Concentrated acetic acid and trifluoroacetic acid (TFA) are commonly used to successfully electrospin chitosan. Other solvents, such as 1,1,1,3,3,3-hexafluoro-2-propanol, have been used in the past. However, such solvents are prohibitively expensive to utilize routinely or in large scale production. The methods using concentrated acetic acid produce nanofibers with poor structure, in which beads are extensively present. The solvent system of TFA/dichloromethane (DCM) is more successful producing continuous, homogenous, bead-free nanofibers. However, the vaporization of the TFA leaves an extensive presence of salt residues immobilized on and in the body of the nanofibers.

Currently, alkaline immersion with or without chemical crosslinking of the chitosan are used to remove immobilized salt residues from chitosan nanofibers. Both approaches suffer significant drawbacks. There are many crosslinking agents for chitosan including glutaraldehyde and genipin. The principle is to crosslink the amino groups of chitosan to prevent the dissolution of chitosan caused by hydrolysis when removing the immobilized salts. However, because the amino groups are extensively occupied by TFA salts, the crosslinking is inefficient because the number of free amino groups in chitosan molecules is too few. Alkaline immersion (e.g. concentrated NaOH or saturated $Na_2CO_3$) may be used to remove the immobilized TFA salts from electrospun chitosan nanofibers since chitosan is insoluble in base, but because water preferentially hydrolyzes the chitosan molecules, swelling and loss of nanofibrous structure of the membranes remains a problem. Despite significant progress made to electrospin chitosan and to stabilize the as-spun fibers against dissolution, the methods using concentrated acetic acid produce nanofibers with poor structure, in which beads were extensively present. The present invention addresses these problems by providing chitosan nanofibers that maintain structural integrity when exposed to hydrophilic solvents and methods of making such compositions without dissolution of the chitosan caused by hydrolysis.

Chitosan is a cationic weak base that is substantially insoluble in water and organic solvents. Typically, chitosan is fairly soluble in acidic solutions, such as acetic, citric, oxalic, proprionic, ascorbic, hydrochloric, formic, and lactic acids, as well as other organic and inorganic acids.

Chitosan nanofibrous membranes may be prepared by electrospinning chitosan dissolved in an acid solution. Electrospinning protocols can be modified to produce chitosan nanofiber membranes (Schiffman and Schauer, Bio macro molecules, 2007. 8 (9): p. 2665-7).

Electrospun chitosan nanofibers typically have a mean diameter of about 100-150 nm or in the range of about 40 nm to about 400 nm (e.g., 40 nm, 100 nm, 130 nm, 200 nm or 400 nm), but can vary widely depending upon a number of factors, such as rotation speed of the spinning mandrel, concentration of the chitosan, electrostatic charge of the solution, etc. Some nanofibers can be as large as 1000 nm in diameter and as small as 5 nm. Some nanofibers have a mean diameter between about 10 nm to about 500 nm. Typically, nanofibers have a mean diameter between about 30 nm to about 500 nm.

In one aspect, the chitosan nanofibers are acylated with an acylating agent, and the acylated chitosan nanofibers are washed with a hydrophilic solvent. These nanofibers typically have a mean diameter of about 150 nm or in the range of about 100 nm to about 200 nm. Typically, nanofibers have a mean diameter between about 50 nm to about 500 nm. In one embodiment, the chitosan nanofibers have a substantially uniform diameter. In another embodiment, the nanofibers have a mean diameter in the range of about 100 to about 200 nm.

In another aspect, the chitosan nanofibers are treated with N-tert-butoxycarbonyl (t-BoC), these nanofibers typically have a mean diameter of about 100 nm or in the range of about 40 nm to about 130 nm. Some nanofibers have a mean diameter between about 10 nm to about 500 nm. Typically, nanofibers have a mean diameter between about 30 nm to about 200 nm. In one embodiment, the chitosan nanofibers have a substantially uniform diameter. In another embodiment, the nanofibers have a mean diameter in the range of about 40 to about 130 nm.

The degree of deacylation of the chitosan used for producing the nanofibers can vary from about 50% to about 99%, with about 70% deacylation preferable. The molecular weight of the chitosan can also vary from less than about 100 kDa to about 900 kDa, with about 300 kDa to about 325 kDa preferable. The chitosan weight volume in solution is from about 0.25 to about 10.0% weight/volume (e.g., 0.1, 0.2, 0.25, 0.3, 0.4, 0.5, 1, 1.25, 1.5, 1.75, 2.0, 2.5, 3.0, 3.5, 4, 4.5, 5, 5.5, 6, 6.5, 7, 7.5, 8, 8.5, 9, 9.5, and 10%). In one embodiment, 5.50% weight volume of chitosan in solution is used for the electrospinning process, where a 5.50% weight volume of chitosan contains 5.50 grams of chitosan per 100 ml solution.

In one aspect, the invention includes a method of preparing chitosan nanofibers that comprises electrospinning an acidic solution comprising chitosan into chitosan nanofibers, acylating one or more of the electrospun chitosan nanofibers with an acylating agent, washing the acylated chitosan nanofibers with a hydrophilic solvent, and deacylating the acylated chitosan nanofibers.

In another embodiment, the invention includes a method of preparing chitosan nanofibers comprises electrospinning an acidic solution comprising chitosan into chitosan nanofibers, removing one or more immobilized salts on the electrospun chitosan nanofibers with an organic solvent, and exposing at least one amino group with an amino protecting reagent to stabilize the chitosan membranes.

For the electrospinning process, the chitosan is dissolved in an acidic solution. The acidic solution includes, but is not limited to, trifluoroacetic acid (TFA), acetic, citric, oxalic, proprionic, ascorbic, hydrochloric, formic, salicylic and/or lactic acids, and any combination of those. In some embodiments, the acidic solutions include other organic compounds or solvents, such as methylene chloride. In one embodiment, the acid solution comprising other organic compounds includes a 90%/10%, 80%/20% 75%/25%, 70%/30%, 60%/40%, or 50%/50% of acidic solution to other organic solvent ratio. In an exemplary embodiment, the chitosan is dissolved in a solution of 70% trifluoroacetic acid and 30% methylene chloride.

In some embodiments, the chitosan solution is loaded into a 10-mL syringe with a blunt 20G, 3.81 cm stainless steel needle tip. The syringe is loaded into the electrospinning apparatus and the flow rate set to a speed appropriate to the desired diameter size, e.g. 20 µL/min. The solution is electrospun at about 25 kV and the fibers are collected on a target (such as about 38.1 cm diameter circular disc of non-stick aluminum foil). The target is positioned about 15 cm from the needle tip and rotated at about 8.4 RPM by an AC motor to ensure even and random distribution of fibers.

The electrospinning apparatus is housed inside a ventilated box, which is vented, preferably to the fume hood. After electrospinning, the nanofibrous membrane is vacuum treated for several hours, e.g. overnight, to remove residual solvent.

The acidic solution, including solvents such as trifluoroacetic acid (TFA), yields immobilized salt residues on and in the chitosan nanofibers (chitosan trifluoroacetate, which may be represented as $R^1$—$NH_3^+CF_3COO^-$). Chitosan/TFA salt is made of the acid, TFA, and base, chitosan, and it readily hydrolyzes in water. The hydrolysis of chitosan/TFA produces free TFA in water and creates an acidic environment which leads to the rapid swelling and dissolution of the electrospun chitosan nanofibers. As a result, chitosan nanofibrous membranes prepared by electrospinning acidic solutions of chitosan are prone to dissolution and swelling in hydrophilic solvents, such as water.

In one embodiment, chitosan nanofiber membranes are fabricated by electrospinning. The fiber orientation may be random or directed in uniform alignment. The fiber orientation may be altered or directed through manipulation of the orientation of the collection target mandrell and/or the speed of rotation.

In another embodiment, the chitosan nanofibers have a water contact angle that is greater than about 90 degrees, 91 degrees, 92 degrees, 93 degrees, 94 degrees, 95 degrees, 96 degrees, 97 degrees, 98 degrees, 99 degrees, 100 degrees, 101 degrees, or greater, or any number in between. In another embodiment, the chitosan nanofibers have a water contact angle in the range of about 93 degrees to about 101 degrees. In yet another embodiment, the chitosan nanofibers have a water contact angle that is greater than about 93 degrees.

Structural integrity of the chitosan can be modified to accommodate the site of injury or tissue being regenerated. Variations in physical properties of polymers, such as chitosan, depend on its molecular weight, number of repeating units in the polymer-chain, and regularity of polymer-chain, side group chemistry, the degree of matrix packing or density, and crosslinking. The physical properties of chitosan can be controlled or altered during manufacture through its molecular weight, degree of deacylation, and crosslinking to affect thermal properties, such as melting point, and physical-mechanical properties, such as tensile strength, Young's modulus, swelling and degradation.

Crosslinking is the process which links polymer chains together. In chitosan, crosslinking induces a three-dimensional matrix of interconnected, linear, polymeric chains. The degree or extent of crosslinking depends on the crosslinking agent. Exemplary crosslinking agents include sodium tripolyphosphate, ethylene glycol diglycidyl ether, ethylene oxide, glutaraldehyde, epichlorohydrin, diisocyanate, and genipin. Crosslinking can also be accomplished using microwave or ultraviolet exposure.

Acylation

In some embodiments, electrospinning acidic solutions of chitosan yields immobilized salt residues on the chitosan nanofibers. However, hydrolysis of the immobilized salts left by the acidic solution and exposure of the chitosan nanofibers to neutralization solutions, e.g., hydrophilic solvents, often results in the nanofibers being prone to dissolution. The chitosan nanofibers swell and lose nanofiber structure and integrity.

The present invention includes methods for preparing chitosan nanofibers by acylating one or more of the electrospun chitosan nanofibers (e.g., a surface of the nanofiber) with an acylating agent. In one embodiment, the electrospun chitosan nanofibers are exposed to an acylating catalyst and acylating agent. The acylating catalyst includes, but is not limited to, pyridine, 4-dimethylamino-pyridine (DMAP), triethylamine, diisopropylethylamine (DIPEA), lutidine, aluminum chloride, aluminum trifluoride, triphenylphosphine, tributylphosphine, and combinations thereof. The acylating agent includes, but is not limited to, acyl chloride, symmetric or mixed acid anhydride, vinyl ester, cyanomethyl ester, S-phenyl thioester, piperidino ester, pyrid-3-yl ester, 4-nitrophenyl ester, 2,4,6-trichlorophenyl ester, 2,3,4,5,6-pentachlorophenyl ester, 2,3,4,5,6-pentafluorophenyl ester, phtalimido ester, succinimido ester, 4-oxo-3,4-dihydrobenzotriazin-3-yl ester, benzotriazolyl ester, and combinations thereof. In certain embodiments, the symmetric or mixed acid anhydride comprises a fatty acid anhydride. In other embodiments, the symmetric or mixed acid anhydride comprises butyric anhydride.

In an exemplary embodiment, one gram of the chitosan nanofibrous membrane is placed in a flask before adding 50 ml of the acylating catalyst, e.g. pyridine, and 50 ml of the acylating agent, e.g. a fatty acid anhydride such as butyric anhydride. The ratio of chitosan material to the pyridine: fatty acid anhydride solution may be adjusted as needed. The mixture is stirred by a magnetic stirrer at 20° C. The degree of acylation on the surface of the nanofibers is controlled by changing the length of the reaction time, wherein longer reaction times increase the level of acylation.

After acylation, the acylated chitosan nanofibers comprise at least one acyl group. Examples of the acyl group include, but are not limited to, formyl, acetyl, propionyl, butyryl, isobutyryl, pivaloyl, pentanoyl, hexanoyl, and benzoyl group. In one embodiment, the acylated chitosan nanofibers are more hydrophobic than unacylated chitosan nanofibers. In another embodiment, the chitosan nanofibers comprise immobilized trifluoroacetate salt residues on the surface of the nanofibers. In yet another embodiment, the immobilized trifluoroacetate salt residues are hydrolyzed when exposed to a hydrophilic solvent.

In another aspect, the invention includes a method of protecting structural integrity of electrospun chitosan nanofibers from dissolution comprising reversibly acylating the chitosan nanofibers. In one embodiment, the reversible acylation prevents or minimizes swelling of the nanofibers when exposed to the hydrophilic solvent. In another embodiment, the reversible acylation protects the nanofibers from dissolution when exposed to the hydrophilic solvent.

Amino Protection

The free amino groups on the chitosan nanofibers are susceptible to hydrolysis or any other unwanted reaction. Protecting the free amino groups, after removing the immobilized salt left from the electrospinning solution, stabilizes the amino group and prevents hydrolysis of the chitosan nanofibers. Amino protection reagents, such as di-tert-butyl dicarbonate, a widely used carbonate ester reagent, can selectively protect free amino groups. Di-tert-butyl dicarbonate reacts with amines to yield N-tert-butoxycarbonyl or N-tert-butoxycarbonyl (t-BoC) derivatives of those amines. These derivatives do not behave as amines, and this prevents certain transformations that could otherwise affect the amine functional group, such as hydrolysis. t-Boc protected groups are stable in neutral or basic conditions, but are deprotected using strong acids. The t-Boc group can later be removed from the amine using strong acids, such as trifluoroacetic acid, $H_2SO_4$ or HCl. Thus, the t-Boc group serves as an amino protective group, since it is unreactive to most bases and nucleophiles.

The methods of the invention also include removing immobilized salts left from the electrospinning solution on the chitosan nanofibers by exposing the chitosan nanofibers to an organic base in an organic solvent. Chitosan nanofibers are susceptible to loss of structural integrity when exposed to hydrophilic solutions that hydrolyze the immobilized salt residues and/or neutralize the chitosan nanofibers. In one embodiment, removing immobilized salts on the chitosan nanofibers comprises neutralizing protonated amino groups on the nanofibers. In another embodiment, removing immobilized salts on the chitosan nanofibers comprises exposing the chitosan nanofibers to an organic solvent.

In one embodiment, the electrospun chitosan nanofibers are immersed in an organic solvent, which may be itself a base or optionally comprises a base, such as triethylamine (TEA) in an acetone solution (FIG. 29B), to remove the immobilized salts. The organic solvent can include, but is not limited to, triethylamine, diisopropylethylamine, trimethylamine or pyridine, or any of these base or any combinations thereof in a liquid such as in acetone, ethyl acetate, tetrahydrofuran and any combinations thereof. As the chitosan nanofibers are insoluble in the organic TEA/acetone solution, they do not swell in such solvent. Triethylamine is a stronger base (pKa~11) than the chitosan amine (pKa~6.5), and thus deprotonates the protonated chitosan amine to form a (trifluoroacetate) TFA salt. The TEA+.TFA− organic salt is soluble in acetone, thus the toxic TFA salt residues are removed from the chitosan nanofibers.

After removal of the TFA salts, the chitosan fibers are highly susceptible to hydrolysis due to the many —OH and, —$NH_2$ or —$NH_3^+$ groups on the chitosan polymer chain. To prevent excessive swelling and dissolution of the chitosan fibers, the amino groups are capped with a protection group by reacting the amino group with a carbonate ester in an organic solvent, such as tetrahydrofuran (THF, FIGS. 28 and 29). The selective protection of the free amino groups with a carbonate ester results in the amine group being protected with a N-tert-butoxycarbonyl group or t-Boc. In one embodiment, the amino protecting reagent comprises a carbonate ester reagent, such as di-tert-butyl dicarbonate. Contacting the chitosan nanofibers with the carbonate ester reagent, such as di-tert-butyl dicarbonate, yields one or more protected amino groups or N-tert-butoxycarbonyl on the chitosan nanofibers.

In certain embodiments, the carbonate ester reagent, such as di-tert-butyl dicarbonate, reacts selectively with one or more of the amino groups that are near surface of the chitosan nanofibers since some carbonate ester reagents may not penetrate deep into the nanofibers. As a result, the amino protected chitosan nanofibers form a seal around the chitosan nanofibers, which retains at least a fraction of unprotected amino groups. The t-BOC modified chitosan polymers are more hydrophobic and less susceptible to hydrolysis in aqueous/physiological solutions, and hence, able to retain nanofibrous structure. In one embodiment, the amino protected chitosan nanofibers are more hydrophobic than unreacted chitosan nanofibers.

The amino protected chitosan nanofibers are also less susceptible to hydrolysis when exposed to the hydrophilic solvent. Thereby, contacting the amino protected chitosan nanofibers with a hydrophilic solvent prevents or minimizes swelling of the chitosan nanofibers. The amine protection reaction can also protect the chitosan nanofibers from dissolution when exposed to a hydrophilic solvent.

Hydrolysis of Immobilized Salts

The methods of the invention also include washing the acylated chitosan nanofibers with a hydrophilic solvent. Acylated chitosan nanofibers that have undergone protection with acylation are not susceptible to loss of structural integrity when exposed to solutions that hydrolyze immobilized salt residues or neutralize the chitosan nanofibers. In one embodiment, washing the acylated chitosan nanofibers comprises hydrolyzing the immobilized salt residues from the chitosan nanofibers.

In an exemplary embodiment, the acylated chitosan nanofibers are isolated from the acylation reaction mixture and dialyzed in distilled water to remove the immobilized salt residues. Other washing methods, such as Soxhlet extraction or Kumagawa extraction in methanol, may also be used to remove immobilized acid salts and/or other contaminants. After hydrolysis of the immobilized salts, the chitosan nanofibers may be dried, such as through lyophilization, air drying or other convenient methods. In one embodiment, the acylated chitosan nanofibers are dried.

Deacylation

The methods included in the invention also include deacylating the acylated chitosan nanofibers. In one embodiment, the acylated chitosan nanofibers are exposed to a deacylating agent. Examples of the deacylating agent include, but are not limited to, a basic solution such as potassium hydroxide, lithium hydroxide, sodium hydroxide, rubidium hydroxide, cesium hydroxide, calcium hydroxide, strontium hydroxide, barium hydroxide, other basic solutions (such as sodium or potassium carbonate), and combinations thereof.

In an exemplary embodiment, one gram of acylated chitosan nanofibers are exposed to 100 ml of a basic solution, such as 5% potassium hydroxide, lithium hydroxide, sodium hydroxide, rubidium hydroxide, cesium hydroxide, calcium hydroxide, strontium hydroxide, barium hydroxide or other basic solutions (such as sodium or potassium carbonate). The ratio of acylated chitosan to base may be adjusted as needed (mol (base):mol (glycosamine unit of chitosan)>10). The mixture is stirred by a magnetic stirrer at 60° C. The degree of deacylation to remove the acyl groups, such as fatty acyl groups, attached to the nanofiber may be controlled by changing the length of the reaction time, wherein longer reaction times increase the level of deacylation. The deacylated chitosan nanofibrous membrane is dialyzed in distilled water to remove excess basic solution. The chitosan nanofibers may be dried, such as through lyophilization, air drying or other convenient methods.

Membranes

Figure 2:
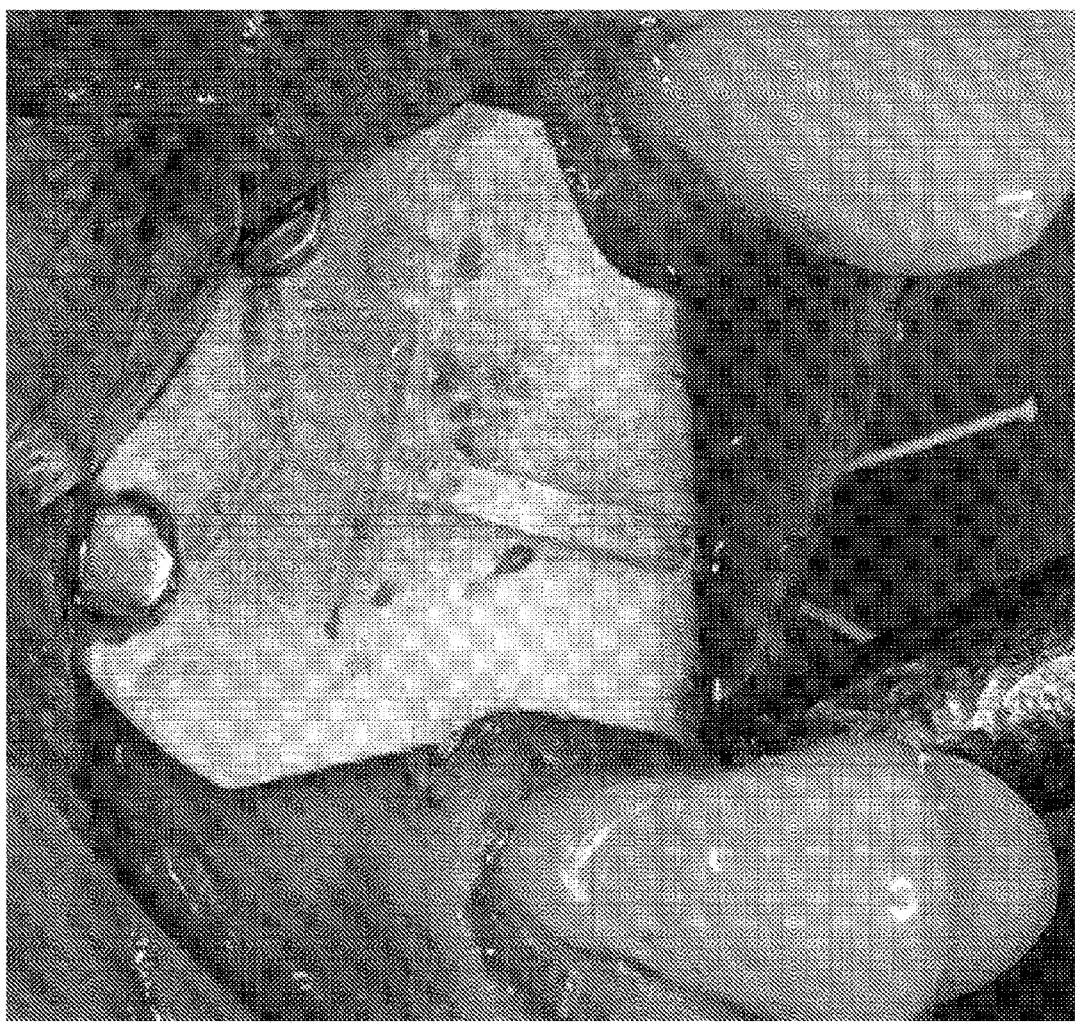
FIG. 2 is an image showing a guided bone regeneration membrane.

The present invention includes membranes or compositions that comprise electrospun chitosan nanofibers. The membranes or compositions of the invention are useful as dressings, barrier membranes, adhesion, three-dimensional scaffolds, etc. Barrier membranes are used to direct the growth of new tissue (FIGS. 1A-1D), such as bone and gingival tissue (FIG. 2), at sites having insufficient volumes or dimensions for proper function, aesthetics or regenerative properties. In one aspect, the electrospun chitosan nanofibers of the barrier membranes may be prepared by acylation, washing and deacylation or a reversible acylation to retain nanofiber structure and integrity when the barrier membrane is exposed to hydrophilic solvents. In another aspect, the electrospun chitosan nanofibers of the barrier membranes may be prepared by exposure to an amino protecting reagent, such as a carbonyl ester, to retain nanofiber structure and integrity when the barrier membrane is exposed to hydrophilic solvents. In one embodiment, the membrane or composition comprises electrospun chitosan nanofibers comprising N-tert-butoxycarbonyl groups. In another embodiment, at least a portion of the chitosan nanofibers comprise amines protected with N-tert-butoxycarbonyl groups.

In one aspect, the barrier membrane comprises electrospun chitosan nanofibers that are reversibly acylated to retain nanofiber structure and integrity when the barrier membrane is exposed to a hydrophilic solvent. When the chitosan nanofibers are electrospun in a solution, such as an acidic solution comprising trifluoroacetic acid, the acidic solution can form salts that become immobilized to the surface of and within the chitosan nanofibers. Exposure to the hydrophilic solvent hydrolyzes the immobilized salt residues, such as trifluoroacetate from the chitosan polymer. The reversible acylation is beneficial by preventing or minimizing swelling of the nanofibers, protecting the nanofibers from dissolution, and protects the nanofibers from loss of nanofiber structure when exposed to the hydrophilic solvent.

Another aspect of the invention includes a membrane comprising electrospun chitosan nanofibers that are reversibly acylated with at least one acyl group. The acyl groups may include formyl, acetyl, propionyl, butyryl, isobutyryl, pivaloyl, pentanoyl, hexanoyl, and benzoyl groups.

In yet another aspect, the barrier membrane comprises electrospun chitosan nanofibers comprising amino protecting groups, such as tert-butoxycarbonyl groups, that retain nanofiber structure and integrity when the barrier membrane is exposed to a hydrophilic solvent. When the chitosan nanofibers are electrospun in a solution, such as an acidic solution comprising trifluoroacetic acid, the acidic solution can form salts that become immobilized to the surface of and within the chitosan nanofibers. Exposure to the hydrophilic solvent hydrolyzes the immobilized salt residues, such as trifluoroacetate from the chitosan polymer. The protection of at least a portion of the amino groups on the chitosan nanofibers is beneficial by preventing or minimizing swelling of the nanofibers, protecting the nanofibers from dissolution, and protects the nanofibers from loss of nanofiber structure when exposed to the hydrophilic solvent. In one embodiment, the amino protected chitosan nanofibers are on an exterior surface of the barrier membrane. When the amino protected chitosan nanofibers are on the exterior surface, the protected nanofibers create a hydrophobic barrier for the barrier membrane against hydrophilic solvents.

The membranes or compositions comprising chitosan nanofibers can be delivered by any method known to the skilled artisan. In one aspect, the chitosan nanofiber membrane or composition is delivered to a target site to promote or direct healing of a tissue at the target site. In another aspect, the chitosan nanofiber membrane or composition is delivered to a target site to promote or direct the formation of tissues at the target site. In one embodiment, the membrane or composition comprises electrospun chitosan nanofibers. In another embodiment, the membrane is a barrier membrane. The tissue at the target site includes epithelial, dental, craniofacial, connective (such as cartilage) and bone tissue. In another embodiment, the subject is suffering from a disease or disorder selected from chronic periodontitis, edentulism, and bone regeneration. In an exemplary embodiment, the barrier membrane of the present invention is implanted for guided bone regeneration.

In some embodiment, the membrane includes electrospun chitosan nanofibers and one or more natural or synthetic materials that include, but are not limited to, collagen, fibrin, elastin, laminin, fibronectin, hyaluronic acid, chondroitin 4-sulfate, chondroitin 6-sulfate, dermatan sulfate, heparin sulfate, heparin, and keratan sulfate, proteoglycans, poly (lactic acid) polymers, poly(glycolic acid) polymers, poly(lactide-co-glycolides) (PLGA), poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol) (PVA), poly(acrylic acid), polyvinyl acetate), polyacrylamide, poly(ethylene-co-vinyl acetate), poly(ethylene glycol), poly(methacrylic acid), polylactic acid (PLA), polyglycolic acids (PGA), nylons, polyamides, polyanhydrides, poly(ethylene-co-vinyl alcohol) (EVOH), polycaprolactone, polyvinyl acetate), polyvinylhydroxide, poly(ethylene oxide) (PEO), and polyorthoesters or a co-polymer formed from at least two members of the group, and any combination thereof.

In some embodiments, the membrane includes at least one agent, such as a therapeutic agent or biological agent. The agent includes, but is not limited to, nucleic acids, antibiotic, anti-inflammatory agent, growth factor, cytokine, enzyme, protein, peptides, amino acids, carbohydrate, lipid, hormone, the like, and any combination thereof. The agent can be incorporated into the membrane during the electrospinning process. For example, the agent can be included in the electrospinning solution. This would allow the agent to be incorporated around and/or in the nanofibers. The agent can also be added to the nanofiber after the electrospinning process. The agent can be absorbed to the nanofibers, such as by exposing the nanofibers to a solution of the agent. The agent can also be immobilized to the nanofibers. The immobilized agent can be bound directly or indirectly to the nanofiber, such as through a covalent bond, a linker, and/or ionic bond. In one embodiment, the nanofibers comprise at least one of a natural material, a synthetic material, and an agent.

As described below, the present invention also features modified chitosan materials with anti-inflammatory and pro-healing properties and methods of making such modified chitosan materials. The invention is based, at least in part, on the discovery that modification of the amino group on chitosan to create an imine bond imparts anti-inflammatory and pro-healing properties to the chitosan material.

Modified Chitosan

Chitosan is a biopolymer composed of N-glucosamine and N-acetyl-glucosamine units. Chitosan is derived from chitin, a naturally occurring polymer. Chitin is a white, hard, inelastic, nitrogenous polysaccharide isolated from fungi, mollusks, or from the exoskeletons of arthropods (e.g., crustaceans, insects). Chitosan is a biodegradable and biocompatible polymer that has much potential and been widely investigated for applications in wound healing, tissue engineering/regenerative medicine, drug delivery and implant applications.

Conventional methods to produce chitosan materials that effectively provide anti-inflammatory and pro-healing properties are inadequate. Chitosan is a cationic weak base that is substantially insoluble in water and organic solvents. Typically, chitosan is fairly soluble in acidic solutions, such as acetic, citric, oxalic, proprionic, ascorbic, hydrochloric, formic, and lactic acids, as well as other organic and inorganic acids. Solubility of chitosan in acidic solutions makes production of chitosan products rather limited. Chitosan is more readily solubilized in low pH solutions, such as concentrated acetic acid and trifluoroacetic acid (TFA). Other solvents, such as 1,1,1,3,3,3-hexafluoro-2-propanol, have also been used in the past. However, such solvents are prohibitively expensive to utilize routinely or in large scale production.

Because chitosan has free amino groups, they may be reacted with other functional groups to produce modified chitosan materials with different properties. Phenyl-containing carbonyl derivatives, such as raspberry ketones, can react with the free amino groups on chitosan to convert the amino group into an imine bond. Raspberry ketone, in particular, is an exemplary embodiment. a natural phenolic compound found in a variety of fruits including raspberries, cranberries and blackberries and is currently used as an additive in foods and cosmetics. Phenyl-containing carbonyl derivatives, such as raspberry ketone, have been shown to modulate the activation of macrophages in cell culture and to reduce effects of stimuli that may lead to chronic inflammation.

The formation of an imine bond on the chitosan molecule maintains many of the advantages of the native chitosan, but includes the ability of the modified chitosan to support/promote the M2 macrophage phenotype for promoting tissue healing/regeneration. For example, promoting healing would have a significant benefit to regenerating bone, cartilage, and nerve tissues for which chitosan materials are broadly investigated. Reducing inflammation around micro- and nano-particles would be important to local drug delivery strategies (e.g. antibiotics, anticancer drugs, etc) by avoiding confounding factors often associated with chronic inflammation that may impede local release rates.

In one aspect, the invention includes a modified chitosan comprising an iminyl group. The iminyl group can have a general structure as shown in Structure I:

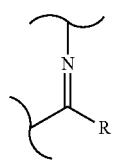

Structure II wherein R can be selected from the group consisting of H, $C_1$-$C_6$ alkyl, $C_1$-$C_6$ alkoxy, phenyl, and any combination thereof. The iminyl group can also be derived from a phenyl-containing carbonyl derivative. The phenyl-containing carbonyl derivative can include a molecule having a general formula of Structure I:

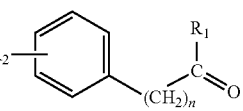

Structure I wherein $R_1$ and $R_2$ are each independently selected from H, $C_1$-$C_6$ alkyl, and $C_1$-$C_6$ alkoxy, and n is an integer selected from 1, 2, 3, 4, 5, and 6. In one embodiment, the phenyl-containing carbonyl derivative is a raspberry ketone. The raspberry ketone or 4-(4-hydroxyphenyl)butan-2-one has the general formula of Structure III:

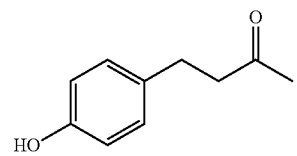

Structure III

In another embodiment, the modified chitosan increases anti-inflammatory properties as compared to unmodified chitosan. Examples of increasing anti-inflammatory properties includes, but is not limited to, decreasing or preventing or inhibiting leukocyte infiltration, nitric oxide production and release by macrophages, edema, redness, pain, and/or neovascularization. The modified chitosan can increase pro-healing properties of the modified chitosan as compared to unmodified chitosan. In another embodiment, the modified chitosan decreases levels of nitric oxide and/or decreases or inhibits macrophage production of nitric oxide.

The invention includes methods for modifying chitosan. In one embodiment, a solution of 2% chitosan by weight (~87% degree of deacetylation) in 2% acetic solution, creating approximately a 0.8:2 ratio, is stirred overnight at 56° C. Oxygen gas is purged from the acidic chitosan solution using nitrogen gas. A phenyl-containing carbonyl derivative, such as a raspberry ketone, is added to the solution and the mixture continues to be oxygen purged. Heat is applied, in the range of about 45° C. to about 90° C., to accelerate the reaction between the chitosan and the phenyl-containing carbonyl derivative. The reaction time may be controlled to control both the degree of modification of the chitosan by the raspberry ketone compound and the water contact angle (hydrophobicity) of the modified chitosan.

In one aspect, a method for modifying chitosan comprises obtaining an oxygen depleted acidic solution comprising chitosan, mixing the oxygen depleted chitosan solution with a phenyl-containing carbonyl derivative, and reacting the phenyl-containing carbonyl derivative with at least one free amino group on the chitosan to create an imine bond that modifies the chitosan. In one embodiment, the acidic solution comprises acetic acid. In another embodiment, obtaining the oxygen depleted chitosan solution comprises removing $O_2$ gas and replacing the $O_2$ gas with $N_2$ gas. In another embodiment, mixing the oxygen depleted chitosan solution with the phenyl-containing carbonyl derivative comprises heating the mixture. In yet another embodiment, the phenyl-containing carbonyl derivative is a raspberry ketone.

Modified Chitosan Microspheres

The invention also includes chitosan microspheres and the method of making chitosan microspheres. One aspect of the invention includes a chitosan microsphere comprising chitosan modified with an iminyl group. Another aspect includes a chitosan microsphere comprising the modified chitosan made by any method described herein.

The chitosan microspheres are generally spherical shells or beads comprising chitosan having a small diameter, in the range of about 50 nm to about 500 μm. One embodiment includes the microsphere having a diameter in the range of about 1 μm to about 500 μm. The diameter includes at least about 50 nm, 100 nm, 150 nm, 200 nm, 250 nm, 300 nm, 350 nm, 400 nm, 500 nm, 600 nm, 700 nm, 800 nm, 900 nm, 1 μm, 5 μm, 10 μm, 15 μm, 16 μm, 17 μm, 18 μm, 19 μm, 20 μm, 21 μm, 22 μm, 23 μm, 24 μm, 25 μm, 26 μm, 27 μm, 28 μm, 29 μm, 30 μm, 31 μm, 32 μm, 33 μm, 34 μm, 35 μm, 36 μm, 37 μm, 38 μm, 39 μm, 40 μm, 41 μm, 42 μm, 43 μm, 44 μm, 45 μm, 46 μm, 47 μm, 48 μm, 49 μm, 50 μm, 51 μm, 52

µm, 53 µm, 54 µm, 55 µm, 56 µm, 57 µm, 58 µm, 59 µm, 60 µm, 61 µm, 62 µm, 63 µm, 64 µm, 65 µm, 66 µm, 67 µm, 68 µm, 69 µm, 70 µm, 71 µm, 72 µm, 73 µm, 74 µm, 75 µm, 76 µm, 77 µm, 78 µm, 79 µm, 80 µm, 81 µm, 82 µm, 83 µm, 84 µm, 85 µm, 86 µm, 87 µm, 88 µm, 89 µm, 90 µm, 91 µm, 92 µm, 93 µm, 94 µm, 95 µm, 96 µm, 97 µm, 98 µm, 99 µm, 100 µm, 150 µm, 200 µm, 250 µm, 300 µm, 350 µm, 400 µm, 450 µm, 500 µm, and any diameter in between.

Another embodiment, the modification increases anti-inflammatory properties of the modified chitosan as compared to unmodified chitosan. In yet another embodiment, the modification increases pro-healing properties of the modified chitosan as compared to unmodified chitosan. In still another embodiment, the modification decreases macrophage production of nitric oxide.

Microspheres are particularly useful for delayed or time release delivery of one or more agents to a target site. In one embodiment, the microsphere further comprises an agent. The microsphere can be hollow and filled with an agent (such as a drug or antibody) that is released upon degradation of the chitosan shell or the microsphere can incorporate the agent into the microsphere with the chitosan molecules and the agent is released as the chitosan degrades. In one embodiment, the microsphere forms a biodegradable shell around the agent or the agent is incorporated into the microsphere.

Another aspect of the invention includes method of producing microspheres of chitosan. The method includes modifying at least one free amino group on the chitosan with an iminyl group and crosslinking the modified chitosan to form chitosan microspheres. In one embodiment, the modified chitosan is crosslinked by exposure to a crosslinking agent, such as glutaraldehyde or genipin.

The method can also include modifying the chitosan by obtaining an oxygen depleted acidic solution comprising chitosan, mixing the oxygen depleted chitosan solution with a phenyl-containing carbonyl derivative, and reacting the phenyl-containing carbonyl derivative with at least one free amino group on the chitosan to create an imine bond that modifies the chitosan.

Modified Chitosan Products

The modified chitosan can also be electrospin by methods known in the art to produce chitosan nanofibers (Schiffman and Schauer, Bio macro molecules, 2007. 8 (9): p. 2665-7). These nanofibers typically have a mean diameter of about 100 nm or in the range of about 40 nm to about 130 nm, but the diameter of the chitosan nanofibers can vary widely depending upon a number of factors, such as rotation speed of the spinning mandrel, concentration of the chitosan, electrostatic charge of the solution, etc. Some nanofibers can be as large as 1000 nm in diameter and as small as 5 nm. Some nanofibers have a mean diameter between about 10 nm to about 500 nm. Typically, nanofibers have a mean diameter between about 30 nm to about 200 nm. In one embodiment, the chitosan nanofibers have a substantially uniform diameter. In another embodiment, the nanofibers have a mean diameter in the range of about 40 to about 130 nm.

The degree of deacylation of the chitosan used for producing the nanofibers can vary from about 50% to about 99%, with about 70% deacylation preferable. The molecular weight of the chitosan can also vary from less than about 100 kDa to about 900 kDa, with about 300 kDa to about 325 kDa preferable. The chitosan weight volume in solution is from about 0.25 to about 10.0% weight/volume (e.g., 0.1, 0.2, 0.25, 0.3, 0.4, 0.5, 1, 1.25, 1.5, 1.75, 2.0, 2.5, 3.0, 3.5, 4, 4.5, 5, 5.5, 6, 6.5, 7, 7.5, 8, 8.5, 9, 9.5, and 10%). In one embodiment, 5.50% weight volume of chitosan in solution is used for the electrospinning process, where a 5.50% weight volume of chitosan contains 5.50 grams of chitosan per 100 ml solution.

In one aspect, the invention includes a method of preparing modified chitosan nanofibers comprises electrospinning an acidic solution comprising modified chitosan into chitosan nanofibers. After the modification of the chitosan, the modified chitosan is dissolved in an acidic solution. The acidic solution includes, but is not limited to, trifluoroacetic acid (TFA), acetic, citric, oxalic, proprionic, ascorbic, hydrochloric, formic, salicylic and/or lactic acids, and any combination of those. In some embodiments, the acidic solutions include other organic compounds or solvents, such as methylene chloride. In one embodiment, the acid solution comprising other organic compounds includes a 90%/10%, 80%/20% 75%/25%, 70%/30%, 60%/40%, or 50%/50% of acidic solution to other organic solvent ratio. In an exemplary embodiment, the chitosan is dissolved in a solution of 70% trifluoroacetic acid and 30% methylene chloride.

In some embodiments, the modified chitosan is loaded into a 10-mL syringe with a blunt 20G, 3.81 cm stainless steel needle tip. The syringe is loaded into the electrospinning apparatus and the flow rate set to a speed appropriate to the desired diameter size, e.g. 20 µL/min. The solution is electrospun at about 25 kV and the fibers are collected on a target (such as about 38.1 cm diameter circular disc of non-stick aluminum foil). The target is positioned about 15 cm from the needle tip and rotated at about 8.4 RPM by an AC motor to ensure even and random distribution of fibers. The electrospinning apparatus is housed inside a ventilated box, which is vented, preferably to the fume hood. After electrospinning, the nanofibrous membrane is vacuum treated for several hours, e.g. overnight, to remove residual solvent.

In one embodiment, modified chitosan nanofiber membranes are fabricated by electrospinning. The fiber orientation may be random or directed in uniform alignment. The fiber orientation may be altered or directed through manipulation of the orientation of the collection target mandrel and/or the speed of rotation.

In another embodiment, the modified chitosan nanofibers have a water contact angle that is greater than about 90 degrees, 91 degrees, 92 degrees, 93 degrees, 94 degrees, 95 degrees, 96 degrees, 97 degrees, 98 degrees, 99 degrees, 100 degrees, 101 degrees, or greater, or any number in between. In another embodiment, the modified chitosan nanofibers have a water contact angle in the range of about 93 degrees to about 101 degrees. In yet another embodiment, the modified chitosan nanofibers have a water contact angle that is greater than about 93 degrees.

Structural integrity of the modified chitosan can be altered to accommodate the proposed use of the chitosan. Variations in physical properties of polymers, such as modified chitosan, depend on its molecular weight, number of repeating units in the polymer-chain, and regularity of polymer-chain, side group chemistry, the degree of matrix packing or density, and crosslinking. The physical properties of modified chitosan can be controlled or altered during manufacture through its molecular weight, degree of deacylation, and crosslinking to affect thermal properties, such as melting point, and physical-mechanical properties, such as tensile strength, Young's modulus, swelling and degradation.

Crosslinking is the process which links polymer chains together. Crosslinking induces a three-dimensional matrix of interconnected, linear, polymeric chains. The degree or extent of crosslinking depends on the crosslinking agent.

Exemplary crosslinking agents include sodium tripolyphosphate, ethylene glycol diglycidyl ether, ethylene oxide, glutaraldehyde, epichlorohydrin, diisocyanate, and genipin. Crosslinking can also be accomplished using microwave or ultraviolet exposure.

The microspheres or membranes comprising the modified chitosan nanofibers can be delivered by any method known to the skilled artisan. In one aspect, the microspheres comprising modified chitosan are delivered to a target site to prevent inflammation or promote healing of tissue at the target site. In another aspect, the chitosan nanofiber membrane or composition is delivered to a target site to decrease nitric oxide levels at the target site. The methods comprise contacting the site with modified chitosan, wherein the modified chitosan is produced according to any of the methods described herein. In one embodiment, modified chitosan is in the form of microspheres.

In some embodiment, the membrane includes microspheres comprise modified chitosan and one or more natural or synthetic materials that include, but are not limited to, collagen, fibrin, elastin, laminin, fibronectin, hyaluronic acid, chondroitin 4-sulfate, chondroitin 6-sulfate, dermatan sulfate, heparin sulfate, heparin, and keratan sulfate, proteoglycans, poly(lactic acid) polymers, poly(glycolic acid) polymers, poly(lactide-co-glycolides) (PLGA), poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol) (PVA), poly(acrylic acid), polyvinyl acetate), polyacrylamide, poly(ethylene-co-vinyl acetate), poly(ethylene glycol), poly(methacrylic acid), polylactic acid (PLA), polyglycolic acids (PGA), nylons, polyamides, polyanhydrides, poly(ethylene-co-vinyl alcohol) (EVOH), polycaprolactone, polyvinyl acetate), polyvinylhydroxide, poly(ethylene oxide) (PEO), and polyorthoesters or a co-polymer formed from at least two members of the group, and any combination thereof.

In some embodiments, the microspheres include at least one agent, such as a therapeutic agent or biological agent. The agent includes, but is not limited to, nucleic acids, antibiotic, anti-inflammatory agent, growth factor, cytokine, enzyme, protein, peptides, amino acids, carbohydrate, lipid, hormone, the like, and any combination thereof. The agent can be encapsulated by the microsphere or incorporated into the microsphere. For example, the agent can be included in the chitosan solution during the production of the microsphere. This would allow the agent to be incorporated around and/or in the microsphere. The agent can be absorbed to the chitosan fibers, such as by exposing the modified chitosan to a solution of the agent. The agent can also be immobilized to the modified chitosan before the production of the microsphere. The immobilized agent can be bound directly or indirectly to the modified chitosan molecule, such as through a covalent bond, a linker, and/or ionic bond. In one embodiment, the microsphere further comprises at least one of a natural material, a synthetic material, and an agent.

Kits

The invention includes kits with reagents for preparing chitosan nanofibers or other modified chitosan materials. In one aspect, the kit includes chitosan nanofibers, acylating catalyst, acylating agent, and hydrophilic solvent. In another aspect, the kit includes a membrane comprising chitosan nanofibers, acylating catalyst, acylating agent, and hydrophilic solvent. In yet another aspect, the kit includes a membrane comprising electrospun chitosan nanofibers comprising acyl groups, and hydrophilic solvent. In one embodiment, the kit further includes a deacylating agent. In another embodiment, the kit further includes at least one of a natural material, a synthetic material, and an agent.

In another aspect, the kit includes chitosan nanofibers, carbonate ester reagent, and organic solvent. In one example, the kit includes a membrane comprising chitosan nanofibers, carbonate ester reagent, such as di-tert-butyl dicarbonate, and organic solvent. In another example, the kit includes a membrane comprising electrospun chitosan nanofibers comprising N-tert-butoxycarbonyl groups. In one embodiment, the kit further includes a hydrophilic solvent.

If desired the chitosan nanofibers and barrier membranes of the invention are provided with instructions for use in a prophylactic or therapeutic method described herein. The instructions will generally include information about the use of the composition in guided tissue regeneration in a subject in need thereof. The instructions may be printed directly on the container (when present), or as a label applied to the container, or as a separate sheet, pamphlet, card, or folder supplied in or with the container.

In another aspect, the kit includes chitosan and a phenyl-containing carbonyl derivative. In one embodiment, the phenyl-containing carbonyl derivative is a raspberry ketone. In another embodiment, the kit further comprises a crosslinking agent. In another aspect, the kit includes reagents for preparing chitosan products with modified chitosan materials. In one embodiment, the kit includes chitosan comprising an iminyl group modification and an acidic solution.

If desired the kit of the invention provides instructions for incorporating the modified chitosan materials in a film, a gel, a membrane, microfibers, nanofibers, and/or nano- or microparticles/spheres as described herein. The instructions will generally include information about the use of the modified chitosan in therapeutic procedures, such as guided tissue regeneration or agent delivery, in a subject in need thereof. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Figure 3:
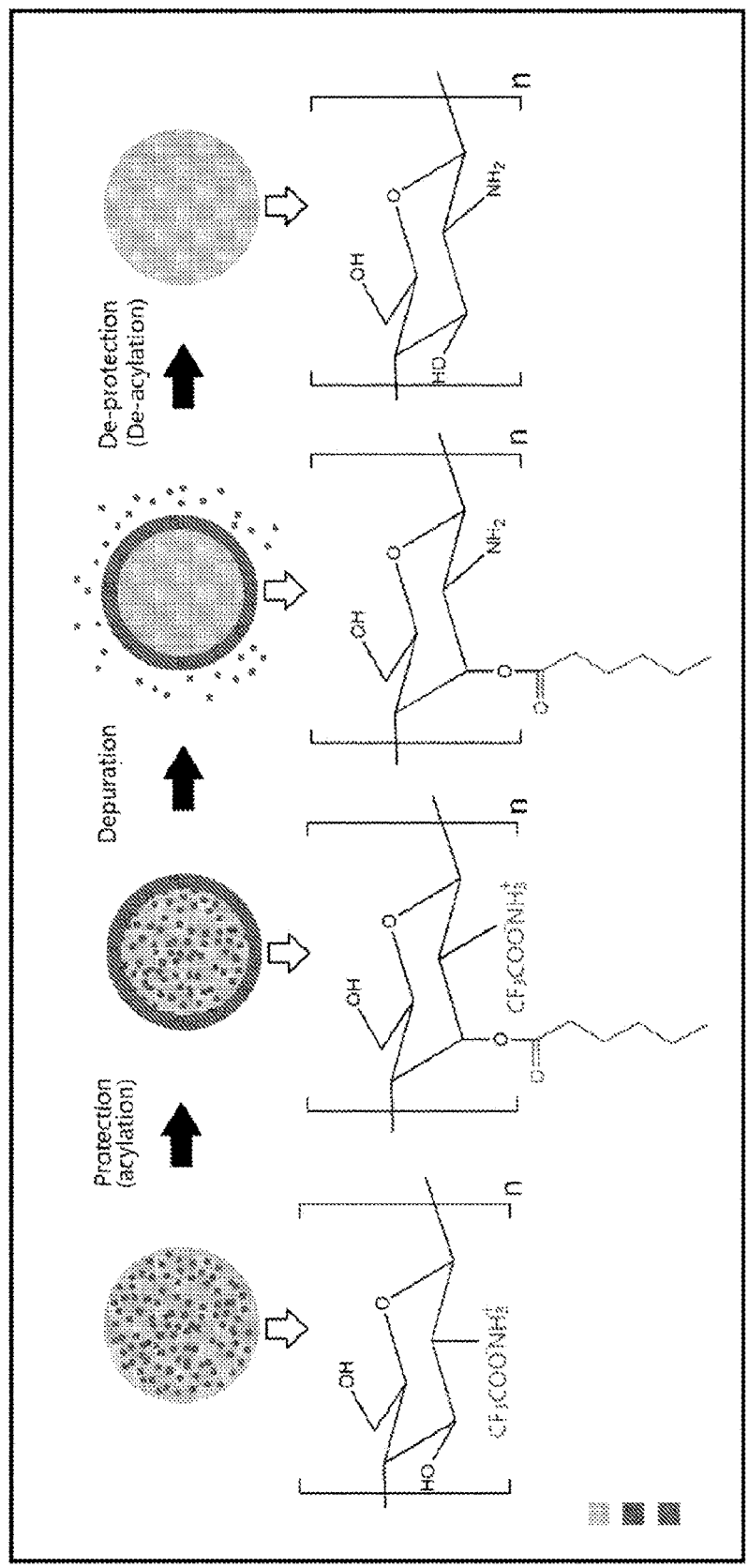
FIG. 3 is a series of cartoon illustrations showing the stabilization process and chemical structure evolution of the chitosan nanofibers (circular disk is a cross-section of the nanofibers; dots represent trifluoroacetate (TFA) salt residues; dark circle is the surface acylated chitosan layer).

Example 1: Removal of Immobilized Salt Residues from Electrospun Chitosan Nanofibers after Protection with Acylation FIG. 3 shows an overview of the stabilization approach. A series of cartoons shows the morphological evolution of the electrospun chitosan nanofibers in cross-sectional view. The change in the chemical structure of the chitosan nanofibers after each process is shown.

The first section shows the interior structure of the electrospun chitosan nanofibers immediately after electrospinning. A large amount of dots, which represent the extensive presence of highly hydrophilic trifluoroacetate salt residues in the body of the electrospun chitosan nanofibers, were present inside the circular disk.

The second section shows the protection of electrospun chitosan nanofibers through acylation. The exterior of the circular disk is protected after the acylation reaction, which represents the exterior region of electrospun chitosan nanofibers become hydrophobic. The hydrophobicity is attributed from the grafted acyl groups.

The third section shows the depuration process or hydrolysis of the trifluoroacetate salt residues. The dots are released from the circular disk while the integrity of the disk circle is maintained. Through the protection of the acyl group, the immobilized trifluoroacetate salt residues are able to be released while the fiber structure is not damaged.

The last cartoon shows the deprotection process or deacylation of the electrospun chitosan nanofibers. The exterior of the circular disk has recovered back to its original state, which indicates the acyl groups have been removed from the chitosan nanofibers.

Example 2: Reversibility of the Acylation Reaction of Chitosan Nanofibers

Figure 4:
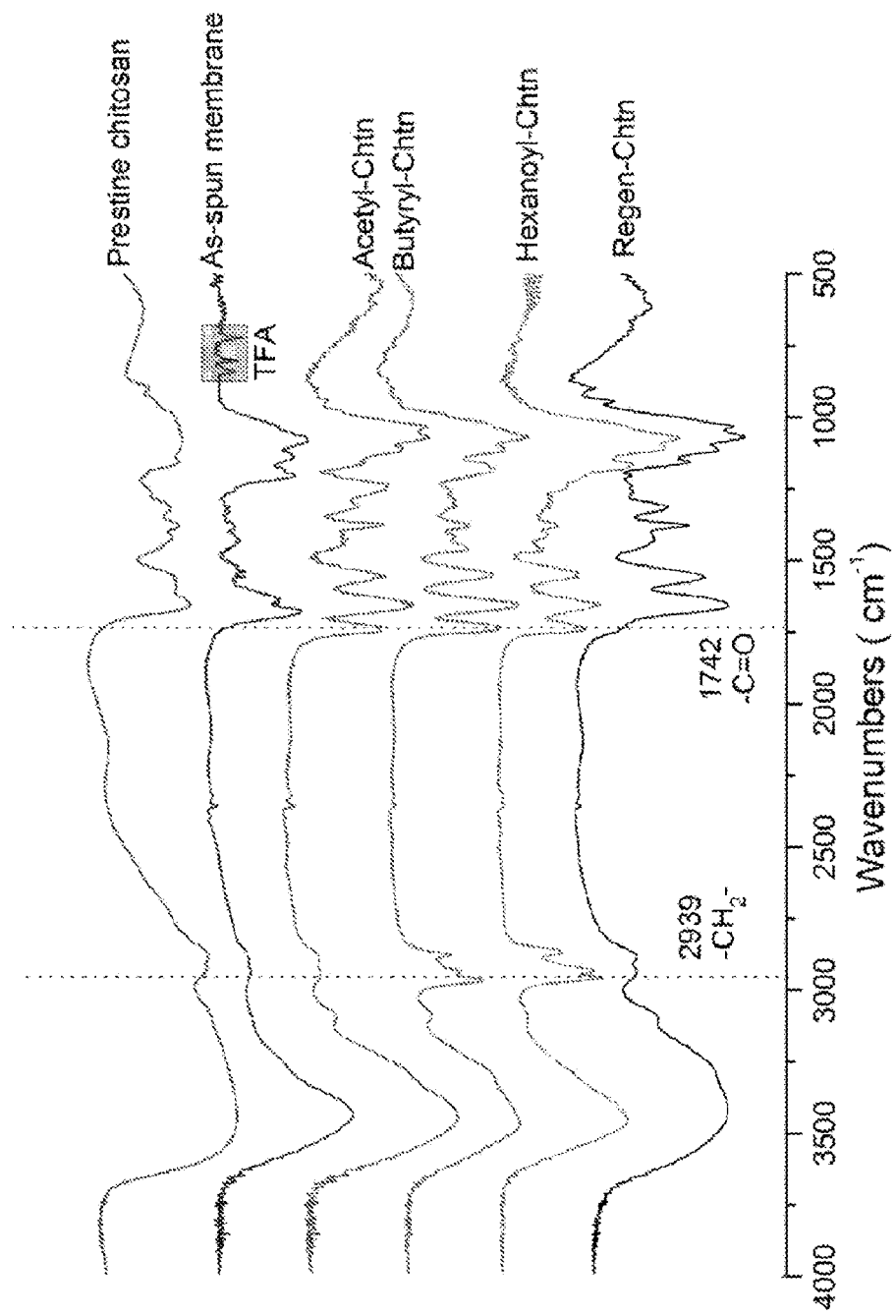
FIG. 4 is a Fourier transform infrared spectroscopy (FTIR) spectra of nanofibrous membranes showing peaks (—$CH_2$—; —C=O) associated with the acylation reaction and disappearance of TFA salts from the fibers.
Figure 5:
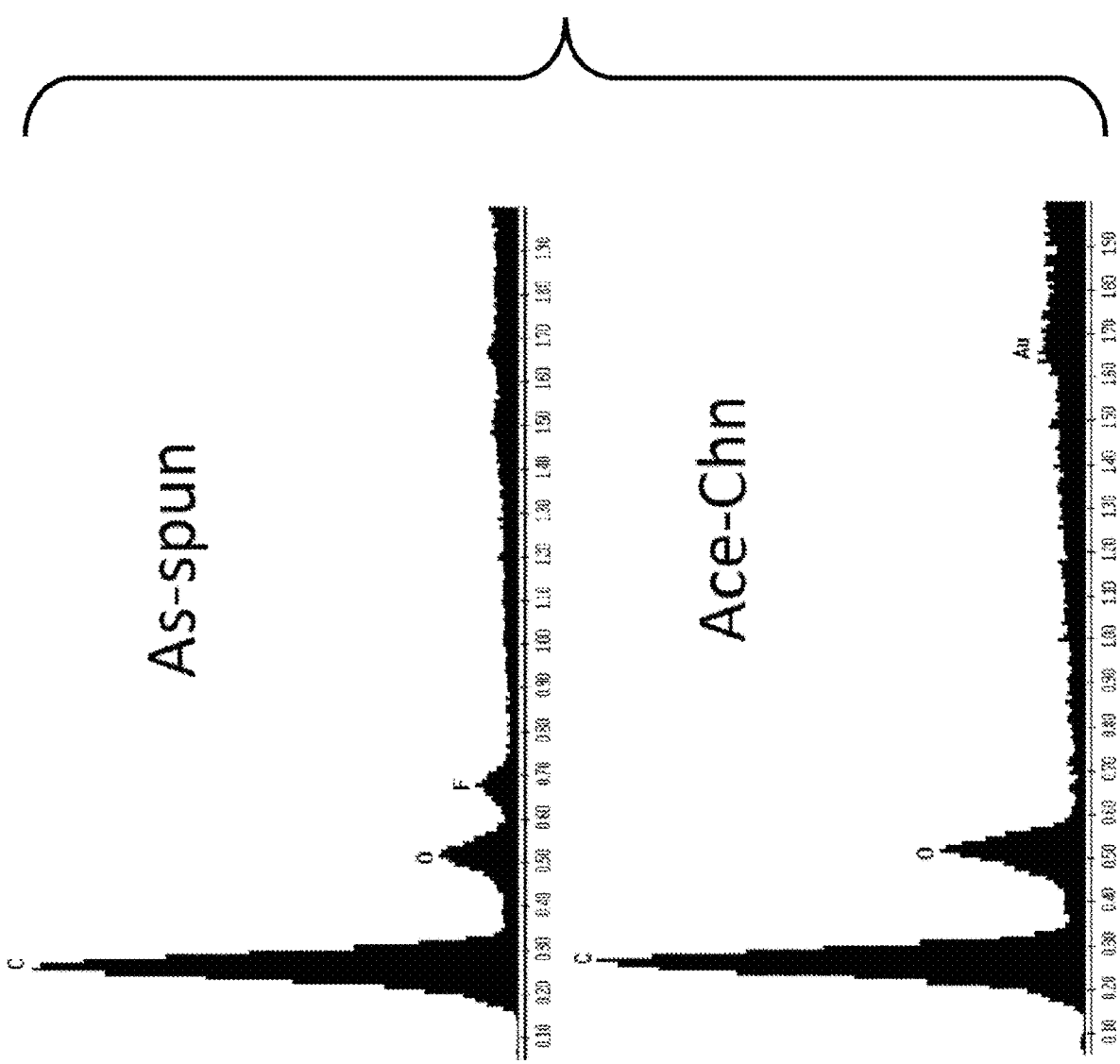
FIG. 5 is a panel of two energy dispersive x-ray spectroscopy analyses of as-spun electrospun chitosan nanofibers and acylated electrospun chitosan nanofibers.

The Fourier transform infrared spectroscopy (FTIR) spectra of pristine chitosan powder, as-spun electrospun chitosan nanofibers, acylated electrospun chitosan nanofibers, and deacylated electrospun chitosan nanofibers were shown in FIG. 4. The broad band at around 3445 $cm^{-1}$ was attributed to the inter- and intra-molecular hydrogen bonding of —$NH_2$ and —OH stretching vibration of chitosan molecules. The hydrogen bonding bands decreased in intensity in as-spun electrospun chitosan nanofibers and acylated electrospun chitosan nanofibers, possibly because the introduction of trifluoroacetic acid (TFA) salt and acyl groups weakened the hydrogen bonding among the chitosan molecules. The absorption peak at 1747 $cm^{-1}$ was assigned to the C=O of —OCOR group which were introduced by acylation between butyric anhydride and —OH groups of chitosan. The peaks at 2921 and 2851 $cm^{-1}$ were assigned to the asymmetrical and symmetrical bending vibrations of methylene groups, which increased in intensity after acylation because of the abundance of methylene structures in butyric groups. The three small peaks at 722, 802 and 841 $cm^{-1}$ and a large peak around 1670 $cm^{-1}$ was attributed to the presence of TFA in the electrospun chitosan nanofibers as amine salts, but these TFA associated peaks were not present in acylated (FIG. 4) and deacylated electrospun chitosan nanofibers. Energy dispersive spectroscopy (EDS) of as-spun electrospun chitosan nanofibers shows a peak identifying presence of fluorine from the TFA salt in the fibers (FIG. 5; top panel). In EDS spectra of the acylated nanofibers (FIG. 5; bottom panel) the peak for fluorine is gone indicating removal of the TFA salts.

Figure 6:
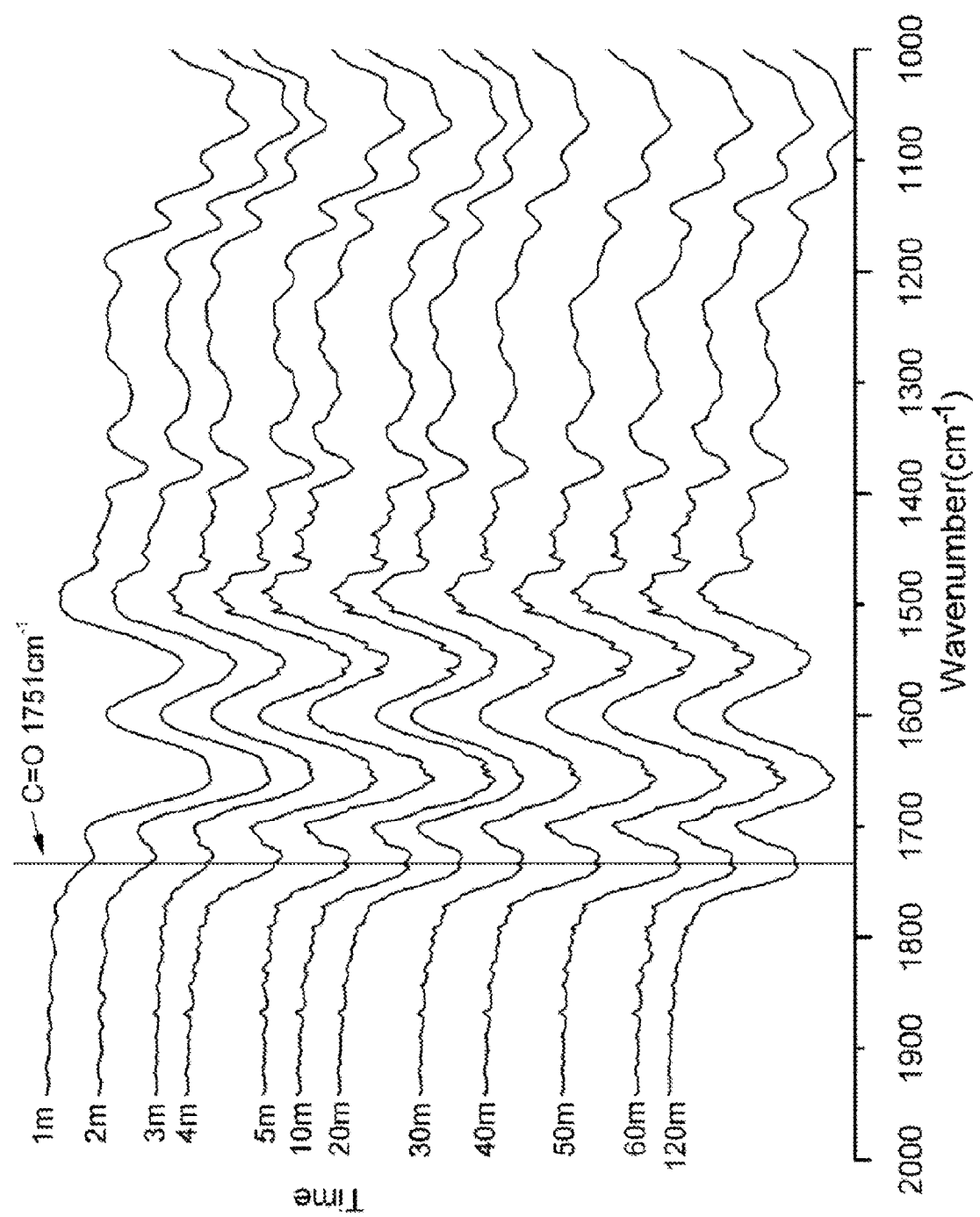
FIG. 6 is a series of FTIR spectra monitoring the effect of reaction time on the degree of substitution (DS) of electrospun chitosan nanofibers.
Figure 7:
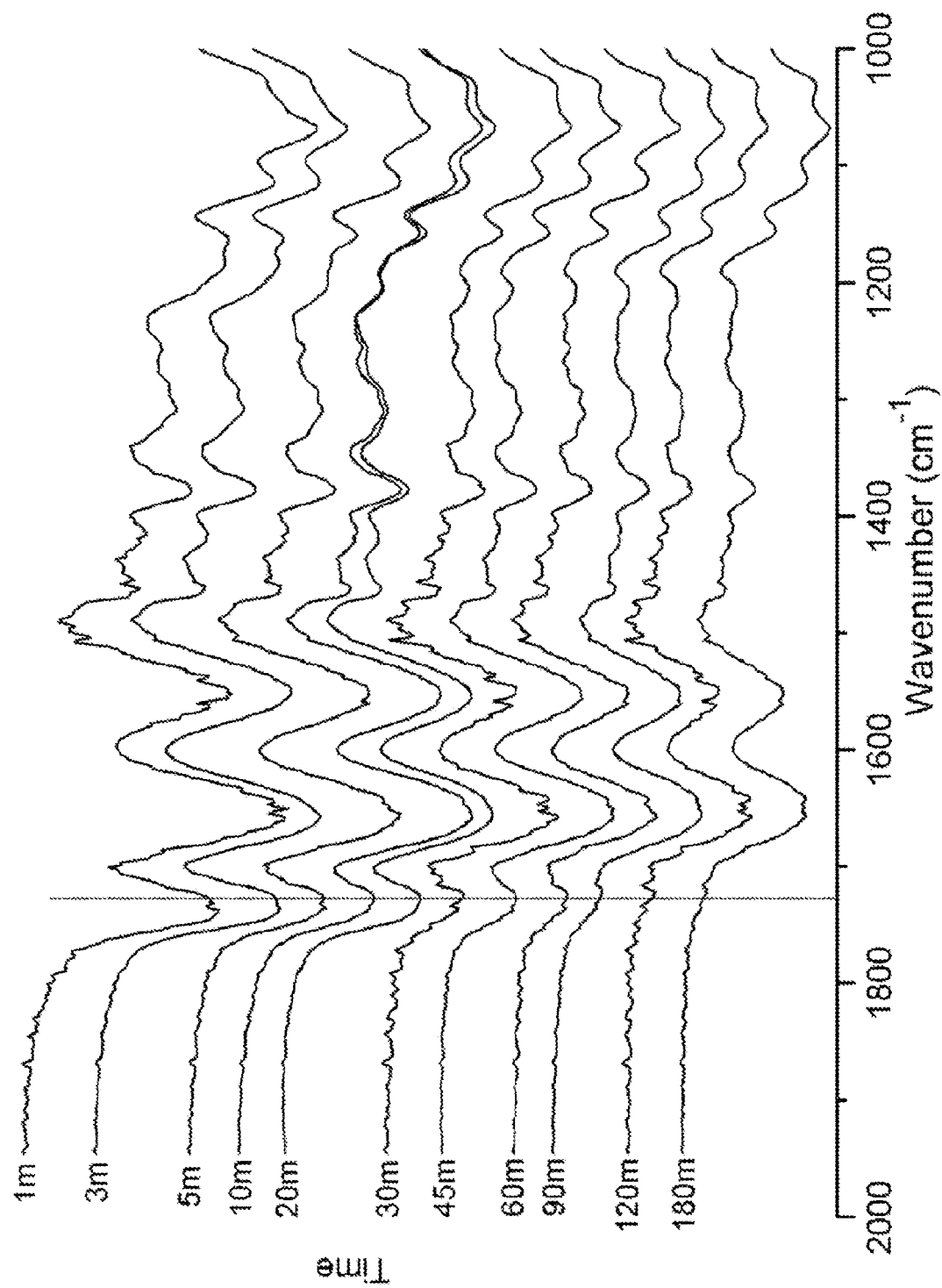
FIG. 7 is a series of FTIR spectra monitoring the effect of reaction time on the degree of substitution (DS) of electrospun chitosan nanofibers.
Figure 8:
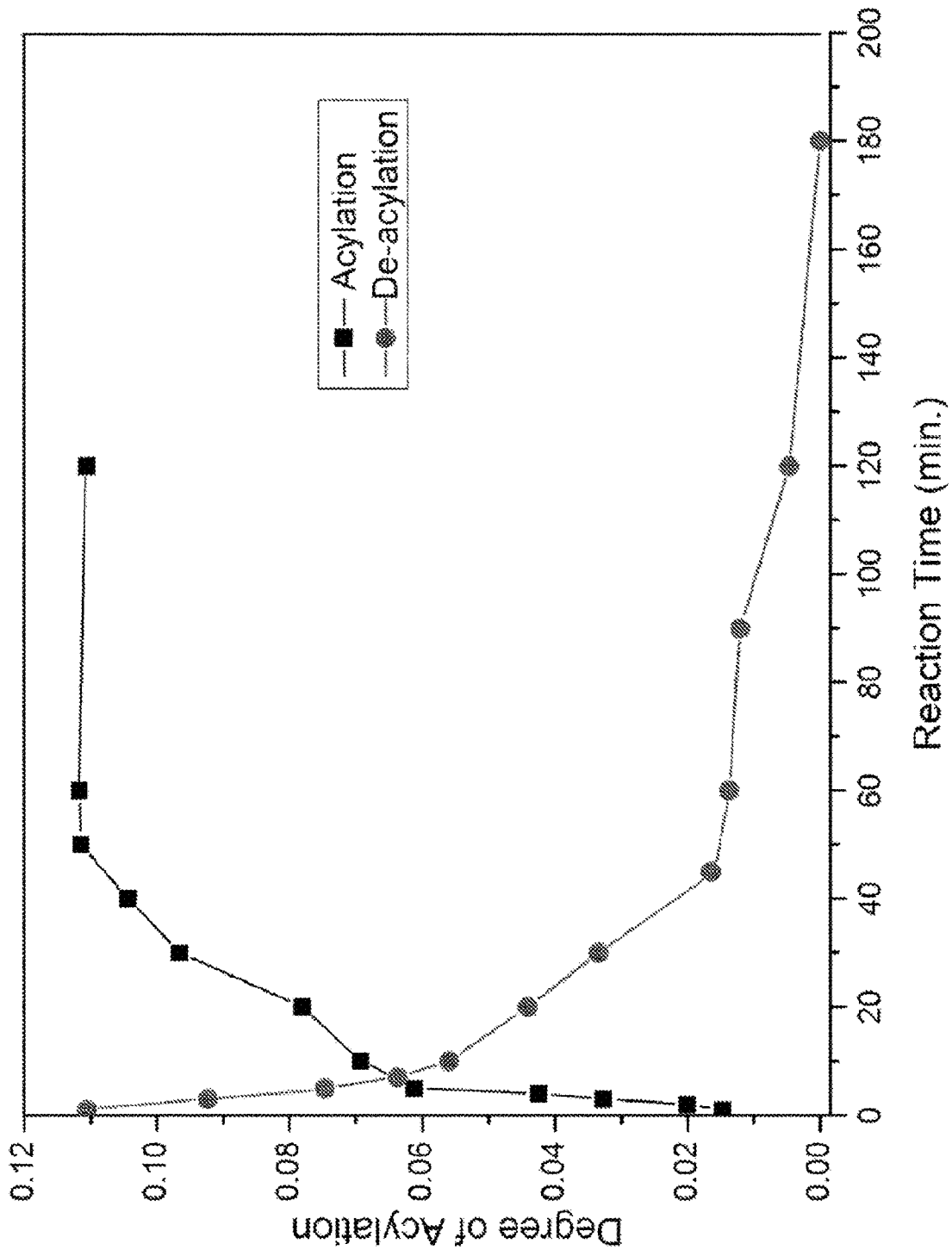
FIG. 8 is a graph showing the quantitative analysis of the FTIR spectras.

FIGS. 6 and 7 show a series of FTIR spectras monitoring the effect of reaction time on the degree of substitution (DS) of electrospun chitosan nanofibers, which was also quantitatively summarized in FIG. 8. During the acylation reaction, the DS value increased rapidly in the first five minutes and slowed until reaching a plateau at 60 minutes. This sample showed a mass increase of 3.48%, equal to the DS of 0.11.

During the deacylation reaction, the DS value dropped rapidly in the first ten minutes and slowed until deacylation was completed at approximately 180 minutes. The reaction kinetics in the described chitosan system were similar to reaction kinetics of other nanomaterials with a high surface to volume ratio. These results indicated that a small gain in mass occurred due to the acyl modification and that the reaction was reversible.

Figure 9A:
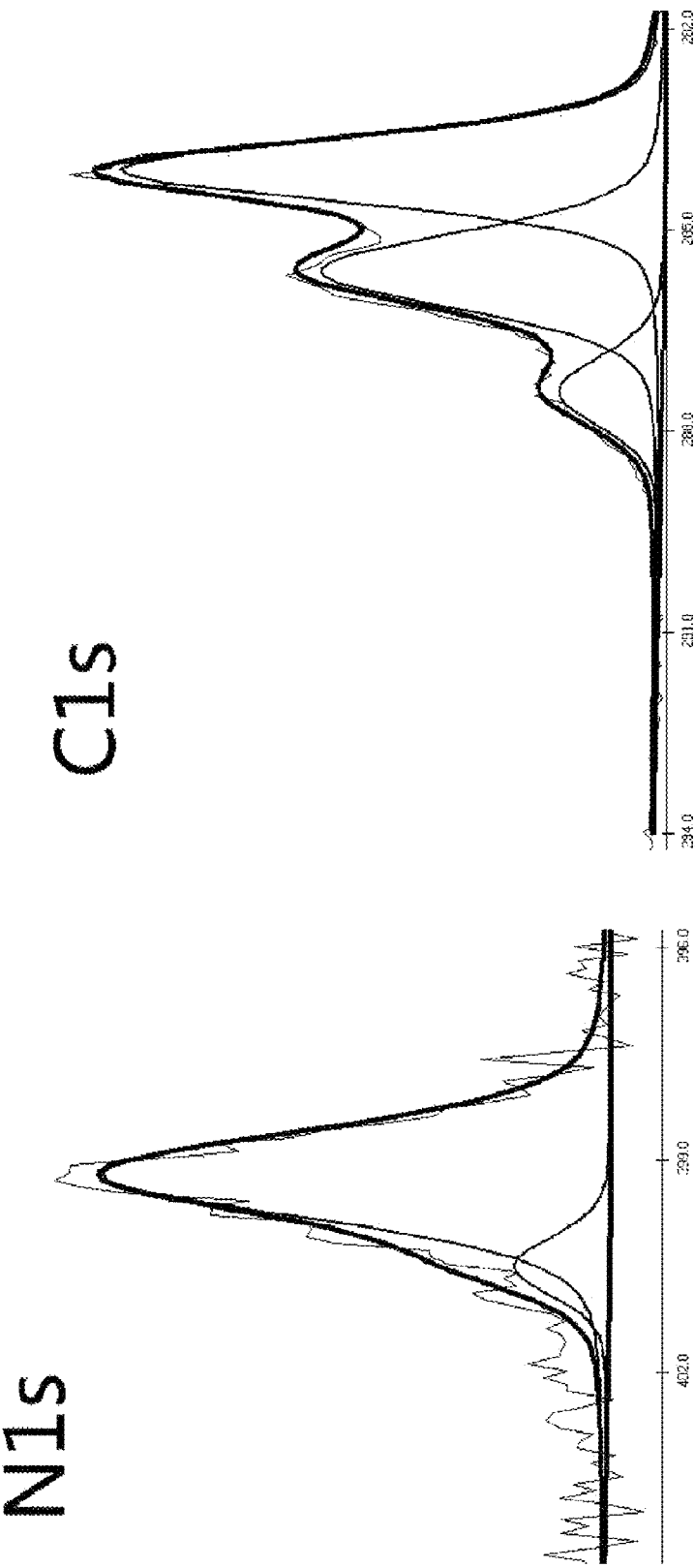
FIG. 9A shows the N 1s and C 1s peaks from x-ray photoelectron spectroscopy of pristine chitosan powder.
Figure 9D:
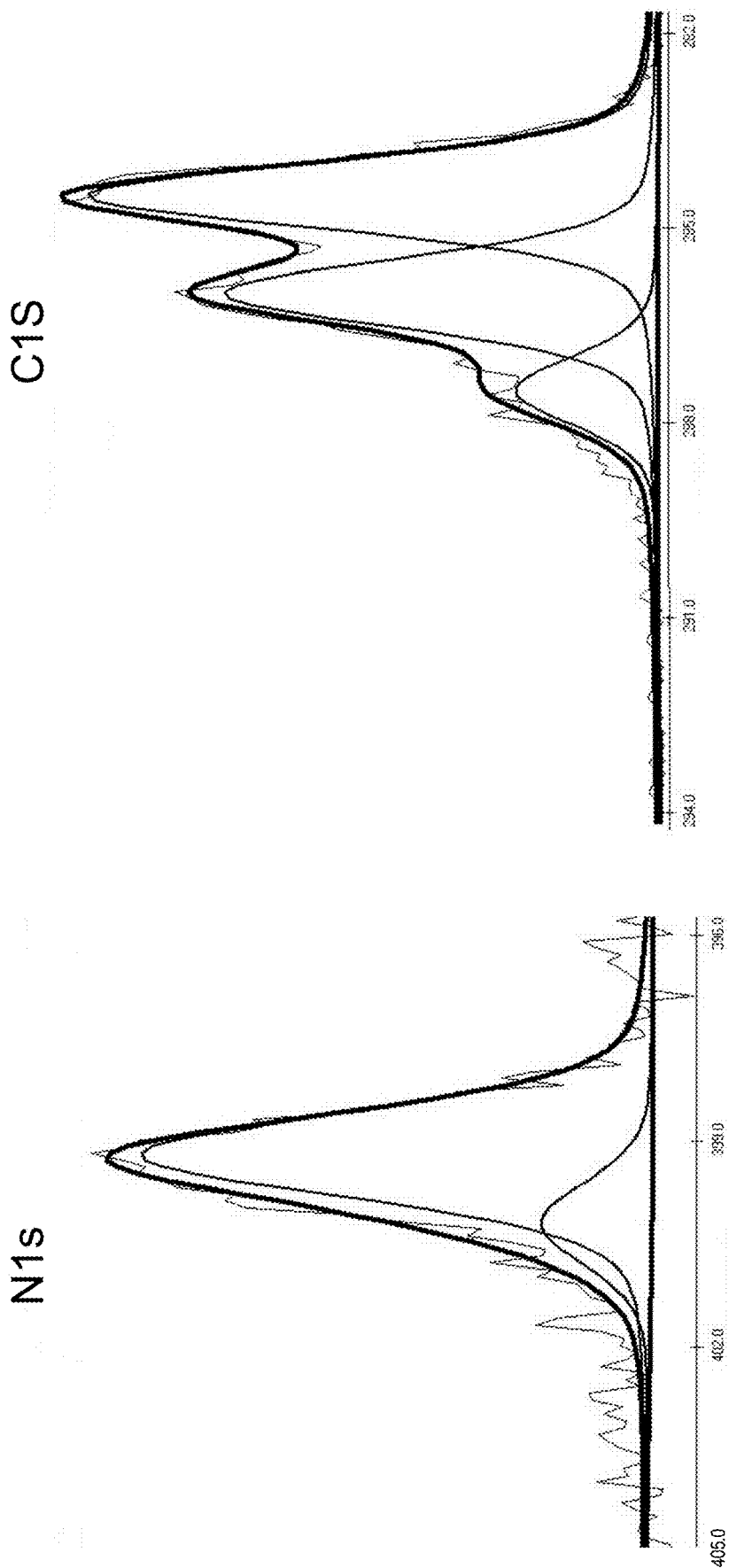
FIG. 9D shows the N 1s and C 1s peaks from x-ray photoelectron spectroscopy of deacylated electrospun chitosan nanofibers.

Example 3: N and C Spectra of Chitosan Nanofibers Support the FTIR Spectra Data The surface chemistry of the membranes was characterized by x-ray photoelectron spectroscopy (XPS). FIGS. 9A-9D show the N 1s and C 1s spectra of pristine chitosan powder (FIG. 9A), as-spun electrospun chitosan nanofibers (FIG. 9B), acylated electrospun chitosan nanofibers (FIG. 9C) and deacylated electrospun chitosan nanofibers (FIG. 9D). The N 1s spectrum of chitosan, acylated and deacylated electrospun chitosan nanofibers showed only two types of nitrogen: primary amine (—$NH_2$, 399.2 eV) and amide (—$NHCOCH_3$, 400.5 eV).

In contrast, the N 1s spectrum of as-spun electrospun chitosan nanofibers (FIG. 9A) showed a strong signal at 401.7 eV, which is attributed to the protonated ammonium ion (—$NH_3^+$) in TFA amine salt. The electrospun chitosan nanofibers had not been analyzed in XPS to date and this evidence agreed with the FTIR observations detailed herein.

Three peaks were present in the C 1s spectrum of chitosan: hydrocarbon at 284.6 eV, a peak at 286.2 eV assigned to both C—OH and C—O—R, and the peak at 287.9 eV assigned to both C=O of the amide and O—C—O of the anomeric carbon of chitosan's sugar residues. Compared with chitosan, two new peaks appeared in the C 1s spectrum of fluorocarbon (291.9 eV) and C=O of TFA (288.5 eV) and a new peak appeared in the C 1s spectrum of C=O of acyl groups (288.3 eV).

Figure 10A:
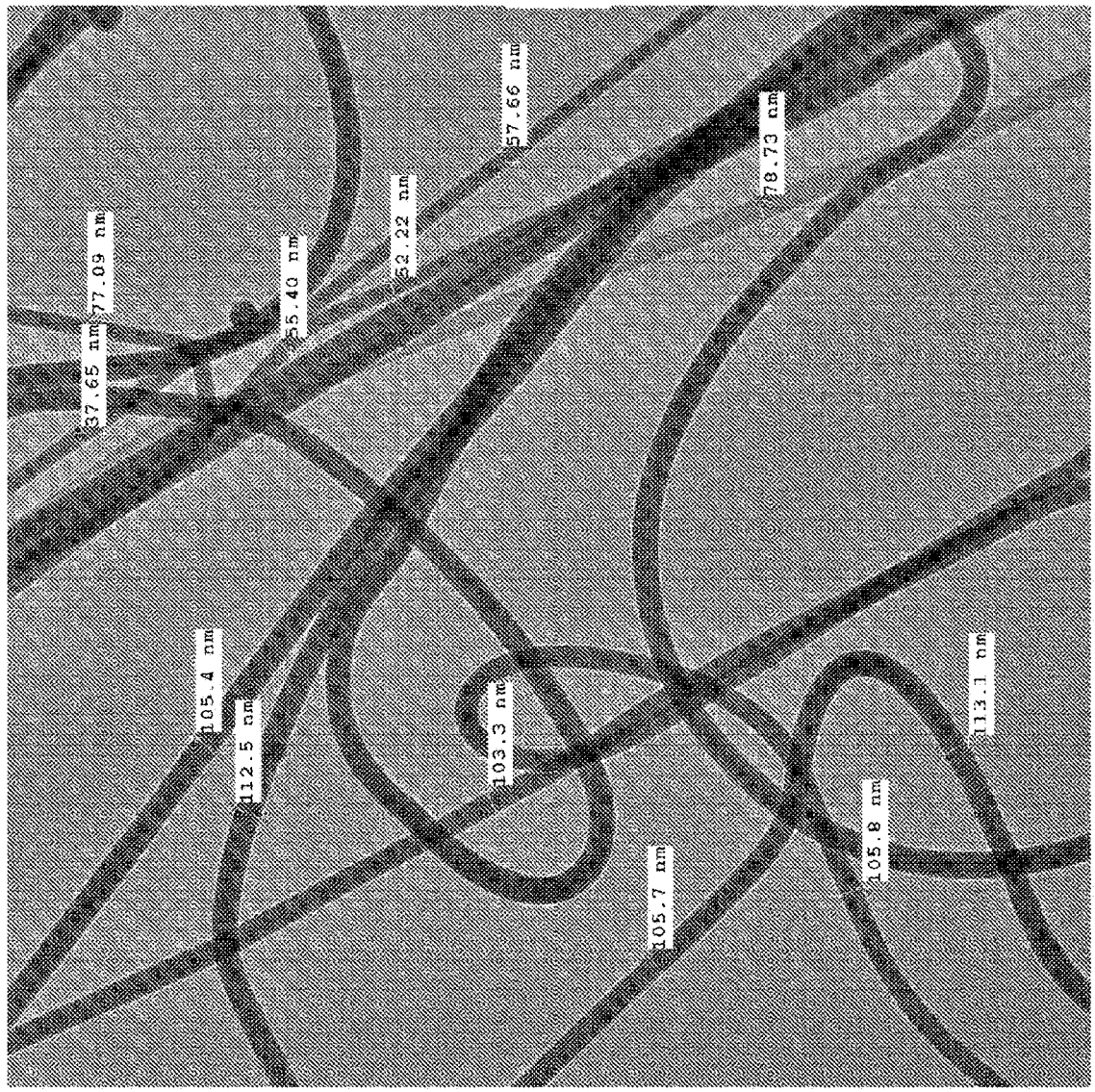
FIG. 10A is an image of a transmission electron micrograph (TEM) of as-spun electrospun chitosan nanofibers.
Figure 10B:
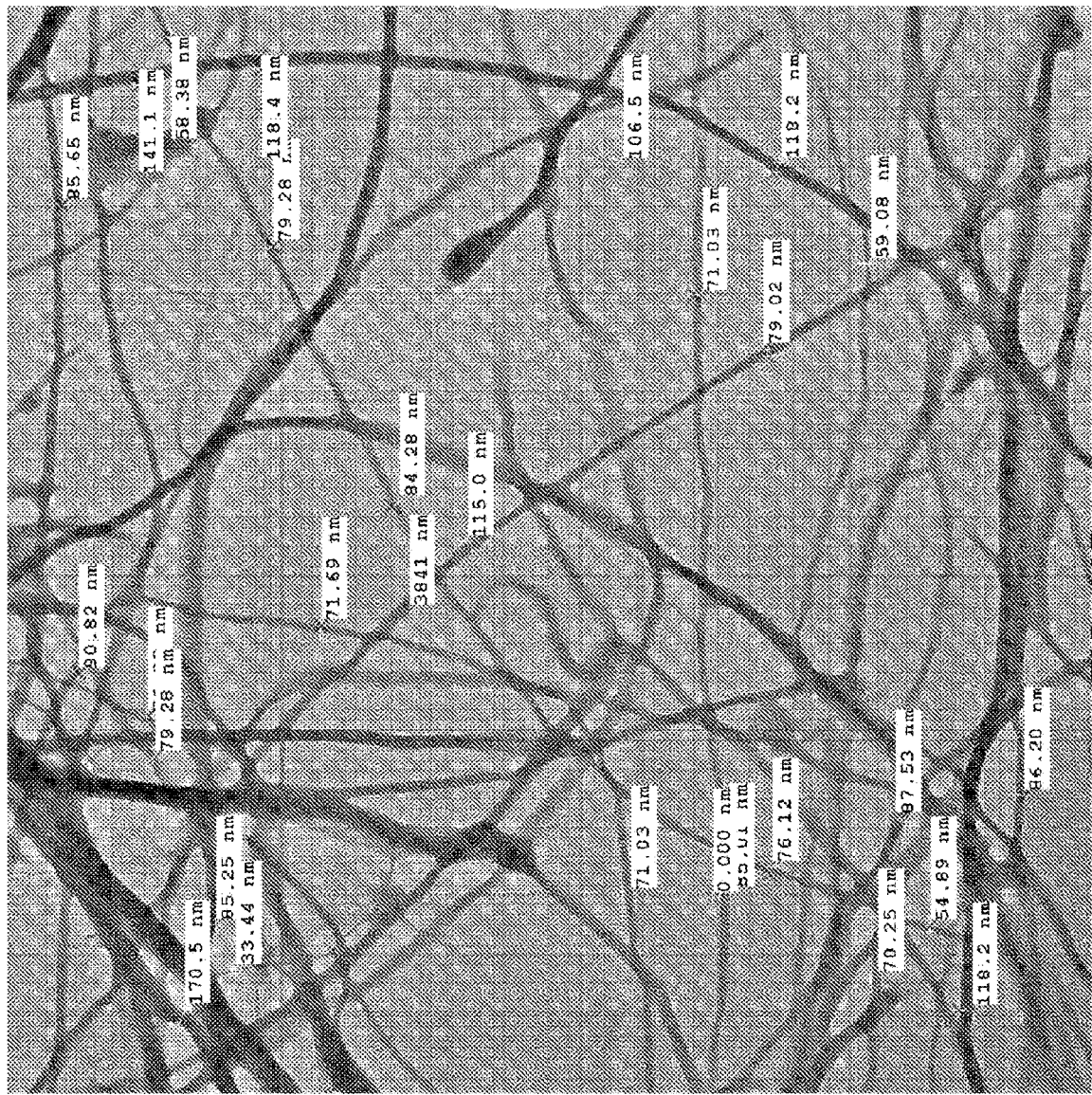
FIG. 10B is an image of a transmission electron micrograph (TEM) of acetyl-chitosan nanofibers.
Figure 10C:
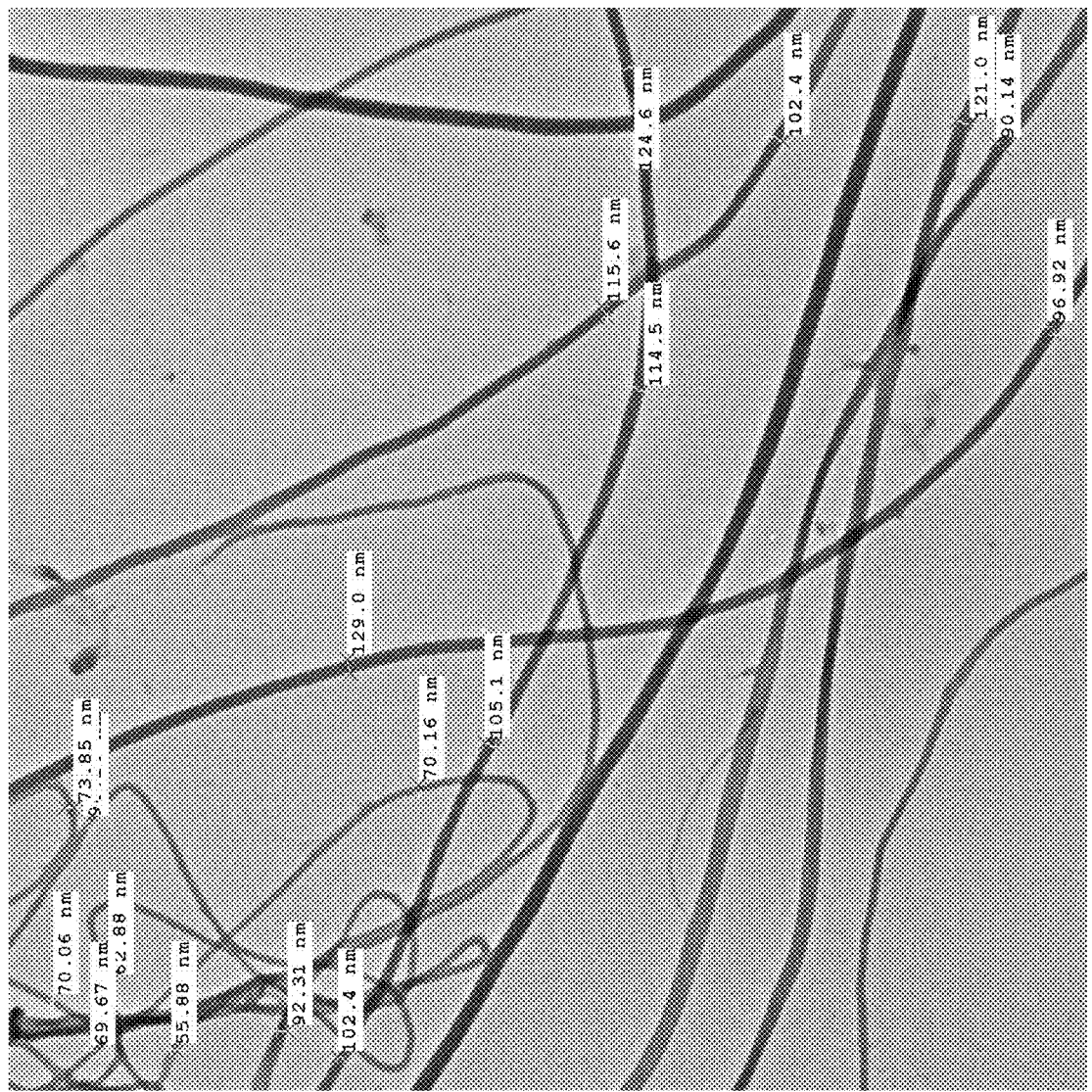
FIG. 10C is an image of a transmission electron micrograph (TEM) of butyryl-chitosan nanofibers.
Figure 10D:
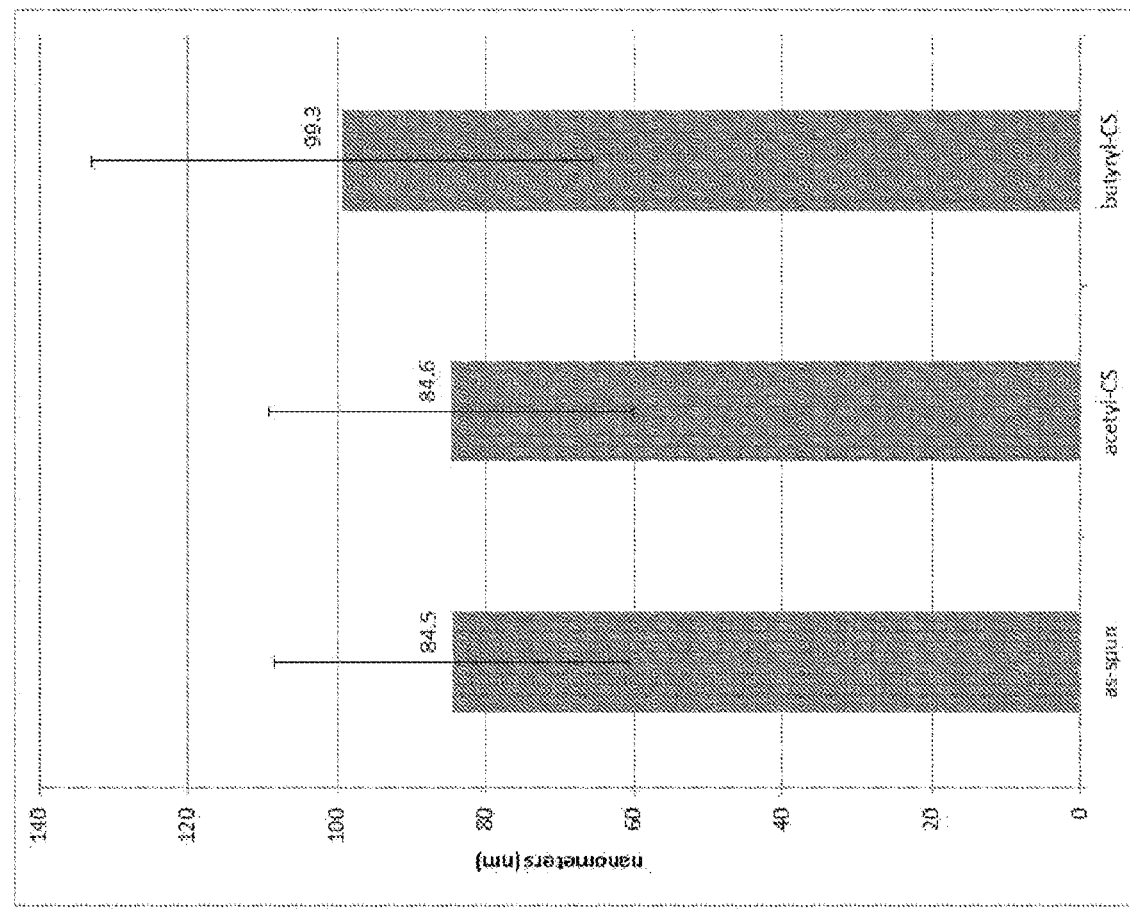
FIG. 10D is a graph showing mean diameters of the electrospun chitosan nanofibers.

Example 4: Unlike NaOH and $Na_2CO_3$ Treated Electrospun Chitosan Nanofibers, Deacylated Electrospun Chitosan Nanofibers Maintained Structural Integrity after Neutralization The structural integrity of electrospun chitosan nanofibers in water was characterized by electron microscopy. FIGS. 10A, 10B and 10C, respectively, show representative transmission electron micrograph images of as-spun electrospun chitosan nanofibers (see also scanning electron micrograph FIG. 11A), acetyl-chitosan (CS) nanofibers and butyryl-chitosan nanofibers which appear to be continuous, homogenous and beads free. The mean diameter is determined to be 150±10 nm by statistical analysis of randomly collectedly images (FIG. 10D).

Although pristine chitosan powder is insoluble in pure water, the as-spun electrospun chitosan nanofibers dissolve quickly in water. When a membrane of as-spun electrospun chitosan nanofibers was placed in a water-containing petri dish, it swelled rapidly and subsequently dissolved. The color of the membrane also changed from pale white to semi-transparent in the process. As suggested by the FTIR and XPS data and findings by other groups, electrospun chitosan nanofibers become water-soluble due to the change in the structure of the chitosan molecules after the electrospinning step. Ionic bonds ($CF_3COO^-NH_3^+$) were formed between the amino groups of the chitosan nanofibers and carboxyl groups of trifluoroacetic acid (TFA).

The TFA salt residues on the chitosan nanofibers cannot be eliminated by a simple physical process, like heating or washing in organic solvents, due to the stable nature of the ionic bonds. Alkaline neutralization is an indispensable treatment step in breaking the ionic bonds between the chitosan and the trifluoroacetate thereby releasing the TFA salt residues. However, the chitosan nanofiber salts undergo a hydrolysis process that partially releases the acid. As a weak-base, the chitosan is less competitive and the hydrolyzed acid is neutralized by the strong base. This process repeats until the acid residue is completely removed. While the alkaline treatment is effective in chemical restoration of chitosan from its salt form, it considerably damages the structure integrity of the treated chitosan materials, especially nanostructured materials.

FIG. 11B shows a SEM image of NaOH treated electrospun chitosan nanofibers. The nanofibrous feature of the electrospun chitosan nanofibers is completely lost. Only a few pores in diameter about hundreds of nanometers and ridges on the rough surfaces were seen in the SEM image.

FIG. 11C shows an image of $Na_2CO_3$ solution treated electrospun chitosan nanofibers. This sample was marginally better than NaOH treated nanofibers at retaining the nanofibrous structure. However, the nanofibrous features still deteriorated greatly, giving the appearance of the fiber melting and fusing together. The fiber diameter also increased greatly, with many irregular clumps emerging. The fiber enlargement problem was also observed in other systems using aqueous alkaline solutions, such as an aqueous ammonia treatment.

Currently, no explanation is available to account for the deterioration of the nanofibrous structure during the alkaline neutralization process. One hypothesis is that there is a lag between the neutralization step and the hydrolysis step. When the as-spun electrospun chitosan nanofibers are in contact with water in the alkaline solution, the hydrolysis of the chitosan/TFA salt proceeded more rapidly than neutralization because TFA is a strong acid. The hydrolyzed TFA then created an acidic environment around the nanofibers. Since the neutralization reaction takes time for base to completely neutralize the acidic environment, a large amount of chitosan molecules were hydrolyzed and released in the acidic environment before being neutralized. This lag results in the enlargement of the fiber thickness due to the release of chitosan molecules into the adjacent spaces of the nanofibers.

Figure 24:
FIG. 24 is an image showing a butyric-chitosan membrane with a water drop having a high (hydrophobic) contact angle.

FIGS. 11D, 11E and 11F show SEM images of electrospun chitosan nanofibers acylated for different lengths of time followed by water immersion. The membranes acylated for 1 min still show significant melt and enlargement, but are less degraded when compared with the alkaline treated groups. Membranes acylated for 10 minutes show a large portion of the fibers maintaining desirable nanofibrous features. All the acylated nanofibers in the membranes treated for 60 minutes appeared as good as the original electrospun chitosan nanofibers. This finding is in agreement with the hypothesis that electrospun chitosan nanofibers can be rendered water insoluble after surface acylation. The contact angle increased to greater than 90° for the 60 min acylated electrospun chitosan nanofiber membranes (FIG. 24), which is considered hydrophobic.

When the water insoluble acylated electrospun chitosan nanofibers were washed in water, the TFA residues were released from the fibers and chitosan molecules were kept intact due to the hydrophobic character of the acylated electrospun chitosan nanofibers. The clearance of the TFA salt residues was evident in the FTIR, EDS and XPS evidences. FIG. 11G shows a SEM image of deacylated electrospun chitosan nanofibers after water immersion. The fibers in the image appeared to be no different than the acylated electrospun chitosan nanofibers. The removal of the acyl groups did not appear to cause damage to the nanofibers, possibly because the presence of acyl groups in the nanofibers is low, which took up only 3.48% of the total mass.

Figure 12:
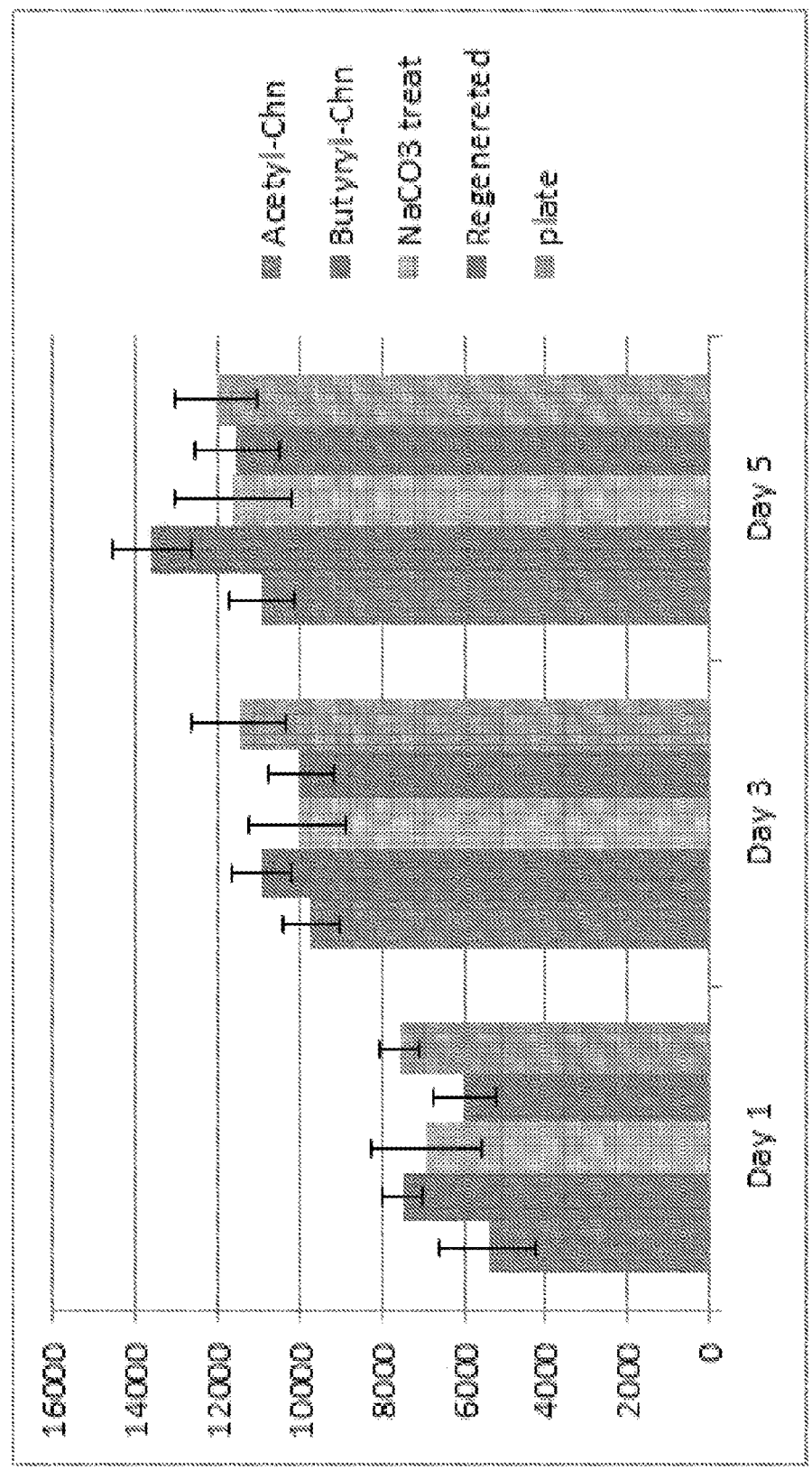
FIG. 12 is a graph showing osteoblast cell growth at day 1, day 3 and day 5 on acetyl-chitosan, butyryl-chitosan nanofiber membranes, $Na_2CO_3$ treated chitosan membrane, regeneration (deacylated) chitosan nanofiber membrane, and a plate control.

Example 5: Osteoblast Cells Proliferation on Electrospun Chitosan Nanofiber Membranes To further explore the potential of the electrospun chitosan nanofibers in tissue engineering applications, osteoblast proliferation on the membrane of electrospun chitosan nanofibers was examined by Celltiter Glo Assay Kit. As shown in FIG. 12, there was no statistical difference in the day 5 growth of cells on chitosan compared with acylated (acetyl- and butyryl-) and deacylated electrospun chitosan nanofiber membranes, suggesting the electrospun chitosan nanofibers membranes were non-toxic.

The cell morphology on the materials was visualized with fluorescence microscope after osteoblast cells were cultured on the top of the materials for 5 days. The cells grown on the electrospun chitosan nanofibers showed characteristic shapes associated with osteoblast cells, such as elongated/stretched shape, suggesting the material did not interfere with the growth of the osteoblasts.

These surprising results suggested that the problems with dissolution and swelling observed with electrospun chitosan fiber membranes can be solved by the reversible acylation method. The mechanisms behind the process were elucidated based on the data obtained from the FTIR, XPS and SEM analyses. The acylation method could potentially be used to synthesize other modified chitoan nanofibrous material containing acyl moieties as well.

Figure 13:
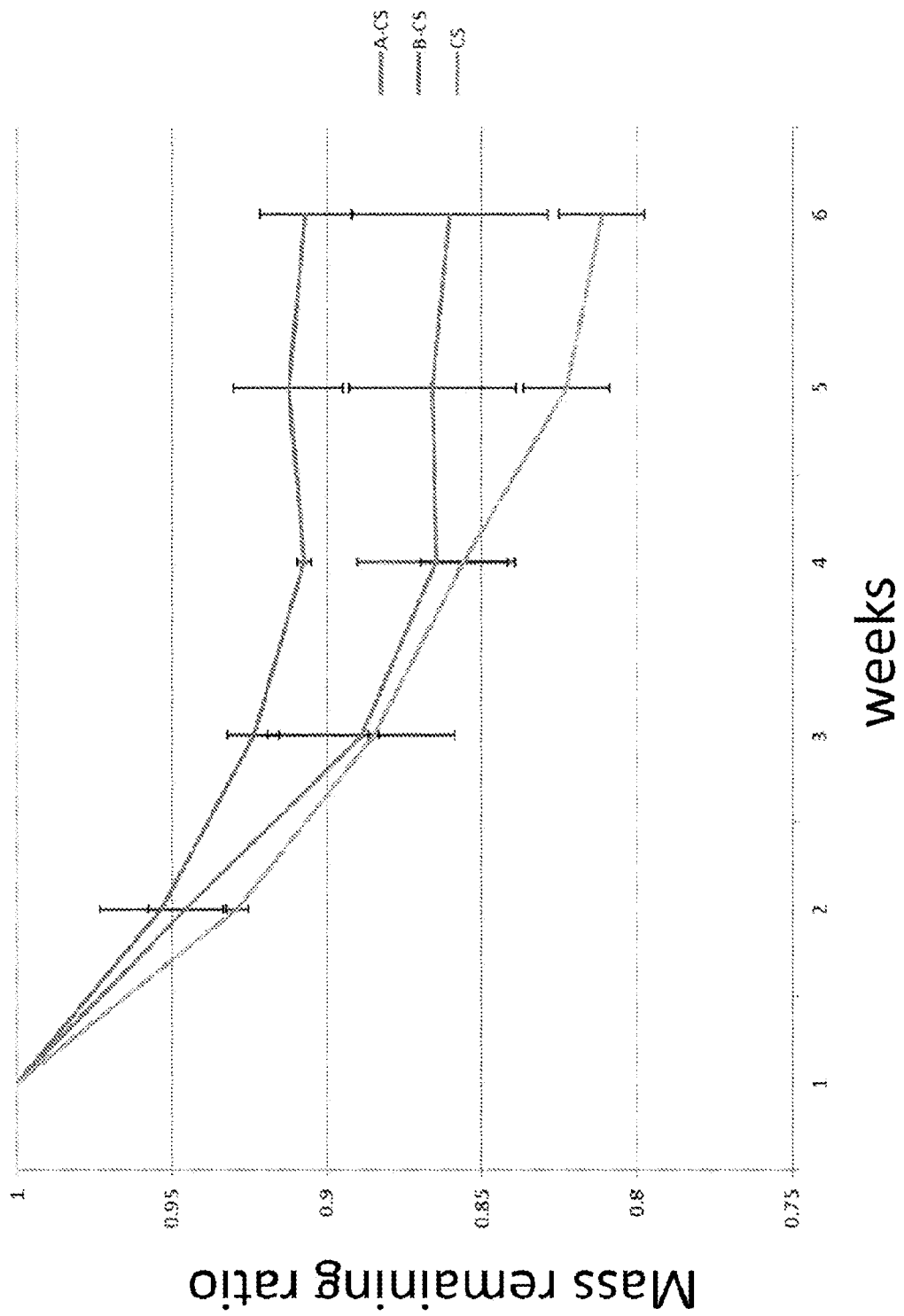
FIG. 13 is a graph showing the in vitro degradation of the acetyl-chitosan, butyryl-chitosan nanofiber membrane and $Na_2CO_3$ treated chitosan membrane.

Example 6: Slower Degradation and Increased Suture Strength of the Acylated Chitosan as Compared to the as-Spun Chitosan FIG. 13 shows the in vitro degradation of the acetyl-chitosan, butyryl-chitosan and $Na_2CO_3$ treated chitosan film when exposed to 100 μg/ml of lysosome in phosphate buffered saline (PBS). Both acetyl-chitosan and butyryl-chitosan resisted degradation and maintained mass longer than $Na_2CO_3$ treated chitosan film.

Figure 14:
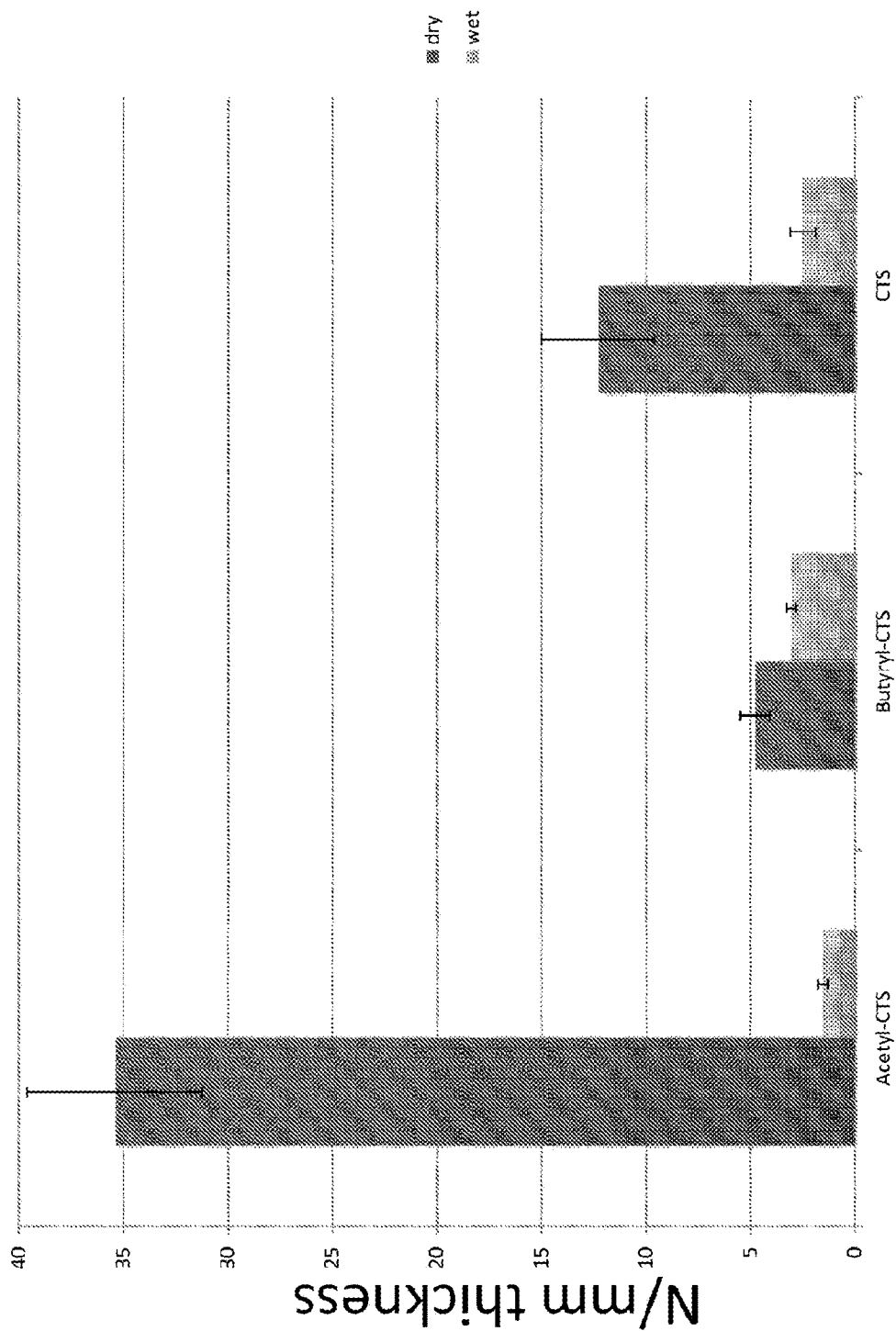
FIG. 14 is a graph showing the ultimate suture pullout load for acetyl-chitosan, butyryl-chitosan and $Na_2CO_3$ treated chitosan membrane when wet or dry.

FIG. 14 shows the ultimate suture pullout load for acetyl-chitosan, butyryl-chitosan and regenerated (deacylated) chitosan when wet or dry.

Figure 15:
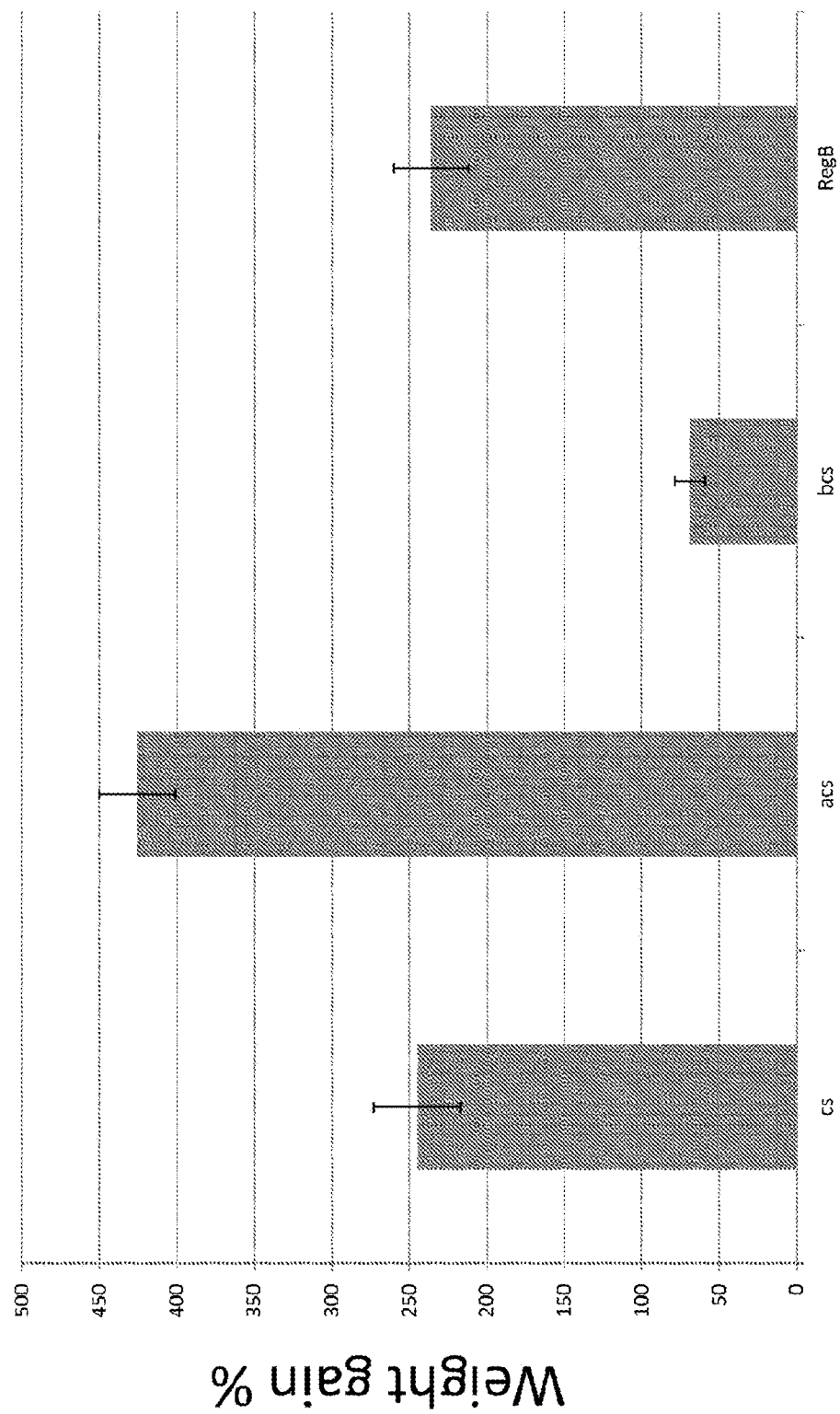
FIG. 15 is a graph showing weight gain or swelling after exposure to a hydrophilic solvent of $Na_2CO_3$ treated chitosan membrane, acetyl-chitosan, butyryl-chitosan and regenerated (deacylated) chitosan.

FIG. 15 shows the weight gain or swelling after exposure to a hydrophilic solvent of $Na_2CO_3$ treated chitosan film, acetyl-chitosan, butyryl-chitosan and regenerated (deacylated) chitosan. The stabilized electrospun chitosan fiber membranes show good cytocompatibility, structural stability, suggesting future exploration in tissue engineering applications.

Example 7: Acylated CSEF Exhibited Nano-Fibrous Morphology after PBS Immersion, but Untreated CSEF Membranes Lost Fibrous Structure There has been a growing interest in the fabrication of nanofibers derived from natural polymers due to their ability to mimic the structure and function of extracellular matrix. Electrospinning is a simple technique to obtain nano-micro fibers with customized fiber topology and composition. The chitosan electrospun nanofibers (CSEF) have recently been extensively studied due to the favorable properties of chitosan such as controllable biodegradation, good biocompatibility, high mechanical strength, lack of toxicity, promotion of cell proliferation; porosity (e.g., nanoscale); and large surface area. Currently, chitosan can be electrospun from a solution of chitosan dissolved in either trifluoroacetic acid (TFA) or acetic acid (HAc). However, processes to remove residual acid and acid salts from the electrospun material generally result in a swelling of fibers and deterioration of the nano-fibrous structure. Crosslinking in combination with neutralization methods also have not been effective at preventing loss of nano-fibrous structure. Surface acylation of cellulose nanowhiskers has been reported to increase hydrophobicity but has not been attempted in chitosan nanofibers. Surface acylation renders CSEF insoluble in water and enables the removal of residual acid from the electrospinning process while maintaining nano-fibrous structure and without causing cytotoxicity. This study aimed to evaluate acylation of CSEF and to characterize the aqueous stability and cytocompatibility of the acylated CSEF.

Figure 16A:
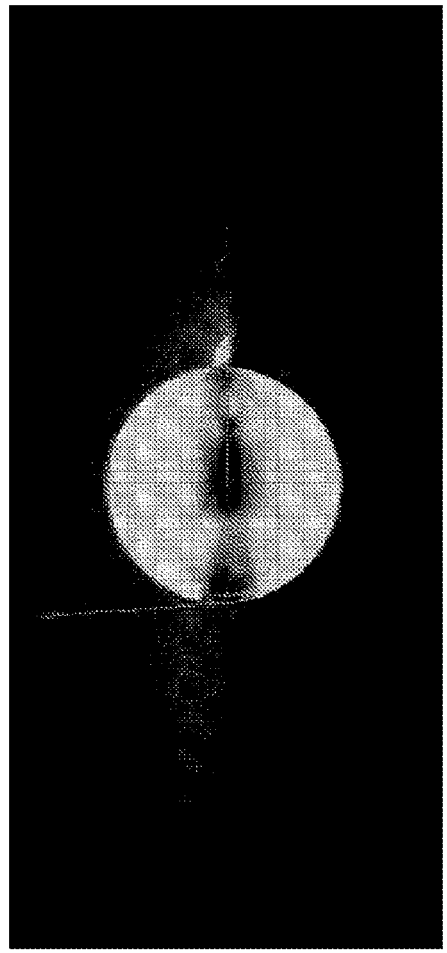
FIG. 16A is an image of the hydrophobicity of a butyryl-chitosan nanofiber membrane as measured by water contact angles.
Figure 16B:
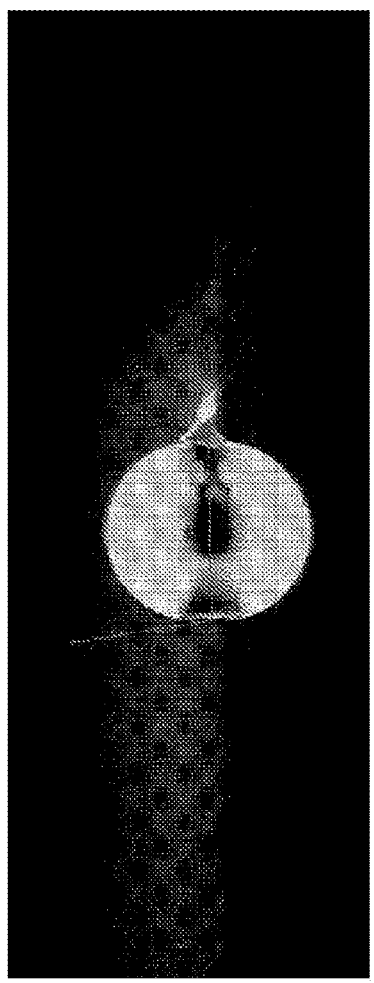
FIG. 16B is an image of the hydrophobicity of the butyryl-chitosan nanofiber membrane as measured by water contact angles.

FIGS. 16A and 16B are images demonstrating the hydrophobicity (about 93.7°-100.3°) of the butyryl-chitosan nanofibers as measured by water contact angles. The contact angle was measured through water, where the liquid/vapor interface meets the surface of the nanofibers. The larger the angle formed, the more hydrophobic the material is. Angles greater than 90° are deemed hydrophobic.

Untreated CSEF swelled and dissolved in PBS. When CSEF membranes were acetylated without pyridine catalyst, only membranes at the 90° C. were stable in PBS, whereas in reactions with pyridine catalyst, even membranes acetylated at room temperature (20° C.) were stable in PBS. SEM evaluation (FIGS. 17A and 17B) showed that acylated CSEF exhibited nano-fibrous morphology after PBS immersion, but untreated CSEF membranes lost fibrous structure. FTIR spectrum of the acylated chitosan nanofibers showed a strong carbonyl absorption peak at 1751 $cm^{-1}$, indicating successful acylation reactions.

Figure 18:
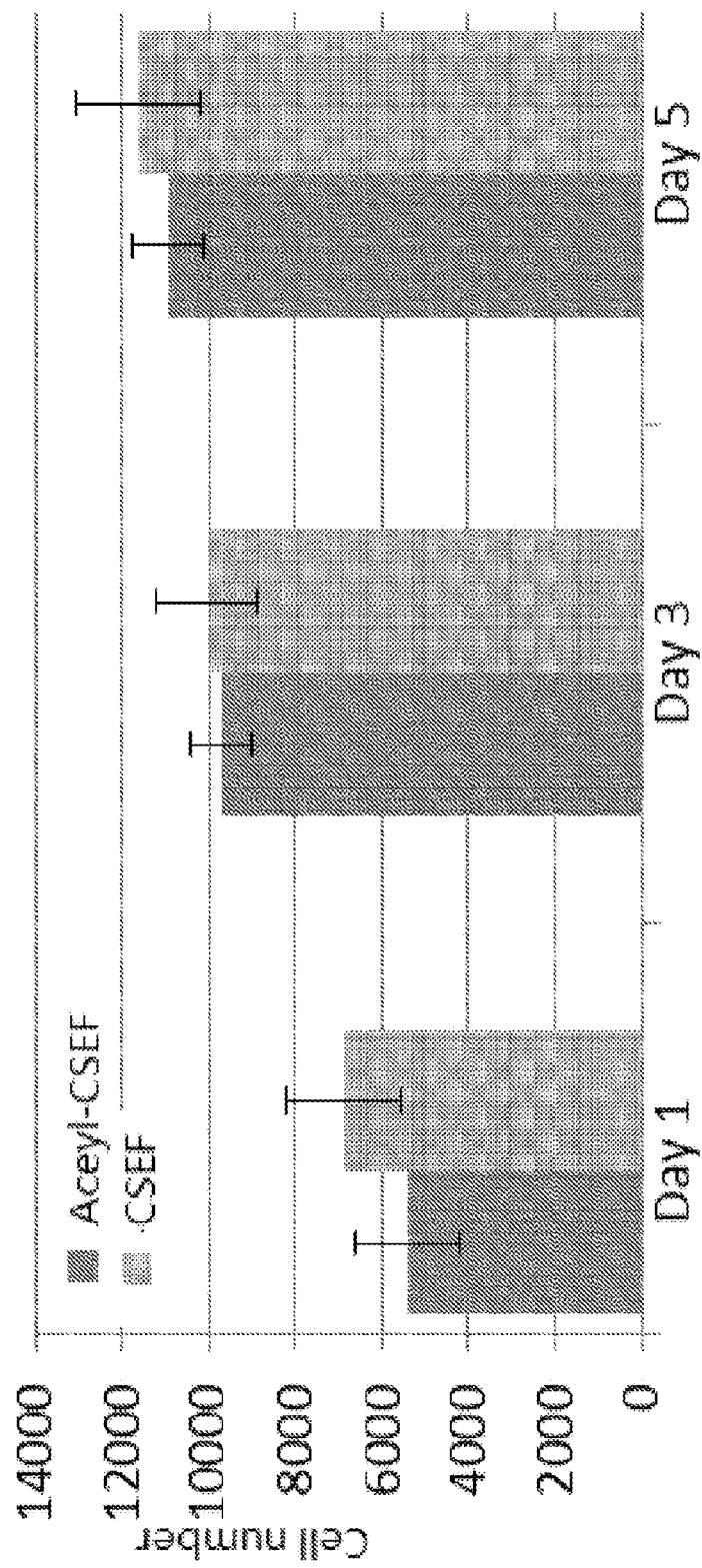
FIG. 18 is a graph showing osteoblasts proliferated by 82% on acylated CSEF over the 5 day culture and there was no difference in growth between the acylated CSEF or cast chitosan film controls.

Example 8: Osteoblasts were Viable and had Low Proportion of Non-Viable Cells when Cultured on Acylated CSEF Over 5 Days Osteoblast cells on acylated CSEF were viable and had low proportion of non-viable cells, as shown by live/dead staining (FIG. 17C). FIG. 18 showed that osteoblasts proliferated by 82% on acylated CSEF over the 5 day culture and there was no difference in growth between the acylated CSEF or cast chitosan film controls.

Chitosan is an extensively studied natural polymer that has been used in tissue engineering and drug delivery applications. Electrospinning provides a new platform to fabricate fibrous biomaterials in a bottom-up approach. CSEF suffers from aqueous instability. Crosslinking by glutaraldehyde has been reported, but its toxicity raises a serious concern. $Na_2CO_3$ and $NH_3OH$ neutralization have been reported, but the fibers deform greatly after neutralization. This study presents a novel method without introducing harmful chemicals into the material to remove bound salts and retain desirable nanofibrous structure of CSEF. As the acyl moiety is chemically inactive and not likely to cause toxicity, extensive cellular proliferation was present in SAOS-2 cells cultured on acylated chitosan nanofibers.

This study identified surface acylation as an effective strategy to stabilize CSEF. The acylated CSEF were cytocompatible suggesting further investigation for tissue engineering.

Example 9: In Vivo Implantation of Nanofibrous Membranes Showed Bone Regeneration in Rat Calvarial Defect An animal study was conducted to evaluate the biocompatibility, biodegradation and soft tissue excluding properties of a butyric anhydride modified electrospun chitosan nanofibrous membrane. The study used a critical size (8-mm) rat calvarial bone defect model. In the rat cranium, the established critical size defect was a circular defect of 8 mm in diameter. Repeated and current studies continued to show that defects of this size in rats failed to heal and fill primarily with fibrous tissue and only minimal bone growth at the edges over a 3-month period. The advantages of this model are; a) the calvarial bone is a plate which is large enough to allow creation of a circular defect that enables convenient radiographic and histological analysis, b) the calvarial bone has a large enough size for easy surgical procedures and specimen handling, c) no fixation is required, and d] the model is well studied and reproducible which enables comparison of variety of implant materials.

The animals were x-rayed at 2, 3, 9 and 12 weeks post implantation. One animal was euthanized by $CO_2$ inhalation at 3-weeks post-implantation and the other animal at 12-weeks post-implantation. The craniotomy sites with implants were excised and fixed in formalin for histological evaluation.

Figure 19B:
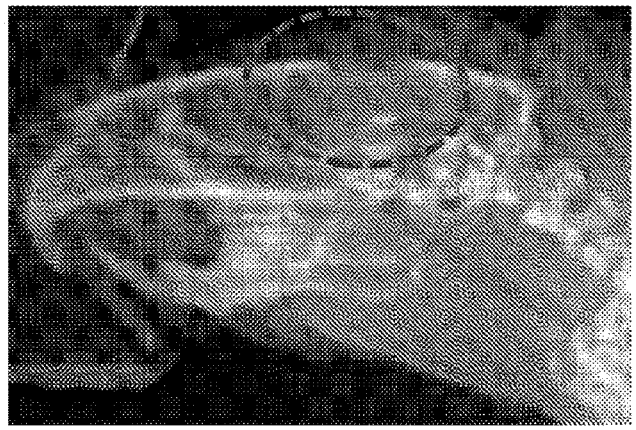
FIG. 19B is an x-ray image (lateral view) of an 8 mm defect covered with membrane 2 weeks post surgery; radiolucent area indicates little to no bone formation.
Figure 19A:
FIG. 19A is an x-ray image (lateral view) of an 8 mm defect covered with membrane 2 weeks post surgery; radiolucent area indicates little to no bone formation.
Figure 19C:
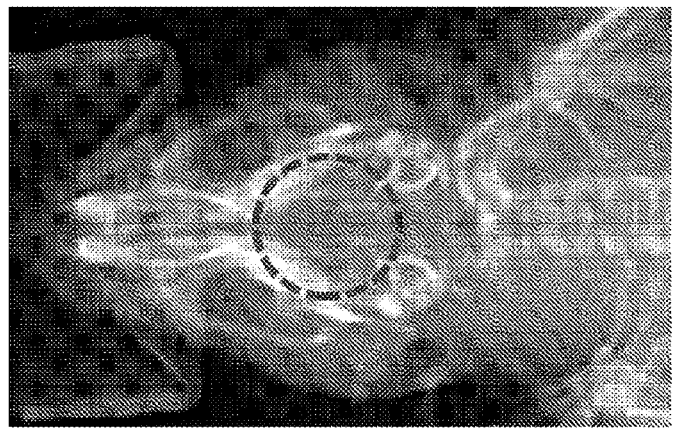
FIG. 19C is an x-ray image of the dorsal-ventral view of the 8 mm defect covered with membrane 2 weeks post surgery; radiolucent area indicates little to no bone formation. The defect is difficult to distinguish due to the thin calvarial bones.
Figure 20B:
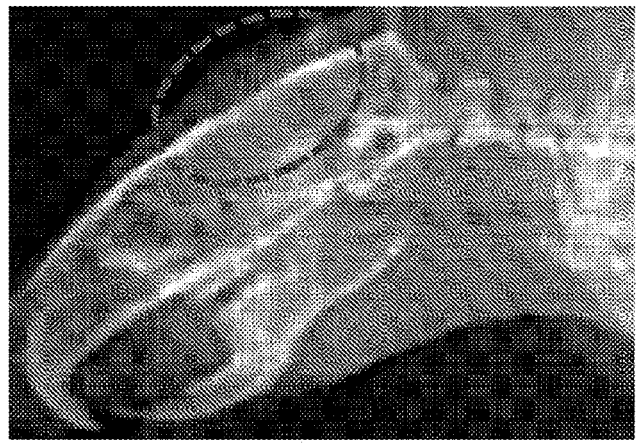
FIG. 20B is an x-ray image of 8 mm defect covered with membrane 3 weeks post surgery; radio-opaque area indicates early bone formation.
Figure 20A:
FIG. 20A is an x-ray image of 8 mm defect covered with membrane 3 weeks post surgery; radio-opaque area indicates early bone formation. Some early tissue healing is indicated by the increase in radio-opaqueness in the defect area.
Figure 21:
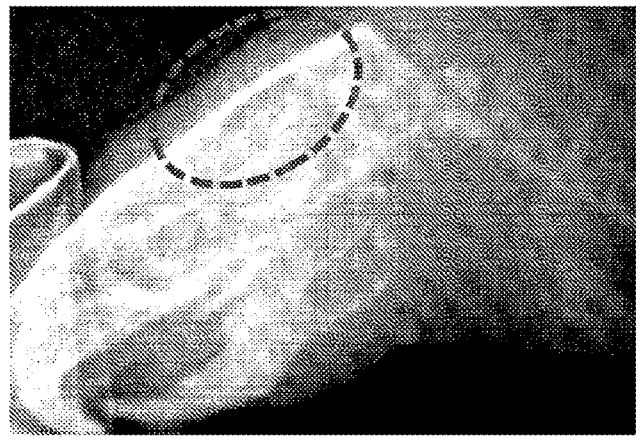
FIG. 21 is an x-ray image of the defect at 9 weeks post surgery; radio-opaque area indicates bone formation. Continued healing is indicated by the continual increase in radio-opaqueness in the defect area.
Figure 22:
FIG. 22 is an x-ray image of the defect at 12 weeks post surgery; radio-opaque area indicates bone formation. Continued healing is indicated by the continual increase in radio-opaqueness in the defect area.

X-rays were taken in the lateral view since this enabled easy viewing of the defect in the thin rat calvarial bone. The membrane was transparent in the x-ray. At two weeks, the calvarial defect was still seen as evidenced by the radiolucent area, indicating little to no bone formation (FIGS. 19A-19C). At three weeks the defect was still apparent but evidence of early fibrous/woven bone was observed as evidenced by increase in radio-opacity in the defect (FIGS. 20A and 20B). At 9 (FIG. 21) and 12 weeks, the radio-opacity increased over the defect indicating development of bone over and along the barrier membrane. Close inspection of the 12 week radiograph revealed that bone was forming along the membrane but not filling the defect (FIG. 22). This was expected since the defect site was not filled with bone graft material. At 9 weeks, the x-ray was taken at different x-ray energy settings so direct comparison between the 2, 3, and 12 week images was not possible.

Figure 23:
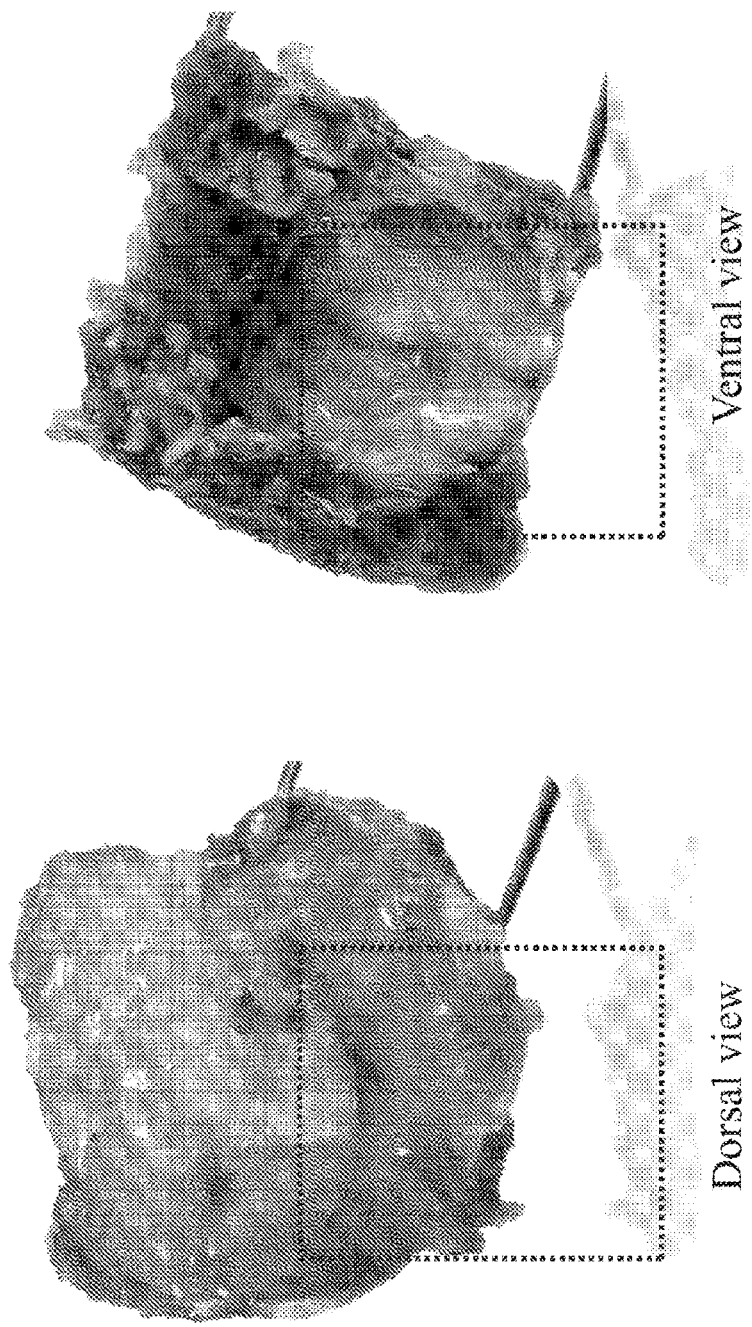
FIG. 23 shows images of tissue sample at 12 weeks (dorsal and ventral views) with no gross inflammation and normal tissue appearance.

Gross Histology of the implant retrieved from animal at the 12 week time point showed no gross inflammation and a normal tissue appearance (FIG. 23). Based on the x-ray images and gross histology, the membranes exhibited biocompatibility and supported bone formation.

Figure 25:
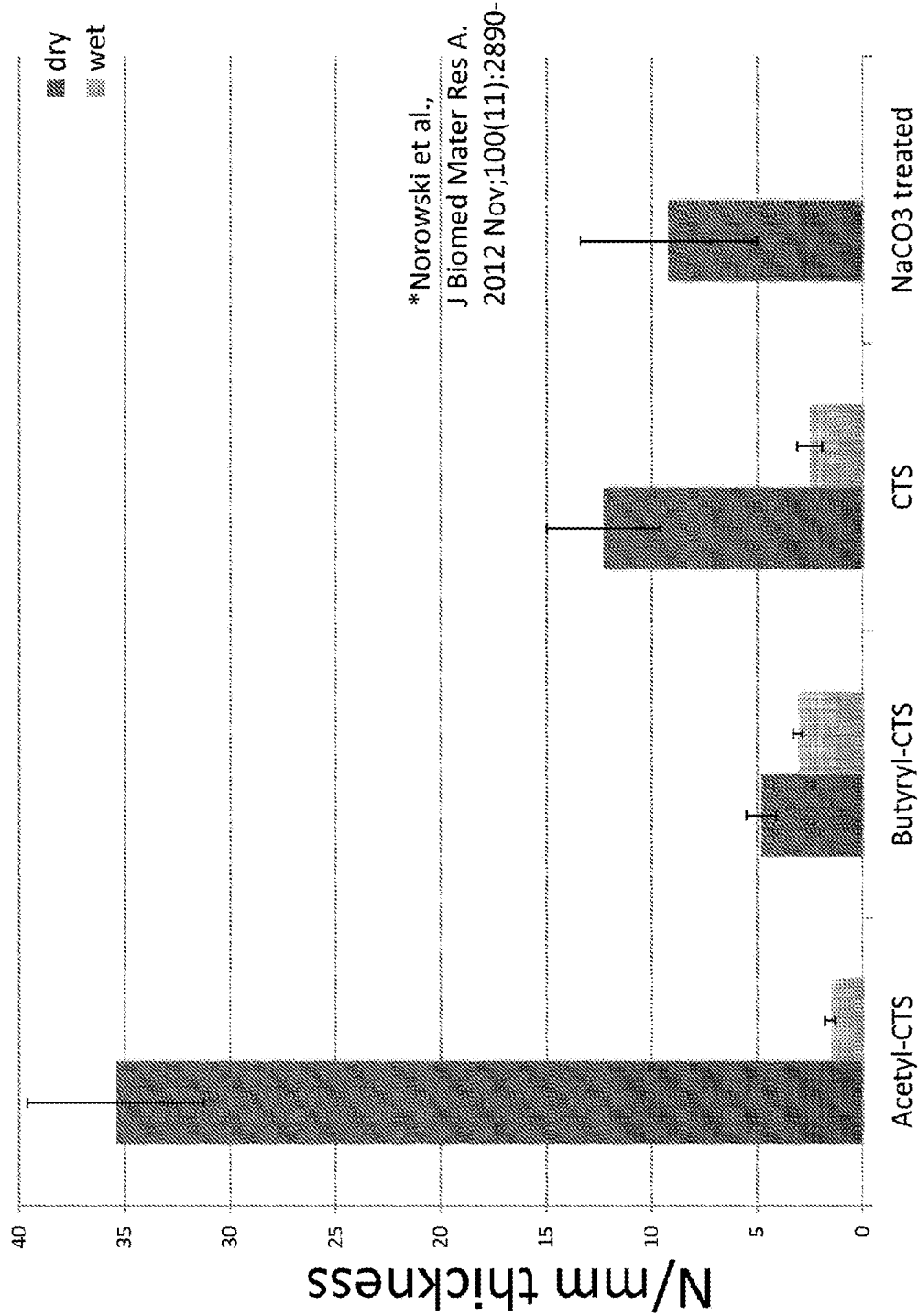
FIG. 25 is graph showing suture pullout strength comparisons between the different chitosan membranes.

Example 10: Characterization of the Chitosan Nanofibers Shows Distinct Differences Between Chitosan Powder, $Na_2CO_3$ Treated Nanofibers and Acetyl-Chitosan Nanofibers FIG. 25 shows the ultimate suture pullout load for acetyl-chitosan, butyryl-chitosan, chitosan powder and $Na_2CO_3$ chitosan when wet or dry.

Figure 26:
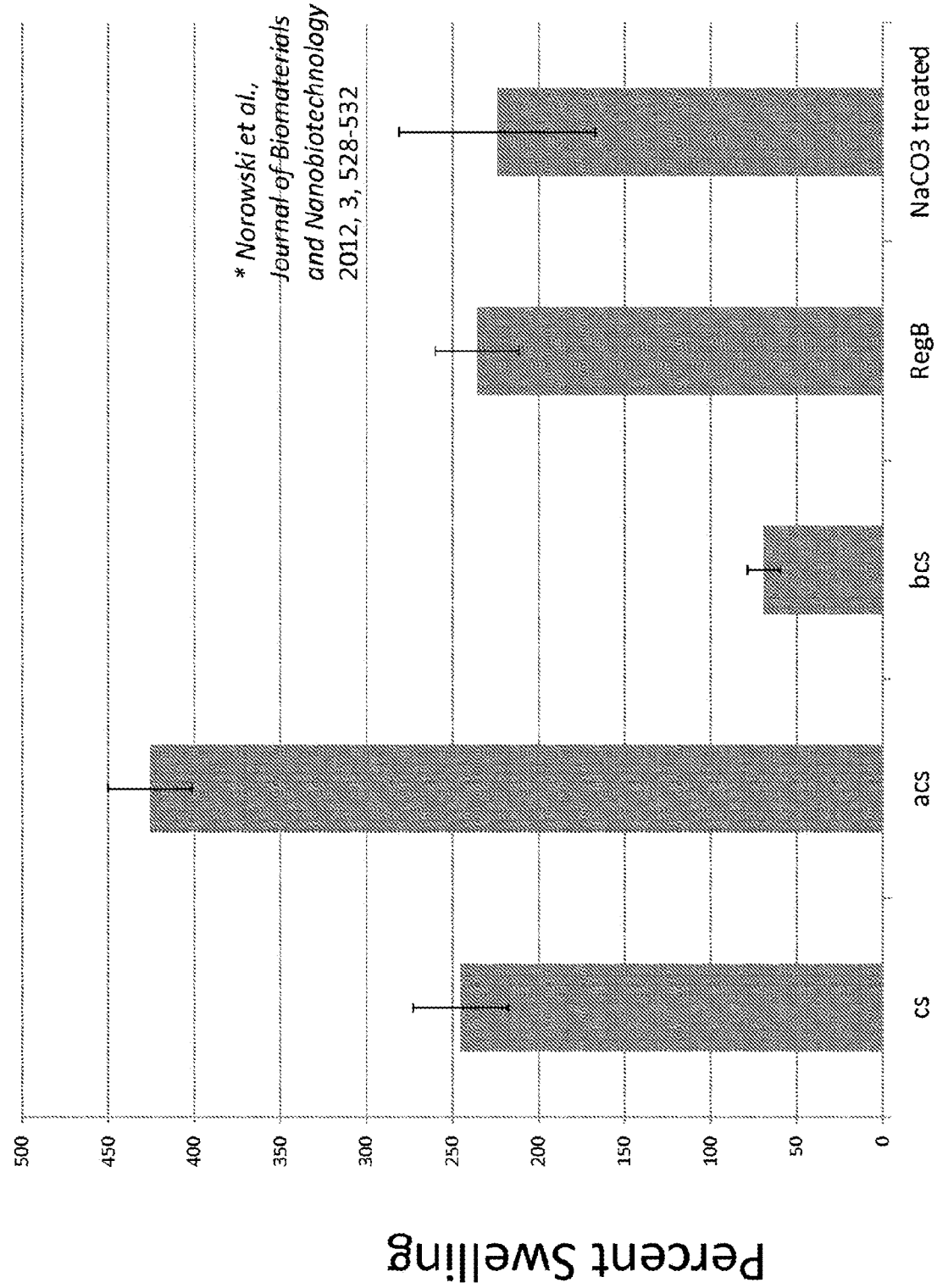
FIG. 26 is a graph showing a comparison of the percentage of swelling between the different chitosan membranes.

FIG. 26 shows the weight gain or swelling after exposure to a hydrophilic solvent of chitosan power, acetyl-chitosan, butyryl-chitosan, regenerated (deacylated) chitosan and $Na_2CO_3$ treated chitosan. The butyryl-chitosan and the regenerated electrospun chitosan nanofibers show good cytocompatibility, structural stability, suggesting future exploration in tissue engineering applications.

Figure 27:
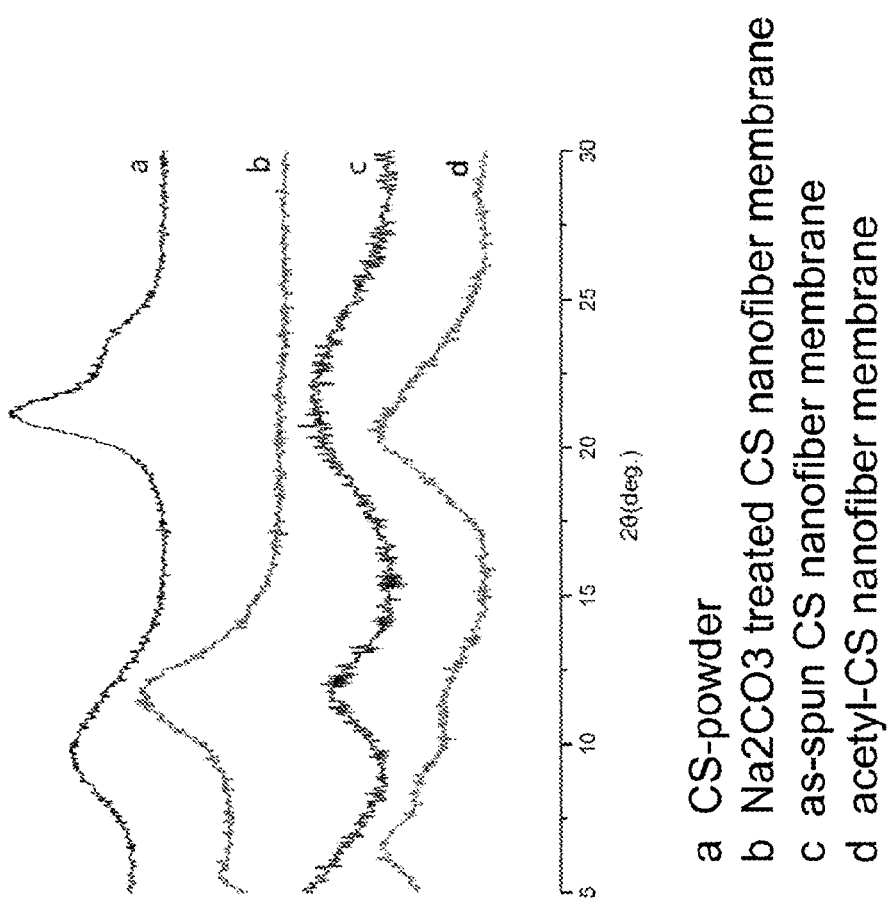
FIG. 27 is an image showing x-ray diffraction (XRD) of the different chitosan membranes.

FIG. 27 shows x-ray diffraction of chitosan power, $Na_2CO_3$ treated chitosan fibers, as-spun chitosan and acetyl-chitosan.

Example 11: Chemical Modification of Chitosan Electrospun Membranes for Guided Tissue Regeneration Guided tissue regeneration (GTR) membranes are employed in dental/maxillofacial treatments combined with bone graft for regeneration of periodontal tissues lost to disease or injury. The membranes act as barriers to soft tissues and prevent their migration into the bone graft site. Chitosan membranes have shown promise in GTR applications due to their biocompatibility and degradability. Electrospinning chitosan into nanofibrous membranes further adds biomimic extracellular matrix structure, and porosity to promote fluid/nutrient exchange between soft and hard tissue compartments while being cell occlusive. Using trifluoroacetic acid (TFA), electrospun chitosan membranes exhibited in vitro and in vivo compatibility and degradability. However, the nanofibrous structure was not optimal due to swelling of the fibers during removal of residual TFA solvent salts post spinning.

Figure 28:
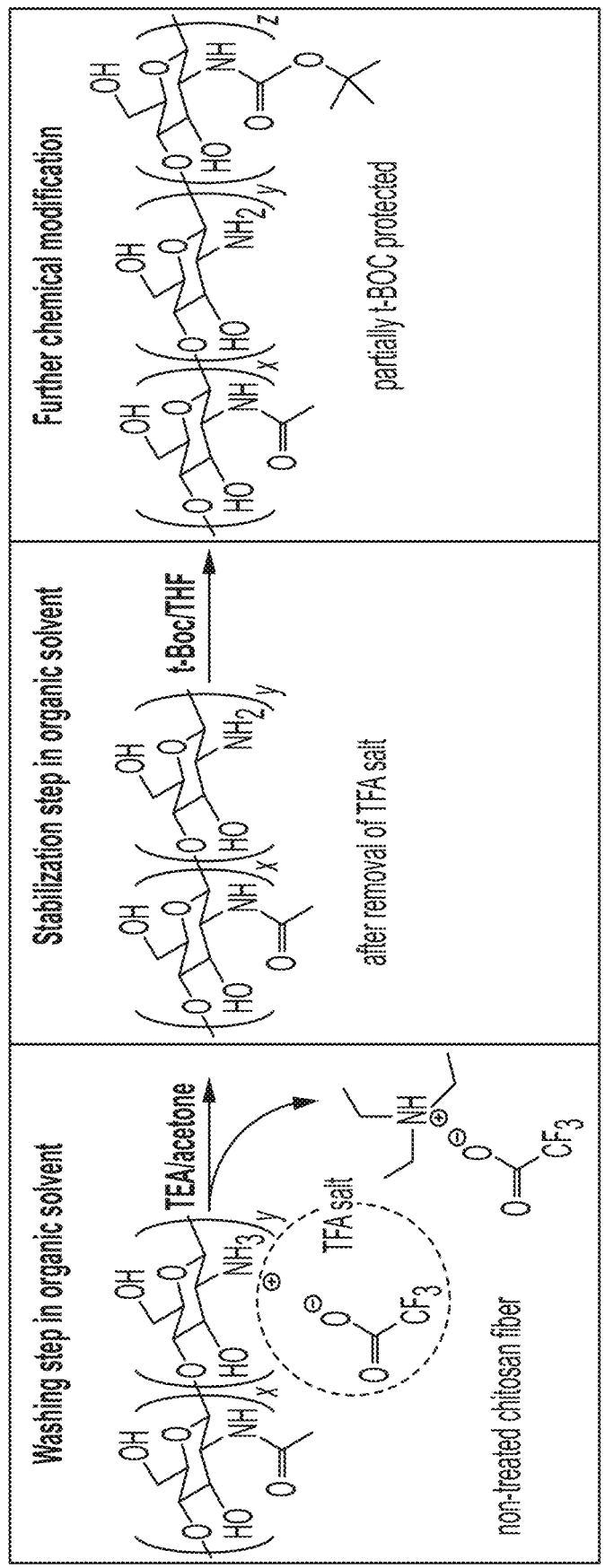
FIG. 28 is a series of chemical illustrations showing the stabilization process and chemical structure evolution of the chitosan nanofibers.

FIG. 28 shows an overview of the stabilization approach. A series of cartoons shows the chemical structure evolution of the electrospun chitosan nanofibers. The first structure shows the chemical structure of the electrospun chitosan nanofibers immediately after electrospinning (as spun). The second structure shows the removal of the immobilized salt or trifluoroacetate salt residues from the as-spun chitosan nanofibers with organic solvent. Triethylamine in acetone acted as stronger nucleophile than the chitosan amino group. The third structure shows the protection of electrospun chitosan nanofibers with an amino protecting reagent, di-t-butyl dicarbonate in tetrahydrofuran. FIG. 29 shows the TEA/t-BoC neutralization method in comparison with the $Na_2CO_3$ neutralization method and the resulting membranes.

Figure 30:
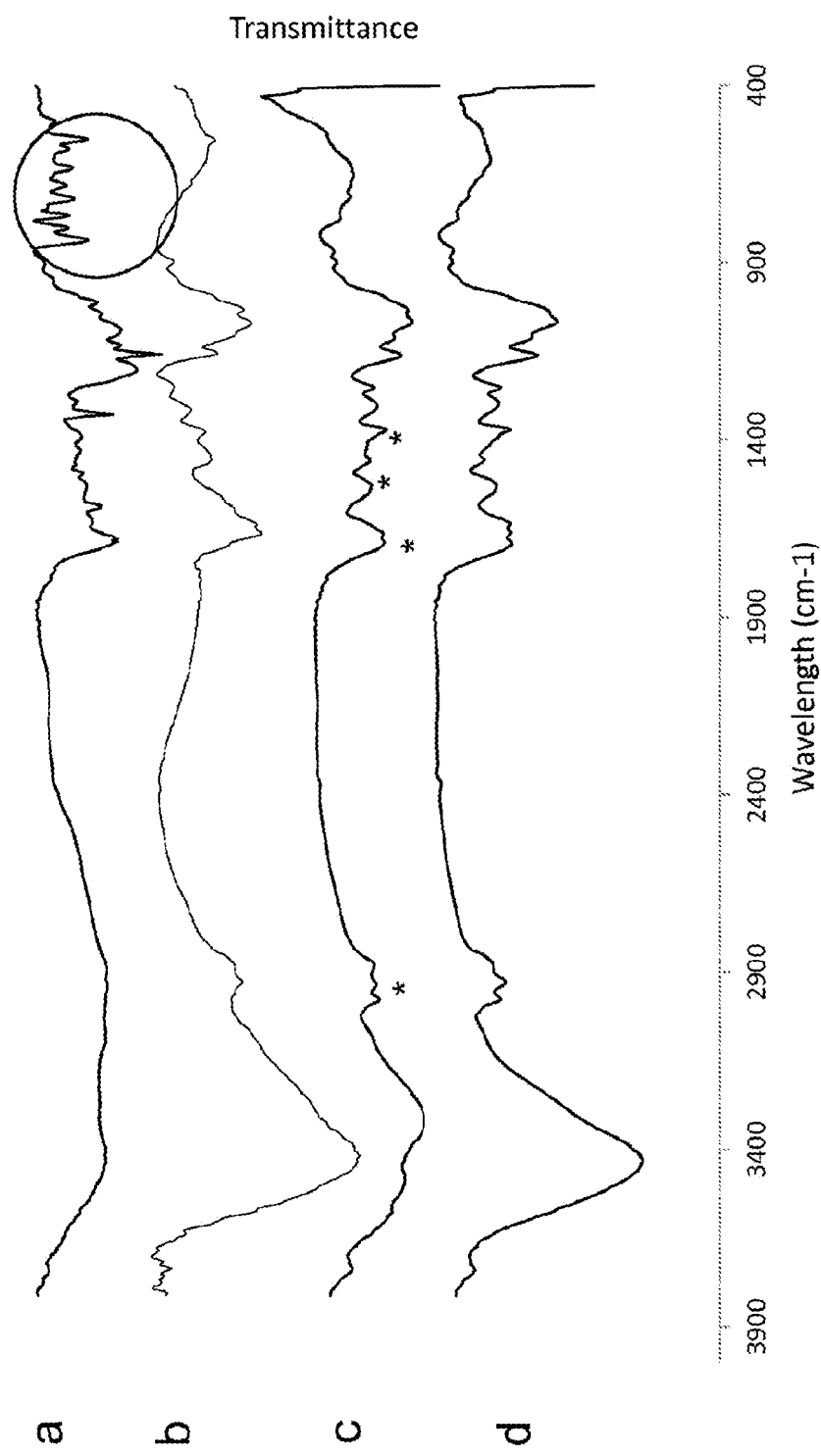
FIG. 30 is a series of spectra generated using Fourier transform infrared spectroscopy analysis (FTIR) of nanofibrous membranes comparing electrospun chitosan membranes at different stages. A=as spun membrane—circle highlights peaks associated with trifluoroacetic acid (TFA) salts. B=after triethylamine (TEA)/acetone washing showing removal of TFA salts. C=after modification of fibers by N-tert-butoxycarbonyl (t-BOC)/tetrahydrofuran (THF)-asterisks in ~1400-1800 $cm^{-1}$ are for: C=O (1688 $cm^{-1}$) CO—$NH_2$ (1527 $cm^{-1}$) and BOC (1368, 1393 $cm^{-1}$); asterisk at ~2980 $cm^{-1}$ is for —$CH_3$ group on attached carbamate from tBOC reaction. D=t-BOC-chitosan nanofiber membranes after approx 12 hours in water—no change in spectra indicating chemical stability.

The Fourier transform infrared spectroscopy (FTIR) spectra shown in FIG. 30 illustrates (a) as-spun electrospun chitosan nanofibers, (b) after triethylamine/acetone treatment, (c) after N-tert-butoxycarbonyl (t-BoC) modification, and (d) after t-Boc modification and soaking in water for 12 hours.

FIG. 31 is a series of FTIR spectra showing the effect of the removal of the immobilized TFA salts on the electrospun chitosan nanofibers. FTIR spectra revealed that the three transmittance peaks related to TFA salts at 720, 796 and 836 $cm^{-1}$ disappeared after the triethanolamine/N-tert-butoxycarbonyl (TEA/tBoC) treatment.

Figure 32:
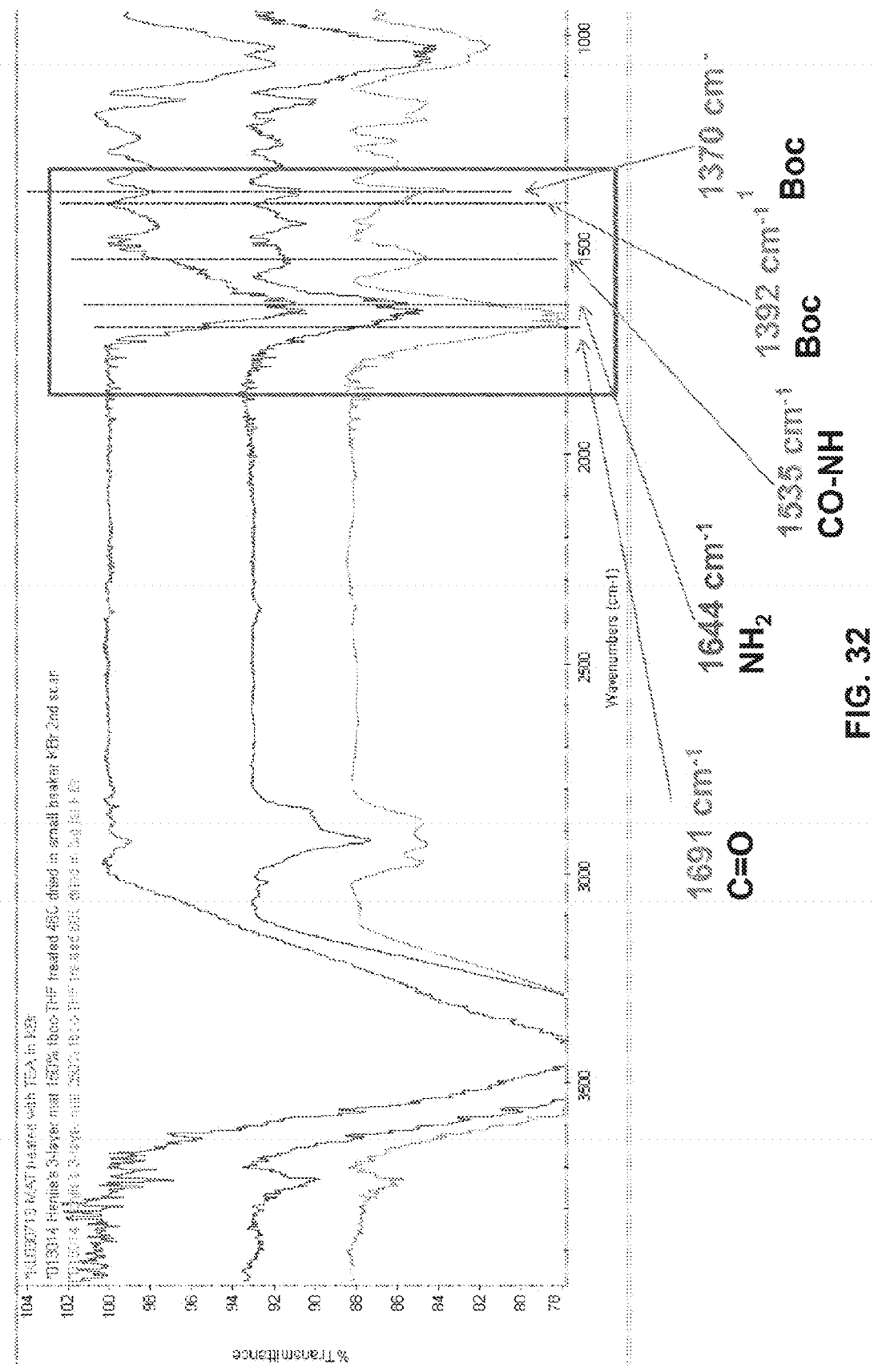
FIG. 32 is a series of FTIR spectra showing the effect of the reaction conditions on the degree of protection. The spectra after the reaction using 150% (w/v) of di-t-butyl dicarbonate in THF at 48° C. and using 250% (w/v) of the reagent at 65° C. revealed the increase of absorbance peaks derived from N-t-Boc groups at 1392, 1535, 1691, and 2980 $cm^{-1}$ as increasing the concentration of reagent and temperature.

FIG. 32 is a series of FTIR spectra showing the effect of the reaction conditions on the degree of protection. The spectra after the reaction using 150% (w/v) of di-t-butyl dicarbonate in tetrahydrofuran (THF) at 48° C. and using 250% (w/v) of the reagent at 65° C. revealed the increase of absorbance peaks derived from N-t-Boc groups at 1392, 1535, 1691, and 2980 $cm^{-1}$ as increasing the concentration of reagent and temperature.

Figure 33A:
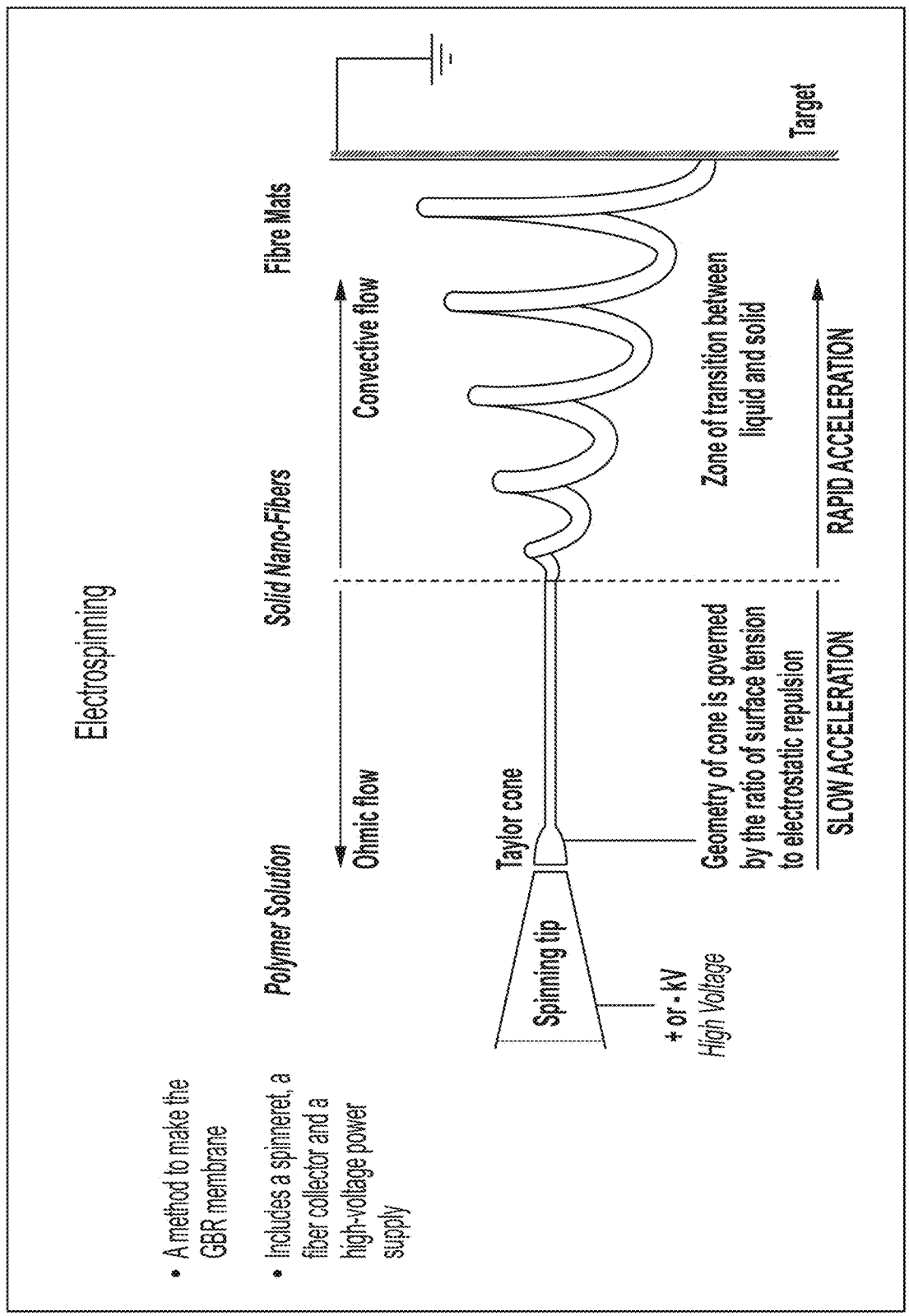
FIG. 33A is a schematic of an electrospinning method.
Figure 33B:
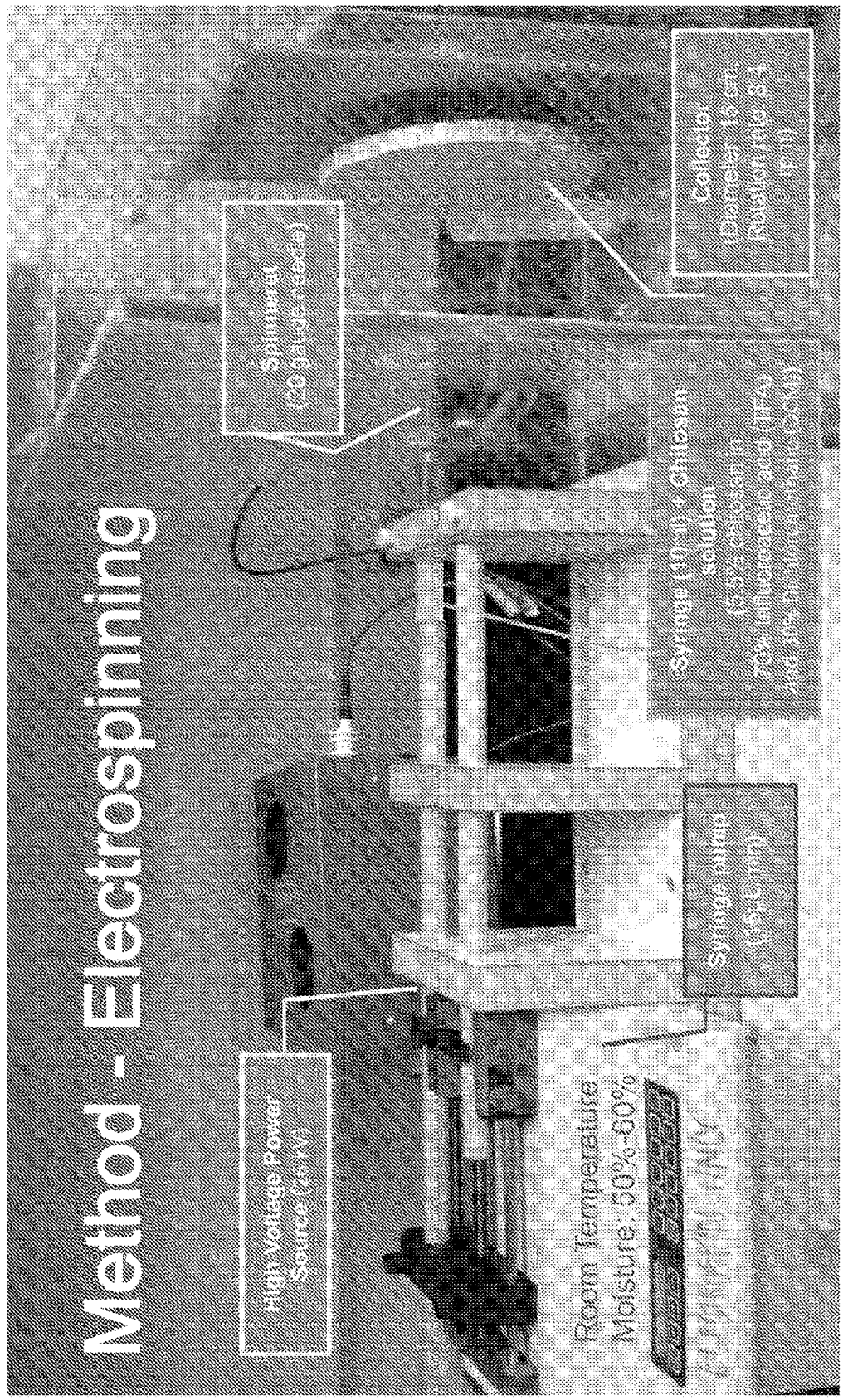
FIG. 33B is an image depicting an electrospinning method.

Example 12: Membranes of t-Boc Chitosan Nanofibers Exhibited Nano-Fibrous Morphology after PBS Immersion, but $Na_2CO_3$ Neutralized Chitosan Nanofiber Membranes Lost Fibrous Structure There has been a growing interest in the fabrication of nanofibers derived from natural polymers due to their ability to mimic the structure and function of extracellular matrix. Electrospinning is a simple technique to obtain nano-micro fibers with customized fiber topology and composition (FIGS. 33A and 33B). The chitosan electrospun nanofibers have recently been extensively studied due to the favorable properties of chitosan such as controllable biodegradation, good biocompatibility and high mechanical strength. Currently, chitosan can be electrospun from a solution of chitosan dissolved in either trifluoroacetic acid (TFA) or acetic acid (HAc). However, processes to remove residual acid and acid salts from the electrospun material generally resulted in a swelling of fibers and deterioration of the nano-fibrous structure. Crosslinking in combination with neutralization methods also had not been effective at preventing loss of nano-fibrous structure.

Figure 33C:
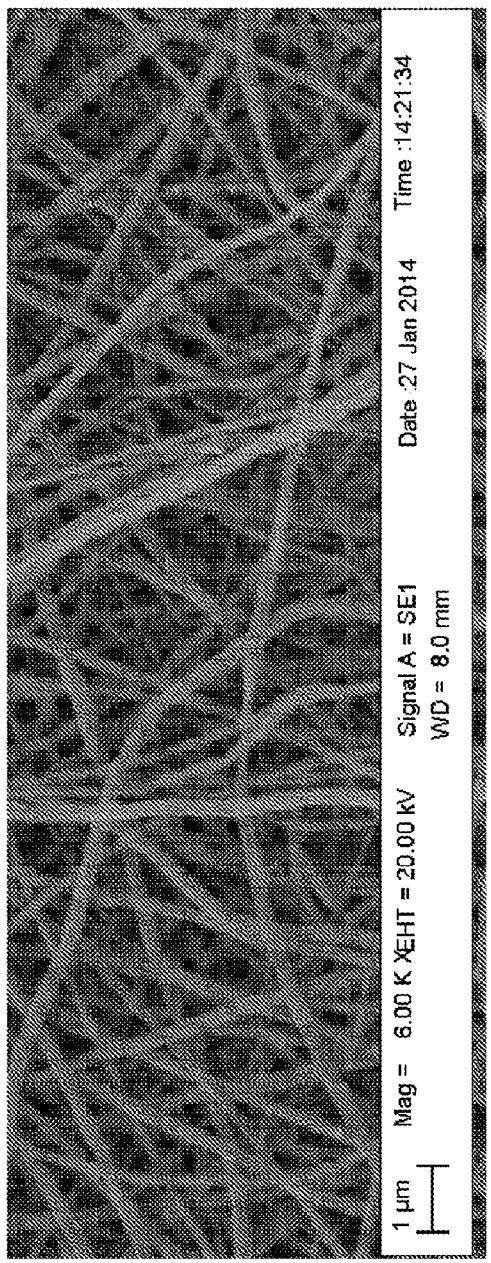
FIG. 33C is an image of a scanning electron micrograph (SEM) of TEA/tboc treated electrospun chitosan nanofibers.
Figure 33D:
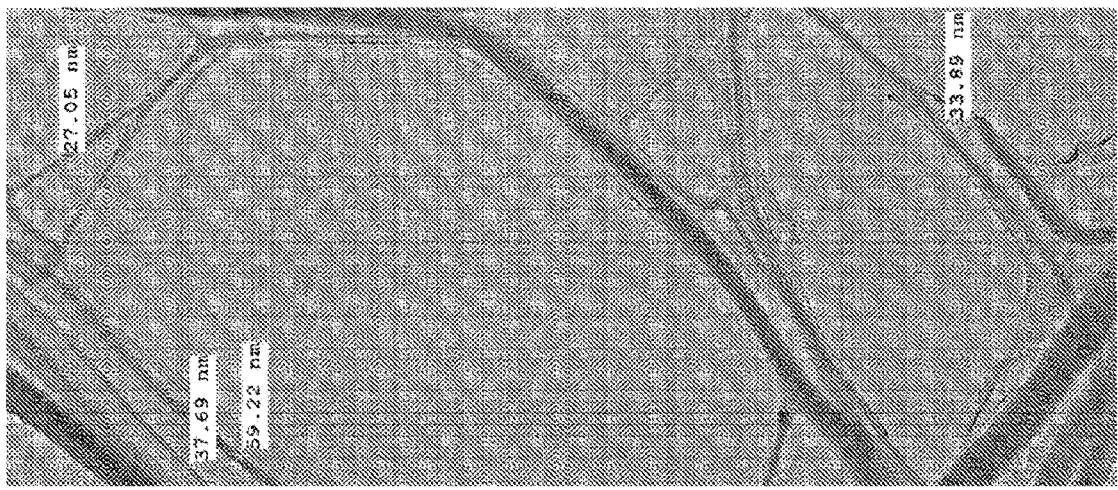
FIG. 33D is an image of a transmission electron micrograph (TEM) of TEA/tboc treated electrospun chitosan nanofibers.
Figures 34A, 34B:
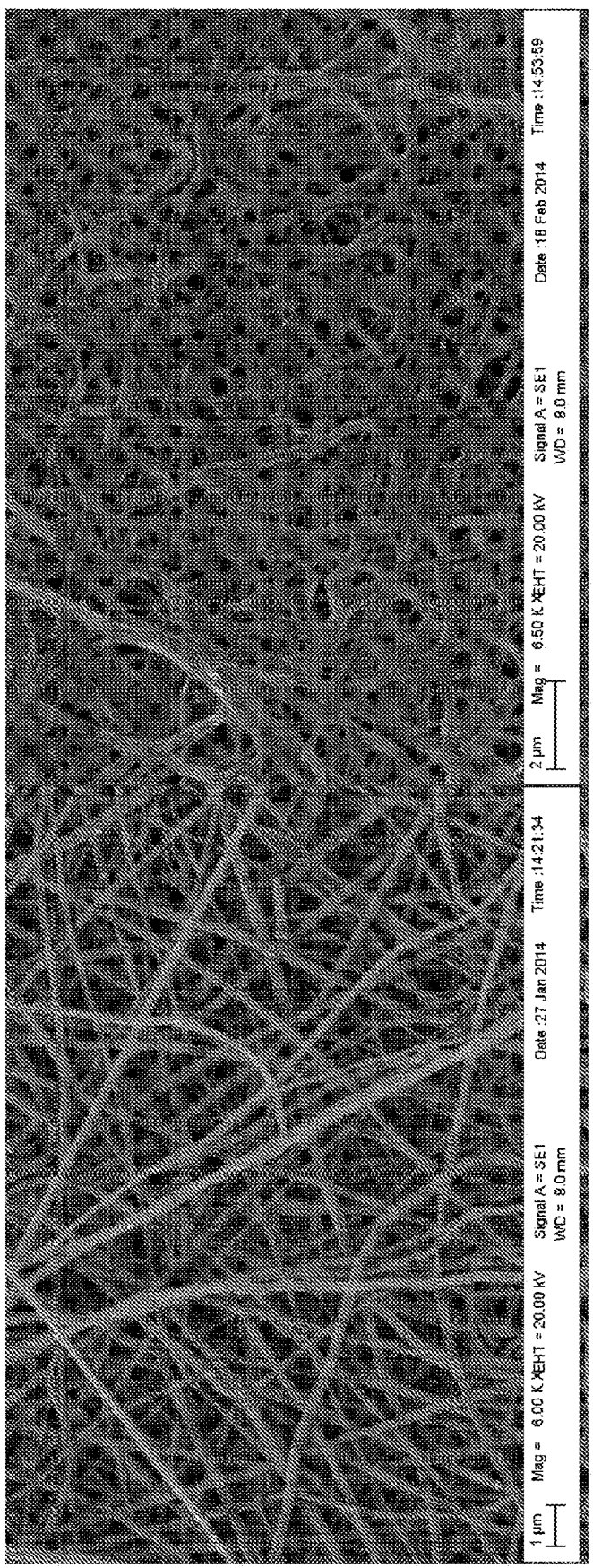
FIG. 34A is a representative scanning electron micrograph (SEM) examination of TEA/tboc treated membranes.
FIG. 34B is a representative scanning electron micrograph (SEM) examination of TEA/tboc treated membranes immersed in PBS for 24 hours.
Figures 35A, 35B:
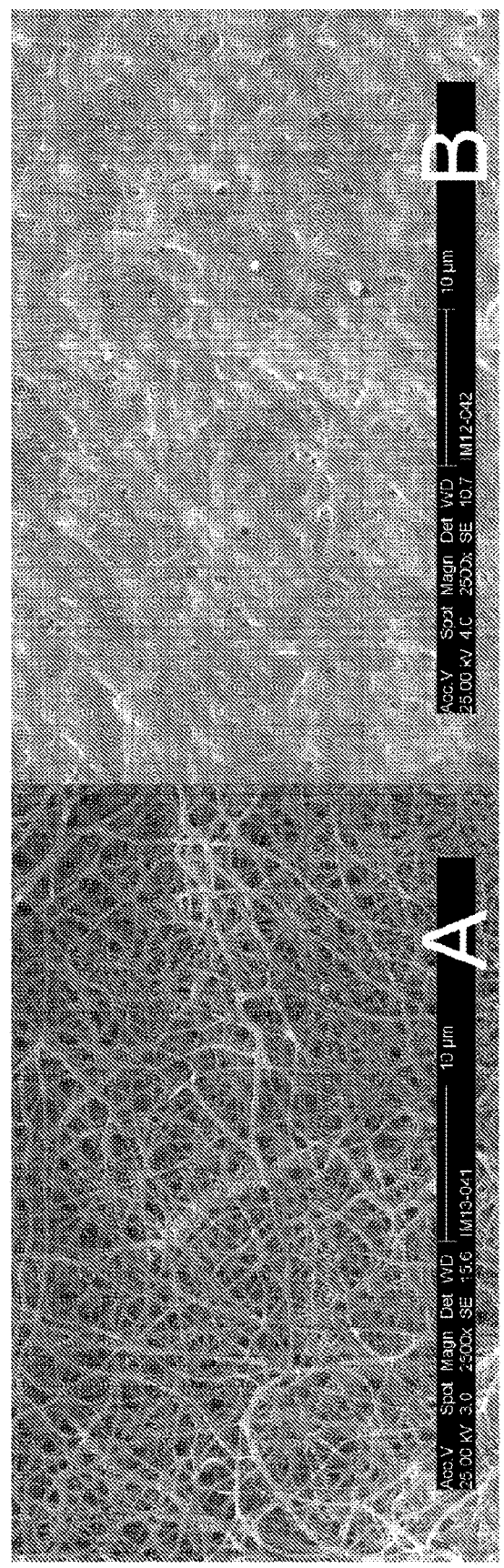
FIG. 35A is a representative scanning electron micrograph (SEM) examination of as-spun chitosan membrane (prior to any post-spinning treatment).
FIG. 35B is a representative scanning electron micrograph (SEM) examination of $Na_2CO_3$ treated membranes.
Figure 35C:
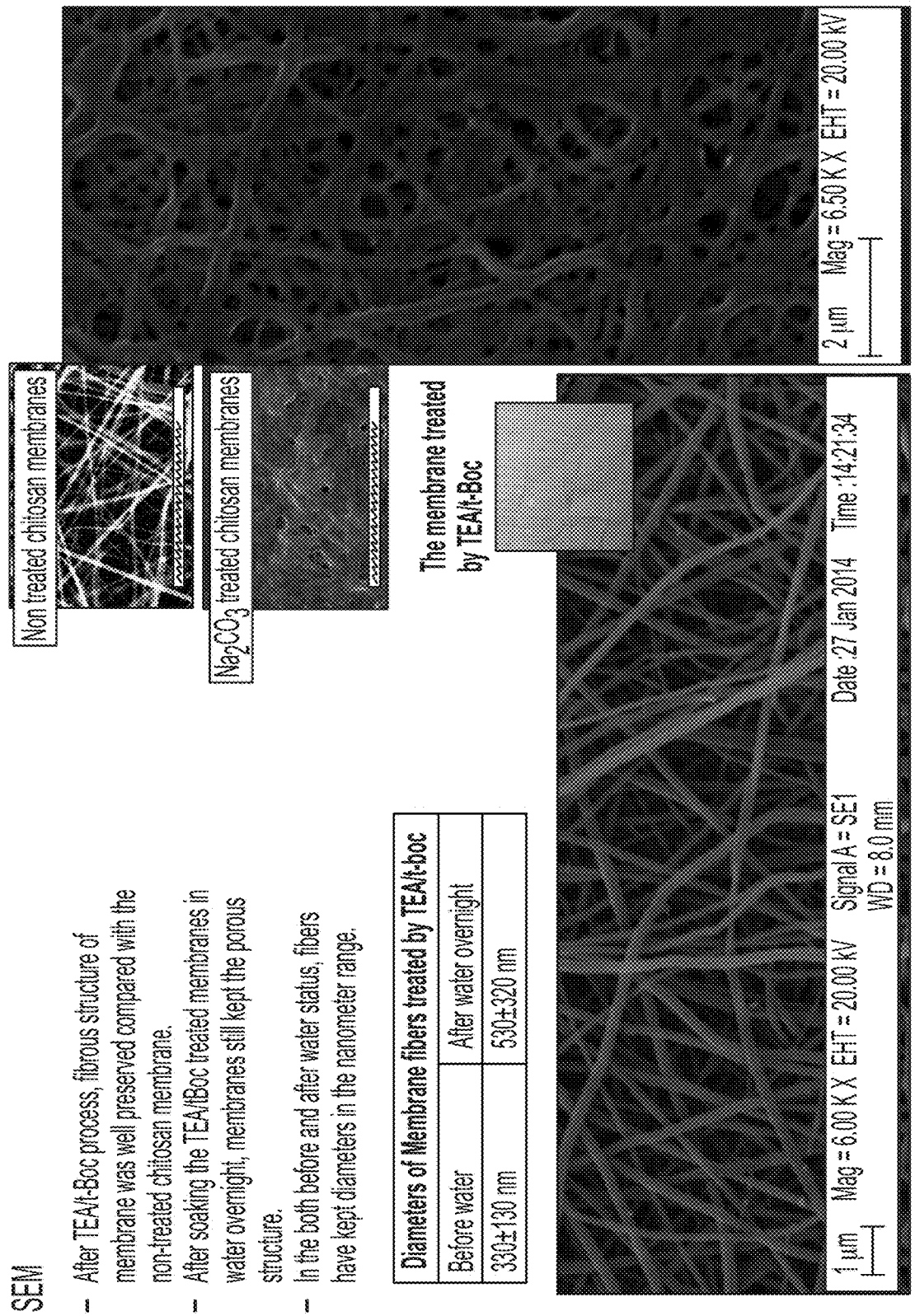
FIG. 35C are representative scanning electron micrographs comparing non-treated, $Na_2CO_3$ treated, and TEA/tboc treated membranes.
Figure 35D:
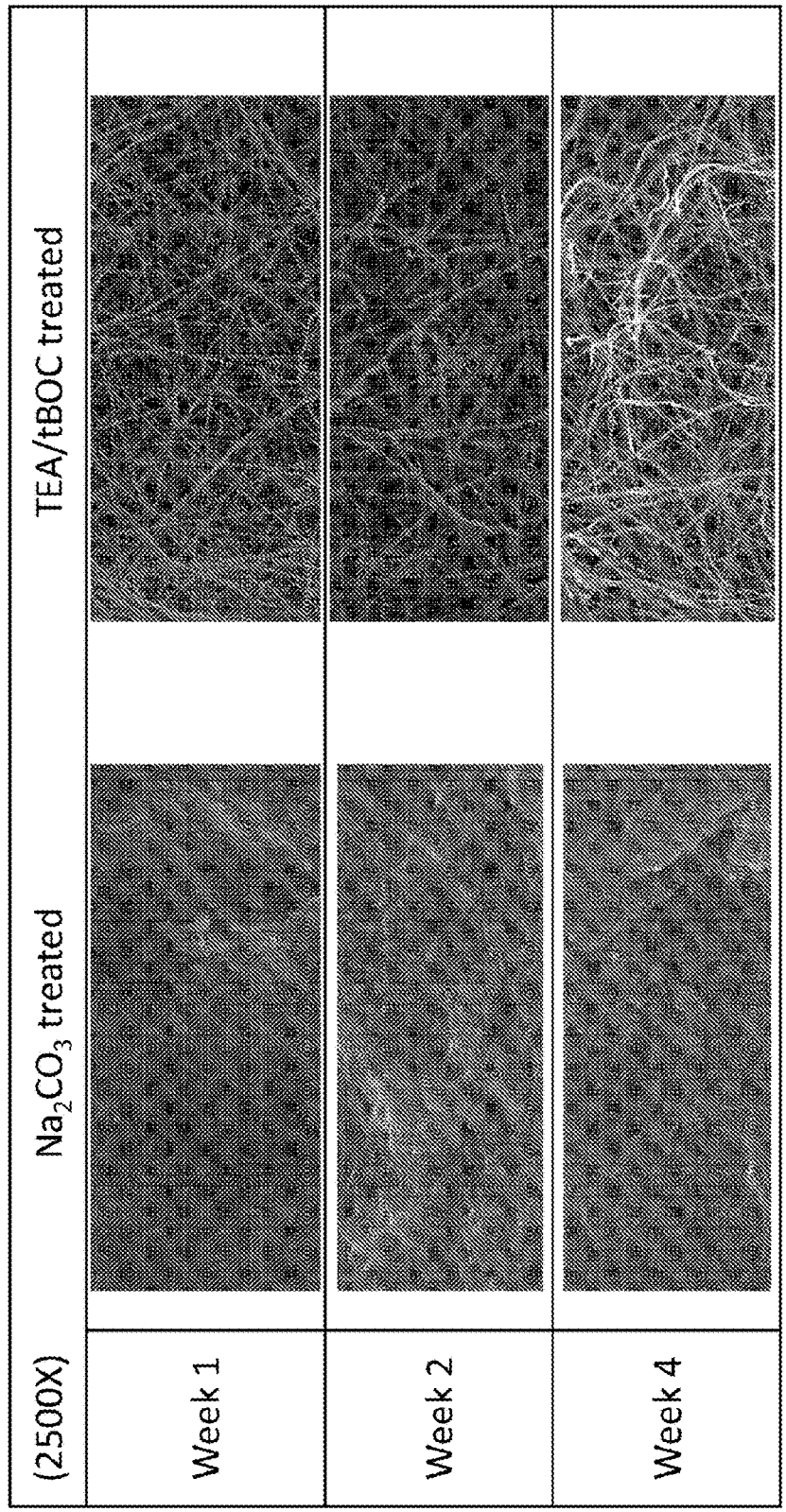
FIG. 35D are representative scanning electron micrographs showing that TEA/tBoC modified nanofiber membranes retain nanofiber structure over 4 weeks in physiological solution as compared to $Na_2CO_3$ treated membranes.

The current study aimed to improve and maintain nano-fibrous and porous structure of the electrospun membranes by introducing a new post electrospinning chemical treatment. Membrane thickness was tripled in this research in order to increase the general tearing strength. Scanning electron micrograph (SEM) examination (FIG. 33C) and transmission electron micrograph (TEM) examination (FIG. 33D) showed Fiber diameters of the triethanolamine/N-tert-butoxycarbonyl (TEA/t-BoC) treated membranes ranged from 40 nm to 130 nm while fiber diameters were not able to be determined for the $Na_2CO_3$ group. Membranes treated by TEA/tboc (FIG. 34A) exhibited more nano-scale fibrous structure than membranes treated by saturated $Na_2CO_3$ (FIGS. 35B-35D, as seen demonstrated in scanning electron micrographs. After immersion in PBS for 24 hours, membranes treated by TEA/tboc exhibited less than 30% swelling (FIG. 34B) and retained their nanofibrous structure, compared with membranes treated by $Na_2CO_3$ (FIGS. 35B-35D) or compared with the non-treated chitosan membrane (FIG. 35A). After soaking the TEA/tBoC treated membranes in water overnight, membranes still kept the porous structure. In both, the before and after water status, fibers kept diameters in the nanometer range (FIG. 35C). TEA/tBoC modified nanofiber membranes also well preserved their fibrous structure over 4 weeks in physiological solution compared with $Na_2CO_3$ treated membranes (FIG. 35D).

Chitosan membranes treated by TEA/tboc showed better nano-fiber morphology characteristics than membranes neutralized by saturated $Na_2CO_3$ solution before and after being soaked in PBS. Retention of the nanofibrous structure for guided tissue regeneration applications may be of benefit for enabling nutrient exchange between soft gingival tissue and bone compartments and for mimicking the natural nanofibrillar components of the extracellular matrix during regeneration.

Example 13: Osteoblast Cells Proliferation on Electrospun Chitosan Nanofiber Membranes To further explore the potential of the electrospun chitosan nanofibers in tissue engineering applications, osteoblast proliferation on the membrane of electrospun chitosan nanofibers was examined using a luminescence based high-throughput method for measuring cell growth based on ATP via the Celltiter Glo Assay Kit. The cell morphology on electrospun chitosan nanofibers membranes treated with triethanolamine/N-tert-butoxycarbonyl (TEA/t-BoC) or $Na_2CO_3$ was visualized with fluorescence microscope after osteoblast cells (SAOS-2 cells) were cultured on the top of the membranes for 5 days. The cells grown on both electrospun chitosan nanofiber membranes showed characteristic shapes associated with osteoblast cells, such as elongated/stretched shape, indicating the material did not interfere with the growth of the osteoblasts.

Figure 36A:
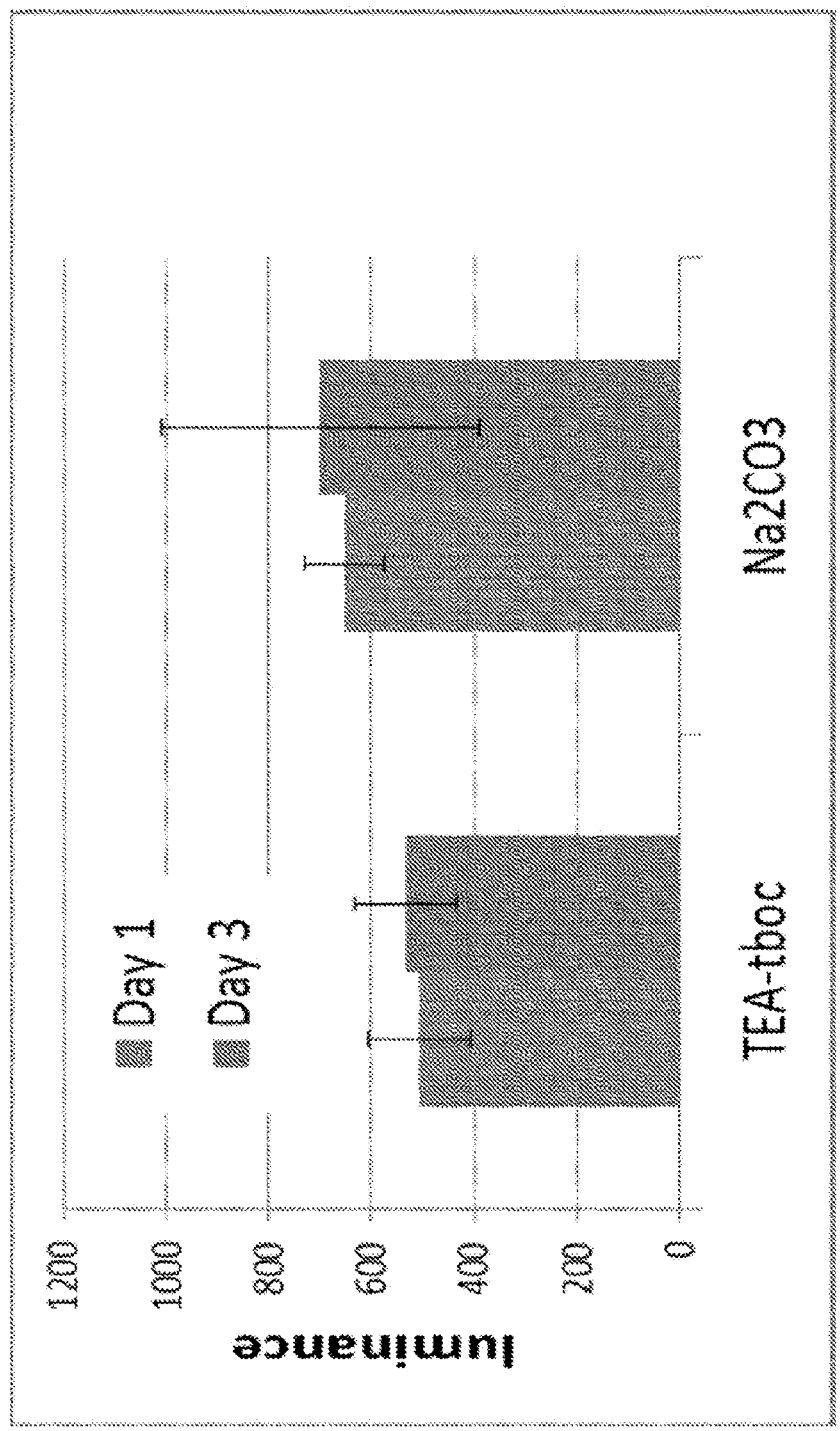
FIG. 36A is a graph showing osteoblast cell growth at day 1 and day 3 on TEA/tboc treated chitosan nanofiber membranes or $Na_2CO_3$ treated chitosan nanofiber membranes.
Figure 36C:
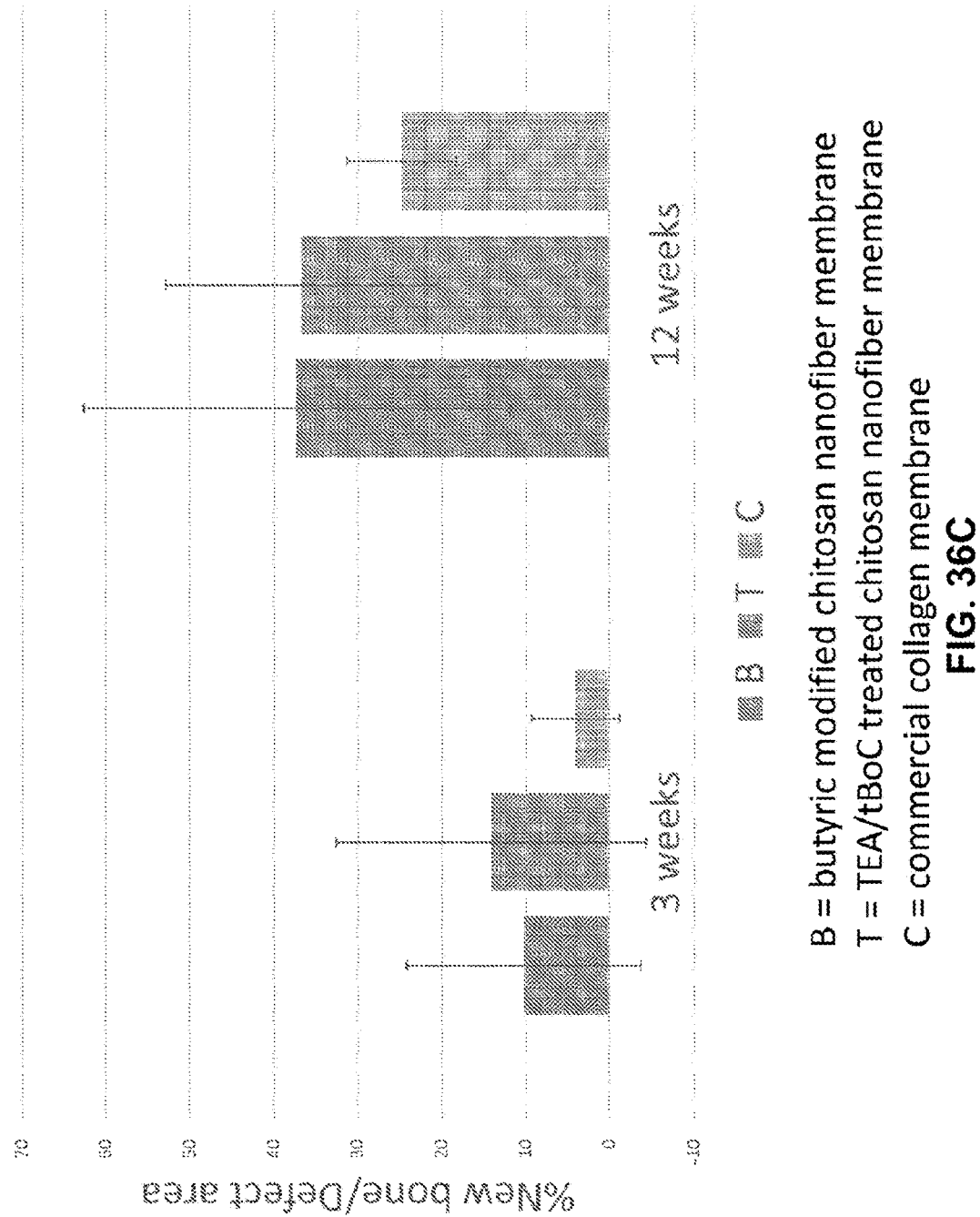
Figure 36D:
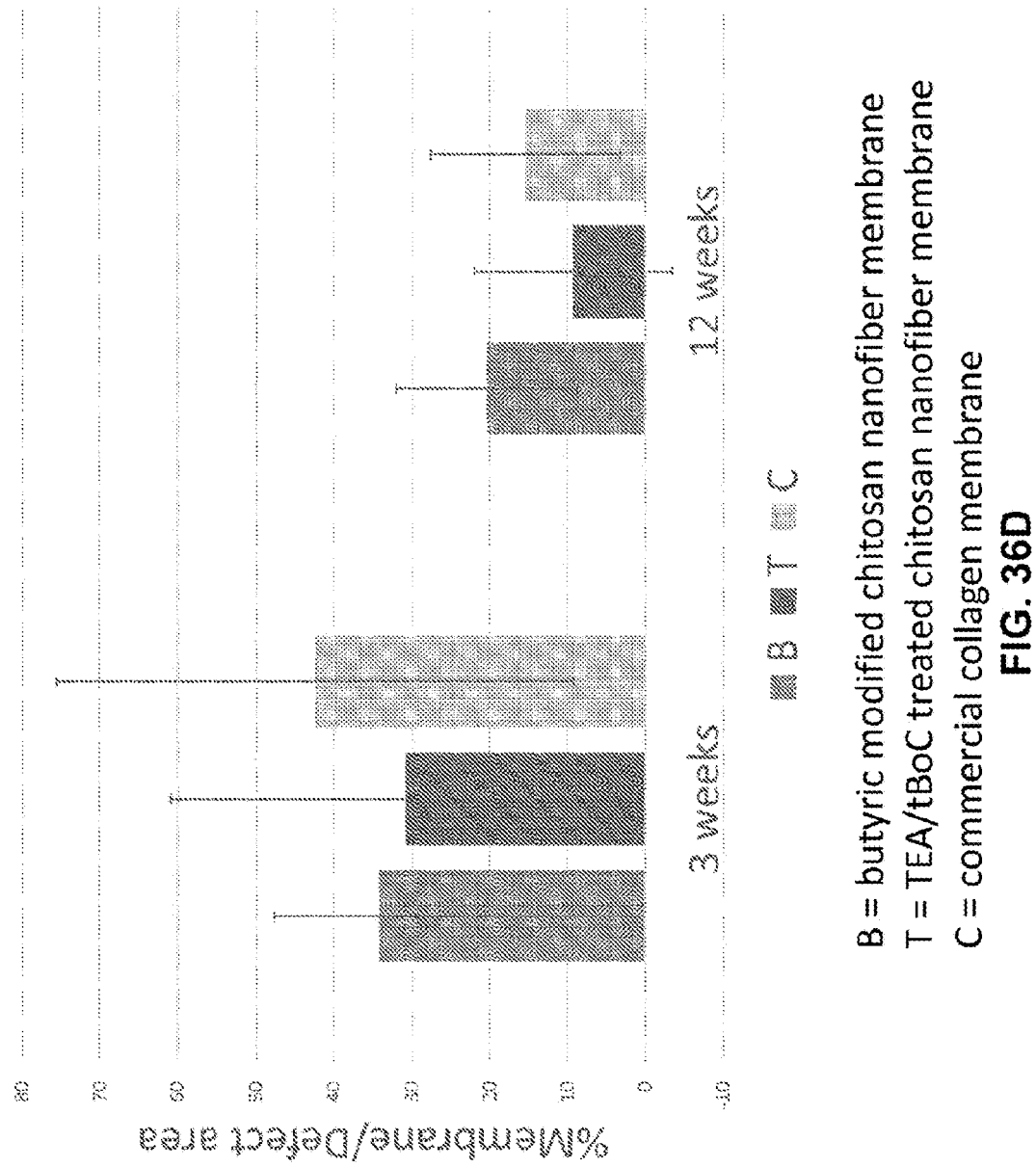
Figures 37A, 37B:
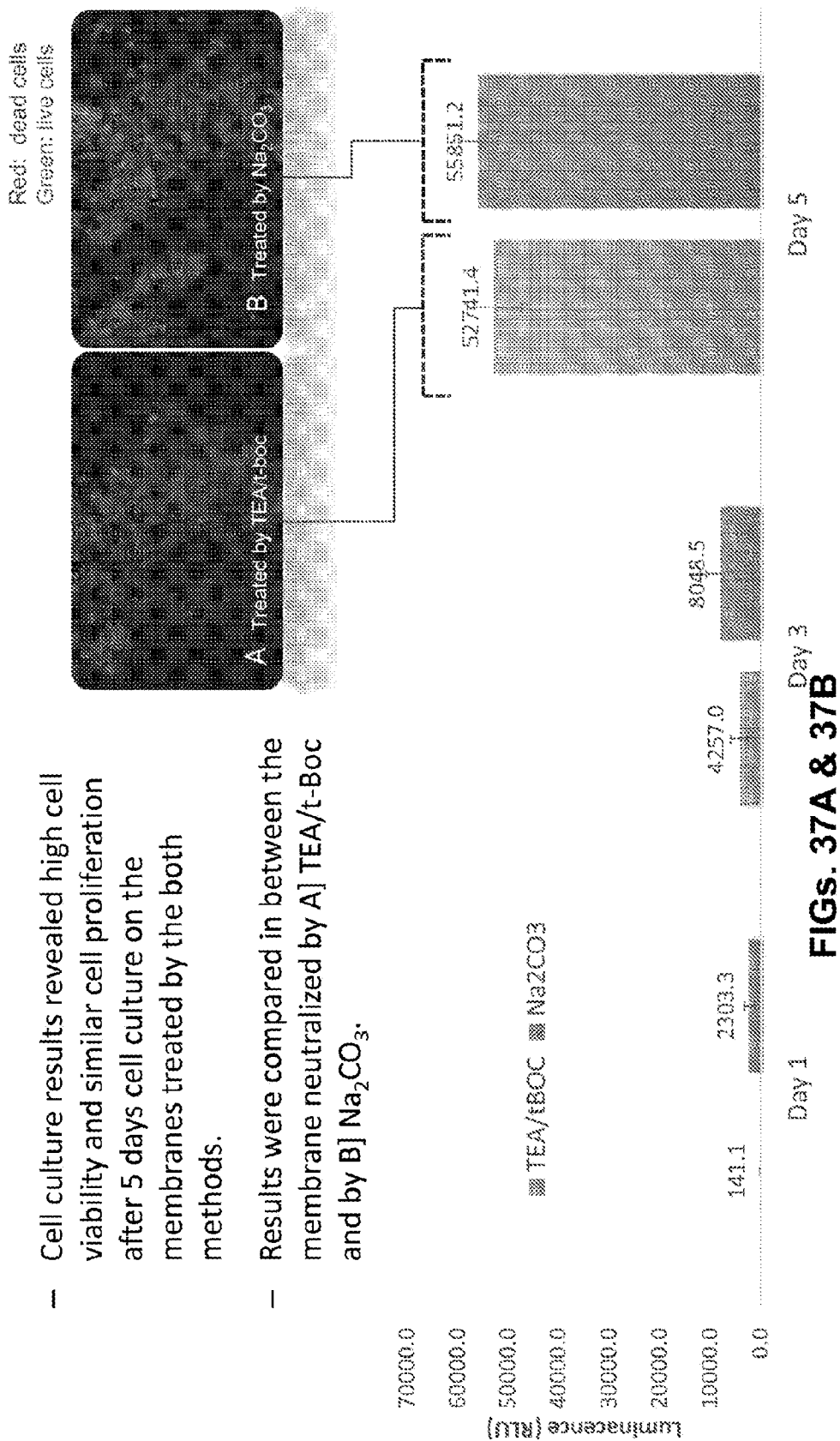
FIGS. 37A and 37B depict two images and a graph comparing cell viability of osteoblast cells cultured on TEA/tboc and $Na_2CO_3$ treated chitosan nanofiber membranes, respectively.
Figure 37C:
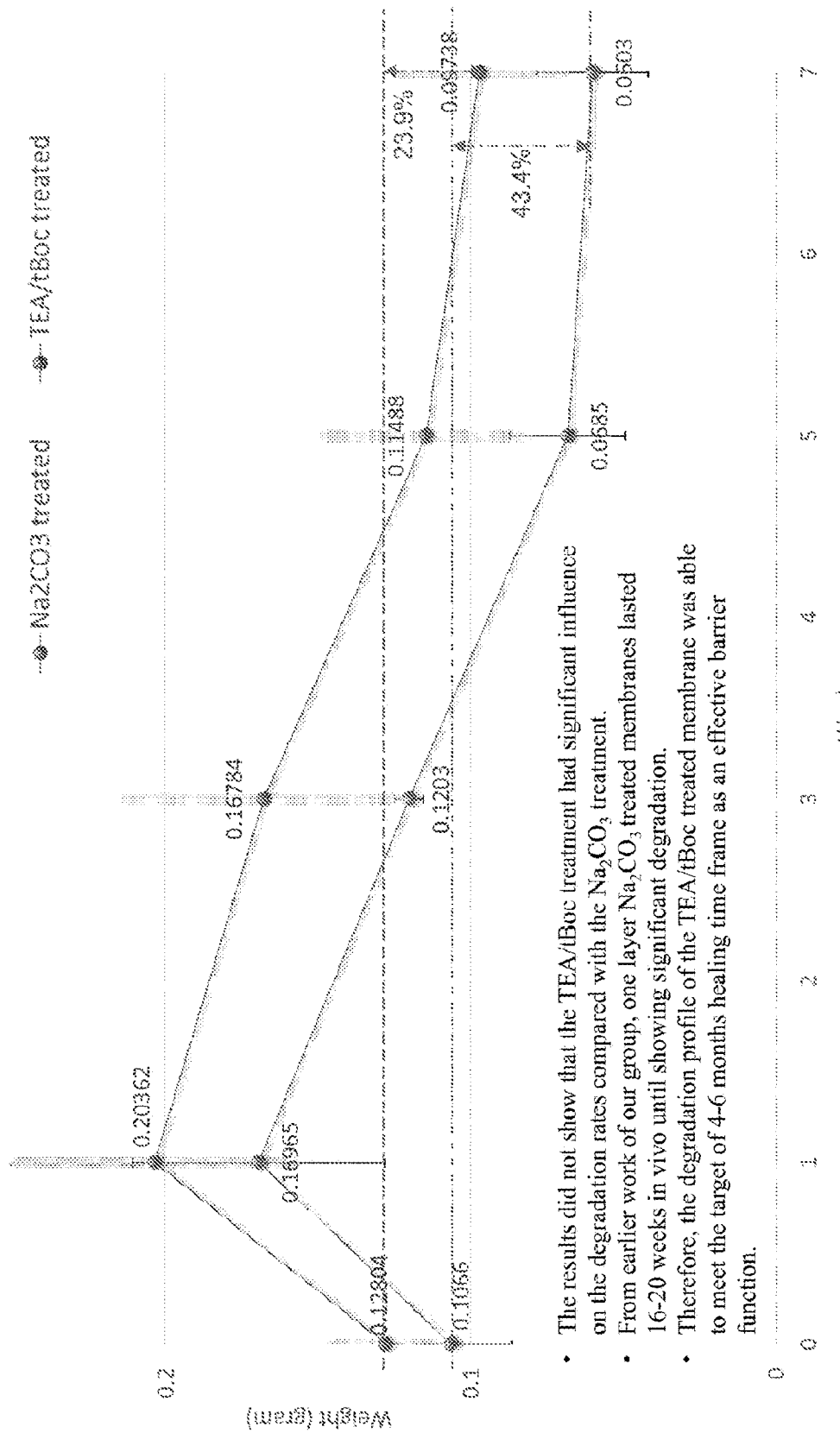
FIG. 37C is a graph comparing degradation rates of non-treated, TEA/tBoc treated and $Na_2CO_3$ treated chitosan nanofiber membranes, respectively over 7 weeks.
Figure 37D:
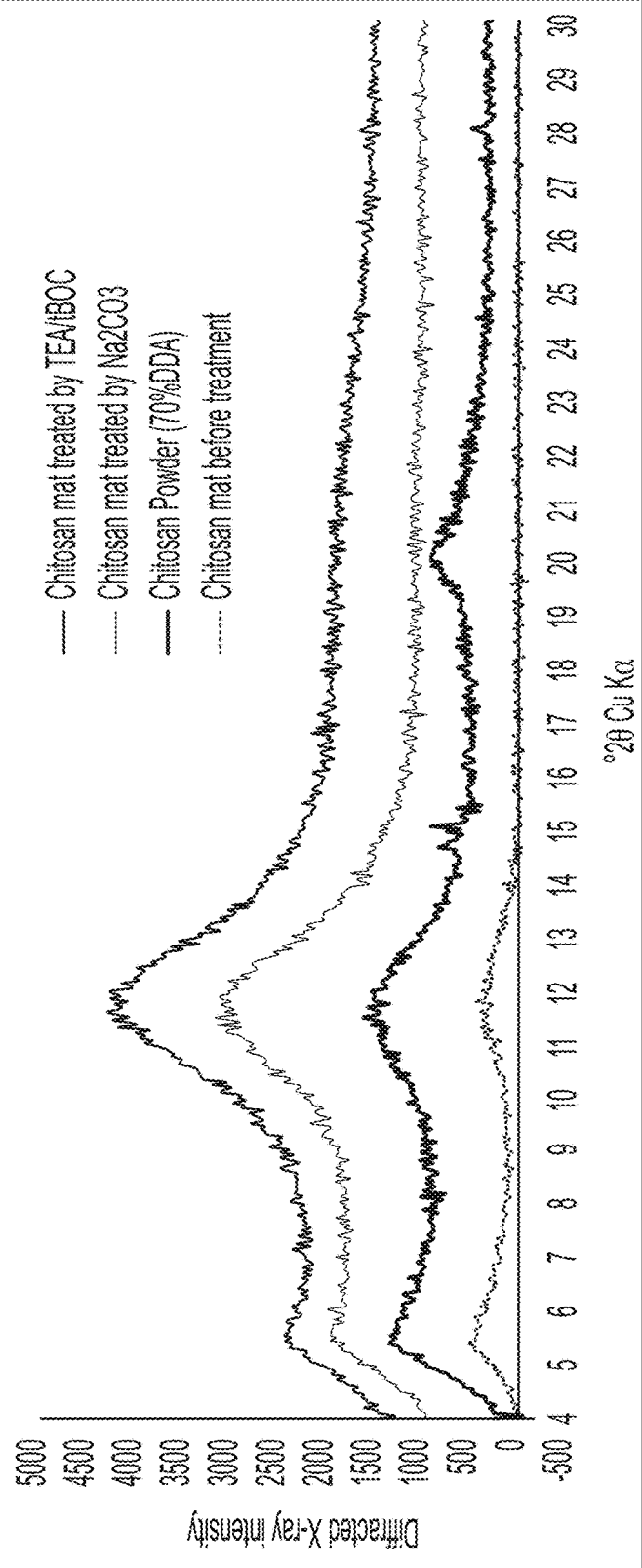
FIG. 37D is a an image showing x-ray diffraction (XRD) of the different chitosan nanofiber membranes.

As shown in FIGS. 37A and 37B, there was no statistical difference in the day 5 growth of cells on chitosan between membranes neutralized by triethanolamine/N-tert-butoxycarbonyl (TEA/t-BoC, left graph of FIG. 37A) and by $Na_2CO_3$ (right graph of FIG. 37A), suggesting the electrospun chitosan nanofibers membranes were non-toxic. Culture results revealed high viability of cells and similar cell proliferation on both types of TEA/t-Boc treated (FIG. 37A) and $Na_2CO_3$ treated (FIG. 37B) membranes after five days cell culture. The cell viability and proliferation results showed that membranes treated by TEA/tboc had no toxicity to SAOS-2 cells. After TEA/t-BoC treatment, the water contact angle with the membrane was larger than that of $Na_2CO_3$ treatment membrane ($p=6.74 \times 10^{-5}$, FIG. 36B). FIG. 37C shows that the TEA/tBoc treatment did not have significant influence on the degradation rates compared with the $Na_2CO_3$ treatment. Earlier work showed that one layer $Na_2CO_3$ treated membranes lasted 16-20 weeks in vivo until showing significant degradation. Therefore, the degradation profile of the TEA/tBoc treated membrane was able to meet the target of 4-6 months healing time frame as an effective barrier function. X-ray diffraction (XRD) showed that crystallinity of the electrospun membranes before TEA/tBoc or $Na_2CO_3$ treatment decreased as compared to the chitosan powder and membrane related to more open molecular structure, which might result in increased degradation, less resistance to swelling and reduced tearing strength. (FIG. 37D).

Figure 37F:
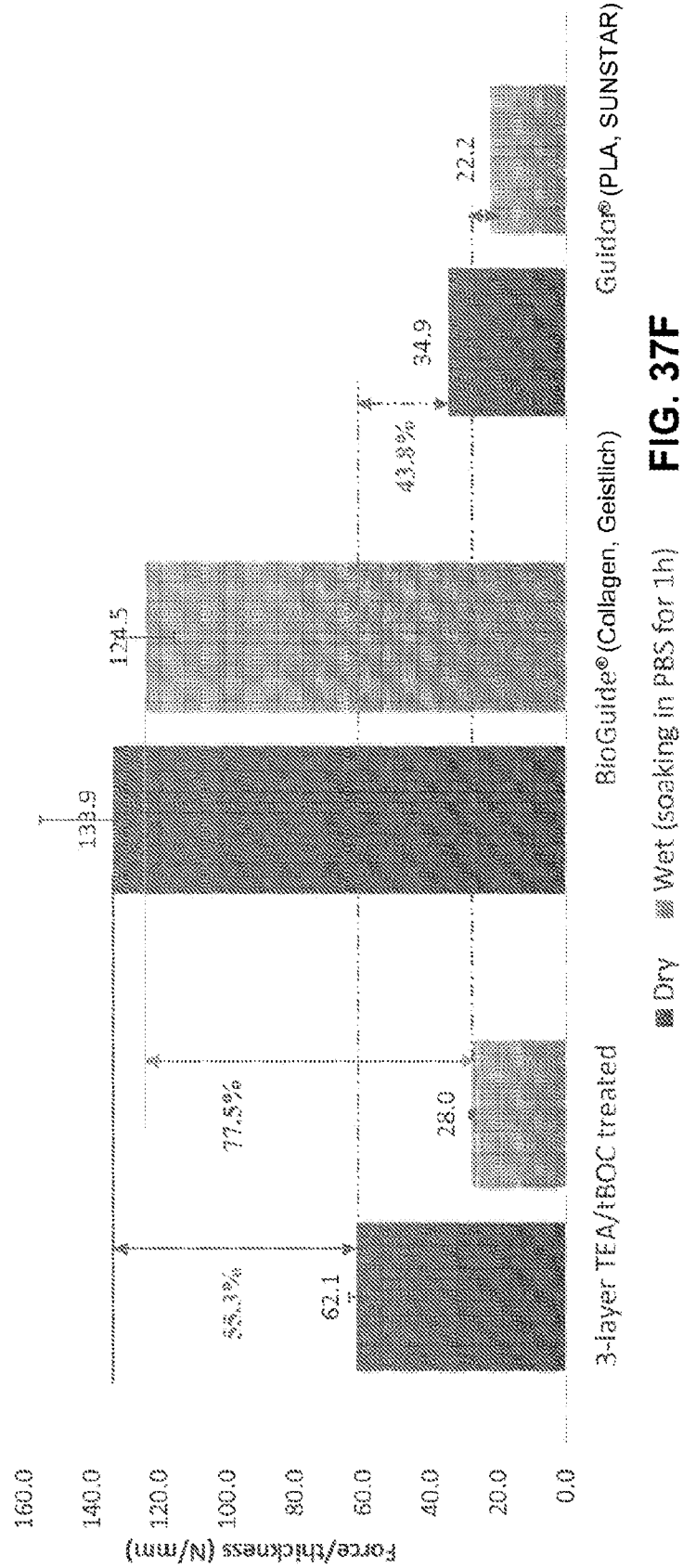
Figure 37H:
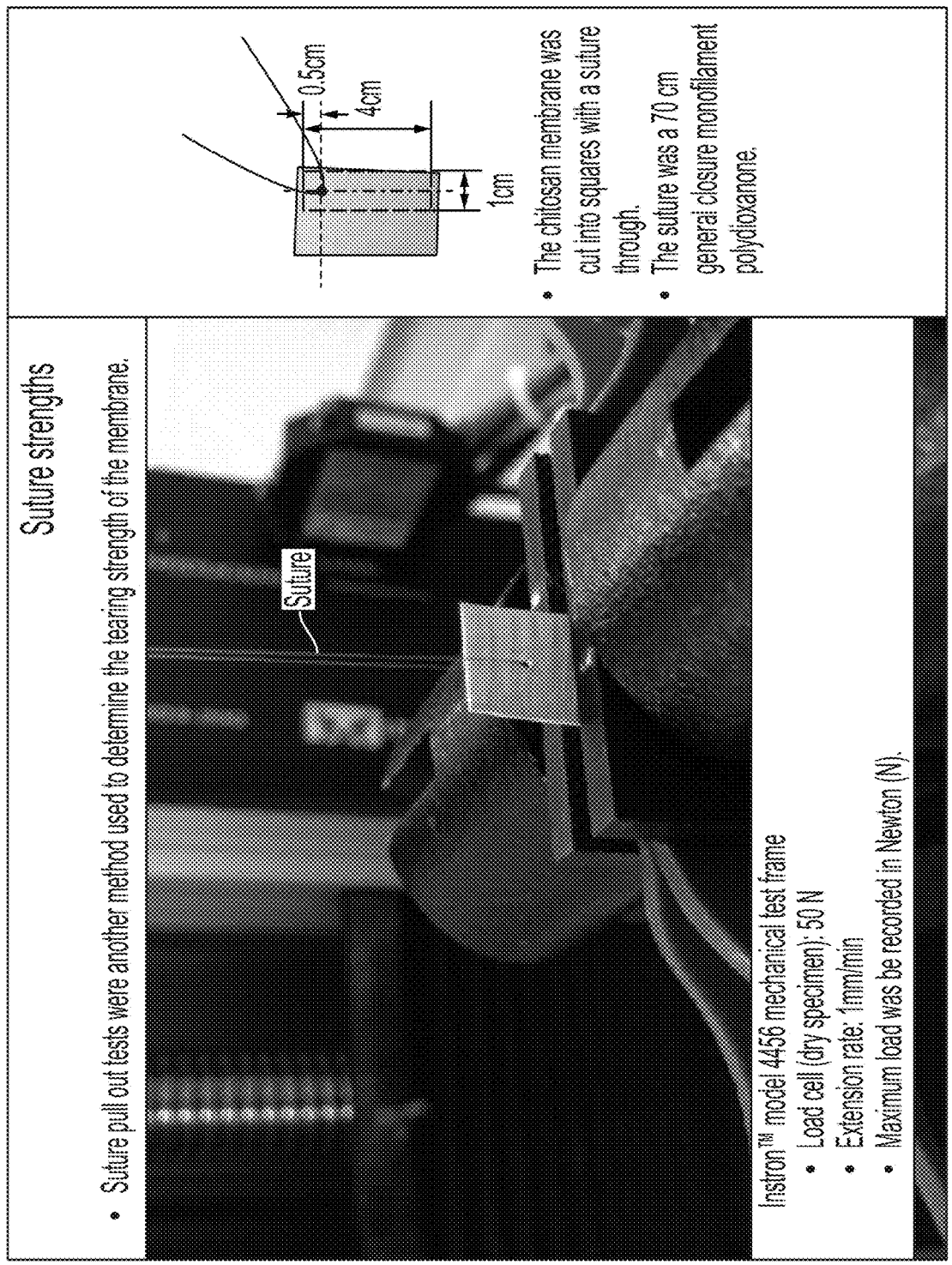
Figure 37I:
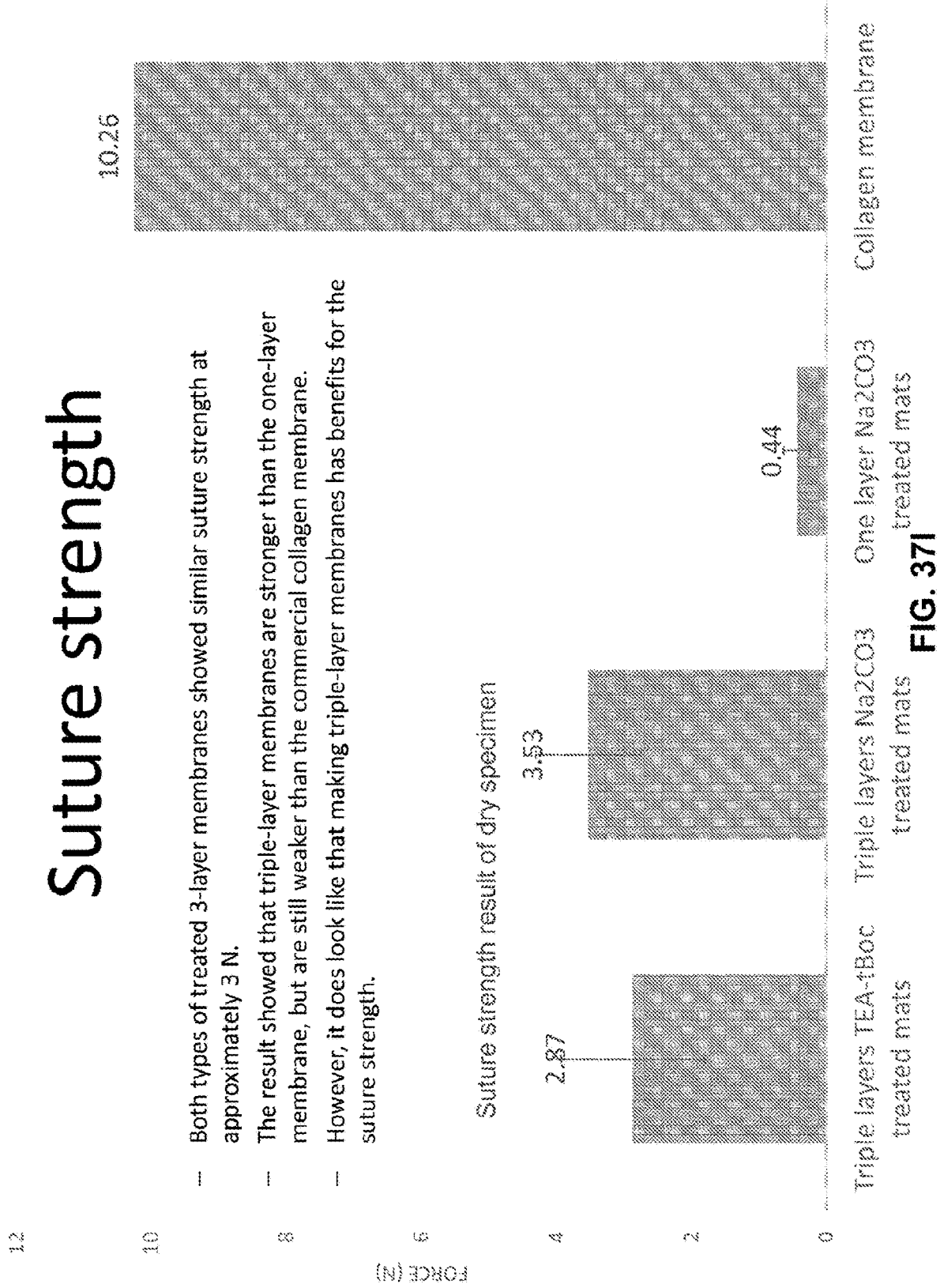
Figure 37J:
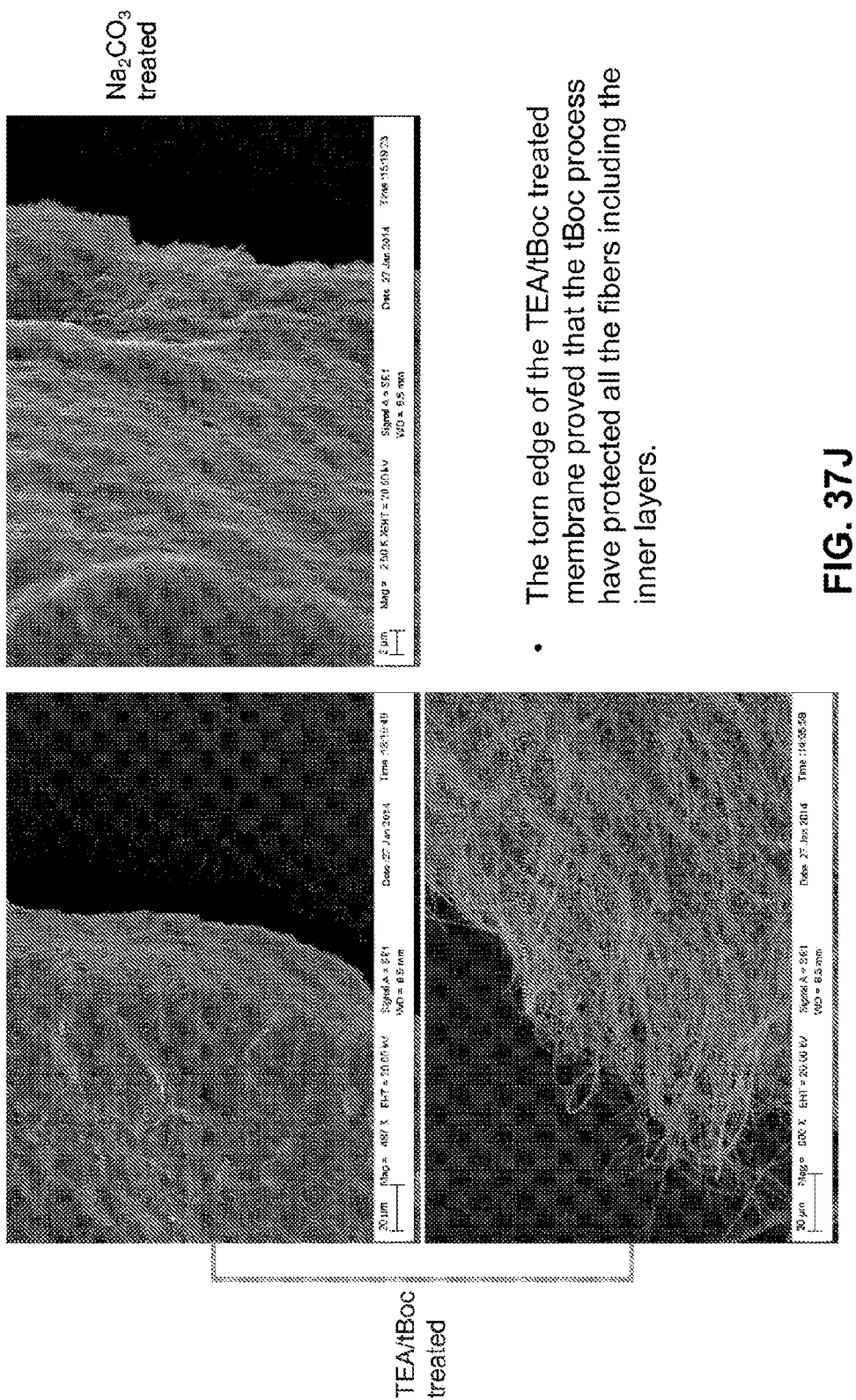

Clinically, surgical tacks are one common method to secure the membrane on the bone during treatment (FIG. 37E). Surgical tacking tests were used to determine the tearing strength of membranes, which could serve as an indicator of clinical handle ability. The tearing strength of TEA/tBoc treated membrane in dry condition was significantly more than that in wet condition, consisting of the fact that swelling decreased the fiber strength. In addition, the tearing strength of TEA/tBoc treated membranes was similar to the result of GUIDOR® polylactic acid (PLA) membranes, which indicated that the tearing strength of TEA/tBoc treated membranes was in the range of clinical requirement (FIG. 37F). The torn patterns related to the clinical handle ability. The Bio-Gide® collagen membrane presented extremely elasticity during the tacking process. TEA/tBoc treated triple layers membranes had the similar torn patterns with the collagen membranes but lower elasticity (FIG. 37G). The GUIDOR® PLA membrane was torn in the middle part of the membrane instead of the tacking edge (FIG. 37G). With the similar tearing strength, TEA/tBoc treated triple layers membranes would be easier fixed in the wound and keep better coverage function than the GUIDOR® PLA membranes. Suture pull out tests were another method used to determine the tearing strength of the membrane. The chitosan membrane was cut into squares with a suture through. The suture was a 70 cm general closure monofilament polydioxanone (FIG. 37H). Both types of treated triple-layer membranes showed similar suture strength at approximately 3 Newton (N, FIG. 37I). The result showed that TEA/tBoc and $Na_2CO_3$ treated membranes were stronger than a one-layer membrane (e.g., Norowski et al., Journal of Biomedical Materials Research Part A., 100(11): 2890-2896, 2012), but were still weaker than the commercial collagen membrane (FIG. 37I). However, the results indicate that making triple-layer membranes had benefits for the suture strength. Examining the suture tearing edge, the torn edge of the TEA/tBoc treated membrane indicated that the tBoc process had protected all the fibers including the inner layers (FIG. 37J).

A new post-electrospinning treatment of the chitosan membrane was explored in this research. The results indicate that this new post-electrospinning TEA/tBoc treatment of the chitosan membrane successfully preserved the porous structure in the water environment with good cell compatibility and degradation rate. In addition, tearing strength of the chitosan membrane was significantly improved compared with the previous study.

Example 14: In Vivo Implantation of Nanofibrous Membranes Showed Bone Regeneration in Rat Calvarial Defect An animal study was conducted to evaluate the biocompatibility, biodegradation and soft tissue excluding properties of a butyric anhydride modified electrospun chitosan nanofibrous membrane. The study used a critical size (8-mm) rat calvarial bone defect model. In the rat cranium, the established critical size defect was a circular defect of 8 mm in diameter. Repeated and current studies continued to show that defects of this size in rats failed to heal and fill primarily with fibrous tissue and only minimal bone growth at the edges over a 3-month period. The advantages of this model are; a) the calvarial bone is a plate which is large enough to allow creation of a circular defect that enables convenient radiographic and histological analysis, b) the calvarial bone has a large enough size for easy surgical procedures and specimen handling, c) no fixation is required, and d] the model is well studied and reproducible which enables comparison of variety of implant materials.

The animals were x-rayed at 2, 3, 9 and 12 weeks post implantation. One group of animals was euthanized by $CO_2$ inhalation at 3-weeks post-implantation and the other group of animals at 12-weeks post-implantation. The craniotomy sites with implants were excised and fixed in formalin for histological evaluation.

Figure 38B:
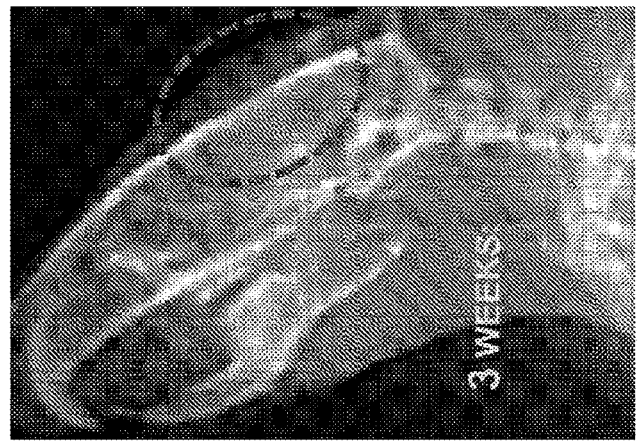
FIG. 38B is an x-ray image of 8 mm defect covered with membrane 3 weeks post surgery; radio-opaque area indicates early bone formation. Some early tissue healing is indicated by the increase in radio-opaqueness in the defect area.
Figure 38A:
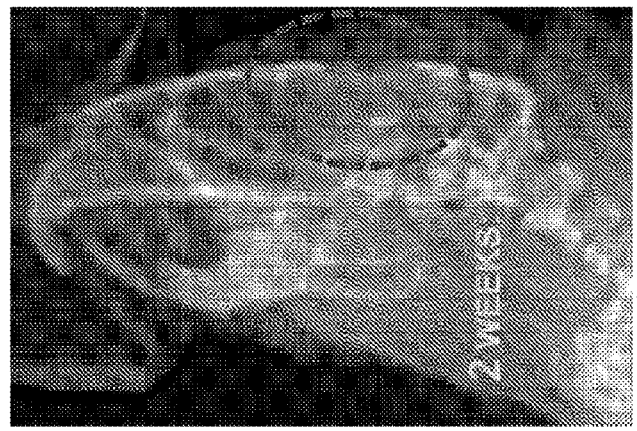
FIG. 38A is an x-ray image of the dorsal-ventral view of the 8 mm defect covered with membrane 2 weeks post surgery; radiolucent area indicates little to no bone formation. The defect is difficult to distinguish due to the thin calvarial bones.
Figure 38D:
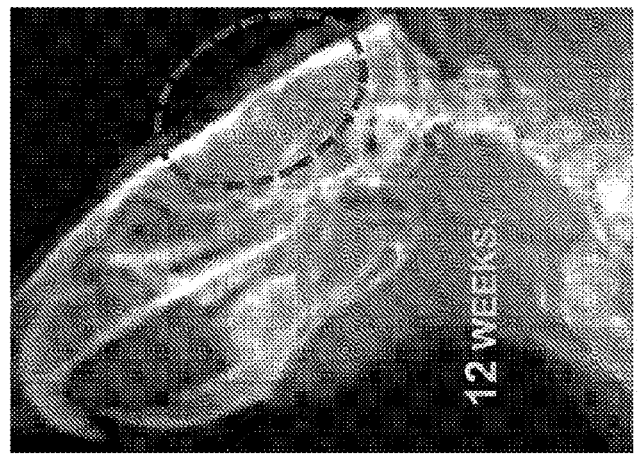
FIG. 38D is an x-ray image of the defect at 12 weeks post surgery; radio-opaque area indicates bone formation. Continued healing is indicated by the continual increase in radio-opaqueness in the defect area.
Figure 38C:
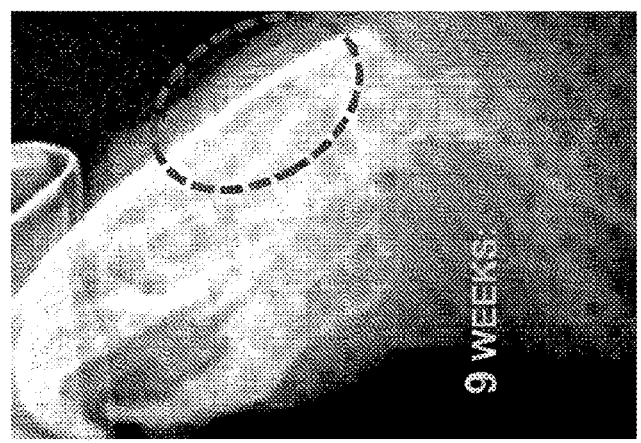
FIG. 38C is an x-ray image of the defect at 9 weeks post surgery; radio-opaque area indicates bone formation. Continued healing is indicated by the continual increase in radio-opaqueness in the defect area.
Figure 38J:
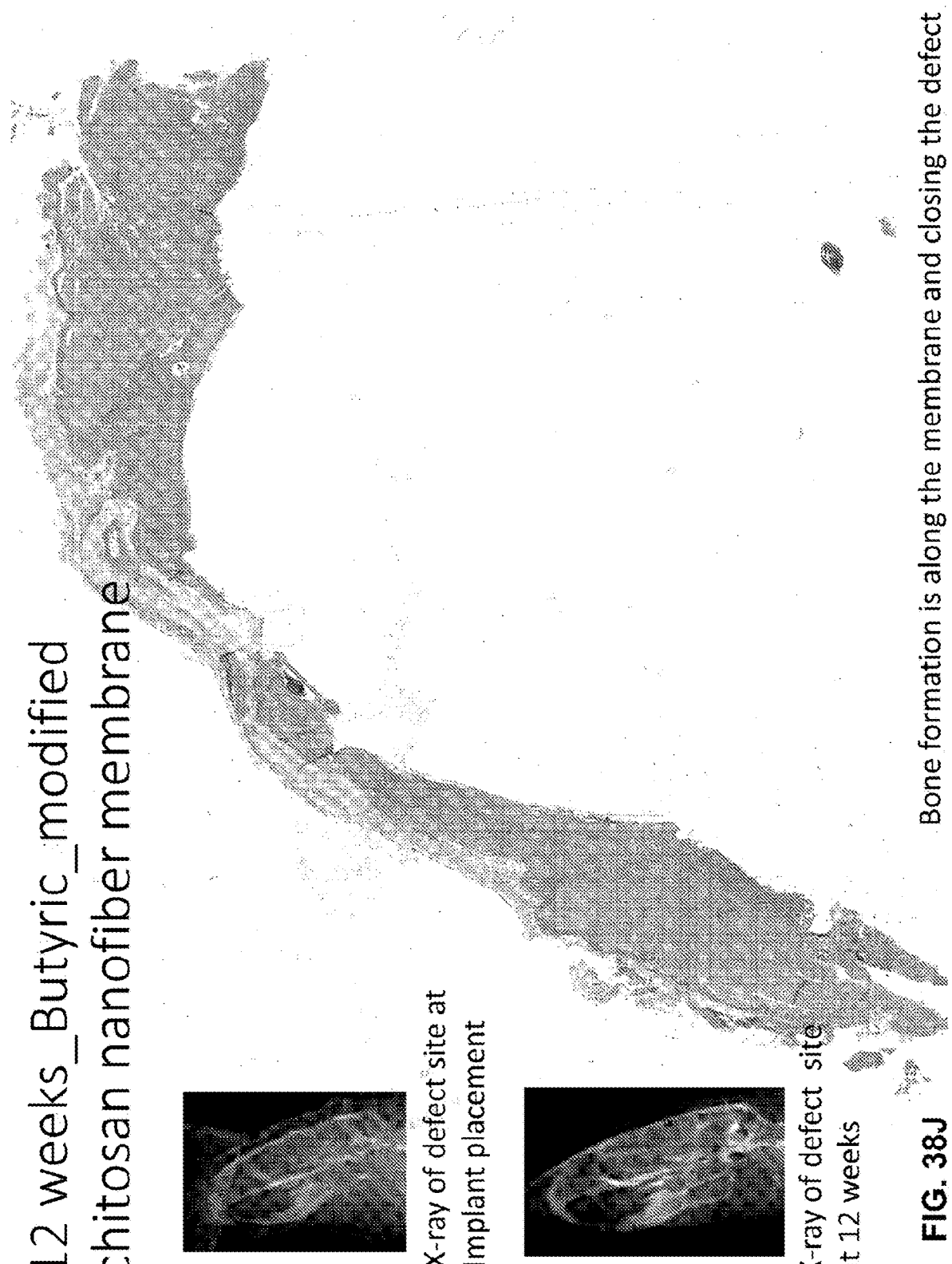
Figure 38K:
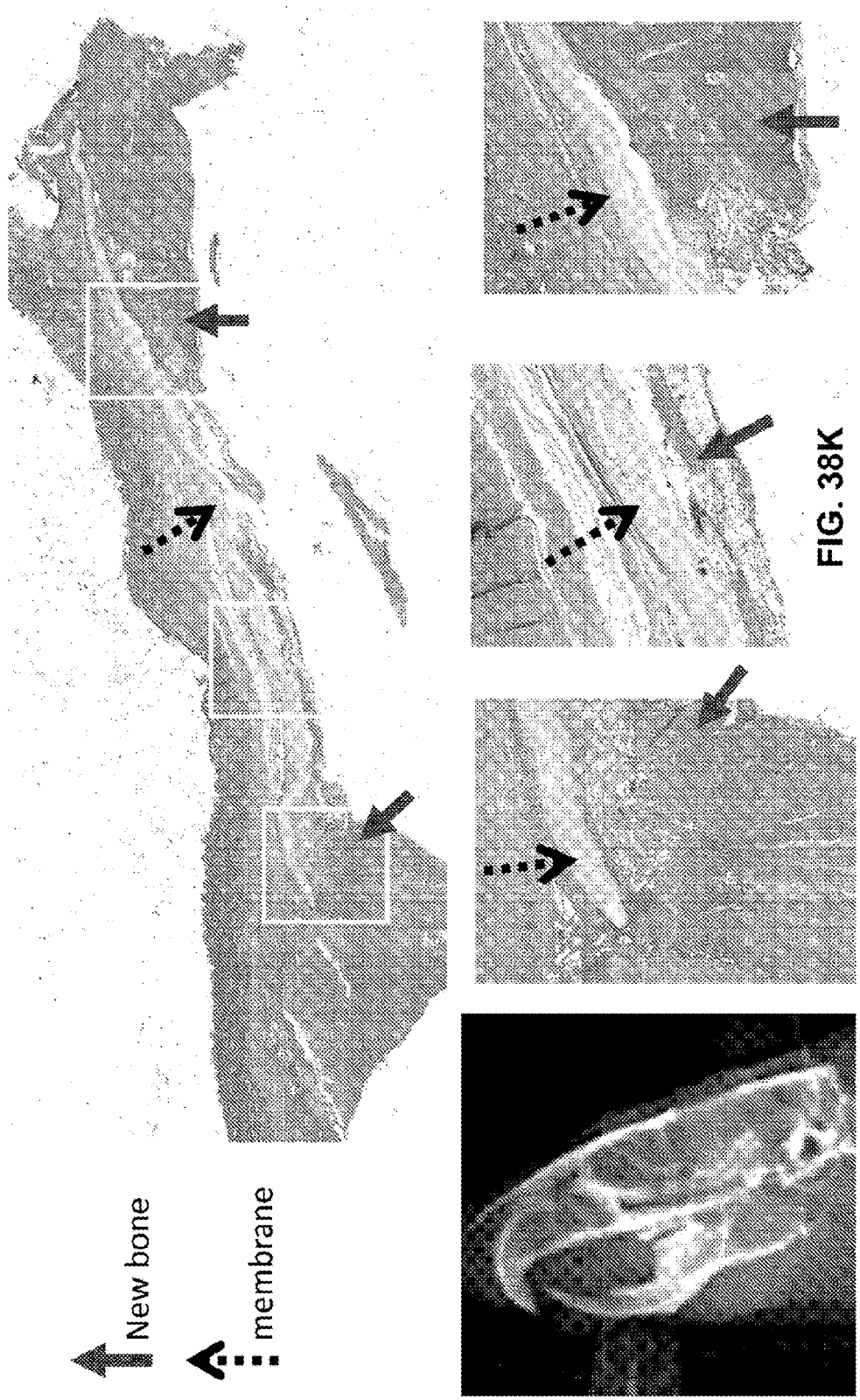
Figure 38L:
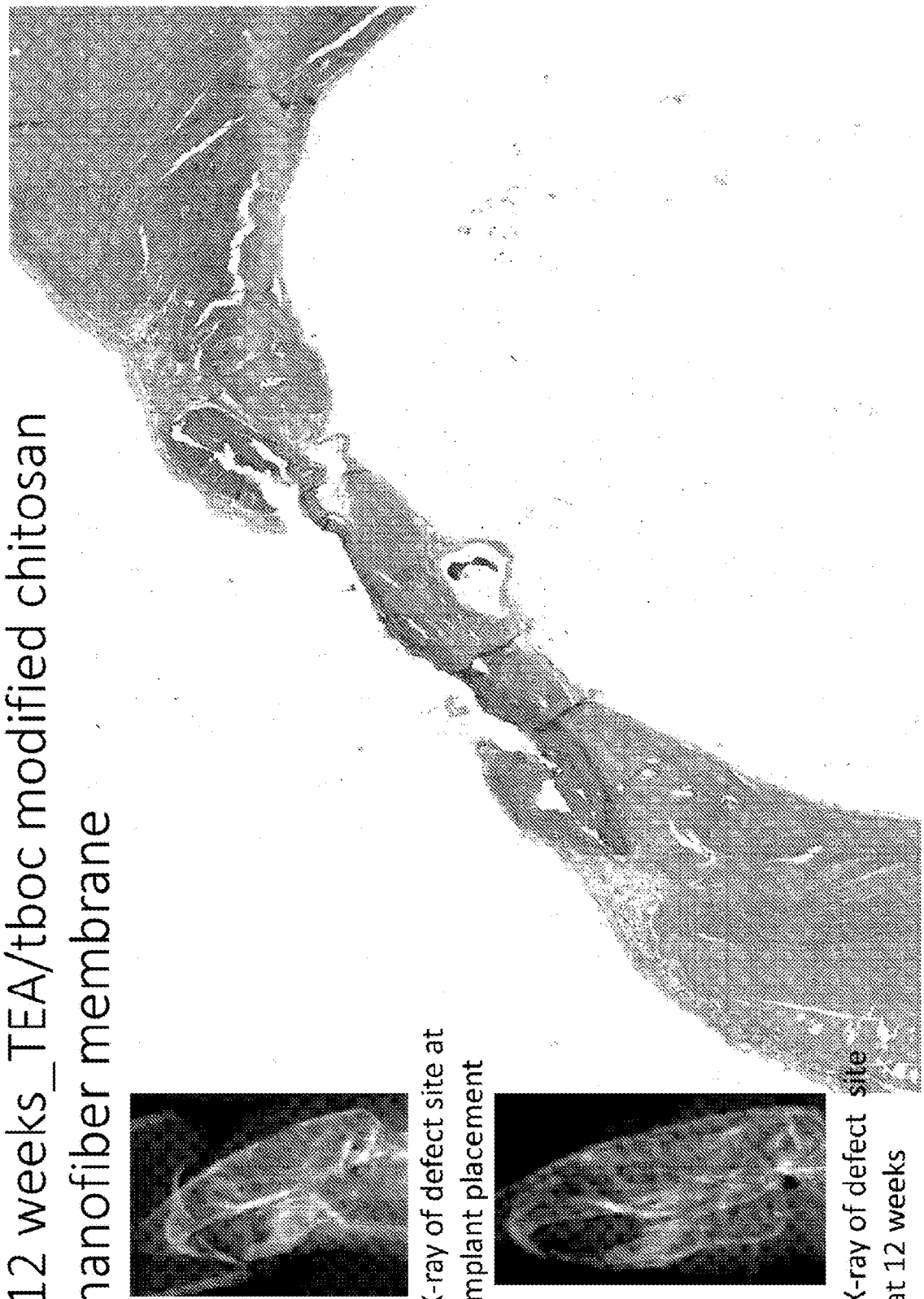
Figure 38M:
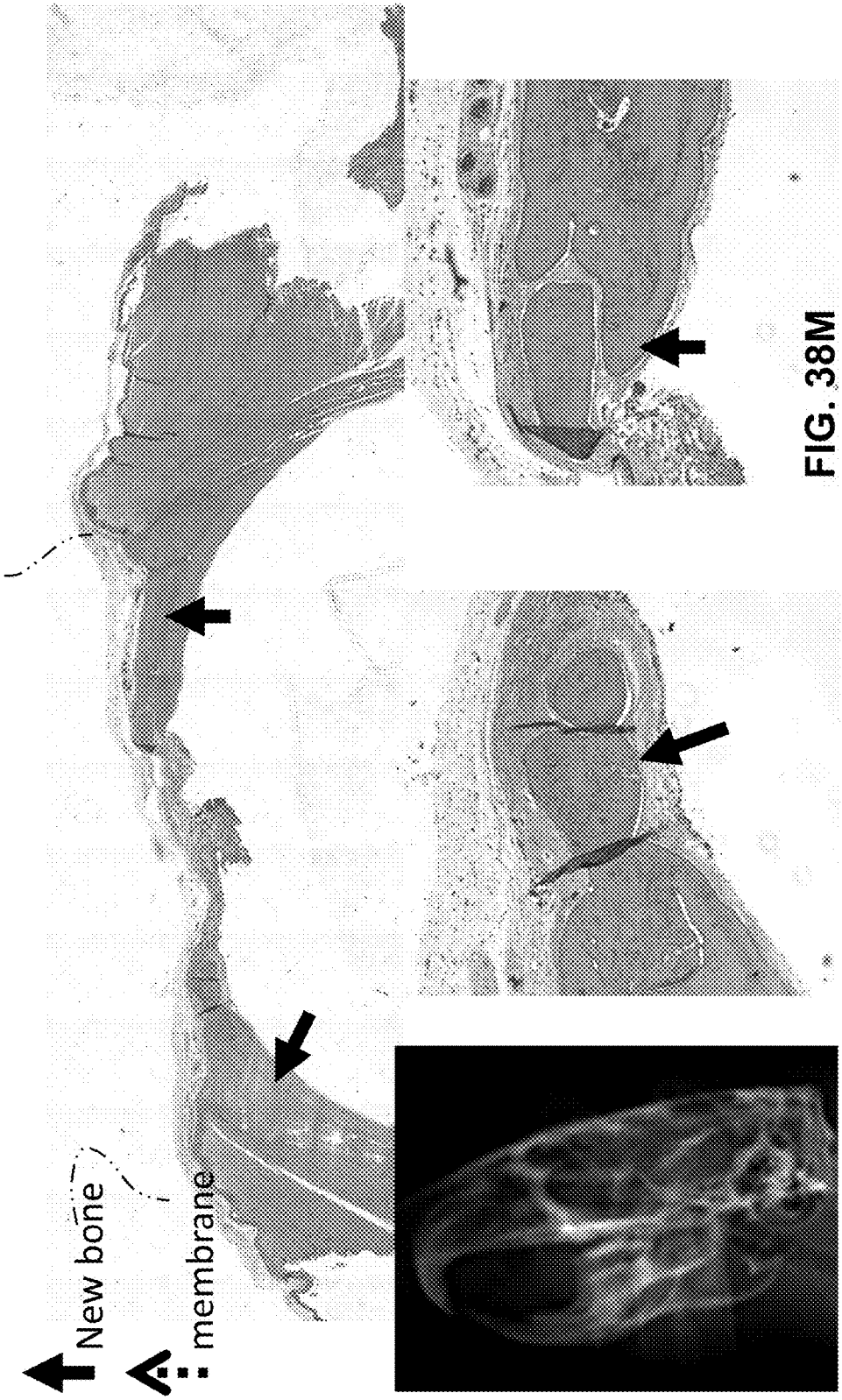

X-rays were taken in the lateral view since this enabled easy viewing of the defect in the thin rat calvarial bone. The membrane was transparent in the x-ray. At two weeks, the calvarial defect was still seen as evidenced by the radiolucent area, indicating little to no bone formation (FIG. 38A). At three weeks the defect was still apparent but evidence of early fibrous/woven bone was observed as evidenced by increase in radio-opacity in the defect (FIG. 38B). At 9 (FIG. 38C) and 12 weeks (FIG. 38D), the radio-opacity increased over the defect indicating development of bone over and along the barrier membrane. Close inspection of the 12 week radiograph revealed that bone was forming along the membrane but not filling the defect. This was expected since the defect site was not filled with bone graft material. At 9 weeks, the x-ray was taken at different x-ray energy settings so direct comparison between the 2, 3, and 12 week images was not possible.

Evaluation of chitosan nanofiber membranes in rat calvarial model showing preliminary x-ray results was done comparing butyric anhydride- and triethanolamine/N-tert-butoxycarbonyl (TEA/t-BoC)-modified nanofibrous chitosans to a commercial collagen membrane. Electrospun chitosan nanofiber guided bone regeneration (GBR) membranes were modified by butyric anhydride or TEA/TBoC mechanisms to stabilize nanofibers in aqueous solutions. 15 mm diameter chitosan nanofiber membranes were implanted to cover 8 mm diameter critical sized rat calvarial defects; a commercial collagen membrane (Biomend Extend, Zimmer Dental) was used as a control. 15 animals (5 animals per membrane type) were x-rayed at implantation (0 week) and at 3 weeks after euthanasia (FIGS. 38E-38G). Samples retrieved from animals at 3 weeks were used to examine initial healing histologically (38E-38G). 15 animals (5 animals per membrane type) were x-rayed at implantation (0 week) and at 4, 8 and at 12 weeks after euthanasia. Samples retrieved from animals at 12 weeks were used to examine bone formation histologically (FIGS. 38H-38M). Histomorphometric analyses and inflammatory response scoring are shown in FIGS. 36C-36F These data showed that TEA/TBoC-modified nanofibrous chitosans had a strong tendency to promote early bone growth over commercially available collagen membranes. In addition, the collagen membranes showed more degradation and less bone formation than TEA/TBoC-modified nanofibrous chitosans and the TEA/TBoC after the onset of early bone formation showed little sign of inflammation (FIGS. 36C-36F). All membranes exhibited limited inflammatory responses. No difference in inflammatory responses based on histological scores to chitosan-based membranes vs collagen membranes was observed. Chitosan membranes exhibited tissue wound healing responses equal to collagen, the gold standard. There appeared to be a slight trend for more bone formation with chitosan-based membranes at 3 and 12 weeks as compared to collagen based on histomorphometric measurements, though there was no statistically significant differences. Increase in bone formation at early time points may be an advantage for stimulating faster healing.

Figure 39B:
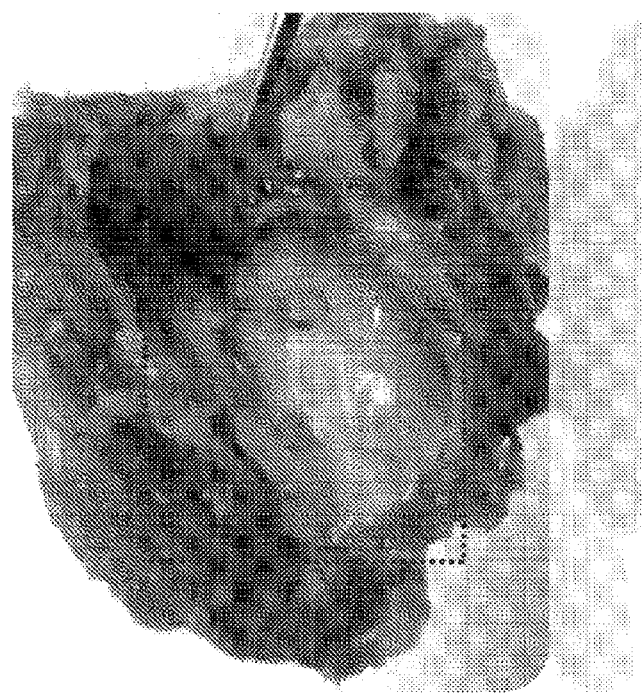
FIG. 39B shows ventral images of tissue sample at 12 weeks with no gross inflammation and normal tissue appearance.
Figure 39A:
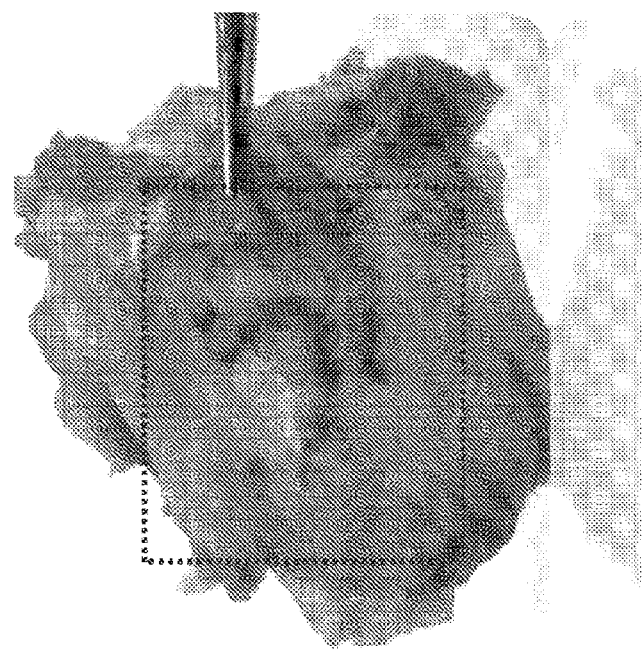
FIG. 39A shows dorsal images of tissue sample at 12 weeks with no gross inflammation and normal tissue appearance.

Gross histology of the implants retrieved from animal at the 12 week time point showed no gross inflammation and a normal tissue appearance (FIG. 39A dorsal view and FIG. 39B ventral view). Based on the x-ray images and gross histology, the membranes exhibited biocompatibility and supported bone formation.

Example 15: Chemical Modification of Chitosan

Figure 40:
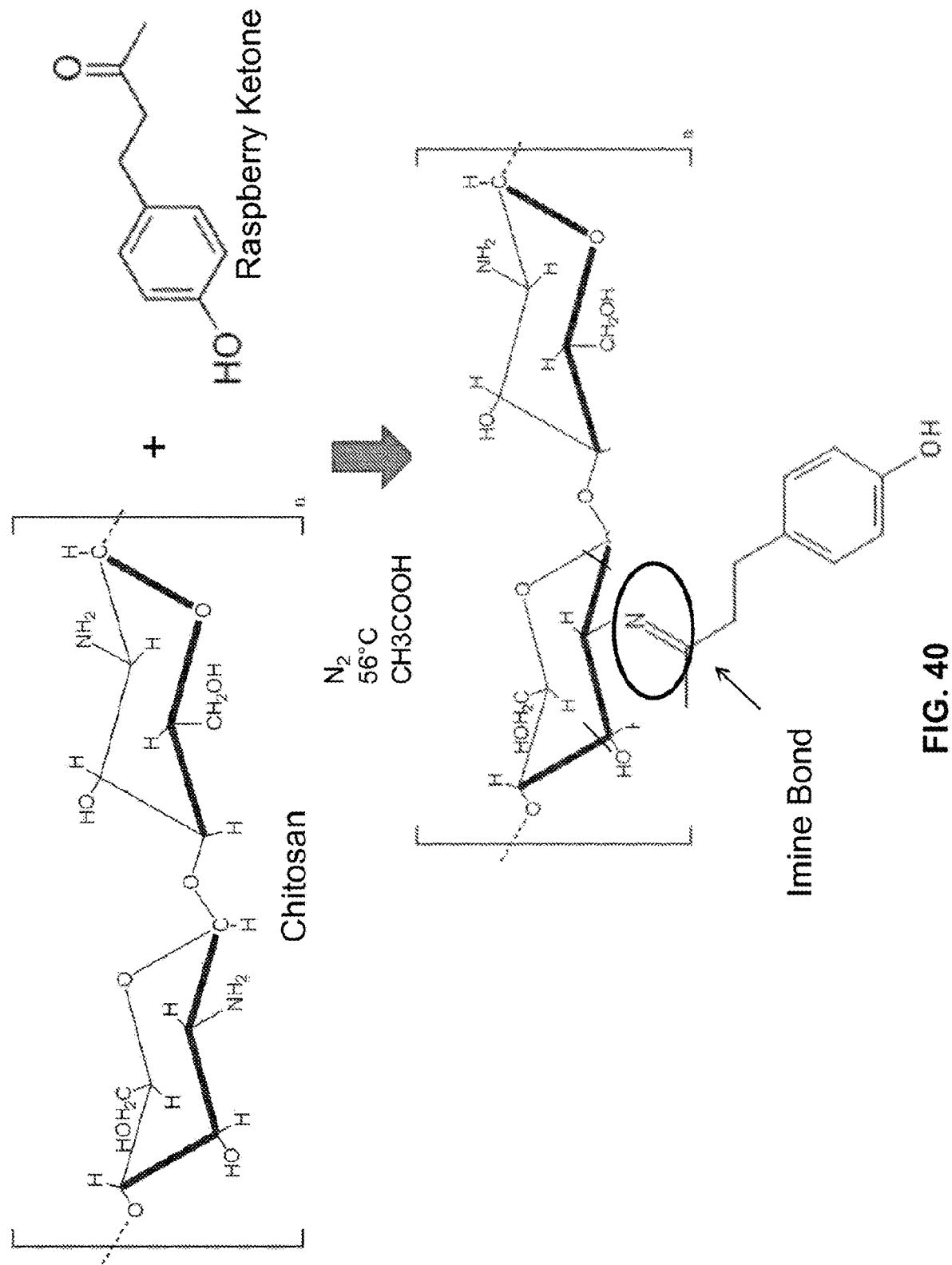
FIG. 40 is a schematic of the chemical reaction to modify the chitosan with raspberry ketone.

Raspberry ketone (Sigma) was added to de-aerated 2% chitosan by weight (87% degree of deacetylation) in 2% acetic solution in 1.6:2 ratio. The mixture was stirred overnight at 85° C. then lyophilized. The lyophilized modified chitosan was combined with unmodified chitosan in a 0:1, 25:75 and 50:50 ratio to make a 4% weight volume polymer in 5% acetic acid solution. FIG. 40 is a schematic of the chemical reaction to modify the chitosan with raspberry ketone.

Figure 41:
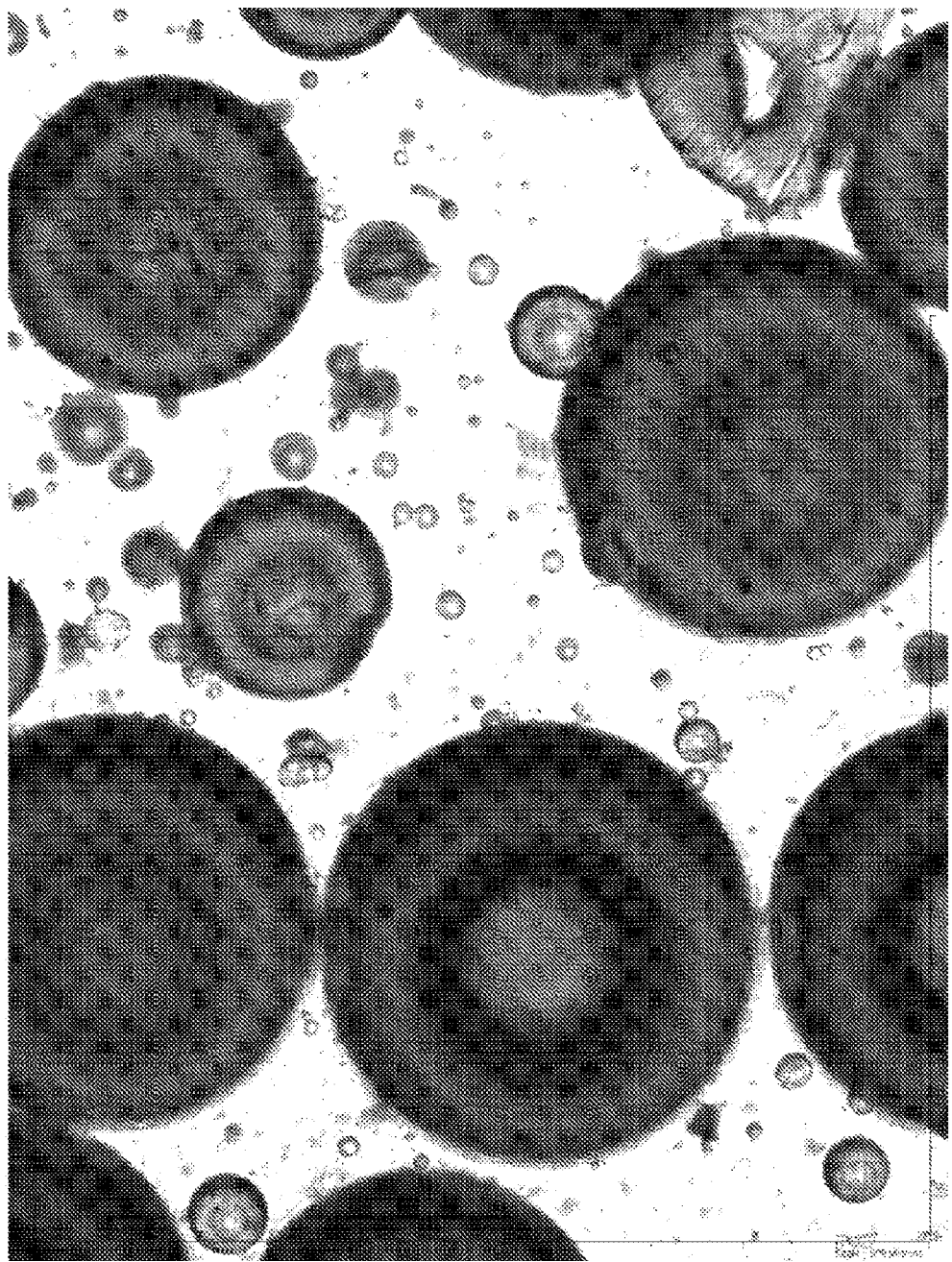
FIG. 41 is a an image showing microspheres at 10× magnification using a light microscope.

Using a water in oil emulsion crosslinking technique (Indian J Pharm Sci. 2007; 69:498-504), the modified chitosan solution was added to liquid paraffin while stirring and then crosslinked by 5 mM genipin (Wako) in acetone for about 12 hours. The microspheres were recovered by centrifugation and size characterization was performed using imaging software (ImageJ, NIH) on images taken under light microscopy. FIG. 41 is a an image showing microspheres at 10× magnification using a light microscope. Light microscopy images of modified chitosan microspheres showed spherical shape with a range of sizes (Table 1). Spheres below 10 μm diameters were excluded as it was difficult to observe microspheres under this size in the light microscope.

TABLE 1

Size distribution of modified chitosan microspheres by percentage.

| Diameter (μm) | % Microspheres |
| --- | --- |
| 10-30 | 17.8 |
| 31-60 | 34.2 |
| 61-100 | 26 |
| >100 | 21.9 |

Figure 42:
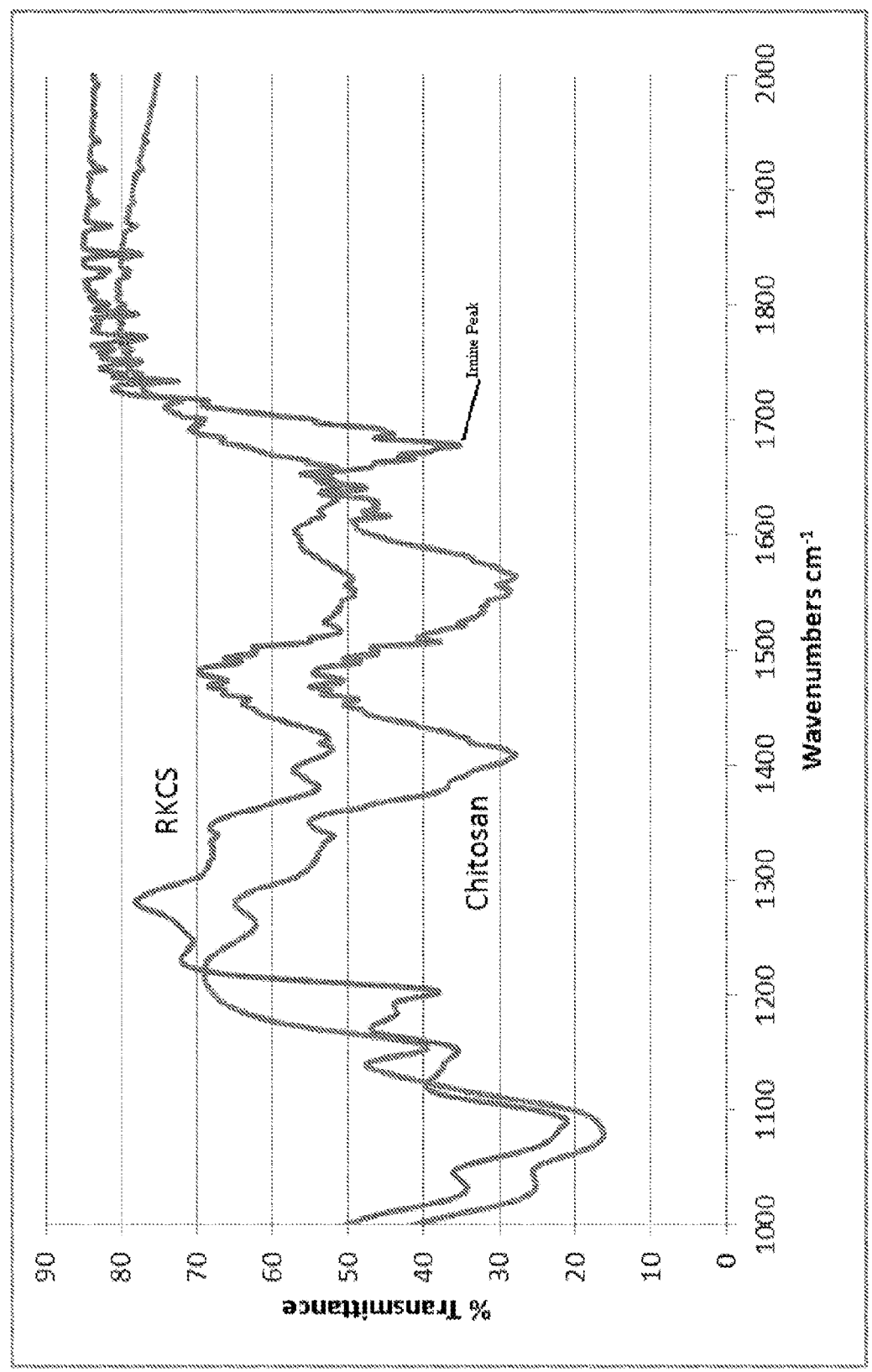
FIG. 42 is an image of Fourier Transform Infrared Spectroscopy (FTIR) of the unmodified chitosan and raspberry ketone chitosan.
Figure 43:
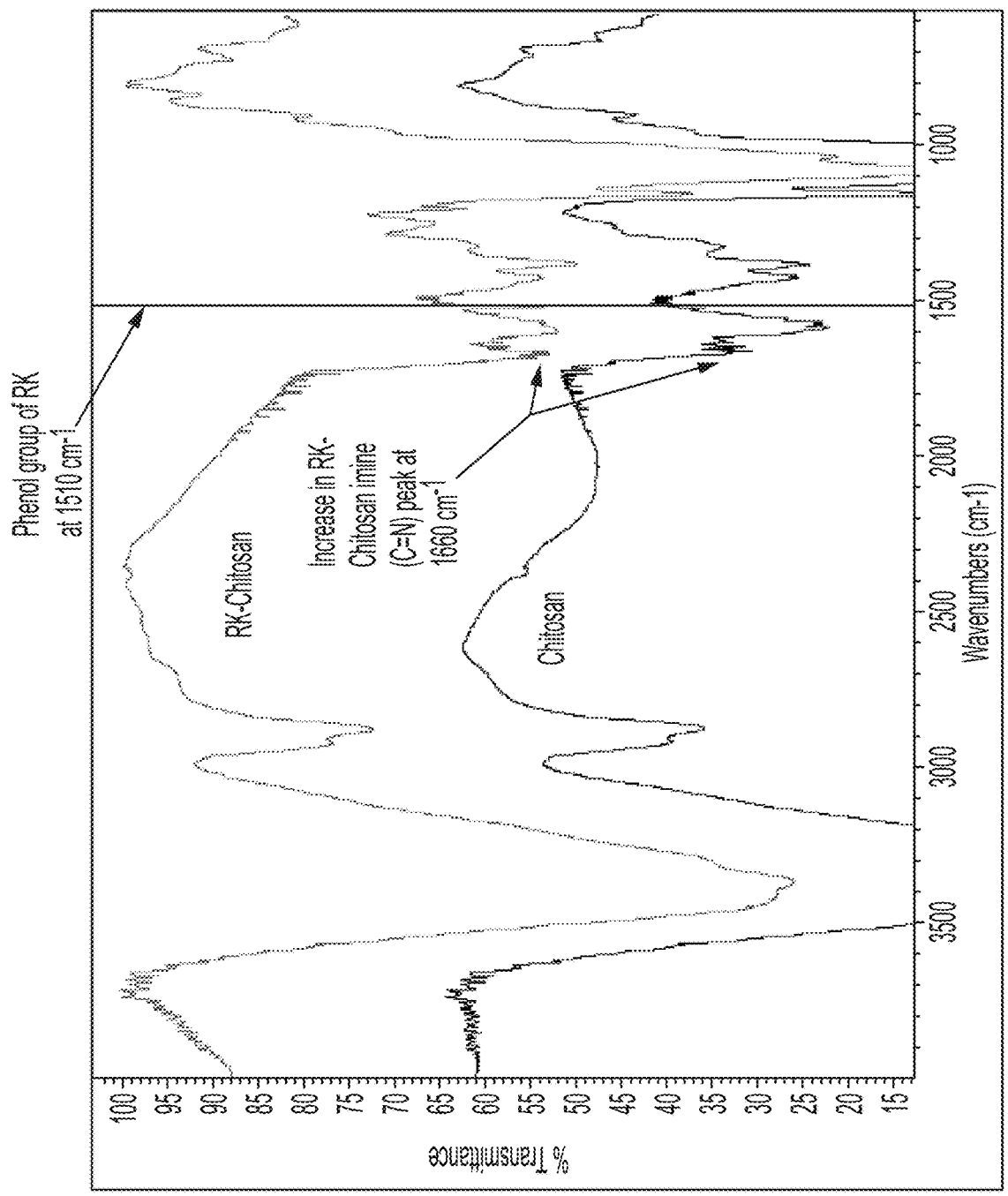
FIG. 43 is a FTIR spectra showing the phenol group from the raspberry ketone on the modified chitosan (upper line) as compared to the unmodified chitosan (lower line).
Figure 44:
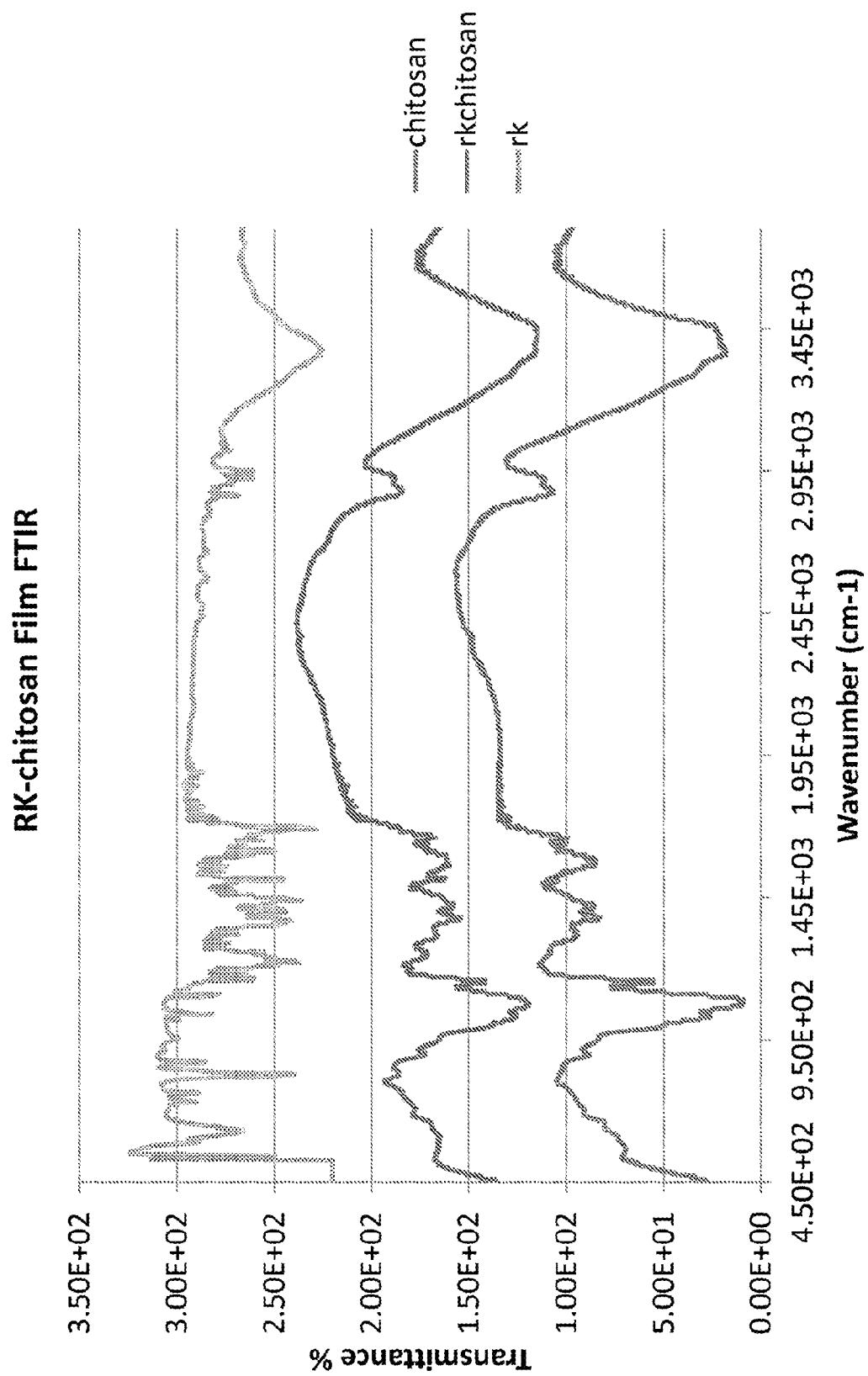
FIG. 44 is a FTIR spectra showing raspberry ketone (upper line), modified chitosan (middle line), and unmodified chitosan (lower line).

Fourier transform infrared spectroscopy (FTIR) was performed to determine if raspberry ketone had attached to the chitosan via an imine bond. FIG. 42 is an image of Fourier Transform Infrared Spectroscopy (FTIR) of the unmodified chitosan and raspberry ketone chitosan. The FTIR spectrum displayed a peak at 1680 cm$^{-1}$ which corresponded to the imine bond between the raspberry ketone and chitosan (FIG. 42). This peak is not present in the unmodified chitosan. FIG. 43 is also a FTIR spectra showing the phenol group from the raspberry ketone on the modified chitosan (upper line) as compared to the unmodified chitosan (lower line). Another FTIR spectra was done on modified chitosan films for convenience in FIG. 44.

Figure 45:
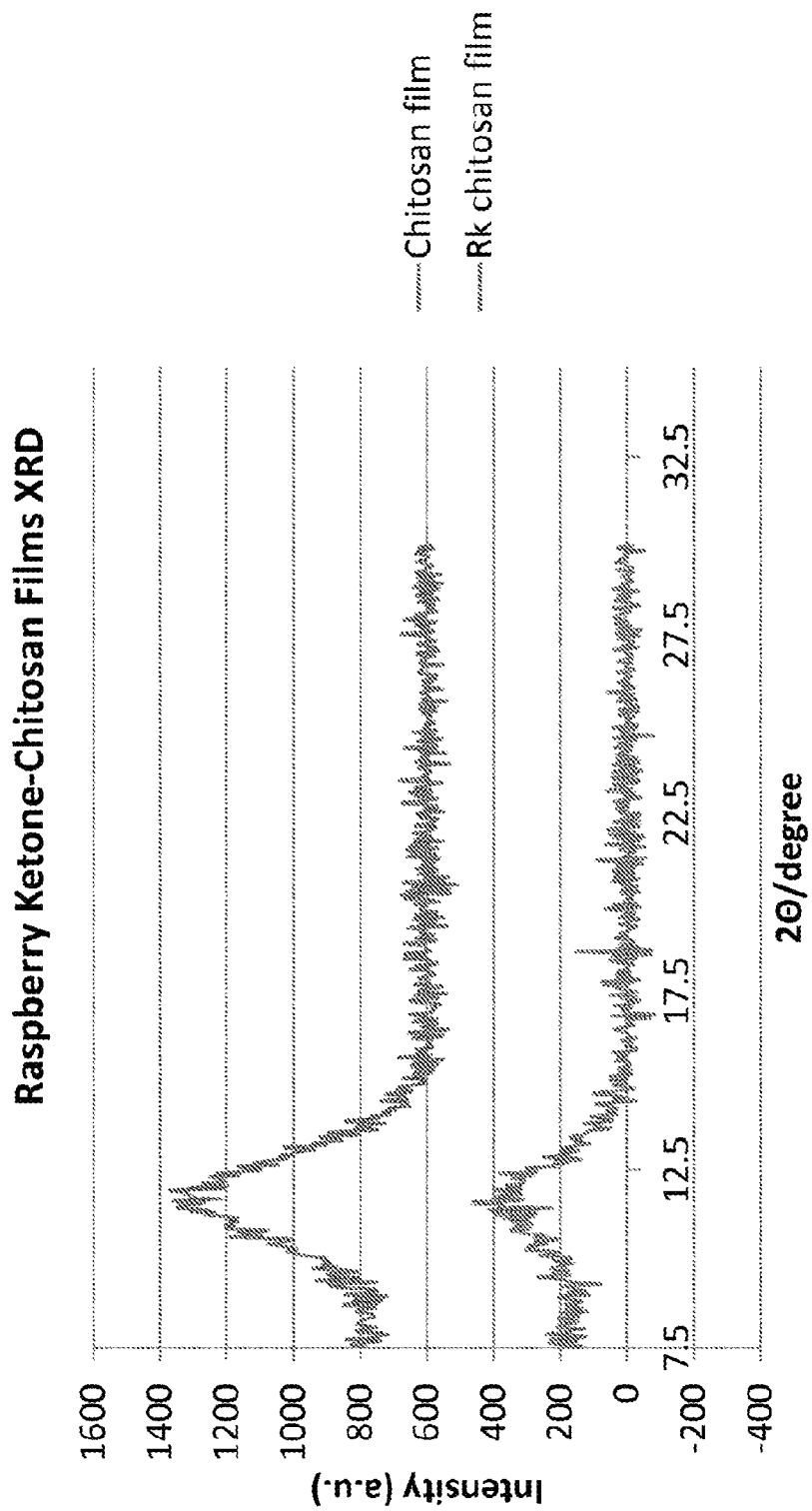
FIG. 45 is a graph showing the X-ray diffraction scattering performed on the unmodified chitosan film (lower line) and the raspberry ketone modified chitosan film (upper line).
Figure 46:
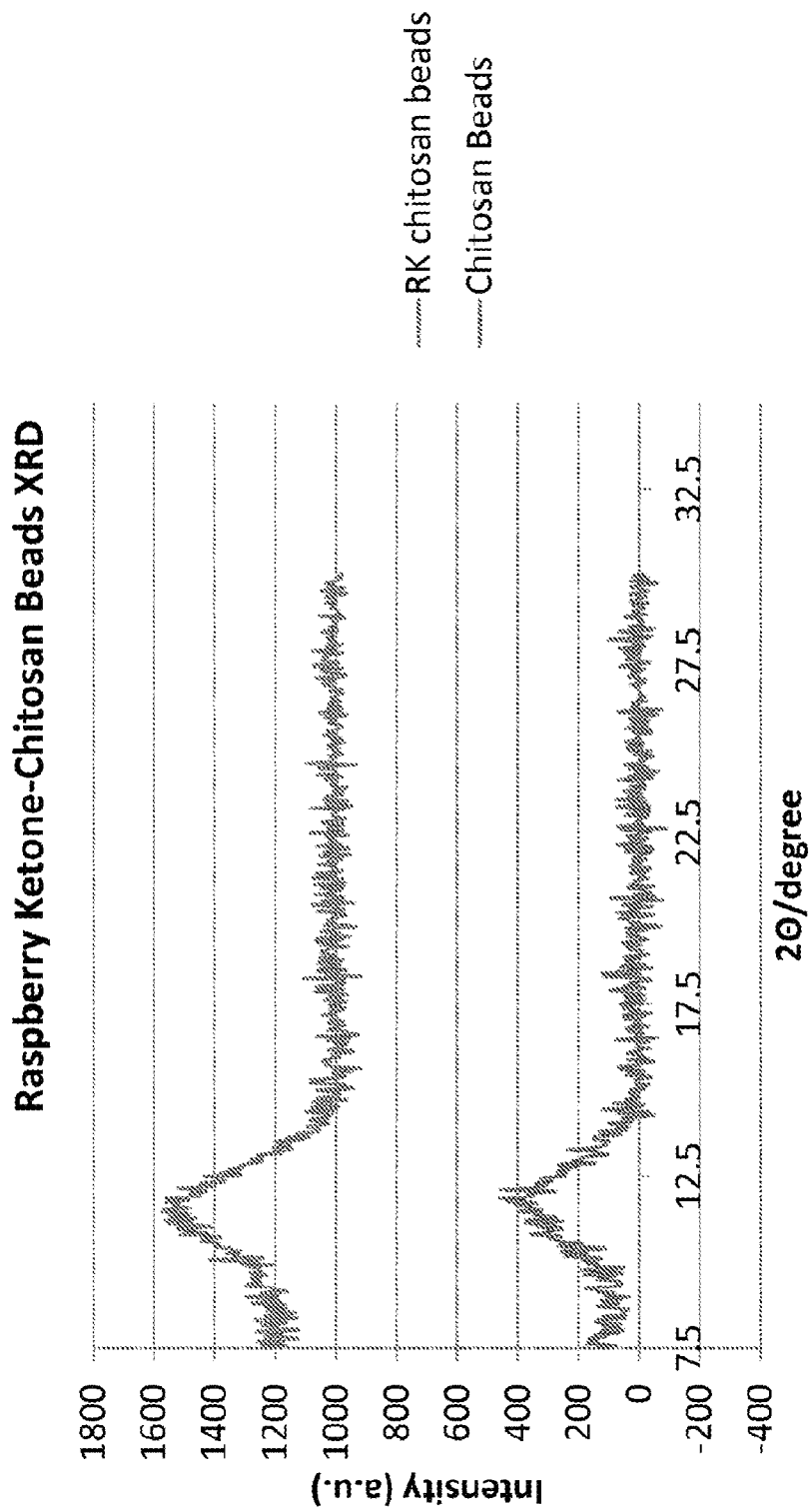
FIG. 46 is a graph showing the X-ray diffraction scattering performed on the unmodified chitosan beads (lower line) and the raspberry ketone modified chitosan beads (upper line).
Figure 47:
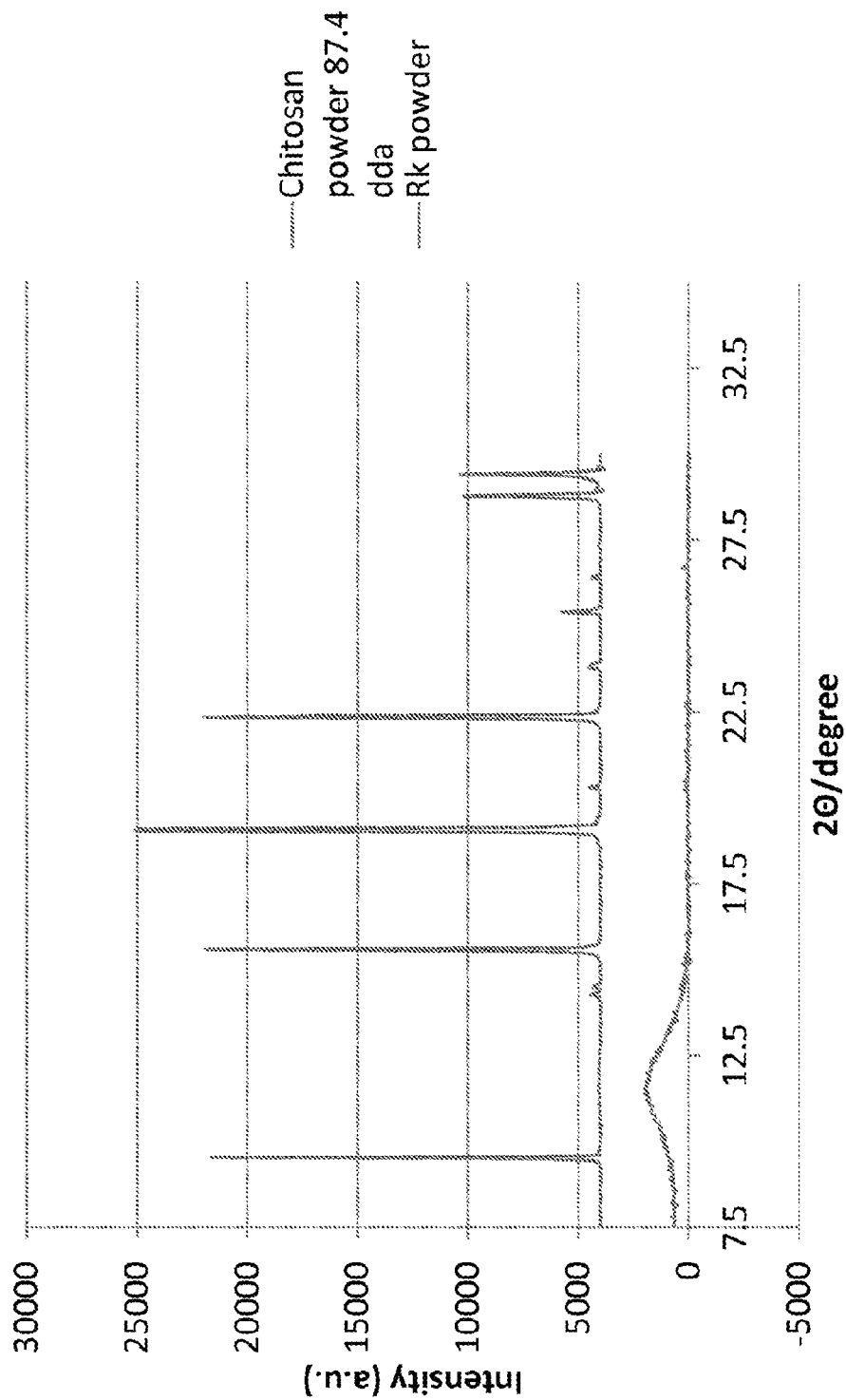
FIG. 47 is a graph showing the X-ray diffraction scattering performed on the unmodified chitosan powder (lower line) and the raspberry ketone modified chitosan powder (upper line).

X-ray diffraction of unmodified chitosan and raspberry ketone modified chitosan was performed. FIG. 45 is a graph showing the X-ray diffraction scattering performed on the unmodified chitosan film (lower line) and the raspberry ketone modified chitosan film (upper line). FIG. 46 is a graph showing the X-ray diffraction scattering performed on the unmodified chitosan beads (lower line) and the raspberry ketone modified chitosan beads (upper line). FIG. 47 is a graph showing the X-ray diffraction scattering performed on the unmodified chitosan powder (lower line) and the raspberry ketone modified chitosan powder (upper line).

Figure 48:
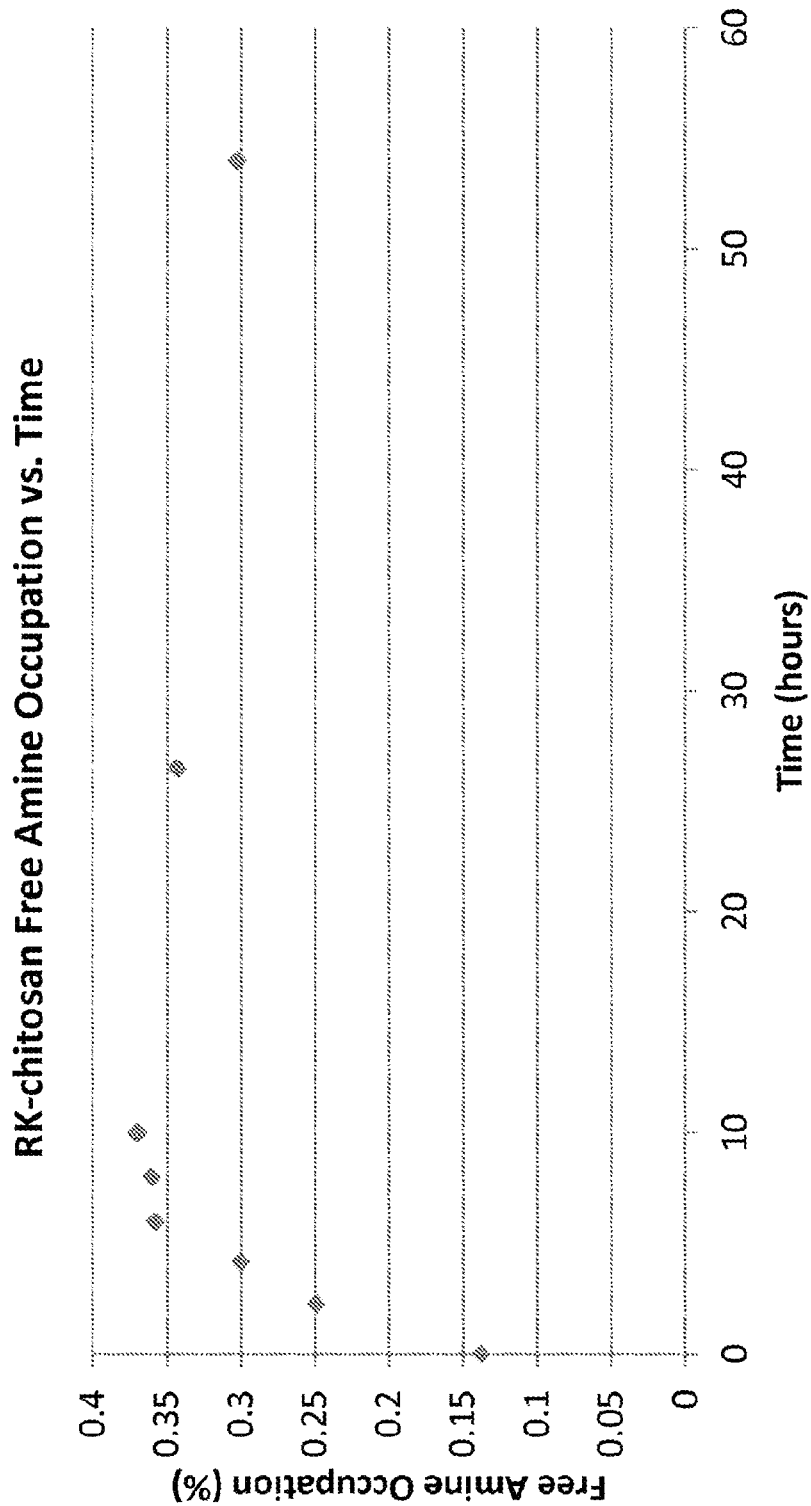
FIG. 48 is a plot showing control over the degree of modification of the chitosan by the raspberry ketone as indicated by the decrease in the number of free aminogroups on the chitosan polymer.

FIG. 48 is a plot showing control over the degree of modification of the chitosan by the raspberry ketone as indicated by the decrease in the number of free amino-groups on the chitosan polymer. As the amino groups on the glucosamine units in the chitosan polymer are reacted with the raspberry ketone, the occupancy of free amino groups increases.

Figure 49:
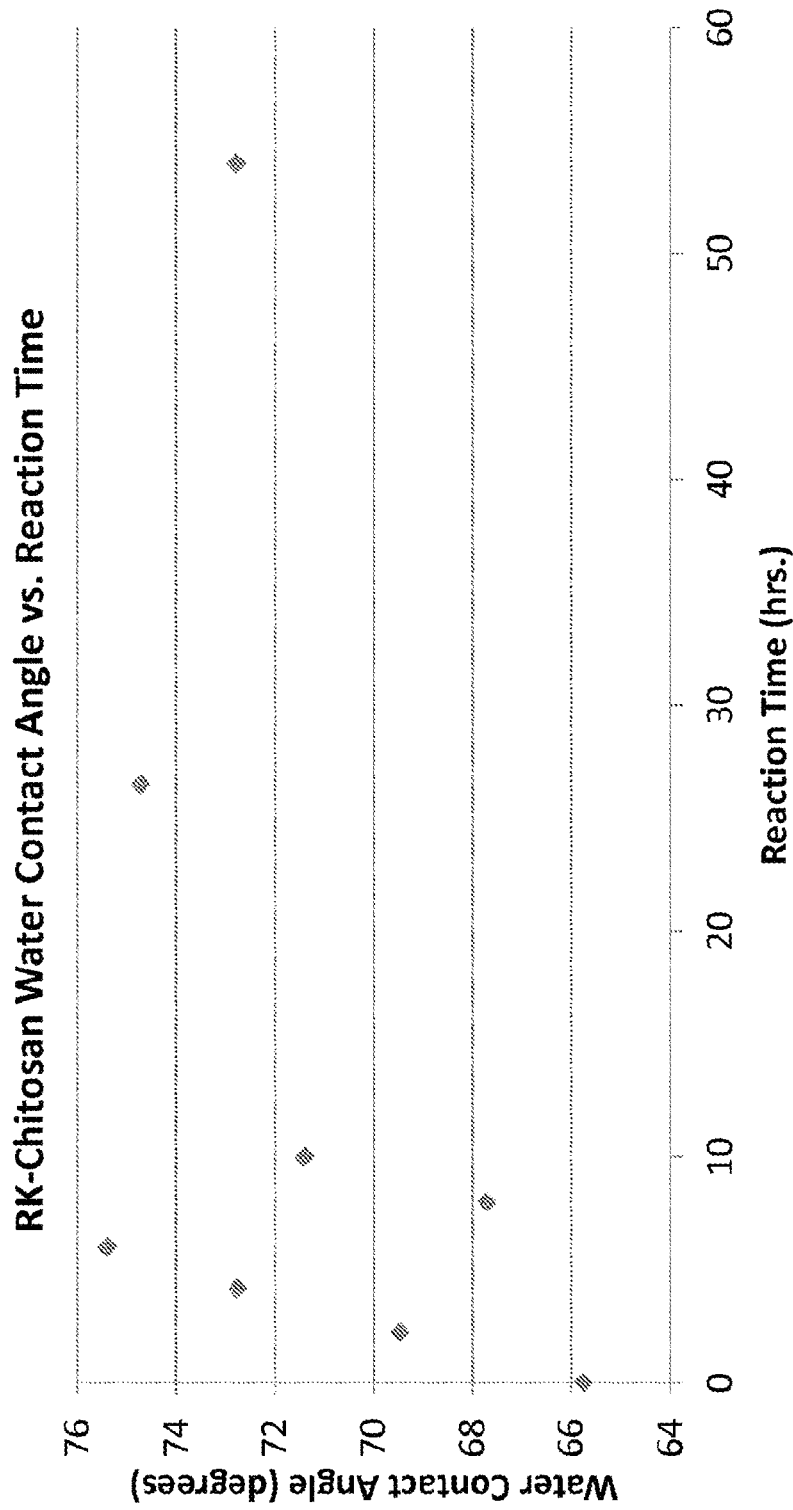
FIG. 49 is a plot showing that the hydrophobic character of the raspberry modified chitosan changes in proportion to the degree of modification.

FIG. 49 is a plot showing that the hydrophobic character of the raspberry modified chitosan changes in proportion to the degree of modification. As the number of raspberry ketone molecules are attached the chitosan molecule, the phenyl groups will increase the hydrophobic character of the polymer proportionally as indicated by the increase in water contact angles.

Figure 50:
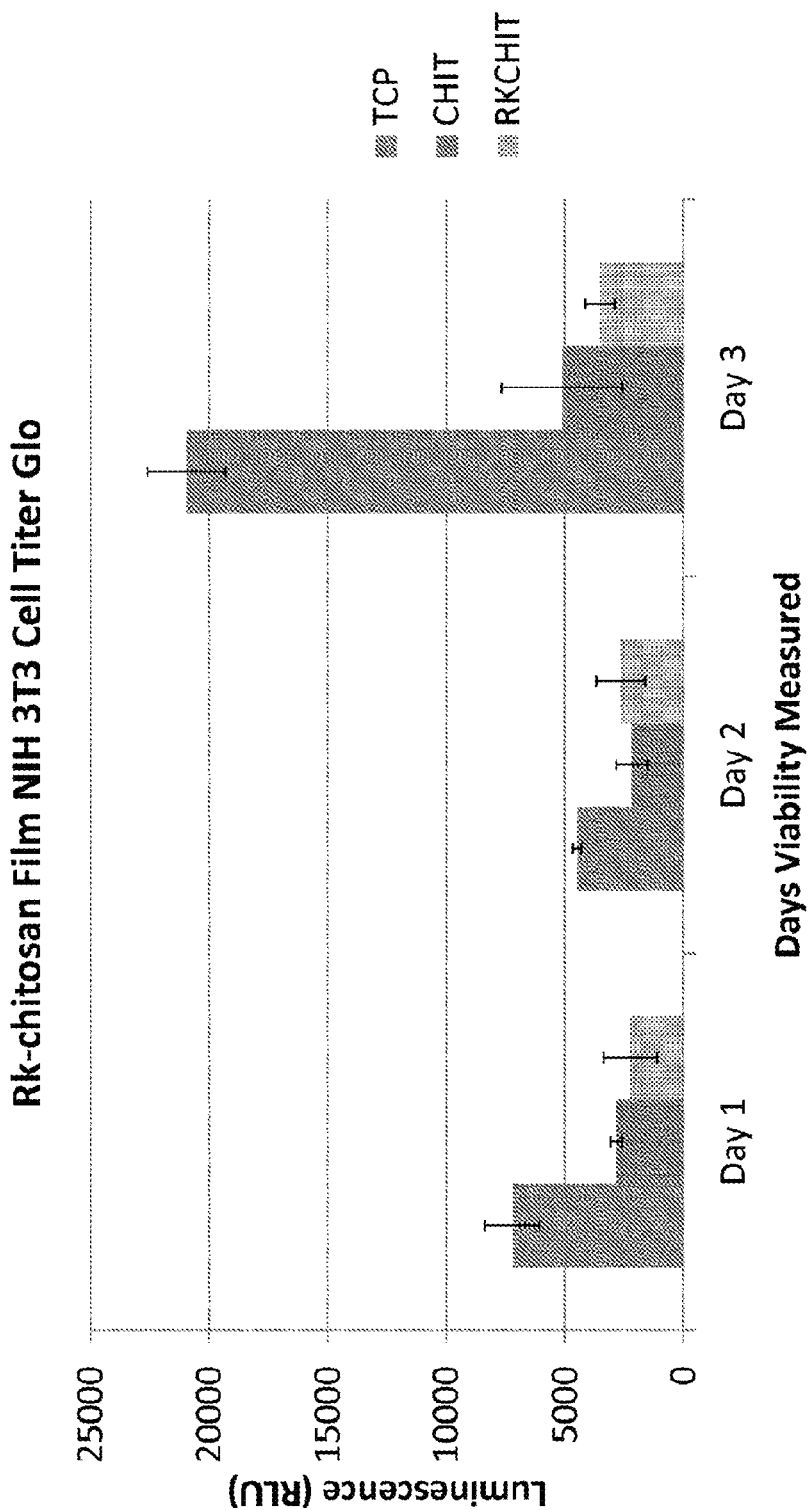
FIG. 50 is a graph showing NIH3T3 cell viability on control tissue culture plastic (TCP, left bar), unmodified chitosan film (CHIT, middle bar), and raspberry ketone modified chitosan films (RKCHIT, right bar).

FIG. 50 is a graph showing NIH3T3 cell viability on control tissue culture plastic (TCP, left bar), unmodified chitosan film (CHIT, middle bar), and raspberry ketone modified chitosan films (RKCHIT, right bar).

Figure 51:
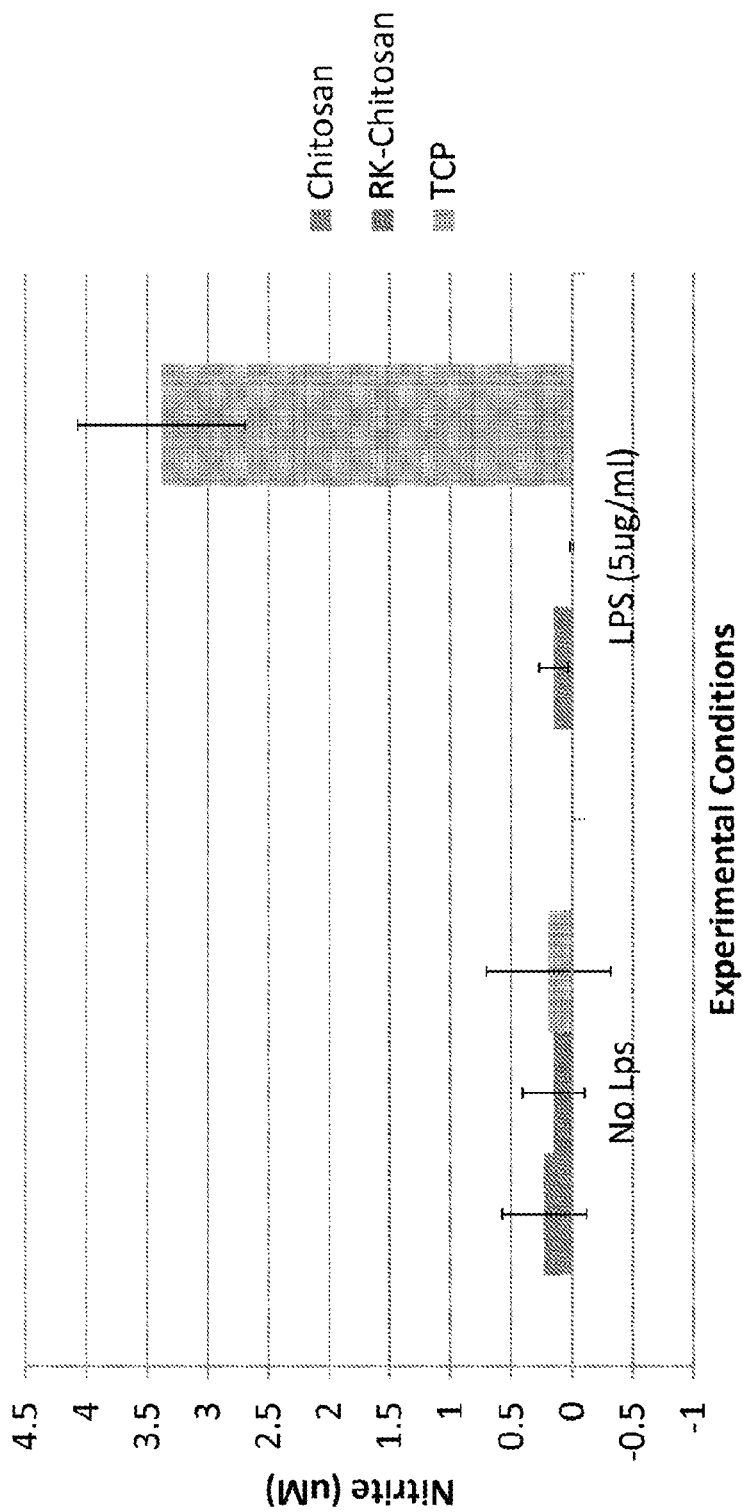
FIG. 51 is a graph showing nitrite levels from macrophages without lipopolysaccharide stimulation or with lipopolysaccharide stimulation when on (TCP, right bar), raspberry ketone modified chitosan films (RKCHIT, middle bar), and unmodified chitosan film (CHIT, left bar).
Figure 52:
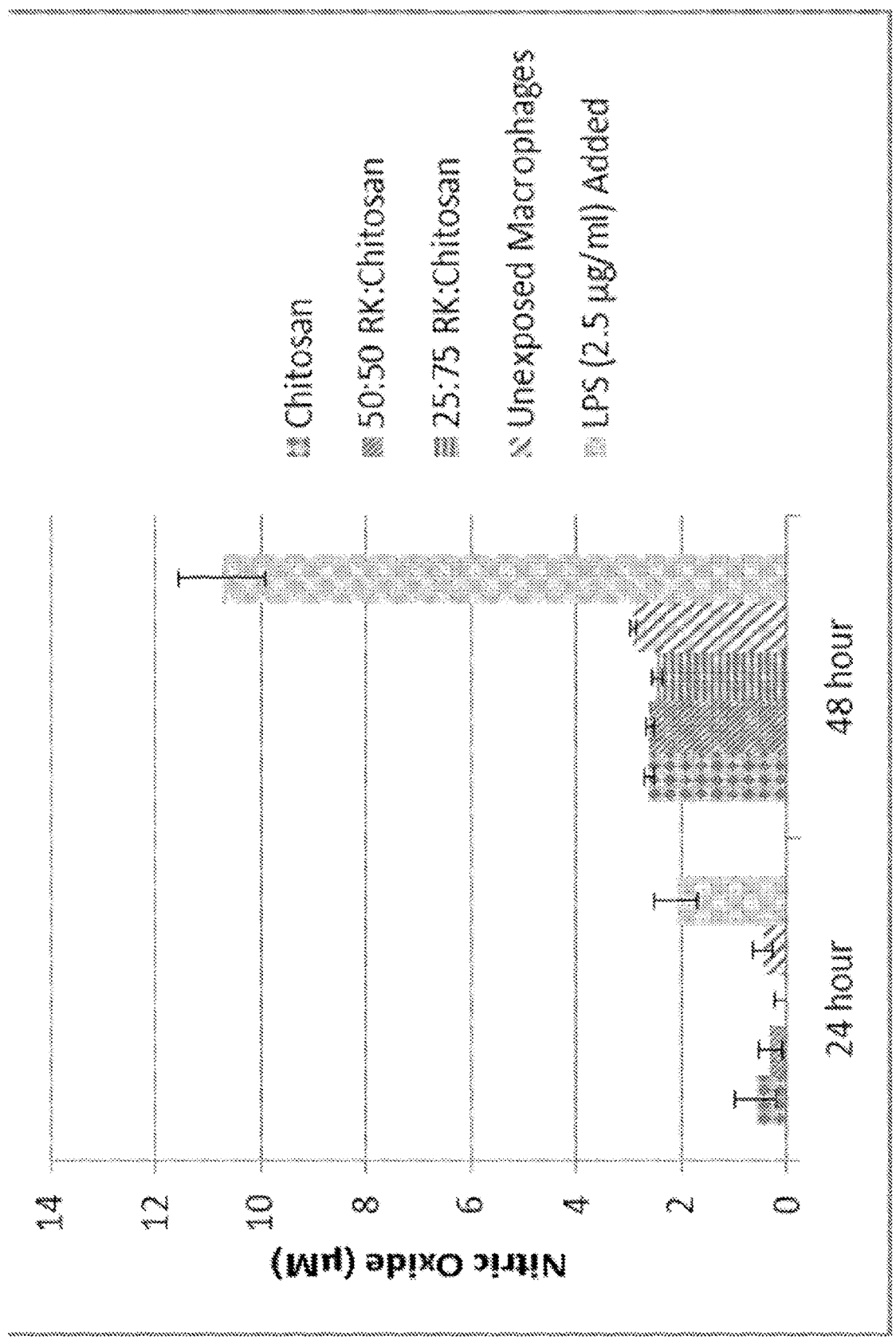
FIG. 52 is a graph showing nitric oxide levels from macrophages after 24 and 48 hours when on unmodified chitosan film, 50:50 ratio of raspberry ketone modified chitosan to unmodified chitosan film, 25:75 ratio of raspberry ketone modified chitosan to unmodified chitosan film, unexposed macrophages without lipopolysaccharide stimulation, and macrophages with lipopolysaccharide stimulation.

In vitro analysis of the modified chitosan microspheres was performed by exposing macrophages (RAW 264.7) to the microspheres for 48 hours and measuring the nitric oxide response. Five groups (n=4) were analyzed. Macrophages were exposed to the microspheres of the different weight ratios including unmodified chitosan microspheres. Cells exposed to 2.5 μg/ml lipopolysaccharide (LPS) were used as positive controls, and cells with no LPS or microspheres were used as negative controls. Samples were taken at 24 and 48 hour intervals and nitric oxide concentration was measured using a Griess Reagent System (Promega). Macrophage cells exposed to all microsphere compositions showed low level nitric oxide production similar to the negative controls. Only the positive control cells exposed to lipopolysaccharide exhibited high levels of nitric oxide production (FIGS. 51, 52 and 53).

Figure 53:
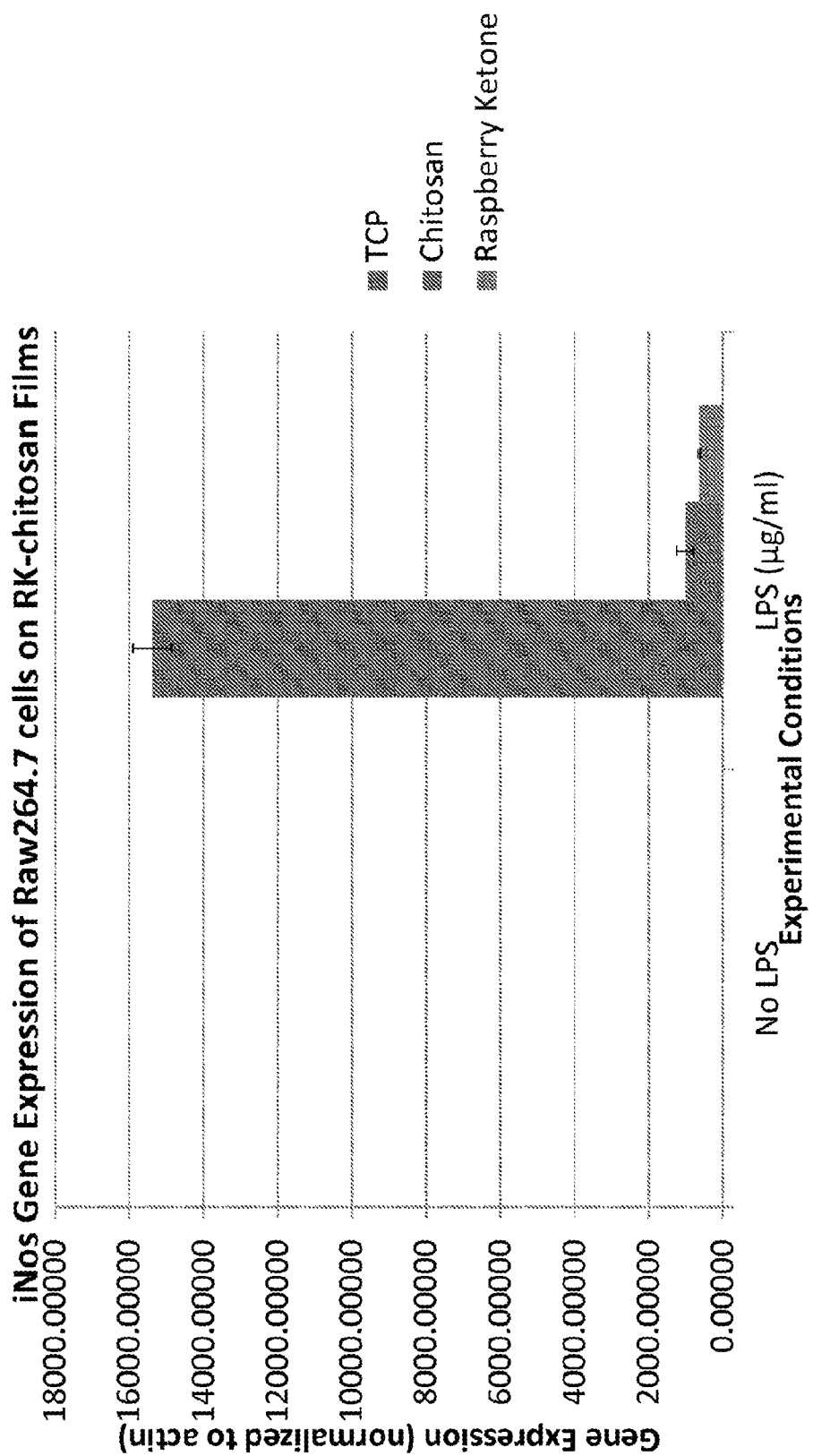
FIG. 53 is a graph showing reduction in inducible nitric oxide synthase gene expression (iNOS) without lipopolysaccharide stimulation or with lipopolysaccharide stimulation when on tissue culture plastic (TCP, left bar), unmodified chitosan film (chitosan, middle bar), and raspberry ketone modified chitosan films (Raspberry Ketone, right bar). The gene expression axis (y-axis) is the calculated gene expression normalized to the expression for the actin gene in each group and relative to the control tissue culture plastic group that was not exposed to LPS.

Inducible nitric oxide syntase (iNos) gene expression in raw264.7 mouse monocytes on chitosan and raspberry ketone modified chitosan were significantly decreased from the control tissue culture plastic group, with raspberry ketone chitosan further reducing iNos expression in the group exposed to LPS (FIG. 53). The group with no LPS added showed no iNos expression which was expected.

A protocol is disclosed herein that allows the preparation of microspheres from raspberry ketone-modified chitosan via water in oil emulsion technique. While the size range is relatively large, the majority of microspheres fell between 30 and 90 μm diameter. The FTIR spectra demonstrated the imine bond peak appeared after modifying the chitosan with raspberry ketone indicating that raspberry ketone was bonded to the chitosan and not just absorbed to the chitosan polymer. The in vitro data demonstrates that the modified microspheres did not activate nitric oxide production at a higher level than the negative controls or unmodified chitosan groups. Further research is needed to explore whether the raspberry ketone modified chitosan microspheres can inhibit an nitric oxide response from macrophages that are exposed to LPS, as well as degradation profiles.

The results described herein relating to acylated chitosan nanofibers were obtained using the following methods and materials.

Electrospinning Procedure: electrospun chitosan nanofiber membrane with random fiber orientation was fabricated by electrospinning. Briefly, a 5.50 (wt/vol) % chitosan (70% deacetylated, MW ¼ 311.5 KDa, Primex Inc.) solution in 70 (v/v) % TFA and 30 (vol/vol) % DCM was gently mixed overnight. The solution was electrospun at 25 kV and the fibers were collected on a non-stick aluminum foil target (Reynolds Wrap VR, 38.1 cm diameter circular disc), positioned 15 cm from needle tip and rotated at 8.4 RPM by an AC motor to ensure even and random distribution of fibers.

Surface acylation: 10 mg of electrospun chitosan nanofibers mats were placed in Petri dish containing 1 ml of butyric anhydride and 1 ml of pyridine. The mixtures were stirred for 1 h at 20° C. After acylation, the electrospun chitosan nanofibers mats were washed by Soxhlet extraction with methanol overnight and dried by lyophilization.

De-acylation: 10 mg of acylated electrospun chitosan nanofibers membrane was placed in a Petri dish containing about 5 ml of 5% KOH solution. The mixtures were stirred for 1 h at 60° C. In another experiment, one gram of acylated chitosan nanofiber membrane was placed in a flask before adding about 100 ml of 5% KOH solution or other base. The ratio of acylated chitosan to base may be adjusted as needed. The mixture was stirred by a magnetic stirrer at 60° C. The degree of deacylation to remove the acyl groups, such as fatty acid anhydrides, attached to the nanofiber surface were controlled by modifying the reaction times. The deacylated chitosan nanofiber membrane was removed from the solution, placed in a dialysis tubing, and dialyzed in distilled water for about 24 hours at room temperature. The membranes were dried by lyophilization. or drying or other convenient method.

Fourier Transform Infrared Spectroscopy (FTIR): electrospun chitosan nanofibers membranes were dried at 80° C. for at least 1 h and grinded with KBr to make pellets. Spectra were recorded on a Spectrum One spectrometer (Perkin-Elmer, Eden Prairie, MN) from about 4000 to about 500 $cm^{-1}$ with a resolution of about 4 $cm^{-1}$ in wave number at room temperature.

Scanning Electron Microscopy (SEM): electrospun chitosan nanofiber membranes were coated with an approximately 20 nm layer of gold by an ion sputter coater and were observed with a SEM (Philips XL-30 ESEM).

Transmission Electron Microscopy (TEM): electrospun chitosan nanofiber membranes were sonicated and loaded on carbon supported copper grids. The grids were freeze-dried and viewed at 120 kV in a electron microscope.

X-ray diffraction: Wide-angle X-ray scattering (WAXS) was recorded on a Bruker D8 diffractometer. Electrospun chitosan nanofibers membranes were ground into a fine powder with a mortar and pestle, after submersion in liquid nitrogen. Powders were scanned in grazing angle reflection mode and data were collected with 2θ from 4 to 30.

Electrospinning: CSEF were prepared by electrospinning 5.5% wt/vol chitosan (71% DDA) in 70% TFA-30% methylene chloride solution at 25 kV onto a non-stick aluminum foil target rotating at 8.4 rpm.

Surface acylation: CSEF were acylated in acetic anhydride with or without pyridine for 1 hr at 20, 50 or 90° C. Pyridine derivatives 4-dimethylaminopyridine (DMAP) and 4-(1-pyrrolidinyl) pyridine may also be used. After reaction, the membranes were washed in sodium carbonate and water to remove by-products and acid contaminants.

Characterization: The acylated CSEF were characterized by immersion in PBS for stability, Fourier transform infrared spectroscopy (FTIR) for chemical structure, and electron microscope (TEM and SEM) for fiber diameter and morphology. Proliferation of osteoblast cells (SaOS-2) on membranes (n=5/membrane) was measured by the CellTitre Glow® (Promega) at 1, 3, and 5 days and compared to cast chitosan film controls. Cell morphology was observed by Live/Dead® staining (Molecular Probes).

Animal study: In the animal study, 10 Sprague Dawley rats weighting 250-280 g (approx. 2 months old) were used. Male animals of this size were selected to be skeletally mature and to avoid confounding factors associated with female estrous cycles. The test membranes were ethylene oxide gas sterilized prior to implantation. Each rat received one implant.

Rats were anesthetized with 4% isoflurane in oxygen for approximately 2 minutes. Maintenance of anesthesia was achieved with 2% isoflurane delivered via nosecone/non-rebreather. The dorsal part of the cranium was shaved and aseptically prepared with a solution of povidone iodine (BETADINE®). A U-shaped incision was made in the posterior part of the cranium, allowed the division of the subcutaneous fascia and the bilateral reflection of the periosteal flaps following blunt dissection, to expose the calvarial bone. Careful drilling with an 8-mm diameter trephine bur, mounted on a low-speed dental hand piece, around the sagittal suture, was used to create a standardized, round, defect. During drilling, the area was continuously irrigated with sterile saline solution. The calvarial disk was carefully removed to avoid tearing of the subjacent cranial structures.

A butyric anhydride modified membrane was placed to cover the circular defect overlapping the defect margin by at least 3-4 mm. There was one implant per animal. The periosteum and skin were carefully closed and secured with nylon sutures (e.g. Ethilon 4-0, Ethicon Endo-Surgery, Bridgewater, NJ) after membrane implantation. After surgery, animals will be housed individually and given subcutaneous injections of buprenorphine (0.15 mg/kg) for postoperative analgesia after surgery. Animals were given free access to rodent chow and water. Sites healed without complication. The study was conducted as part of the animal protocol (#0732) that was reviewed and approved by the Institutional Animal Care and Use Committee at The University of Memphis in compliance with the NIH Guide for the Care and Use of Laboratory Animals.

The results described herein related to chitosan nanofibers treated with tboc were obtained using the following methods and materials.

Manufacture of chitosan nonwoven nanofiber membranes: nanofibrous chitosan membranes with random fiber orientation are fabricated by electrospinning. Briefly, a 5.50 weight per volume percentage (w/v) chitosan (70% deacetylated, MW=311.5 KDa, Primex Inc.) solution in 70 (v/v) % trifluoroacetic acid and 30 (v/v) % methylene chloride was gently mixed overnight. Chitosans with other degrees of deacetylation (DDA)'s and MW may be used, though the exact weight percent of chitosan in the solvent spinning solution may need to be adjusted. The solution was loaded into a 10-mL syringe with a blunt 20 G, 3.81 cm stainless steel needle tip. The syringe was loaded into a syringe pump and the flow rate set to 20 µL/min. The solution was electrospun at 25 kV and the fibers were collected on a non-stick aluminum foil target (REYNOLDS WRAP®, 38.1 cm diameter circular disc), positioned 15 cm from needle tip and rotated at 8.4 RPM by an AC motor to ensure even and random distribution of fibers. The electrospinning apparatus was housed inside a ventilated box, which was vented to the fume hood. After electrospinning, the nanofibrous mat was put under vacuum overnight to remove residual solvent and carefully removed from the foil. Note that aligned or other fiber orientations may also be made through simple manipulation of the orientation of the collection target mandrell and speed of rotation.

Electrospinning chitosan: chitosan solution was prepared by dissolving 5.5% (w/v) weight per volume Chitosan (71% DDA) in 70% (v/v) trifluoroacetic acid (TFA) and 30% (v/v) dichloromethane (DCM). Solution was loaded with 25 kV voltage and electrospun with a pumping rate of 15 µL/min. Membranes were collected by non-stick aluminum foil in the distance of 15 cm.

Removal of TFA using TEA/acetone: in the post-electrospinning treatment, the membrane is treated in the circumstance of pure organic solvent to avoid swelling in aqueous solutions. The membrane is immersed in 10% (v/v) triethylamine (TEA)/Acetone solution for 8 hours under mild magnetic stirring to completely remove all trifluoroacetate ions and rinsed in pure acetone for 2 hours. The rinsing procedure is repeated two times in order to remove excess TEA. The purified chitosan membrane is placed in between two pieces of nylon net and quickly pressed to remove most of acetone. The membrane is immediately forwarded to the next protection step.

t-BOC protection of chitosan amino group in tetrahydrofuran (THF): the salt free chitosan membrane is then soaked in tetrahydrofuran solution containing di-t-butyl dicarbonate (Boc2O) (25 g/10 mL) in round bottom flask equipped with reflux condenser. The reaction is kept under mild magnetic stirring at the temperature of 65 degree Celsius. After 8 hours, the membrane is rinsed by pure tetrahydrofuran for 2 hours and repeated 2 times to fully remove unreacted di-t-butyl dicarbonate. The membrane is placed in between two pieces of nylon net and gently pressed to remove the solvent and then air-dried and stored in desiccator. The amount of t-BOC capping on the chitosan amino groups can be controlled by changing the di-t-butyl dicarbonate concentration and reaction conditions such as time and temperature. Additionally, 4-Dimethylaminopyridine (DMAP) or other cyclic amine catalyst may be used to increase reaction rate and or shorten reaction times for the t-BOC reaction.

Fourier Transform Infrared Spectroscopy (FTIR): electrospun chitosan nanofibers membranes were dried at 80° C. for at least 1 hour and grinded with KBr to make pellets. Spectra were recorded on a Spectrum One spectrometer (Perkin-Elmer, Eden Prairie, MN) from about 4000 to about 500 $cm^{-1}$ with a resolution of about 4 $cm^{-1}$ in wave number at room temperature.

Scanning Electron Microscopy (SEM): electrospun chitosan nanofiber membranes were coated with an approximately 20 nm layer of gold by an ion sputter coater and were observed with a SEM (Philips XL-30 ESEM).

Transmission Electron Microscopy (TEM): electrospun chitosan nanofiber membranes were sonicated and loaded on carbon supported copper grids. The grids were freeze-dried and viewed at 120 kV in a electron microscope.

X-ray diffraction (XRD): Wide-angle X-ray scattering (WAXS) was recorded on a Bruker D8 diffractometer. Electrospun chitosan nanofibers membranes were ground into a fine powder with a mortar and pestle, after submersion in liquid nitrogen. Powders were scanned in grazing angle reflection mode and data were collected with 2θ from 4 to 30.

Post-operation: Electrospun membranes (n=4/treatment) were treated by 1] using saturated $Na_2CO_3$ solution (control) or 2] our novel method based on using triethylamine (TEA) and tert-butyl dicarbonate (tboc). The TEA is used to extract the TFA salts while the tboc is used to protect the —$NH_2$ groups on the chitosan to reduce fiber swelling and maintain nanofibrous structure.

Characterization: Morphology and diameter of fibers in membranes was examined by scanning electron microscope (SEM) and transmission electron microscope (TEM). Fourier transform infrared spectroscopy (FTIR) spectra used to evaluate the removal of the TFA salts and changes in chitosan chemistry pre- and post-treatments. SAOS-2 (ATCC catalogue #HTB-85') osteoblast cells were seeded on both types of treated membranes (n=4/treatment group) and cell proliferation and viability evaluated over three days using the CellTitre Glow® (Promega) and LIVW/DEAD® stain (Molecular Probes), which are proliferation and viability assays, respectively.

Animal study: In the animal study, 10 Sprague Dawley rats weighting 250-280 g (approx. 2 months old) were used. Male animals of this size were selected to be skeletally mature and to avoid confounding factors associated with female estrous cycles. The test membranes were ethylene oxide gas sterilized prior to implantation. Each rat received one implant.

Rats were anesthetized with 4% isoflurane in oxygen for approximately 2 minutes. Maintenance of anesthesia was achieved with 2% isoflurane delivered via nosecone/non-rebreather. The dorsal part of the cranium was shaved and aseptically prepared with a solution of povidone iodine (BETADINE®). A U-shaped incision was made in the posterior part of the cranium, allowed the division of the subcutaneous fascia and the bilateral reflection of the periosteal flaps following blunt dissection, to expose the calvarial bone. Careful drilling with an 8-mm diameter trephine bur, mounted on a low-speed dental hand piece, around the sagittal suture, was used to create a standardized, round, defect. During drilling, the area was continuously irrigated with sterile saline solution. The calvarial disk was carefully removed to avoid tearing of the subjacent cranial structures.

A TEA/t-boc modified membrane was placed to cover the circular defect overlapping the defect margin by at least 3-4 mm. There was one implant per animal. The periosteum and skin were carefully closed and secured with nylon sutures (e.g. ETHILON® 4-0, ETHICON® Endo-Surgery, Bridgewater, NJ) after membrane implantation. After surgery, animals were housed individually and given subcutaneous injections of buprenorphine (0.15 mg/kg) for postoperative analgesia after surgery. Animals were given free access to rodent chow and water. Sites healed without complication. The study was conducted as part of the animal protocol (#0732) that was reviewed and approved by the Institutional Animal Care and Use Committee at The University of Memphis in compliance with the NIH Guide for the Care and Use of Laboratory Animals.

The results described herein relating to chitosan compositions treated with a phenyl-containing carbonyl derivative (e.g., raspberry ketone) were obtained using the following methods and materials.

Modification of chitosan material: 2% weight volume of chitosan (87.4% deacetylated, MW=470 kDa, Vanson Halosource) solution in 2% weight volume of acetic acid solution was mixed overnight to allow for homogeneous solution. 300 ml of the chitosan solution was stirred with magnetic stirrer/hot plate at 300 rpm while $O_2$ was purged from the solution using $N_2$ for two hours. 2.4 g of a phenyl-containing carbonyl derivative, such as raspberry ketone, was added to the solution and the mixture was purged using $N_2$ for an additional 30 minutes. The mixture was covered with parafilm to keep $O_2$ from being reintroduced to the system, and the hot plate was set to 85° C. and allowed to stir for 24 hours. Other chitosans with other degrees of deacetylation and molecular weights may be used and the weight percentage of chitosan and or acetic acid may be adjusted. Pyridine, pyridine derivatives 4-dimethylaminopyridine (DMAP) and 4-(1-pyrrolidinyl) pyridine and other catalysts may also be used. The reaction time may be controlled to control both the degree of modification of the chitosan by the raspberry ketone compound and the water contact angle (hydrophobicity) of the modified chitosan.

After 24 hours, the solution was aliquoted and frozen at −80° C., then lyophilized for 2-3 days, or enough all water content to be removed. The lyophilized raspberry ketone modified chitosan was washed with 100% ethanol to remove excess raspberry ketone, then dried in vacuum oven at 60° C. to remove the ethanol. Other drying methods such as air or vacuum drying may also be used to collect the modified material from reaction solution.

The final product can then be redissolved into acetic acid or other solvents for various uses such as films, gels, fibers, and or nano-micro-particles/spheres.

Fourier Transform Infrared Spectroscopy (FTIR): modified chitosan microspheres were dried at 80° C. for at least 1 hour and grinded with KBr to make pellets. Spectra were recorded on a Spectrum One spectrometer (Perkin-Elmer, Eden Prairie, MN) from about 4000 to about 500 $cm^{-1}$ with a resolution of about 4 $cm^{-1}$ in wave number at room temperature.

Scanning Electron Microscopy (SEM): modified chitosan microspheres were coated with an approximately 20 nm layer of gold by an ion sputter coater and were observed with a SEM (PHILIPS XL-30 ESEM).

X-ray diffraction: Wide-angle X-ray scattering (WAXS) was recorded on a Bruker D8 diffractometer. Modified chitosan was ground into a fine powder with a mortar and pestle, after submersion in liquid nitrogen. Powders were scanned in grazing angle reflection mode and data were collected with 2θ from 4 to 30.

Characterization: Morphology and diameter of modified chitosan was examined by scanning electron microscope (SEM). Fourier transform infrared spectroscopy (FTIR) spectra used to evaluate the addition of the phenyl group and changes in chitosan chemistry pre- and post-treatments. Proliferation of NIH3T3 cells on modified chitosan films (n=5/membrane) was measured by the CELLTITRE GLOW® (Promega) at 1, 2, and 3 days and compared to cast chitosan film controls. Cell morphology was observed by Live/Dead® staining (Molecular Probes). Inducible nitric oxide syntase (iNos) gene expression of raw264.7 cells on raspberry ketone chitosan films was performed by seeding raw264.7 mouse monocytes on chitosan and raspberry ketone chitosan films as well as tissue culture plastic as a control onto multiwell plate. After seeding, half of the cells were exposed to 5 µg/ml lipopolysaccharide (LPS) and the other half were left as a negative control for LPS conditions. The LPS treatment activated the production of inducible nitric oxide syntase (iNos). After a 24 hours incubation, the cells were lysed and RNA extracted for use to synthesize cDNA, then Real Time PCR to measure iNos gene expression.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of preparing an electrospun chitosan nanofiber, the method comprising:
 (a) electrospinning an acidic solution comprising chitosan to produce a chitosan nanofiber comprising immobilized salt residues;
 (b) removing one or more immobilized salt residues on the electrospun chitosan nanofiber with an organic solvent, thereby generating one or more free amino groups on the chitosan nanofibers; and
 (c) contacting at least one free amino group with an amino protecting reagent, wherein the organic solvent comprises triethylamine and, optionally, acetone.

2. The method of claim 1, wherein the organic solvent further comprises acetone.

3. A method of preparing an electrospun chitosan nanofiber, the method comprising:
 (a) electrospinning an acidic solution comprising chitosan to produce a chitosan nanofiber comprising immobilized salt residues;
 (b) removing one or more immobilized salt residues on the electrospun chitosan nanofiber with an organic solvent, thereby generating one or more free amino groups on the chitosan nanofibers; and (c) contacting at least one free amino group with di-tert-butyl decarbonate.

4. A method of producing an electrospun chitosan nanofiber comprising N-tert-butoxycarbonyl (t-Boc), the method comprising:
   (a) electrospinning a trifluoroacetic acid solution comprising chitosan to produce a chitosan nanofiber comprising immobilized salt residues;
   (b) removing one or more immobilized salt residues from the chitosan nanofiber with an organic solvent comprising triethylamine and, optionally, acetone, thereby generating one or more free amino groups on the chitosan nanofibers; and
   (c) contacting the free amino groups with di-tert-butyl dicarbonate, thereby producing a chitosan nanofiber comprising N-tert-butoxycarbonyl (t-Boc).

5. A composition comprising electrospun chitosan nanofibers comprising one or more N-tert-butoxycarbonyl groups.

6. The composition of claim 5, wherein the chitosan nanofibers resist dissolution when exposed to a hydrophilic solvent and/or exhibits minimal loss of chitosan nanofiber structure when exposed to a hydrophilic solvent.

7. The composition of claim 5, wherein the N-tert-butoxycarbonyl groups are on an exterior surface of the chitosan nanofibers.

8. A method of promoting or directing formation of a tissue in a subject at a target site comprising contacting the site with a barrier membrane comprising electrospun chitosan nanofibers produced according to a method comprising:
   (a) electrospinning an acidic solution comprising chitosan to produce a chitosan nanofiber comprising immobilized salt residues;
   (b) removing one or more immobilized salt residues on the electrospun chitosan nanofiber with an organic solvent, thereby generating one or more free amino groups on the chitosan nanofibers; and
   (c) contacting at least one free amino group with an amino protecting reagent, wherein the tissue is selected from the group consisting of epithelial, dental, craniofacial, and bone.

9. A method of promoting or directing formation of a tissue in a subject at a target site comprising contacting the site with a barrier membrane comprising electrospun chitosan nanofibers produced according to a method comprising:
   (a) electrospinning an acidic solution comprising chitosan to produce a chitosan nanofiber comprising immobilized salt residues;
   (b) removing one or more immobilized salt residues on the electrospun chitosan nanofiber with an organic solvent, thereby generating one or more free amino groups on the chitosan nanofibers; and
   (c) contacting at least one free amino group with an amino protecting reagent, wherein contacting the site comprises implanting the membrane for guided bone regeneration.

10. A method of promoting or directing formation of a tissue in a subject at a target site comprising contacting the site with a barrier membrane comprising electrospun chitosan nanofibers produced according to a method comprising:
    (a) electrospinning an acidic solution comprising chitosan to produce a chitosan nanofiber comprising immobilized salt residues;
    (b) removing one or more immobilized salt residues on the electrospun chitosan nanofiber with an organic solvent, thereby generating one or more free amino groups on the chitosan nanofibers; and
    (c) contacting at least one free amino group with an amino protecting reagent, wherein the tissue is bone tissue and the method prevents soft tissue migration into the target site.

* * * * *